(12) United States Patent
Al-Awar et al.

(10) Patent No.: US 11,174,250 B2
(45) Date of Patent: Nov. 16, 2021

(54) SUBSTITUTED CARBOXAMIDES AS INHIBITORS OF WDR5 PROTEIN-PROTEIN BINDING

(71) Applicant: PROPELLON THERAPEUTICS INC., Toronto (CA)

(72) Inventors: Rima Al-Awar, Toronto (CA); Carlos Armando Zepeda-Velazquez, Mississauga (CA); Gennady Poda, Toronto (CA); Methvin Isaac, Brampton (CA); David Uehling, Toronto (CA); Brian Wilson, Mississauga (CA); Babu Joseph, Oakville (CA); Yong Liu, Oakville (CA); Pandiaraju Subramanian, Oakville (CA); Ahmed Mamai, Mississauga (CA)

(73) Assignee: Propellon Therapeutics Inc., Toronto (CA)

( * ) Notice: Subject to any disclaimer, the term of this patent is extended or adjusted under 35 U.S.C. 154(b) by 0 days.

(21) Appl. No.: 16/080,851

(22) PCT Filed: Mar. 1, 2017

(86) PCT No.: PCT/CA2017/050271
§ 371 (c)(1),
(2) Date: Aug. 29, 2018

(87) PCT Pub. No.: WO2017/147701
PCT Pub. Date: Sep. 8, 2017

(65) Prior Publication Data
US 2019/0119264 A1    Apr. 25, 2019

Related U.S. Application Data

(60) Provisional application No. 62/301,678, filed on Mar. 1, 2016.

(51) Int. Cl.
| | | |
|---|---|---|
| A61K 31/167 | (2006.01) |
| C07C 233/57 | (2006.01) |
| C07C 233/64 | (2006.01) |
| C07D 413/12 | (2006.01) |
| C07D 401/12 | (2006.01) |
| C07D 405/12 | (2006.01) |
| C07D 401/14 | (2006.01) |
| C07D 491/08 | (2006.01) |
| C07D 237/14 | (2006.01) |
| C07D 213/81 | (2006.01) |
| C07D 295/135 | (2006.01) |
| C07D 405/14 | (2006.01) |
| A61K 45/06 | (2006.01) |
| C07D 213/82 | (2006.01) |
| C07D 235/08 | (2006.01) |

(Continued)

(52) U.S. Cl.
CPC ............ *C07D 413/12* (2013.01); *A61K 45/06* (2013.01); *C07D 213/81* (2013.01); *C07D 213/82* (2013.01); *C07D 235/08* (2013.01); *C07D 235/24* (2013.01); *C07D 237/14* (2013.01); *C07D 237/24* (2013.01); *C07D 295/135* (2013.01); *C07D 401/12* (2013.01); *C07D 401/14* (2013.01); *C07D 405/12* (2013.01); *C07D 405/14* (2013.01); *C07D 413/10* (2013.01); *C07D 471/04* (2013.01); *C07D 491/08* (2013.01)

(58) Field of Classification Search
CPC .... A61K 31/167; C07C 233/57; C07C 233/64
USPC .......................................... 514/613; 564/123
See application file for complete search history.

(56) References Cited

U.S. PATENT DOCUMENTS

| | | |
|---|---|---|
| 5,981,537 A | 11/1999 | Nugent et al. |
| 6,288,055 B1 | 9/2001 | Natarajan et al. |

(Continued)

FOREIGN PATENT DOCUMENTS

| | | |
|---|---|---|
| CA | 2944959 A1 | 10/2015 |
| CL | 201802360 | 9/2018 |

(Continued)

OTHER PUBLICATIONS

Jordan, V. C. Nature Reviews: Drug Discovery, 2, 2003, 205.*

(Continued)

*Primary Examiner* — Douglas M Willis
(74) *Attorney, Agent, or Firm* — Cooley LLP; J. Dean Farmer; Serge R. Banini

(57) ABSTRACT

The present application is directed to compounds of Formula I:

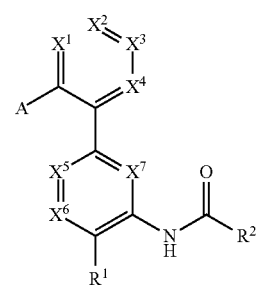

compositions comprising these compounds and their uses, for example as medicaments for the treatment of diseases, disorders or conditions mediated or treatable by inhibition of binding between WDR5 protein and its binding partners.

23 Claims, 1 Drawing Sheet

(51) Int. Cl.
*C07D 235/24* (2006.01)
*C07D 237/24* (2006.01)
*C07D 413/10* (2006.01)
*C07D 471/04* (2006.01)

(56) References Cited

U.S. PATENT DOCUMENTS

| | | | |
|---|---|---|---|
| 7,169,791 | B2 | 1/2007 | Breitenstein et al. |
| 7,230,001 | B1 | 6/2007 | Rudolf et al. |
| 7,312,341 | B2 | 12/2007 | DeSimone et al. |
| 7,547,804 | B2 | 6/2009 | Bajji et al. |
| 7,745,437 | B2 | 6/2010 | Ren et al. |
| 7,807,679 | B2 | 10/2010 | Cassayre et al. |
| 7,947,696 | B2 | 5/2011 | Eggenweiler et al. |
| 8,193,239 | B2 | 6/2012 | Ford et al. |
| 8,748,423 | B2 | 6/2014 | Hangauer, Jr. et al. |
| 9,079,866 | B2 | 7/2015 | Bacani et al. |
| 10,160,763 | B2 | 12/2018 | Fesik et al. |
| 10,501,466 | B2 | 12/2019 | Fesik et al. |
| 2001/0051719 | A1 | 12/2001 | Bromidge et al. |
| 2007/0254894 | A1 | 11/2007 | Kane, Jr. et al. |
| 2009/0069327 | A1 | 3/2009 | Ding et al. |
| 2009/0105250 | A1 | 4/2009 | Sim et al. |
| 2009/0233905 | A1 | 9/2009 | Burke et al. |
| 2010/0184765 | A1 | 7/2010 | Huang et al. |
| 2012/0208815 | A1 | 8/2012 | Burger et al. |
| 2015/0266881 | A1 | 9/2015 | Tomita et al. |
| 2016/0311807 | A1 | 10/2016 | Treon et al. |
| 2016/0318878 | A1 | 11/2016 | Treon et al. |
| 2019/0112290 | A1 | 4/2019 | Al-Awar et al. |
| 2019/0330274 | A1 | 10/2019 | Mahr et al. |
| 2020/0385371 | A1 | 12/2020 | Al-Awar et al. |

FOREIGN PATENT DOCUMENTS

| | | |
|---|---|---|
| CN | 100355751 C | 12/2007 |
| CN | 101875617 | 11/2010 |
| CN | 105175284 A | 12/2015 |
| CN | 105585565 A | 5/2016 |
| JP | 9-59236 A | 3/1997 |
| JP | 2010/520228 A | 6/2010 |
| WO | WO 01/72745 A1 | 10/2001 |
| WO | WO 2002/044153 A1 | 6/2002 |
| WO | WO 2002/088101 A2 | 11/2002 |
| WO | WO 2006/124731 A2 | 11/2006 |
| WO | WO 2011/149874 A2 | 12/2011 |
| WO | WO 2011/156557 A2 | 12/2011 |
| WO | WO 2011/159685 A2 | 12/2011 |
| WO | WO 2012/066065 A1 | 5/2012 |
| WO | WO 2014/003124 A1 | 1/2014 |
| WO | WO 2014/048878 A1 | 4/2014 |
| WO | WO 2014/121055 A2 | 8/2014 |
| WO | WO 2016/112846 A1 | 7/2016 |
| WO | WO 2017/147700 A1 | 9/2017 |
| WO | WO 2017/221092 A1 | 12/2017 |
| WO | WO 2020/086857 A1 | 4/2020 |
| WO | WO 2021/028806 A1 | 2/2021 |

OTHER PUBLICATIONS

Vippagunta, et al. Advanced Drug Delivery Reviews, 48, 2001, 18.*
Bolshan, Y. et al. (2013) "Synthesis, Optimization, and Evaluation of Novel Small Molecules as Antagonists of WDR5-MLL Interaction" *ACS Medicinal Chemistry Letters*, 4:353-357.
Getlik, M. et al. (Mar. 9, 2016) "Structure-Based Optimization of a Small Molecule Antagonist of the Interaction between WD Repeat-Containing Protein 5 (WDR5) and Mixed-Lineage Leukemia 1 (MLL1)" *J Med Chem*, 59(6):2478-2496.
Grebien, F. et al. (Aug. 2015) "Pharmacological targeting of the Wdr5-MLL interaction in C/EBPα N-terminal leukemia" *Nat Chem Biol*, 11(8):571-578; plus 2 pages supplemental information and 1 page correction.

Karatas, H. et al. (2010) "Analysis of the Binding of Mixed Lineage Leukemia 1 (MLLI) and Histone 3 Peptides to WD Repeat Domain 5 (WDR5) for the Design of Inhibitors of the MLL1-WDR5 Interaction" *J Med Chem*, 53:5179-5185.
Karatas, H. et al. (2015) "Structure-based design of conformationally constrained cyclic peptidomimetics to target the MLL1-WDR5 protein-protein interaction as inhibitors of the MLL1 methyltransferase activity" *Chinese Chemical Letters*, 26:455-458.
Senisterra, G. et al. (2013) "Small-molecule inhibition of MLL activity by disruption of its interaction with WDR5" *Biochem J*, 449:151-159; plus 4 pages supplemental information.
Song, Ji-Joon and Kingston, R.E. (Dec. 12, 2008) "WDR5 Interacts with Mixed Lineage Leukemia (MLL) Protein via the Histone H3-binding Pocket" *J Biol Chem*, 283(50):35258-35264; plus 4 pages supplemental information.
Li, DD., et al. "Structure-based design and synthesis of small molecular inhibitors disturbing the interaction of MLL1-WDR5." *European Journal of Medicinal Chemistry* vol. 118 (2016): pp. 1-8.
Wermuth, C.G., et al. "Molecular Variations Based on Isosteric Replacements." *Practice of Medicinal Chemistry* (1996): pp. 203-237.
Carugo, et al. "In Vivo Functional Platform Targeting Patient-Derived Xenografts Identifies WDR5-Myc Association as a Critical Determinant of Pancreatic Cancer." Cell Rep. Jun. 28, 2016;16(1):133-147. doi: 10.1016/j.celrep.2016.05.063.
Cheung, et al. "Methylation of an intronic region regulates miR-199a in testicular tumor malignancy." Oncogene. Aug. 4, 2011;30(31):3404-15. doi: 10.1038/onc.2011.60.
Costa, et al. "Reversing HOXA9 oncogene activation by PI3K inhibition: epigenetic mechanism and prognostic significance in human glioblastoma." Cancer Res. Jan. 15, 2010;70(2):453-62. doi: 10.1158/0008-5472.CAN-09-2189.
Dorwald. "Side Reactions in Organic Synthesis: A Guide to Successful Synthesis Design." Weinheim: WILEY-VCH Verlag GmbH & Co. KGaA, 2005, Preface.
Dubuc, et al. "Aberrant patterns of H3K4 and H3K27 histone lysine methylation occur across subgroups in medulloblastoma." Acta Neuropathol. Mar. 2013;125(3):373-84. doi: 10.1007/s00401-012-1070-9.
Gallo, et al. "A tumorigenic MLL-homeobox network in human glioblastoma stem cells." Cancer Res. Jan. 1, 2013;73(1):417-27. doi: 10.1158/0008-5472.CAN-12-1881.
Hackam, et al. "Translation of research evidence from animals to humans." JAMA. Oct. 11, 2006;296(14):1731-2.
Irizarry, et al. "The human colon cancer methylome shows similar hypo- and hypermethylation at conserved tissue-specific CpG island shores." Nat Genet. Feb. 2009;41(2):178-186. doi: 10.1038/ng.298.
Kim, et al. "A role for WDR5 in integrating threonine 11 phosphorylation to lysine 4 methylation on histone H3 during androgen signaling and in prostate cancer." Mol Cell. May 22, 2014;54(4):613-25. doi: 10.1016/j.molcel.2014.03.043.
Li, et al. "Pygo2 siRNA Inhibit the Growth and Increase Apoptosis of U251 Cell by Suppressing Histone H3K4 Trimethylation." J Mol Neurosci. Aug. 2015;56(4):949-955. doi: 10.1007/s12031-015-0558-x.
Molyneux, et al. "Burkitt's lymphoma." Lancet. Mar. 31, 2012;379(9822):1234-44. doi: 10.1016/S0140-6736(11)61177-X.
Sausen, et al. "Clinical implications of genomic alterations in the tumour and circulation of pancreatic cancer patients." Nat Commun. Jul. 7, 2015;6:7686. doi: 10.1038/ncomms8686.
Schneider and Saur. "In Vivo RNAi Screening for Pancreatic Cancer Drivers: PILOTing the WDR5-MYC Axis." Trends Cancer. Aug. 2016;2(8):391-392. doi: 10.1016/j.trecan.2016.07.002.
Sun, et al. "LncRNA GClnc1 Promotes Gastric Carcinogenesis and May Act as a Modular Scaffold of WDR5 and KAT2A Complexes to Specify the Histone Modification Pattern." Cancer Discov. Jul. 2016;6(7):784-801. doi: 10.1158/2159-8290.CD-15-0921.
Thomas, et al. "Interaction with WDR5 promotes target gene recognition and tumorigenesis by MYC." Mol Cell. May 7, 2015;58(3):440-52. doi: 10.1016/j.molcel.2015.02.028.
Zhao, et al. "Methylation of DACT2 promotes papillary thyroid cancer metastasis by activating Wnt signaling" PLoS One. Nov. 6, 2014;9(11):e112336. doi: 10.1371/journal.pone.0112336.

(56) References Cited

OTHER PUBLICATIONS

Zhao, et al. "Expression and clinical role of RBQ3 in gliomas." J Neurol Sci. Dec. 15, 2015;359(1-2):177-84. doi: 10.1016/j.jns.2015.10.058.

Zhou, et al. "Pygo2 functions as a prognostic factor for glioma due to its up-regulation of H3K4me3 and promotion of MLL1/MLL2 complex recruitment." Sci Rep. Feb. 23, 2016;6:22066. doi: 10.1038/srep22066.

* cited by examiner

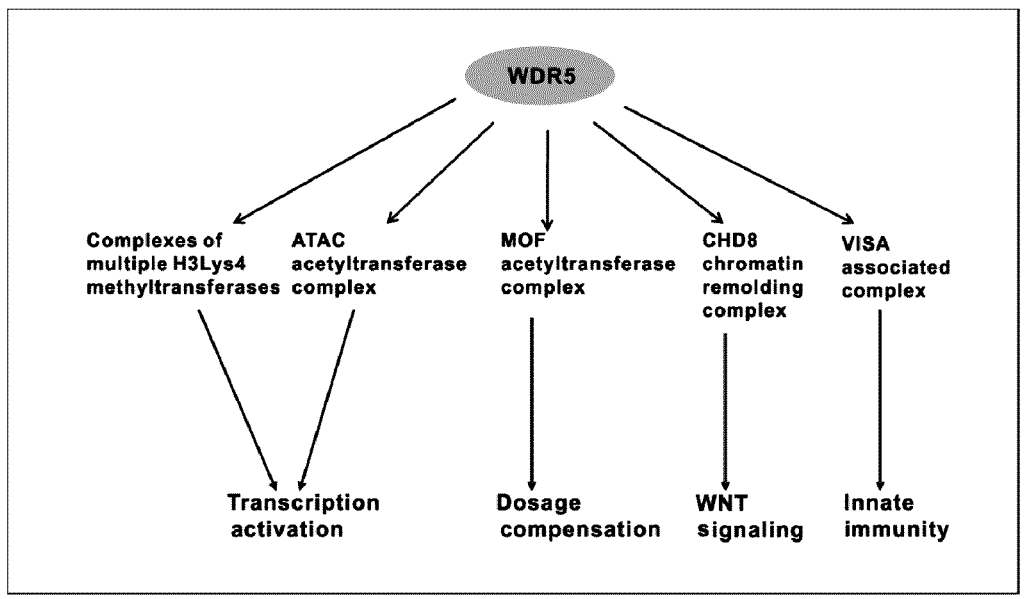

SUBSTITUTED CARBOXAMIDES AS INHIBITORS OF WDR5 PROTEIN-PROTEIN BINDING

CROSS-REFERENCE TO RELATED APPLICATIONS

This application is a national stage application, filed under 35 U.S.C. 371, of International Application No. PCT/CA2017/050271, filed Aug. 29, 2018, which claims priority to, and the benefit of U.S. provisional patent application No. 62/301,678, filed on Mar. 1, 2016, the contents of each of the aforementioned patent applications are incorporated herein by reference in their entireties.

FIELD

The present application relates to compounds, to processes for their preparation, to compositions comprising them and their use for the treatment of diseases and conditions related to interactions between WDR5 and its binding partners including, but not limited to, MLL.

BACKGROUND

Histones are the most basic units for packing DNA into nucleosomes and covalent modifications of histones, such as methylation, acetylation and phosphorylation, play a central role for regulation of gene transcription [*Nat. Rev. Mol. Cell Biol.* 2001, 2: 422-432; *Cell* 2007, 128:693-705]. Epigenetics refers to the heritable changes that control how the genome is accessed in different cell types during embryonic development and cellular differentiation [*Genes. Dev.* 2009; 23: 781-3]. This capability permits specialization of function between cells without altering the DNA sequence.

It is now well recognized that misregulation of histone modifications plays a key role in a wide range of human diseases, including but not limited to cancer [*Cell.*, 2007, 10: 693-705; *Nat. Rev. Cancer.*, 2010, 10:457-469]. Mixed Lineage Leukemia 1 (MLL1) protein is a Histone H3 Lysine 4 (H3K4) methyltransferase and is frequently misregulated in a subset of acute leukemia [*Trends Mol. Med.*, 2004, 10: 500-507, *Cell. Stem. Cell.*, 2007, 1:324-337]. MLL1 itself has a weak H3K4 methyltransferase activity but its enzymatic activity is dramatically enhanced when MLL1 is present in a core complex, made up of MLL1, WD repeat domain 5 protein (WDR5), Absent, Small, or Homeotic-2-Like (ASH2L) and Retinoblastoma Binding Protein 5 (RbBP5). Recent studies have clearly shown that the interaction between MLL1 and WDR5 proteins is essential for the activity of MLL1 but dispensable for the activity of other MLL family members, including MLL2, MLL3 and MLL4 [*Mol. Cell.*, 2014, 53:247-261]. Hence, blocking the MLL1-WDR5 protein-protein interaction can specifically inhibit the activity of MLL1 H3K4 methyltransferase activity and such inhibition has the potential for the treatment of human diseases, such as, a subset of acute leukemia, whose development and progression depend upon MLL1 activity.

WDR5 is a common subunit of all six mammalian histone H3K4 methyltransferases [*Dev. Biol.*, 2010, 339 (2):240-249]. WDR5 has 334 amino acids and contains seven typical WD40 repeat domains, each approximately 40 amino acids [*Nat. Struct. Mol. Biol.*, 2009, 16 (7):678-680]. Structural studies suggest that the WD40 repeats form a seven-bladed propeller fold, with each blade made up of a four-stranded antiparallel sheet. This structural property suggests that WDR5 has many exposed surfaces making it a useful adaptor to interact with other proteins. Further, pulldown assays indicate that WDR5 prefers to bind dimethylated histone H3K4 peptide [*Nat. Struct. Mol. Biol.*, 2009, 16 (7):678-680].

Because WDR5 is an essential component of the histone methylation, acetylation, and chromatin remodeling complexes, while not wishing to be limited by theory, WDR5 is believed to serve as an adaptor protein for complex assembly. However, it may also contribute to other physiological phenomena. WDR5 is an important component for assembly or stability of the virus-induced signaling adapter (VISA) associated complex, which plays a key role in virus-triggered induction of type I interferons (IFNs) and antiviral innate immune response [*Proc. Natl. Acad. Sci. USA.*, 2010, 107(2):815-820]. Previous studies have demonstrated that VISA is located at the outer membrane of mitochondria. Interestingly, this study revealed that WDR5 was not only localized in the nucleus as believed before, but also abundantly localized in the cytoplasm. Viral infection induces translocation of WDR5 from the nucleus to the mitochondria located VISA complex, where it played a role in the assembly and stability of the VISA complex. These studies demonstrate for the first time a cytoplasmic function for WDR5, specifically in virus-triggered signaling resulting in induction of type I IFNs [*Proc. Natl. Acad. Sci. USA.*, 2010, 107(2):815-820].

(A) MLL1-WDR5 Complex in Leukemogenesis

Leukemia is characterized by an abnormal increase of white blood cells in the blood or bone marrow. Among all types of cancers, the morbidity of leukemia is the highest for patients below 35 years old. Over 70% of infant leukemia patients bear a translocation involving chromosome 11, resulting in the fusion of the MLL1 gene with other genes [*Nat. Rev. Cancer.*, 2007, 7(11):823-833]. MLL1 translocations are also found in approximately 10% of adult acute myeloid leukemia (AML) patients, who were previously treated with topoisomerase II inhibitors for other types of cancers [*Nat. Rev. Cancer.*, 2007, 7(11):823-833].

MLL1 is the human homologue of *Saccharomyces cerevisiae* gene Set1 and the *Drosophila* gene Trx. The genes encode an enzyme to catalyze the methylation of H3K4 [*Nat. Rev. Cancer.*, 2007, 7(11):823-833]. Trimethylation of histone H3K4 is a hallmark of active gene transcription, and alteration of this process often causes changes in gene expression pattern. MLL1 translocation is also linked to altered transcription of important genes involved in stem cell maintenance and development and, thus, leads to leukemogenesis. The MLL1 gene was first discovered in leukemia patients in 1991 [*Nat. Rev. Cancer.*, 2007, 7(11):823-833]. cDNA of the MLL1 gene contains ~12 kb nucleotides and encodes a peptide over 4000 amino acids in length. In the cell, the premature MLL1 protein is digested by taspase, which results in two peptides: a 300 kDa N-terminal fragment and a 170 kDa C-terminal fragment. The two cleaved peptides form a heterodimer, which is complexed with other components, including WDR5, RBBP5, ASH2L and DPY30. In some leukemia patients, chromosomal translocation results in fusion of ~4.2 kb DNA of the MLL1 N-terminal coding region with some other genes [Cancer. Cell., 2003, 4(3):197-207].

The generation of MLL1 fusion protein is sufficient to induce leukemia, which has been demonstrated in animal models [*Nat. Rev. Cancer.*, 2007, 7(11):823-833]. The mechanisms of MLL1 fusion-mediated leukemia has been studied extensively in the past twenty years. The MLL/SET1 family members are most enzymatically active when part of the "core complex" (WRAD2), comprising the catalytic SET-domain-containing subunits bound to a sub-complex made up of the proteins WDR5, RbBP5, Ash2L and a homodimer of DPY-30. The necessity of MLL/SET1 members to bind WRAD2 for full activity is the basis of a particular drug development strategy, which seeks to disrupt the interaction between the MLL/SET1 subunits and WDR5. Recent efforts to pharmacologically target the MLL1 catalytic activity has centered on attempts to disrupt the MLL1-WDR5 interaction by means of Win-motif mimicking peptides and small-molecule peptidomimetics [*J. Med. Chem.*, 2010, 53: 5179-5185; *J. Am. Chem. Soc.*, 2013, 135: 669-682; *Mol Cell.*, 2014; 53:247-261]. However, as with most peptide based inhibitors, MLL1-WDR5 peptidic inhibitors exhibit poor cell-based activity and lack oral bioavailability due to poor cell-permeability and their susceptibility to peptidases.

(b) Role of WDR5 in Other Cancers (i) Bladder Cancer

WDR5 also plays a critical role in embryonic stem cell self-renewal [*Cell.* 2011; 145 (2):183-97] and Epithelial-Mesenchymal Transition [*Mol. Cell.*, 2011; 43(5):811-22]. A recent study finds that H2A.Z is overexpressed in bladder cancer and activates oncogenic transcription by recruiting WDR5 and Bromodomain PHD Finger Transcription Factor (BPTF) to its target genes [*Epigenetics. Chromatin.*, 2013; 6 (1):34.], suggesting that WDR5 may play a role in bladder cancer, but its expression pattern, role and mechanism in bladder cancer remain unclear. WDR5 is upregulated in bladder cancer tissues compared with normal tissues as determined by immunohistochemistry (IHC), and is correlated with advanced tumor stage and overall survival of bladder cancer patients. A recent study found that WDR5 is overexpressed in prostate cancer tissue compared with normal tissues [*Mol. Cell.*, 2014 May 22; 54 (4):613-25]. Taken together, high expression levels of WDR5 may serve as a novel molecular marker for bladder cancer.

WDR5 silencing reduces cell growth in breast cancer and prostate cancer [*Mol. Cell.*, 2014, 54 (4):613-25; *Cell Rep.*, 2013 5 (2):302-13], but the detailed mechanism and role in vivo is still unknown. Through gain or loss of function, WDR5 was found to promote bladder cancer cell proliferation in vitro and tumor growth in vivo, and that silencing WDR5 mainly induces the G0/G1 phase cell cycle arrest. The cell cycle is regulated by cyclins and cyclin-dependent kinases. Cyclin E1 and Cyclin E2 regulate the G1 to S-phase transition, while Cyclin B1 regulates the G2 to M-phase transition. Moreover, Cyclin E is associated with high-grade, high-stage and invasive bladder cancer [*Cell. Cycle.*, 2012; 11(7):1468-76; *Am. J. Pathol.*, 2000; 157(3):787-94]. UHMK1 (also named KIS) is overexpressed in leukemia and promotes the G1 to S-phase transition [*Leuk. Res.*, 2008; 32 (9):1358-65]. Mechanistically, WDR5 knockdown inhibited cyclin E1, cyclin E2 and UHMK1 leading to G0/G1 phase cell cycle arrest, which might disturb the effect of cyclin B1 downregulation on G2 to M-phase transition. Additional studies showed that knockdown of MLL1, another core component of the MLL/SET1 complexes, suppressed HeLa cell proliferation by reducing the expression of cyclin B and inducing the G2/M phase cell cycle arrest [*Oncogene.* 2013; 32(28):3359-70]. Thus, the data reported suggests that WDR5 promotes bladder cancer cell proliferation in vitro and in vivo by regulating the cell cycle, but the role and mechanism are not the same as MLL1.

WDR5 is believed to play an essential role in cancer stem cells (CSCs). CSCs are a small subpopulation of cells in a tumor that can self-renew and differentiate into multiple lineages, and possess strong tumor-initiating capacity. CSCs have been widely identified in a number of malignancies, and the existence of CSCs in bladder cancer was found by Chan et al [*Proc. Natl. Acad. Sci. USA.*, 2009; 106 (33): 14016-21]. Several studies have found that sphere culture is an effective way to enrich cancer stem cells [*Cell.* 2007; 131(6):1109-23; *Urol Oncol.* 2012; 30(3):314-8]. It was observed that WDR5 and pluripotency transcription factors were upregulated in UM-UC-3 and T24 spheres. Through gain or loss of function, it was demonstrated that WDR5 promoted UM-UC-3 and T24 cells self-renewal in vitro and upregulated Nanog. Emerging evidence shows that Nanog is overexpressed in poorly differentiated tumors and correlated with poor survival outcome of patients with various types of cancer, including bladder cancer [*Nat. Genet.*, 2008; 40(5): 499-507; *Onco. Targets. Ther.*, 2013; 6:1207-20]. Moreover, Nanog plays a key role in CSCs self-renewal and targeting. Nanog has shown promising therapeutic potential in several types of cancer [*Cell Stem Cell.* 2011; 9 (1):50-63; *Oncogene.* 2013; 32(37):4397-405]. WDR5 directly activates Nanog by mediating its promoter H3K4me3 level. Taken together, recent findings suggest that WDR5 plays a vital role in self-renewal of bladder cancer cells by regulating Nanog.

Further studies have demonstrated that WDR5 silencing increased cell apoptosis and decreases bladder cancer cells resistance to cisplatin. Conversely, overexpression of WDR5 enhanced chemoresistance to cisplatin. Moreover, WDR5 directly regulates important inhibitors of apoptotic proteins, MCL1 [*FEBS Lett.* 2010; 584(14):2981-9; *Sci Rep.* 2014; 4:6098] and BIRC3 [*Expert Opin Ther Targets.* 2009; 13(11):1333-45], by H3K4me3.

In summary, WDR5 is upregulated in bladder cancer, and promotes bladder cancer cell proliferation, self-renewal and chemoresistance via activating a series of oncogenes by H3K4me3. Therefore, WDR5 is a potential biomarker for bladder cancer and a promising target for drug development [*Sci Rep.* 2015; 5: 8293, *Genom Data.* 2015; 5:27-9.].

(II) Acute Myeloid Leukemia (AML)

The CEBPA gene is mutated in 9% of patients with acute myeloid leukemia (AML). Selective expression of a short (30-kDa) CCAAT-enhancer binding protein-α (C/EBPα) translational isoform, termed p30, represents the most common type of CEBPA mutation in AML. The molecular mechanisms underlying p30-mediated transformation remain incompletely understood. Recent studies have shown that C/EBPα p30, but not the normal p42 isoform, preferentially interacts with WDR5, a key component of SET/MLL (SET-domain/mixed-lineage leukemia) histone-methyltransferase complexes. Accordingly, p30-bound genomic regions were enriched for MLL-dependent H3K4me3 marks. The p30-dependent increase in self-renewal and inhibition of myeloid differentiation required WDR5, as downregulation of the latter inhibited proliferation and restored differentiation in p30-dependent AML models. Small-molecule inhibitors of the WDR5-MLL interaction selectively inhibited proliferation and induced differentiation in p30-expressing human AML cells revealing the mechanism of p30-dependent transformation and establish the essential p30 cofactor WDR5 as a therapeutic target in CEBPA-mutant AML [*Nat Chem Biol.* 2015; 11(8):571-8].

(III) MYCN-Amplified Neuroblastoma

MYCN gene amplification in neuroblastoma drives a gene expression program that correlates strongly with aggressive disease. Mechanistically, trimethylation of histone H3 lysine 4 (H3K4) at target gene promoters is a strict prerequisite for this transcriptional program to be enacted. WDR5 is a histone H3K4 presenter that has been found to have an essential role in H3K4 trimethylation [*Cancer Res* 2015; 75(23); 5143-54]. For this reason, in this study, the relationship between WDR5-mediated H3K4 trimethylation and N-Myc transcriptional programs in neuroblastoma cells were investigated. N-Myc upregulated WDR5 expression in neuroblastoma cells. Gene expression analysis revealed that WDR5 target genes included those with MYC-binding elements at promoters such as MDM2. WDR5 was demonstrated to form a protein complex at the MDM2 promoter with N-Myc, but not p53, leading to histone H3K4 trimethylation and activation of MDM2 transcription. RNAi-mediated attenuation of WDR5 upregulated expression of wild-type but not mutant p53, an effect associated with growth inhibition and apoptosis. Similarly, a small-molecule antagonist of WDR5 reduced N-Myc/WDR5 complex formation, N-Myc target gene expression, and cell growth in neuroblastoma cells. In MYCN-transgenic mice, WDR5 was overexpressed in precancerous ganglion and neuroblastoma cells compared with normal ganglion cells. Clinically, elevated levels of WDR5 in neuroblastoma specimens were an independent predictor of poor overall survival. Overall, these results identify WDR5 as a key cofactor for N-Myc-regulated transcriptional activation and tumorogenesis and as a novel therapeutic target for MYCN-amplified neuroblastomas [*Cancer Res* 2015; 75(23); 5143-54, *Mol Cell.* 2015; 58(3):440-52.].

SUMMARY

The structural features as described above suggest that the WDR5-MLL binding is a desirable drug target. Hence, agents that bind to the WDR5 protein and compete for binding with WDR5-interacting partners can reverse the transcriptional activities of WDR5 containing complexes. Considering the challenges generally associated with inhibiting protein-protein interactions, along with the current need to treat WDR5-driven tumor types such as leukemias, bladder cancers and neuroblastomas, complementary screening approaches namely virtual screening, focused library screening and traditional structure activity relationship (SAR) studies were conducted. These studies led to the identification of compounds which inhibit the WDR5 protein-protein binding. In addition, structure-activity relationship studies demonstrated that specific chemical features contribute to longer residence times for the binding of these compounds with WDR5. Studies indicate that longer residence times can be designed into WDR5 inhibitors and contribute to the ligand-induced anti-proliferative effects observed in hematologic and solid tumors.

A novel class of compounds of Formula (I) have been prepared that show potent disruption of WDR5-MLL1 protein-protein binding and therefore have utility in the treatment of cancers and other WDR5-mediated diseases, disorders and conditions.

Therefore, in one aspect, the present application includes a compound of Formula (I) or a pharmaceutically acceptable salt and/or solvate thereof:

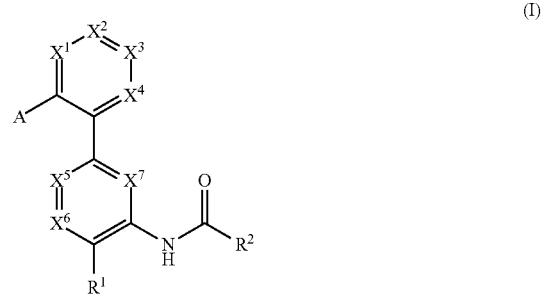

wherein:
$R^1$ is a heterocycloalkyl that is unsubstituted or substituted with one or more substituents selected from halo, $C_{1-6}$alkyl, $C_{1-6}$fluoroalkyl, $C_{3-10}$cycloalkyl, $OR^4$, $SR^4$, $NR^5R^6$, $C_{1-6}$alkyleneOR$^4$, $C_{1-6}$alkyleneSR$^4$ and $C_{1-6}$alkyleneNR$^5$R$^6$, provided that $R^1$ comprises at least one basic nitrogen atom;
$R^2$ is selected from $C_{6-10}$aryl and heteroaryl, and $R^2$ is unsubstituted or substituted with one or more substituents selected from halo, $C_{1-6}$alkyl, $C_{1-6}$fluoroalkyl, =O, =S, $OR^7$, $SR^7$ and $NR^8R^9$;
$R^4$ and $R^7$ are independently selected from H, $C_{1-6}$alkyl, $C_{1-6}$fluoroalkyl, $C(O)C_{1-6}$alkyl and $C(O)C_{1-6}$fluoroalkyl;
$R^5$ and $R^6$ are independently selected from H, $C_{1-6}$alkyl, $C_{1-6}$fluoroalkyl, heterocycloalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneNHC$_{1-6}$alkyl, $C_{1-6}$alkyleneN(C$_{1-6}$alkyl)(C$_{1-6}$alkyl), $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl, or $R^5$ and $R^6$ together with the nitrogen atom to which they are attached form a 3-10 membered heterocycle that is unsubstituted or substituted with one or more substituents selected from halo, OH, CN, $C_{1-6}$alkyl, $OC_{1-6}$alkyl, $C_{1-6}$fluoroalkyl, $OC_{1-6}$fluoroalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneNHC$_{1-6}$alkyl, $C_{1-6}$alkyleneN(C$_{1-6}$alkyl)(C$_{1-6}$alkyl), $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl;
$R^8$ and $R^9$ are independently selected from H, $C_{1-6}$alkyl, $C_{1-6}$fluoroalkyl, $C(O)C_{1-6}$alkyl and $C(O)C_{1-6}$fluoroalkyl, or $R^8$ and $R^9$ together with the nitrogen atom to which they are attached form a 3-10 membered heterocycle that is unsubstituted or substituted with one or more substituents selected from halo, CN, OH, $C_{1-6}$alkyl $OC_{1-6}$alkyl, $C_{1-6}$fluoroalkyl and $OC_{1-6}$fluoroalkyl;
$X^1$, $X^2$, $X^3$ and $X^4$ are each independently selected from $CR^{10}$ and N;
$X^5$, $X^6$ and $X^7$ are each independently selected from CH and N;
$R^{10}$ is selected from H, halo, CN, $C_{1-6}$alkyl, $C_{1-6}$fluoroalkyl, $OR^{11}$, $SR^{11}$, $NR^{12}R^{13}$, $R^{14}$, $C_{1-6}$alkyleneR$^{14}$, $OC_{1-6}$alkyleneR$^{14}$, $SC_{1-6}$alkyleneR$^{14}$, $C_{1-6}$alkyleneNR$^{12}$R$^{13}$, $C_{1-6}$alkyleneOR$^{11}$, $C_{1-6}$alkyleneSR$^{11}$, $OC_{1-6}$alkyleneNR$^{12}$R$^{13}$, $SC_{1-6}$alkyleneNR$^{12}$R$^{13}$, $OC_{1-6}$alkyleneOR$^{11}$, $SC_{1-6}$alkyleneOR$^{11}$, $OC_{1-6}$alkyleneSR$^{11}$, $SC_{1-6}$alkyleneSR$^{11}$, $C(O)OR^{11}$, $C(S)OR^{11}$, $C(S)NR^{12}R^{13}$ and $C(O)NR^{12}R^{13}$;
$R^{11}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{11}$ is other than H, it is unsubstituted or substituted with one or more substituents selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$ alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{15}$, $C_{1-6}$alkyleneOR$^{15}$, $C_{1-6}$alkyleneSR$^{15}$ and $C_{1-6}$alkyleneNR$^{16}R^{17}$;

$R^{12}$ and $R^{13}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and when $R^{12}$ and $R^{13}$ are other than H they are each independently unsubstituted or substituted with one or more substituents selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{15}$, $C_{1-6}$alkyleneOR$^{15}$, $C_{1-6}$alkyleneSR$^{15}$ and $C_{1-6}$alkyleneNR$^{16}R^{17}$, or $R^{12}$ and $R^{13}$ together with the nitrogen atom to which they are attached form a 3-10 membered heterocycle that is unsubstituted or substituted with one or more substituents independently selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{15}$, $C_{1-6}$alkyleneOR$^{15}$, $C_{1-6}$alkyleneSR$^{15}$ and $C_{1-6}$alkyleneNR$^{16}R^{17}$;

$R^{14}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl, and when $R^{14}$ is other than H it is unsubstituted or substituted with one or more substituents independently selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{15}$, $C_{1-6}$alkyleneOR$^{15}$, $C_{1-6}$alkyleneSR$^{15}$ and $C_{1-6}$alkyleneNR$^{16}R^{17}$;

$R^{15}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and when $R^{15}$ is other than H it is unsubstituted or substituted with one or more substituents selected from halo, $C_{1-6}$alkyl, CN, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)C_{1-6}$fluoroalkyl, $C(O)$OH, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN($C_{1-6}$alkyl)($C_{1-6}$alkyl);

$R^{16}$ and $R^{17}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl and when $R^{16}$ and $R^{17}$ are other than H they are each unsubstituted or substituted with one or more substituents independently selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)$OH, $C(O)OC_{1-6}$alkyl, $C(O)C_{1-6}$fluoroalkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN($C_{1-6}$alkyl)($C_{1-6}$alkyl), or $R^{16}$ and $R^{17}$ together with the nitrogen atom to which they are attached form a 3-10 membered heterocycle that is unsubstituted or substituted with one or more substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)C_{1-6}$fluoroalkyl, $C(O)$OH, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN($C_{1-6}$alkyl) ($C_{1-6}$ alkyl);

A is fluoro; and all alkyl and alkylene groups are optionally fluorosubstituted.

In another aspect, the present application includes a composition comprising one or more compounds of the application and a carrier.

In another aspect, the present application includes a method for inhibition of binding of WDR5 to its binding partners in a cell, either in a biological sample or in a patient, comprising administering an effective amount of one or more compounds of the application to the cell.

The present application also includes a method of treating a disease, disorder or condition that is mediated or treatable by inhibition of binding between WDR5 protein and its binding partners comprising administering a therapeutically effective amount of one or more compounds of the application to a subject in need thereof. In an embodiment of the present application, the disease, disorder or condition mediated or treatable by inhibition of binding between WDR5 protein and its binding partners is cancer.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 illustrates WDR5 as an adaptor protein in multiple complexes and related biological processes.

DETAILED DESCRIPTION (A) Definitions

Unless otherwise indicated, the definitions and embodiments described in this and other sections are intended to be applicable to all embodiments and aspects of the present application herein described for which they are suitable as would be understood by a person skilled in the art.

The term "compound of the application" or "compound of the present application" and the like as used herein refers to a compound of Formula I, including compounds of Formula Ia, Ib, Ic, Id and Ie, and pharmaceutically acceptable salts and/or solvates thereof.

The term "composition of the application" or "composition of the present application" and the like as used herein refers to a composition, such a pharmaceutical composition, comprising one or more compounds of Formula I, including compounds of Formula Ia, Ib, Ic, Id and/or Ie, or pharmaceutically acceptable salts and/or solvates thereof.

The term "and/or" as used herein means that the listed items are present, or used, individually or in combination. In effect, this term means that "at least one of" or "one or more" of the listed items is used or present. The term "and/or" with respect to pharmaceutically acceptable salts and/or solvates thereof means that the compounds of the application exist as individual salts and hydrates, as well as a combination of, for example, a salt of a solvate of a compound of the application.

As used in the present application, the singular forms "a", "an" and "the" include plural references unless the content clearly dictates otherwise. For example, an embodiment including "a compound" should be understood to present certain aspects with one compound, or two or more additional compounds.

In embodiments comprising an "additional" or "second" component, such as an additional or second compound, the second component as used herein is chemically different from the other components or first component. A "third" component is different from the other, first, and second components, and further enumerated or "additional" components are similarly different.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "consisting" and its derivatives as used herein are intended to be closed terms that specify the presence of the stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The term "suitable" as used herein means that the selection of the particular compound or conditions would depend on the specific synthetic manipulation to be performed, the identity of the molecule(s) to be transformed and/or the specific use for the compound, but the selection would be well within the skill of a person trained in the art.

In embodiments of the present application, the compounds described herein may have at least one asymmetric center. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (for example, less than 20%, suitably less than 10%, more suitably less than 5%) of compounds of the present application having an alternate stereochemistry. It is intended that any optical isomers, as separated, pure or partially purified optical isomers or racemic mixtures thereof are included within the scope of the present application.

The compounds of the present application may also exist in different tautomeric forms and it is intended that any tautomeric forms which the compounds form, as well as mixtures thereof, are included within the scope of the present application.

The compounds of the present application may further exist in varying polymorphic forms and it is contemplated that any polymorphs, or mixtures thereof, which form are included within the scope of the present application.

The present description refers to a number of chemical terms and abbreviations used by those skilled in the art. Nevertheless, definitions of selected terms are provided for clarity and consistency.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies or unless the context suggests otherwise to a person skilled in the art.

The expression "proceed to a sufficient extent" as used herein with reference to the reactions or process steps disclosed herein means that the reactions or process steps proceed to an extent that conversion of the starting material or substrate to product is maximized. Conversion may be maximized when greater than about 5, 10, 15, 20, 25, 30, 35, 40, 45, 50, 55, 60, 65, 70, 75, 80, 85, 90, 95 or 100% of the starting material or substrate is converted to product.

The term "basic nitrogen" as used herein refers to a nitrogen atom that has a lone pair of electrons available to participate in an interaction with a hydrogen atom. In an embodiment, the interaction is a hydrogen bond, an ionic bond or a covalent bond. In general, the basic nitrogen atom will be either a primary, secondary or tertiary alkyl amine nitrogen atom, either in a linear, branched or cyclic group. In some embodiments, the pKa of the conjugate acid of the basic nitrogen atom will be greater than about 8-10.

The term "alkyl" as used herein, whether it is used alone or as part of another group, means straight or branched chain, saturated alkyl groups. The number of carbon atoms that are possible in the referenced alkyl group are indicated by the prefix "$C_{n1-n2}$". For example, the term $C_{1-10}$alkyl means an alkyl group having 1, 2, 3, 4, 5, 6, 7, 8, 9 or 10 carbon atoms.

The term "alkylene", whether it is used alone or as part of another group, means straight or branched chain, saturated alkylene group, that is, a saturated carbon chain that contains substituents on two of its ends. The number of carbon atoms that are possible in the referenced alkylene group are indicated by the prefix "$C_{n1-n2}$". For example, the term $C_{2-6}$alkylene means an alkylene group having 2, 3, 4, 5 or 6 carbon atoms.

The term "alkenyl" as used herein, whether it is used alone or as part of another group, means straight or branched chain, unsaturated alkyl groups containing at least one double bond. The number of carbon atoms that are possible in the referenced alkylene group are indicated by the prefix "$C_{n1-n2}$". For example, the term $C_{2-6}$alkenyl means an alkenyl group having 2, 3, 4, 5 or 6 carbon atoms and at least one double bond.

The term "fluoroalkyl" as used herein refers to an alkyl group wherein one or more, including all of the hydrogen atoms are replaced by a halogen atom. In an embodiment, the halogen is fluorine. In another embodiment, the haloalkyl comprises at least one —$CHF_2$ group. In another embodiment, the haloalkyl comprises at least one —$CF_3$ group.

The term "fluorosubstituted" as used herein refers to a chemical group wherein one or more, including all of the hydrogen atoms, are replaced by a fluorine atom.

The term "cycloalkyl," as used herein, whether it is used alone or as part of another group, means a saturated carbocyclic group containing a number of carbon atoms and one or more rings. The number of carbon atoms that are possible in the referenced cycloalkyl group are indicated by the numerical prefix "$C_{n1-n2}$". For example, the term $C_{3-10}$cycloalkyl means a cycloalkyl group having 3, 4, 5, 6, 7, 8, 9 or 10 carbon atoms.

The term "aryl" as used herein, whether it is used alone or as part of another group, refers to cyclic groups containing from 6 to 20 carbon atoms and at least one aromatic ring. In an embodiment of the application, the aryl group contains from 6, 9 or 10 carbon atoms, such as phenyl, indanyl or naphthyl.

The term "heterocycloalkyl" as used herein, whether it is used alone or as part of another group, refers to cyclic groups containing 3 to 20 atoms, suitably 3 to 10 atoms, and at least one non-aromatic, ring in which one or more of the atoms are a heteromoiety selected from O, S, S(O), $SO_2$, N, NH and $NC_{1-6}$alkyl, suitably O, S, N, NH and $NC_{1-6}$alkyl. Heterocycloalkyl groups are either saturated or unsaturated (i.e. contain one or more double bonds) and contain one or more than one ring (i.e. are polycyclic). When a heterocycloalkyl group contains more than one ring, the rings may be fused, bridged, spirofused or linked by a bond. When a heterocycloalkyl group contains the prefix $C_{n1-n2}$ this prefix indicates the number of carbon atoms in the corresponding carbocyclic group, in which one or more, suitably 1 to 5, of the ring atoms is replaced with a heteromoiety as defined above. Heterocycloalkyl includes, monocyclic heterocycloalkyls such as but not limited to aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. Additionally, heterocycloalkyl includes polycyclic heterocycloalkyls such as but not limited to pyrolizidinyl and quinolizidinyl. In addition to the polycyclic heterocycloalkyls described above, heterocycloalkyl includes polycyclic heterocycloalkyls wherein the ring fusion between two or more rings includes more than one bond common to both rings and more than two atoms common to both rings. Examples of such bridged heterocycles include but are not limited to quinuclidinyl, diazabicyclo[2.2.1]heptyl and 7-oxabicyclo[2.2.1]heptyl.

A first ring group being "fused" with a second ring group means the first ring and the second ring share at least two atoms there between.

The term "heteroaryl" as used herein refers to cyclic groups containing from 5 to 20 atoms, suitably 5 to 10 atoms, at least one aromatic ring and at least one a heteromoiety selected from O, S, S(O), $SO_2$, N, NH and $NC_{1-6}$alkyl, suitably O, S, N, NH and $NC_{1-6}$alkyl. Heteroaryl groups contain one or more than one ring (i.e. are polycyclic). When a heteroaryl group contains more than one ring, the rings may be fused, bridged, spirofused or linked by a bond. When a heteroaryl group contains the prefix $C_{n1-n2}$ this prefix indicates the number of carbon atoms in the corresponding carbocyclic group, in which one or more, suitably 1 to 5, of the ring atoms is replaced with a heteromoiety as defined above.

The term "available", as in "available hydrogen atoms" or "available atoms" refers to atoms that would be known to a person skilled in the art to be capable of replacement by a substituent.

The terms "halo" or "halogen" as used herein, whether it is used alone or as part of another group, refers to a halogen atom and includes fluoro, chloro, bromo and iodo.

The term "amine" or "amino," as used herein, whether it is used alone or as part of another group, refers to groups of the general formula NRR', wherein R and R' are each independently selected from hydrogen and an alkyl group, such as $C_{1-6}$alkyl.

The term "atm" as used herein refers to atmosphere.

The term "MS" as used herein refers to mass spectrometry.

The term "aq." as used herein refers to aqueous.

DCM as used herein refers to dichloromethane.

DIPEA as used herein refers to N,N-diisopropyl ethylamine

DMF as used herein refers to dimethylformamide.

DMSO as used herein refers to dimethylsulfoxide.

EtOAc as used herein refers to ethyl acetate.

HATU as used herein refers to 1-[Bis(dimethylamino)methylene]-1H-1,2,3-triazolo[4,5-b]pyridinium 3-oxid hexafluorophosphate.

MeOH as used herein refers to methanol.

MeCN as used herein refers to acetonitrile.

HCl as used herein refers to hydrochloric acid.

TFA as used herein refers to trifluoroacetic acid.

TBAF as used herein refers to tetra-n-butylammonium fluoride.

CsF as used herein is cesium fluoride.

μwave as used herein refers to a microwave reaction vessel.

SnAr as used herein represents nucleophilic aromatic substitution.

LCMS as used herein refers to liquid chromatography-mass spectrometry.

The term "protecting group" or "PG" and the like as used herein refers to a chemical moiety which protects or masks a reactive portion of a molecule to prevent side reactions in those reactive portions of the molecule, while manipulating or reacting a different portion of the molecule. After the manipulation or reaction is complete, the protecting group is removed under conditions that do not degrade or decompose the remaining portions of the molecule. The selection of a suitable protecting group can be made by a person skilled in the art. Many conventional protecting groups are known in the art, for example as described in "Protective Groups in Organic Chemistry" McOmie, J. F. W. Ed., Plenum Press, 1973, in Greene, T. W. and Wuts, P. G. M., "Protective Groups in Organic Synthesis", John Wiley & Sons, 3rd Edition, 1999 and in Kocienski, P. Protecting Groups, 3rd Edition, 2003, Georg Thieme Verlag (The Americas).

The term "subject" as used herein includes all members of the animal kingdom including mammals, and suitably refers to humans. Thus the methods of the present application are applicable to both human therapy and veterinary applications. In an embodiment, the subject is a mammal. In another embodiment, the subject is human.

The term "pharmaceutically acceptable" means compatible with the treatment of subjects, for example humans.

The term "pharmaceutically acceptable carrier" means a non-toxic solvent, dispersant, excipient, adjuvant or other material which is mixed with the active ingredient in order to permit the formation of a pharmaceutical composition, i.e., a dosage form capable of administration to a subject.

The term "pharmaceutically acceptable salt" means either an acid addition salt or a base addition salt which is suitable for, or compatible with, the treatment of subjects.

An acid addition salt suitable for, or compatible with, the treatment of subjects is any non-toxic organic or inorganic acid addition salt of any basic compound. Basic compounds that form an acid addition salt include, for example, compounds comprising an amine group. Illustrative inorganic acids which form suitable salts include hydrochloric, hydrobromic, sulfuric, nitric and phosphoric acids, as well as acidic metal salts such as sodium monohydrogen orthophosphate and potassium hydrogen sulfate. Illustrative organic acids which form suitable salts include mono-, di- and tricarboxylic acids. Illustrative of such organic acids are, for example, acetic, trifluoroacetic, propionic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, mandelic, salicylic, 2-phenoxybenzoic, p-toluenesulfonic acid and other sulfonic acids such as methanesulfonic acid, ethanesulfonic acid and 2-hydroxyethanesulfonic acid. In an embodiment, the mono- or di-acid salts are formed, and such salts exist in either a hydrated, solvated or substantially anhydrous form. In general, acid addition salts are more soluble in water and various hydrophilic organic solvents, and generally demonstrate higher melting points in comparison to their free base forms. The selection criteria for the appropriate salt will be known to one skilled in the art. Other non-pharmaceutically acceptable salts such as but not limited to oxalates may be used, for example in the isolation of compounds of the application for laboratory use, or for subsequent conversion to a pharmaceutically acceptable acid addition salt.

A base addition salt suitable for, or compatible with, the treatment of subjects is any non-toxic organic or inorganic base addition salt of any acidic compound. Acidic compounds that form a basic addition salt include, for example, compounds comprising a carboxylic acid group. Illustrative inorganic bases which form suitable salts include lithium, sodium, potassium, calcium, magnesium or barium hydroxide as well as ammonia. Illustrative organic bases which form suitable salts include aliphatic, alicyclic or aromatic organic amines such as isopropylamine, methylamine, trimethylamine, picoline, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, ethanolamine, trimethylamine, dicyclohexylamine, choline, and caffeine. [See, for example, S. M. Berge, et al., "Pharmaceutical Salts," *J. Pharm. Sci.* 1977, 66, 1-19]. The selection of the appropriate salt may be useful, for example, so that an ester functionality, if any, elsewhere in a compound is not hydrolyzed. The selection criteria for the appropriate salt will be known to one skilled in the art.

The term "solvate" as used herein means a compound, or a salt or prodrug of a compound, wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate". The formation of solvates of the compounds of the application will vary depending on the compound and the solvate. In general, solvates are formed by dissolving the compound in the appropriate solvent and isolating the solvate by cooling or using an antisolvent. The solvate is typically dried or azeotroped under ambient conditions. The selection of suitable conditions to form a particular solvate can be made by a person skilled in the art.

The term "treating" or "treatment" as used herein and as is well understood in the art, means an approach for obtaining beneficial or desired results, including clinical results. Beneficial or desired clinical results include, but are not limited to alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. "Treating" and "treatment" as used herein also include prophylactic treatment. For example, a subject with early cancer can be treated to prevent progression, or alternatively a subject in remission can be treated with a compound or composition of the application to prevent recurrence. Treatment methods comprise administering to a subject a therapeutically effective amount of one or more of the compounds of the application and optionally consist of a single administration, or alternatively comprise a series of administrations. For example, the compounds of the application are administered at least once a week. However, in another embodiment, the compounds are administered to the subject from about one time per two weeks, three weeks or one month. In another embodiment, the compounds are administered about one time per week to about once daily. In another embodiment, the compounds are administered 2, 3, 4, 5 or 6 times daily. The length of the treatment period depends on a variety of factors, such as the severity of the disease, disorder or condition, the age of the subject, the concentration and/or the activity of the compounds of the application, and/or a combination thereof. It will also be appreciated that the effective dosage of the compound used for the treatment may increase or decrease over the course of a particular treatment regime. Changes in dosage may result and become apparent by standard diagnostic assays known in the art. In some instances, chronic administration is required. For example, the compounds are administered to the subject in an amount and for duration sufficient to treat the subject.

"Palliating" a disease, disorder or condition means that the extent and/or undesirable clinical manifestations of a disease, disorder or condition are lessened and/or time course of the progression is slowed or lengthened, as compared to not treating the disorder.

The term "prevention" or "prophylaxis", or synonym thereto, as used herein refers to a reduction in the risk or probability of a patient becoming afflicted with a disease, disorder or condition or manifesting a symptom associated with a disease, disorder or condition.

The "disease, disorder or condition" as used herein refers to a disease, disorder or condition mediated or treatable by inhibition of binding between WDR5 protein and its binding partners, in particular MLL1, and in particular using a WDR5 protein inhibitor, such as a compound of the application herein described.

The term "mediated or treatable by inhibition of binding between WDR5 protein and its binding partners" as used herein means that the disease, disorder or condition to be treated is affected by, modulated by and/or has some biological basis, either direct or indirect, that includes WDR5 binding, in particular, increased WDR5 binding, to its binding partners, such as MLL1. Such biological basis includes, for example, WDR5 and/or MLL1 gene overexpression or WDR5 and/or MLL1 protein over-accumulation or overexpression of proteins that are products of or precursors to WDR5-mediated and/or MLL1 gene expression. In a refined context, "mediated or treatable by inhibition of binding between WDR5 protein and its binding partners" refers to an effect mediated through inhibition of binding between WDR5 and MLL1. In a broader context, "mediated or treatable by inhibition of binding between WDR5 protein and its binding partners" can include the large number of diseases that are caused by aberrant methylation of histone 3 lysine 4 (H3K4) residues, as results from aberrant WDR5 and/or MLL1 activity. As used herein, WDR5 refers to the protein identified as GenBank Accession number NM_017588 [*J. Biol. Chem.* 2001, 276 (49), 46515-46522] and isoforms that include this sequence, and shorter versions. Similarly, the other WDR5 proteins are characterized and described in any of the protein databases. As used herein, MLL1 refers to the protein identified as GenBank Accession number NM_005933 [*Proc. Natl. Acad. Sci. U.S.A.* 1991, 88 (23), 10735-10739; *DNA Cell Biol.* 1995, 14 (6), 475-483] and isoforms that include this sequence, and shorter versions. Similarly, the other MLL1 proteins are characterized and described in any of the protein databases.

The term "binding" as used herein refers to any interaction between two entities, such as two proteins, that leads to a functional effect.

As used herein, the term "effective amount" or "therapeutically effective amount" means an amount of one or more compounds of the application that is effective, at dosages and for periods of time necessary to achieve the desired result. For example in the context of treating a disease, disorder or condition mediated or treatable by inhibition of binding between WDR5 protein and its binding partners, an effective amount is an amount that, for example, increases said inhibition compared to the inhibition without administration of the one or more compounds. In an embodiment, effective amounts vary according to factors such as the disease state, age, sex and/or weight of the subject. In a further embodiment, the amount of a given compound or compounds that will correspond to an effective amount will vary depending upon factors, such as the given drug(s) or compound(s), the pharmaceutical formulation, the route of administration, the type of condition, disease or disorder, the identity of the subject being treated, and the like, but can nevertheless be routinely determined by one skilled in the art.

The term "administered" as used herein means administration of a therapeutically effective amount of one or more compounds or compositions of the application to a cell, tissue, organ or subject.

The term "neoplastic disorder" as used herein refers to a disease, disorder or condition characterized by cells that have the capacity for autonomous growth or replication, e.g., an abnormal state or condition characterized by proliferative cell growth. The term "neoplasm" as used herein refers to a mass of tissue resulting from the abnormal growth and/or division of cells in a subject having a neoplastic disorder. Neoplasms can be benign (such as uterine fibroids and melanocytic nevi), potentially malignant (such as carcinoma in situ) or malignant (i.e. cancer). Exemplary neoplastic disorders include the so-called solid tumours and liquid tumours, including but not limited to carcinoma, sarcoma, metastatic disorders (e.g., tumors arising from the prostate), hematopoietic neoplastic disorders, (e.g., leukemias, lymphomas, myeloma and other malignant plasma cell disorders), metastatic tumors and other cancers.

The term "cancer" as used herein refers to cellular-proliferative disease states.

(b) Compounds and Compositions of the Application

The present application includes a compound of Formula (I) or a pharmaceutically acceptable salt and/or solvate thereof:

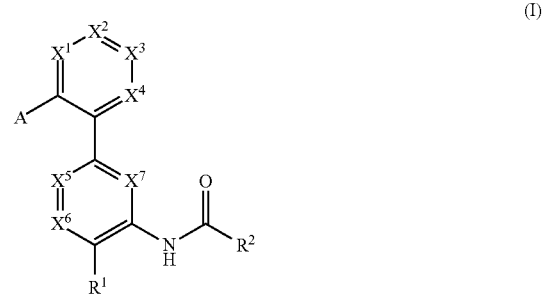

(I)

wherein:
$R^1$ is a heterocycloalkyl that is unsubstituted or substituted with one or more substituents selected from halo, $C_{1-6}$alkyl, $C_{1-6}$fluoroalkyl, $C_{3-10}$cycloalkyl, $OR^4$, $SR^4$, $NR^5R^6$, $C_{1-6}$alkyleneOR$^4$, $C_{1-6}$alkyleneSR$^4$ and $C_{1-6}$alkyleneNR$^5R^6$, provided that $R^1$ comprises at least one basic nitrogen atom;
$R^2$ is selected from $C_{6-10}$aryl and heteroaryl, and $R^2$ is unsubstituted or substituted with one or more substituents selected from halo, $C_{1-6}$alkyl, $C_{1-6}$fluoroalkyl, =O, =S, $OR^7$, $SR^7$ and $NR^8R^9$;
$R^4$ and $R^7$ are independently selected from H, $C_{1-6}$alkyl, $C_{1-6}$fluoroalkyl, $C(O)C_{1-6}$alkyl and $C(O)C_{1-6}$fluoroalkyl;
$R^5$ and $R^6$ are independently selected from H, $C_{1-6}$alkyl, $C_{1-6}$fluoroalkyl, heterocycloalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneNHC$_{1-6}$alkyl, $C_{1-6}$alkyleneN(C$_{1-6}$alkyl)(C$_{1-6}$alkyl), $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl, or $R^5$ and $R^6$ together with the nitrogen atom to which they are attached form a 3-10 membered heterocycle that is unsubstituted or substituted with one or more substituents selected from halo, OH, CN, $C_{1-6}$alkyl, $OC_{1-6}$alkyl, $C_{1-6}$fluoroalkyl, $OC_{1-6}$fluoroalkyl, $C(O)C_{1-6}$alkyl, $C(O)C_{1-6}$fluoroalkyl, $C(O)OC_{1-6}$alkyl, $C(O)NHC_{1-6}$alkyl, $SO_2C_{1-6}$alkyl, $SO_2HNC_{1-6}$alkyl, $C_{1-6}$alkyleneOC$_{1-6}$alkyl, $C_{1-6}$alkyleneNHC$_{1-6}$alkyl, $C_{1-6}$alkyleneN(C$_{1-6}$alkyl)(C$_{1-6}$alkyl), $C_{1-6}$alkyleneC$_{6-10}$aryl, $C_{1-6}$alkyleneheteroaryl, $C_{1-6}$alkyleneheterocycloalkyl and $C_{1-6}$alkyleneC$_{3-6}$cycloalkyl;

$R^8$ and $R^9$ are independently selected from H, $C_{1-6}$alkyl, $C_{1-6}$fluoroalkyl, $C(O)C_{1-6}$alkyl and $C(O)C_{1-6}$fluoroalkyl, or $R^8$ and $R^9$ together with the nitrogen atom to which they are attached form a 3-10 membered heterocycle that is unsubstituted or substituted with one or more substituents selected from halo, CN, OH, $C_{1-6}$alkyl $OC_{1-6}$alkyl, $C_{1-6}$fluoroalkyl and $OC_{1-6}$fluoroalkyl;

$X^1$, $X^2$, $X^3$ and $X^4$ are each independently selected from $CR^{10}$ and N;

$X^5$, $X^6$ and $X^7$ are each independently selected from CH and N;

$R^{10}$ is selected from H, halo, CN, $C_{1-6}$alkyl, $C_{1-6}$fluoroalkyl, $OR^{11}$, $SR^{11}$, $NR^{12}R^{13}$, $R^{14}$, $C_{1-6}$alkyleneR$^{14}$, $OC_{1-6}$alkyleneR$^{14}$, $SC_{1-6}$alkyleneR$^{14}$, $C_{1-6}$alkyleneNR$^{12}R^{13}$, $C_{1-6}$alkyleneOR$^{11}$, $C_{1-6}$alkyleneSR$^{11}$, $OC_{1-6}$alkyleneNR$^{12}R^{13}$, $SC_{1-6}$alkyleneNR$^{12}R^{13}$, $OC_{1-6}$alkyleneOR$^{11}$, $SC_{1-6}$alkyleneOR$^{11}$, $OC_{1-6}$alkyleneSR$^{11}$, $SC_{1-6}$alkyleneSR$^{11}$, $C(O)OR^{11}$, $C(S)OR^{11}$, $C(S)NR^{12}R^{13}$ and $C(O)NR^{12}R^{13}$;

$R^{11}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{11}$ is other than H, it is unsubstituted or substituted with one or more substituents selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$ alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{12}$ and $R^{13}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{12}$ and $R^{13}$ are other than H they are each independently unsubstituted or substituted with one or more substituents selected from halo, CN, $OR^{15}$, $SR^{15}$, $NR^{16}R^{17}$, $C_{1-6}$alkyl, $C(O)R^{15}$, $C(O)R^5$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$, or $R^{12}$ and $R^{13}$ together with the nitrogen atom to which they are attached form a 3-10 membered heterocycle that is unsubstituted or substituted with one or more substituents independently selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{14}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl, and when $R^{14}$ is other than H it is unsubstituted or substituted with one or more substituents independently selected from halo, CN, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{15}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and when $R^{15}$ is other than H it is unsubstituted or substituted with one or more substituents selected from halo, $C_{1-6}$alkyl, CN, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)(C$_{1-6}$alkyl), $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl)(C$_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl);

$R^{16}$ and $R^{17}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl and when $R^{16}$ and $R^{17}$ are other than H they are each unsubstituted or substituted with one or more substituents independently selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)(C$_{1-6}$alkyl), $C(O)C_{1-6}$alkyl, $C(O)OH$, $C(O)OC_{1-6}$alkyl, $C(O)C_{1-6}$fluoroalkyl, $C(O)NH_2$, $C(O)NHC_{1-6}$alkyl, $C(O)N(C_{1-6}$alkyl)(C$_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl), or $R^{16}$ and $R^{17}$ together with the nitrogen atom to which they are attached form a 3-10 membered heterocycle that is unsubstituted or substituted with one or more substituents selected from halo, CN, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)(C$_{1-6}$alkyl), $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl)(C$_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$ alkyl);

A is fluoro; and all alkyl and alkylene groups are optionally fluorosubstituted.

The present application also includes a compound of Formula (I) or a pharmaceutically acceptable salt and/or solvate thereof:

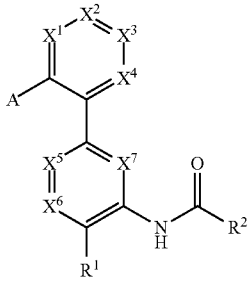

(I)

wherein:

$R^1$ is a heterocycloalkyl that is unsubstituted or substituted with one or more substituents selected from halo, $C_{1-6}$alkyl, $C_{1-6}$fluoroalkyl, $OR^4$, $SR^4$, $NR^5R^6$, $C_{1-6}$alkyleneOR$^4$, $C_{1-6}$alkyleneSR$^4$ and $C_{1-6}$alkyleneNR$^5R^6$, provided that $R^1$ comprises at least one basic nitrogen atom;

$R^2$ is selected from $C_{6-10}$aryl and heteroaryl, and $R^2$ is unsubstituted or substituted with one or more substituents selected from halo, $C_{1-6}$alkyl, $C_{1-6}$fluoroalkyl, =O, =S, $OR^7$, $SR^7$ and $NR^8R^9$;

$R^4$ and $R^7$ are independently selected from H, $C_{1-6}$alkyl, $C_{1-6}$fluoroalkyl, $C(O)C_{1-6}$alkyl and $C(O)C_{1-6}$fluoroalkyl;

$R^5$ and $R^6$ are independently selected from H, $C_{1-6}$alkyl, $C_{1-6}$fluoroalkyl, heterocycloalkyl, $C(O)C_{1-6}$alkyl and $C(O)C_{1-6}$fluoroalkyl, or $R^5$ and $R^6$ together with the nitrogen atom to which they are attached form a 3-10 membered heterocycle that is unsubstituted or substituted with one or more substituents selected from halo, OH, $C_{1-6}$alkyl, $OC_{1-6}$alkyl, $C_{1-6}$fluoroalkyl, $OC_{1-6}$fluoroalkyl, $C(O)C_{1-6}$alkyl and $C(O)C_{1-6}$fluoroalkyl;

$R^8$ and $R^9$ are independently selected from H, $C_{1-6}$alkyl, $C_{1-6}$fluoroalkyl, $C(O)C_{1-6}$alkyl and $C(O)C_{1-6}$fluoroalkyl, or $R^8$ and $R^9$ together with the nitrogen atom to which they are attached form a 3-10 membered heterocycle that is unsubstituted or substituted with one or more substituents selected from halo, OH, $C_{1-6}$alkyl, $OC_{1-6}$alkyl, $C_{1-6}$fluoroalkyl and $OC_{1-6}$fluoroalkyl;

$X^1$, $X^2$, $X^3$ and $X^4$ are each independently selected from $CR^{10}$ and N;

$X^5$, $X^6$ and $X^7$ are each independently selected from CH and N;

$R^{10}$ is selected from H, halo, CN, $C_{1-6}$alkyl, $C_{1-6}$fluoroalkyl, $OR^{11}$, $SR^{11}$, $NR^{12}R^{13}$, $R^{14}$, $C_{1-6}$alkyleneR$^{14}$, $OC_{1-6}$alkyleneR$^{14}$, $SC_{1-6}$alkyleneR$^{14}$, $C_{1-6}$alkyleneNR$^{12}R^{13}$, $C_{1-6}$alkyleneOR$^{11}$, $C_{1-6}$alkyleneSR$^{11}$, $OC_{1-6}$alkyleneNR$^{12}R^{13}$, $SC_{1-6}$alkyleneNR$^{12}R^{13}$, $OC_{1-6}$alkyleneOR$^{11}$, $SC_{1-6}$alkyleneOR$^{11}$, $OC_{1-6}$alkyleneSR$^{11}$, $SC_{1-6}$alkyleneSR$^{11}$, $C(O)OR^{11}$, $C(S)OR^{11}$, $C(S)NR^{12}R^{13}$ and $C(O)NR^{12}R^{13}$;

$R^{11}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{11}$ is other than H, it is unsubstituted or substituted with one or more substituents selected from halo, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{12}$ and $R^{13}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{12}$ and $R^{13}$ are other than H they are each independently unsubstituted or substituted with one or more substituents selected from halo, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$, or $R^{12}$ and $R^{13}$ together with the nitrogen atom to which they are attached form a 3-10 membered heterocycle that is unsubstituted or substituted with one or more substituents independently selected from halo, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{14}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl, and when $R^{14}$ is other than H it is unsubstituted or substituted with one or more substituents independently selected from halo, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{15}$, $C_{1-6}$alkyleneOR$^{15}$, $C_{1-6}$alkyleneSR$^{15}$ and $C_{1-6}$alkyleneNR$^{16}R^{17}$;

$R^{15}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and when $R^{15}$ is other than H it is unsubstituted or substituted with one or more substituents selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)C_{1-6}$fluoroalkyl, C(O)OH, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN($C_{1-6}$alkyl)($C_{1-6}$alkyl);

$R^{16}$ and $R^{17}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl and when $R^{16}$ and $R^{17}$ are other than H they are each unsubstituted or substituted with one or more substituents independently selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, C(O)OH, $C(O)OC_{1-6}$alkyl, $C(O)C_{1-6}$fluoroalkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$ alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl), or $R^{16}$ and $R^{17}$ together with the nitrogen atom to which they are attached form a 3-10 membered heterocycle that is unsubstituted or substituted with one or more substituents selected from halo, $C_{1-6}$alkyl, $C_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl);

A is halo; and all alkyl and alkylene groups are optionally fluorosubstituted.

In some embodiments, $R^1$ is a heterocycloalkyl that is unsubstituted or substituted with one, two or three substituents selected from halo, $C_{1-6}$alkyl, $C_{1-6}$fluoroalkyl, $C_{1-6}$alkyleneOR$^4$, NR$^5$R$^6$ and $C_{1-6}$alkyleneNR$^5$R$^6$, provided that $R^1$ comprises at least one basic nitrogen atom. In some embodiments, $R^1$ is a heterocycloalkyl that is substituted with one, two or three substituents selected from halo, $C_{1-6}$alkyl, $C_{1-6}$alkyleneOR$^4$ and NR$^5$R$^6$, provided that $R^1$ comprises at least one basic nitrogen atom. In some embodiments, $R^1$ is a heterocycloalkyl that is substituted with one or two substituents selected from $C_{1-6}$alkyl, $C_{1-6}$alkyleneOR$^4$ and NR$^5$R$^6$, provided that $R^1$ comprises at least one basic nitrogen atom.

In some embodiments, $R^1$ is selected from:

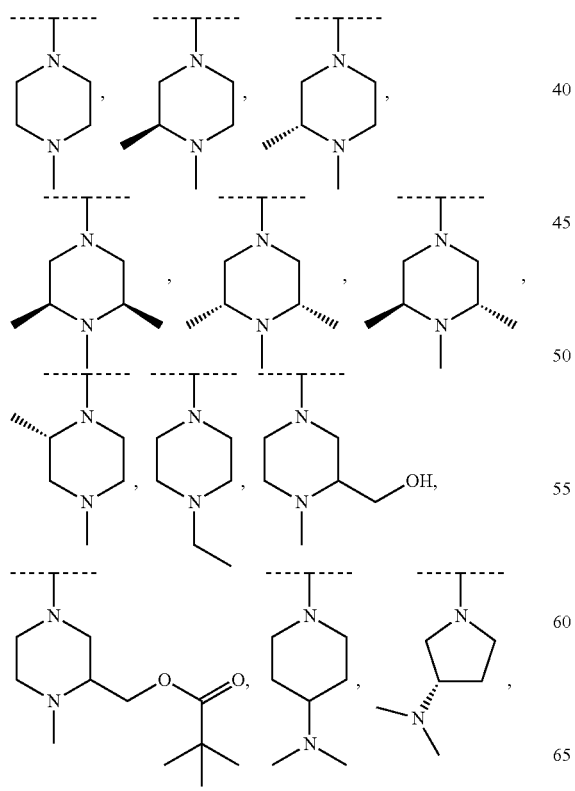

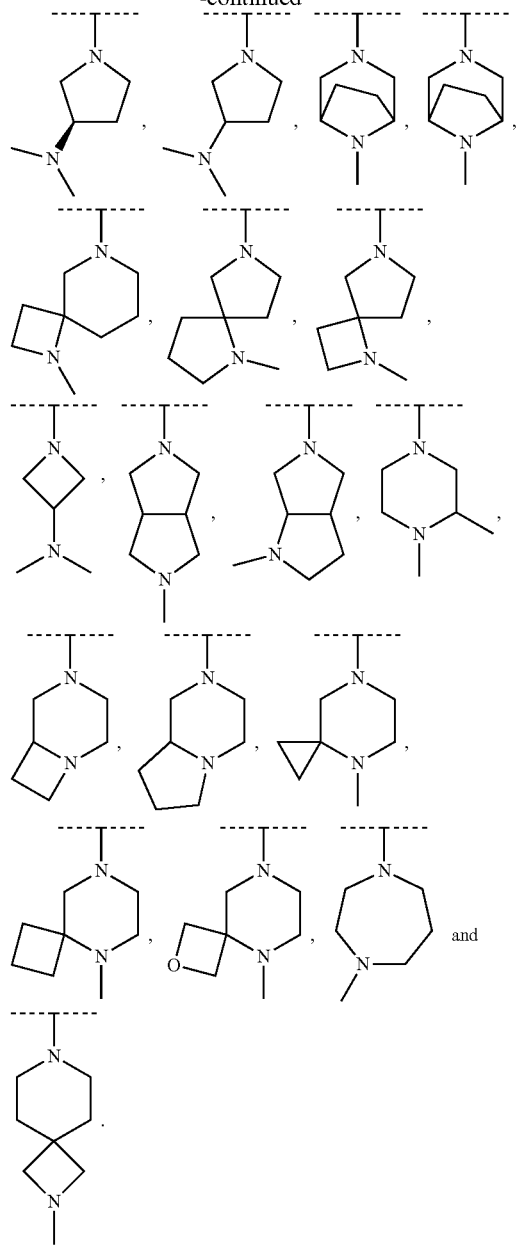

In some embodiments, $R^1$ is selected from:

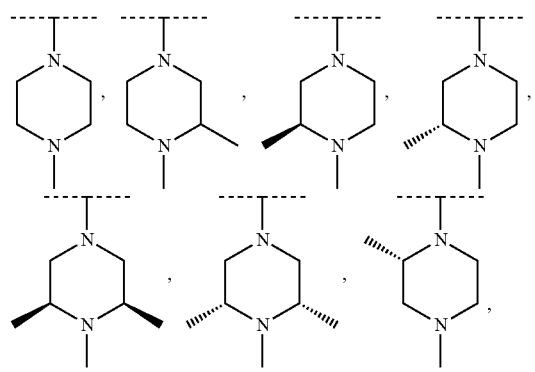

-continued

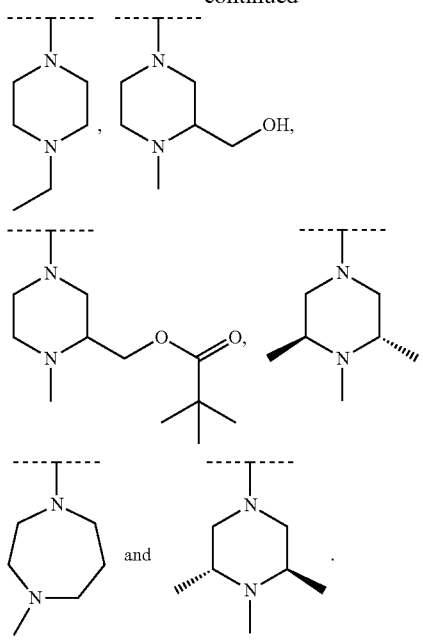

In some embodiments, $R^1$ is selected from:

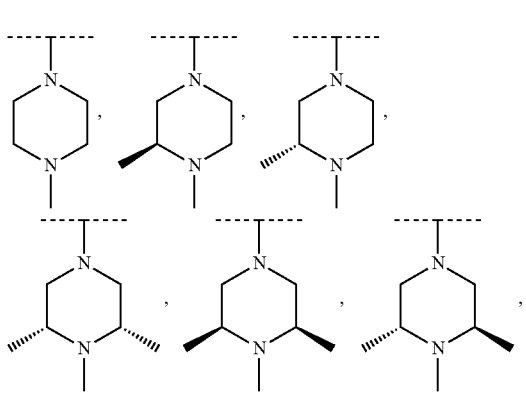

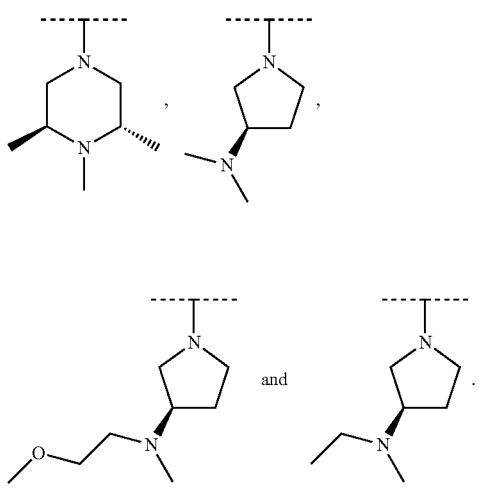

In some embodiments, $R^1$ is selected from:

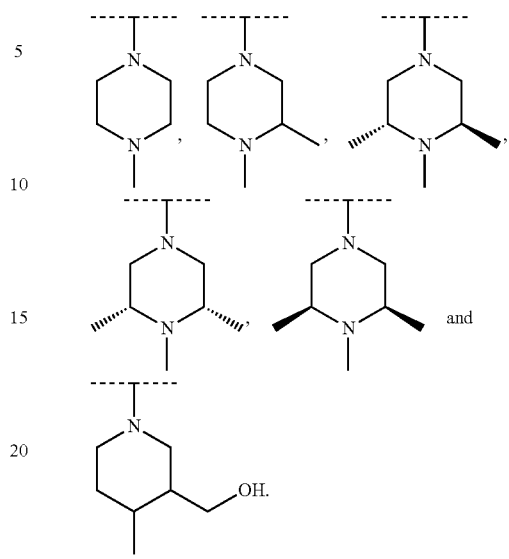

In some embodiments, $R^1$ is selected from:

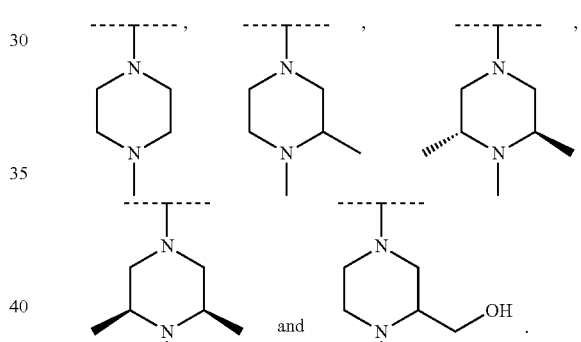

In some embodiments, $R^1$ is selected from:

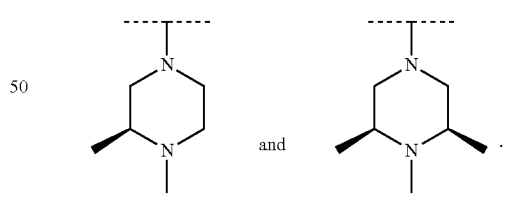

In some embodiments, $R^2$ is selected from $C_{6-10}$aryl and heteroaryl, and $R^2$ is unsubstituted or substituted with one, two or three substituents selected from halo, $C_{1-6}$alkyl, $C_{1-6}$fluoroalkyl, $=O$, $OR^7$, $SR^7$ and $NR^8R^9$. In some embodiments, $R^2$ is selected from $C_{6-10}$aryl and heteroaryl, and $R^2$ is unsubstituted or substituted with one, two or three substituents selected from halo, $C_{1-6}$alkyl, $C_{1-6}$fluoroalkyl, $=O$, $OR^7$ and $NR^8R^9$. In some embodiments, $R^2$ is selected from $C_{6-10}$aryl and heteroaryl, and $R^2$ is unsubstituted or substituted with one or two substituents selected from halo, $C_{1-6}$alkyl, $C_{1-6}$fluoroalkyl, $=O$ and $OR^7$. In some embodiments, R² is selected from phenyl and C₆-heteroaryl, and R² is substituted with one to three substituents selected from F, CF₂H, CF₃ and =O.
In some embodiments, R² is selected from:
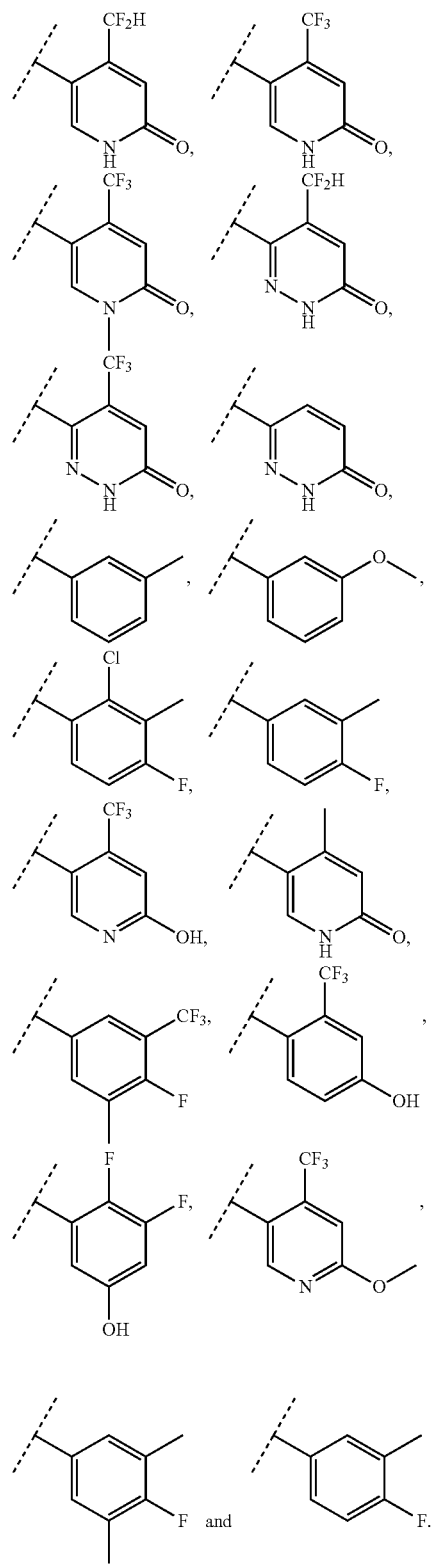
In some embodiments, R² is selected from:
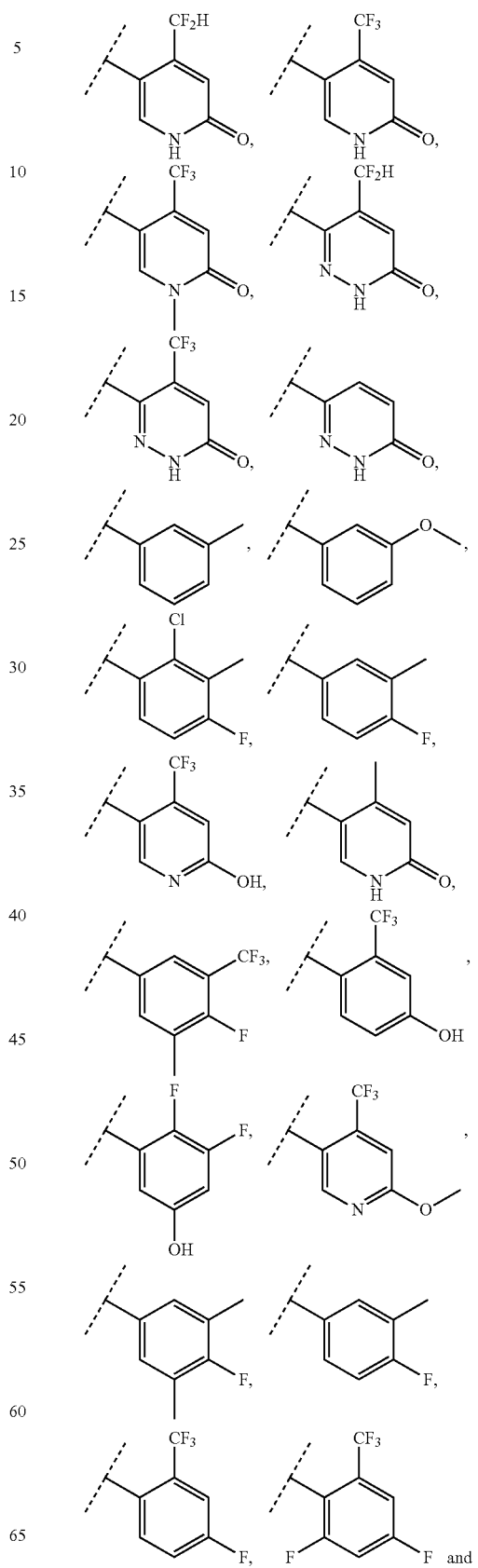

-continued
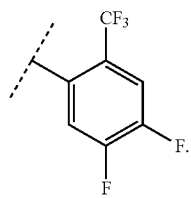
In some embodiments, R² is selected from:
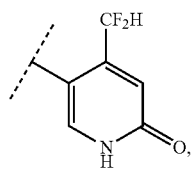
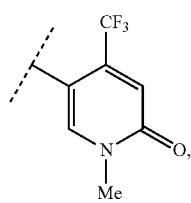
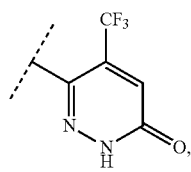
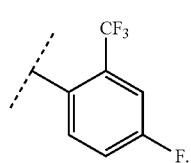
In some embodiments, R¹ is selected from:
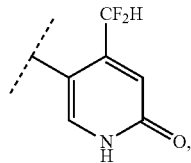

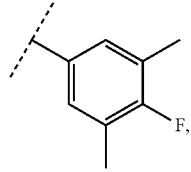
and tautomers thereof.
In some embodiments, R² is selected from:
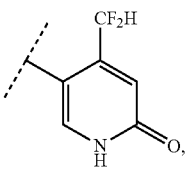
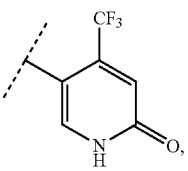
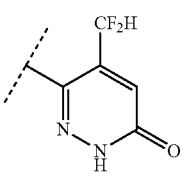
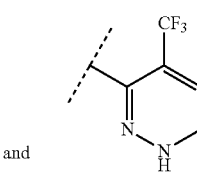
or a tautomer thereof.
In some embodiments, R² is selected from:
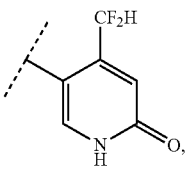
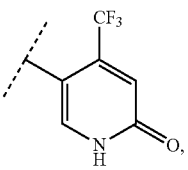
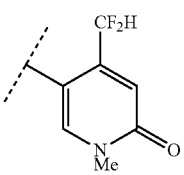
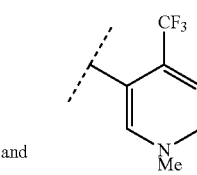
or a tautomer thereof.
In some embodiments, R² is selected from:
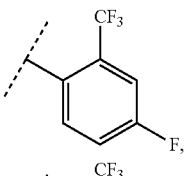
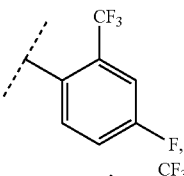
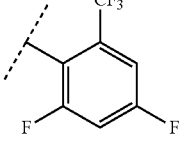
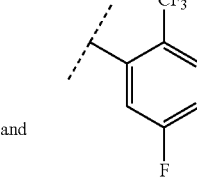
In some embodiments, R² is
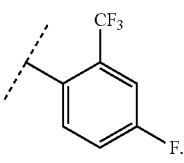

In an embodiment, $R^2$ is

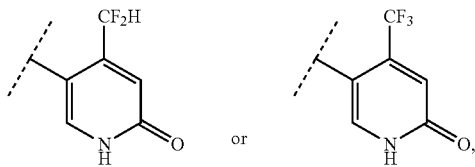

and the corresponding tautomers are

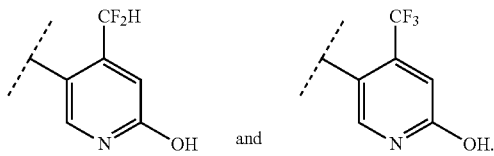

In some embodiments, $R^4$ is selected from H, $C_{1-6}$alkyl, $C_{1-6}$fluoroalkyl and $C(O)C_{1-6}$alkyl. In some embodiments, $R^4$ is selected from H, $C_{1-6}$alkyl and $C(O)C_{1-6}$alkyl. In some embodiments, $R^4$ is selected from H, $CH_3$ and $C(O)CH_3$. In some embodiments, $R^4$ is selected from H and $CH_3$.

In some embodiments, $R^5$ and $R^6$ are independently selected from H, $C_{1-6}$alkyl and heterocycloalkyl. In some embodiments, $R^5$ and $R^6$ are independently selected from H and $C_{1-6}$alkyl. In some embodiments, $R^5$ and $R^6$ together with the nitrogen atom to which they are attached form a 3-10 membered heterocycle that is unsubstituted or substituted with one or two substituents selected from halo and $C_{1-6}$alkyl. In some embodiments, $R^5$ and $R^6$ together with the nitrogen atom to which they are attached form a 3-10 membered heterocycle that is unsubstituted. In some embodiments, $R^5$ and $R^6$ together with the nitrogen atom to which they are attached form an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^7$ is selected from H, $C_{1-6}$alkyl, $C_{1-6}$fluoroalkyl and $C(O)C_{1-6}$alkyl. In some embodiments, $R^7$ is selected from H, $CH_3$ and $C(O)CH_3$. In some embodiments, $R^7$ is selected from H and $C_{1-6}$alkyl. In some embodiments, $R^7$ is selected from H and $CH_3$.

In some embodiments, one of $X^1$, $X^2$, $X^3$ and $X^4$ is N and the others of $X^1$, $X^2$, $X^3$ and $X^4$ are $CR^{10}$. In some embodiments, $X^1$, $X^2$, $X^3$ and $X^4$ are $CR^{10}$. In some embodiments, $X^1$ and $X^4$ are CH. In some embodiments one of $X^2$ and $X^3$ is $CR^{10}$ and $R^{10}$ is other than H.

In some embodiments, one of $X^5$, $X^6$ and $X^7$ is N and the others of $X^5$, $X^6$ and $X^7$ are CH. In some embodiments, $X^5$, $X^6$ and $X^7$ are CH.

In some embodiments, $R^{10}$ is selected from H, halo, CN, $C_{1-6}$alkyl, $C_{1-6}$fluoroalkyl, $OR^{11}$, $NR^{12}R^{13}$, $R^{14}$, $C_{1-6}$alkyleneR$^{14}$, $OC_{1-6}$alkyleneR$^{14}$, $C_{1-6}$alkyleneNR$^{12}R^{13}$, $C_{1-6}$alkyleneOR$^{11}$, $OC_{1-6}$alkyleneNR$^{12}R^{13}$, $OC_{1-6}$alkyleneOR$^{11}$, $C(O)OR^{11}$ and $C(O)NR^{12}R^{13}$. In some embodiments, $R^{10}$ is selected from H, halo, CN, $OR^{11}$, $NR^{12}R^{13}$, $R^{14}$, $C_{1-6}$alkyleneR$^{14}$, $OC_{1-6}$alkyleneR$^{14}$, $C_{1-6}$alkyleneNR$^{12}R^{13}$, $C_{1-6}$alkyleneOR$^{11}$, $OC_{1-6}$alkyleneNR$^{12}R^{13}$, $OC_{1-6}$alkyleneOR$^{11}$, $C(O)OR^{11}$ and $C(O)NR^{12}R^{13}$. In some embodiments, $R^{10}$ is selected from H, halo, CN, $OR^{11}$, $R^{14}$, $OC_{1-6}$alkyleneR$^{14}$, $C_{1-6}$alkyleneNR$^{12}R^{13}$, $OC_{1-6}$alkyleneOR$^{11}$, $C(O)OR^{11}$ and $C(O)NR^{12}R^{13}$. In some embodiments, $R^{10}$ is selected from $OR^{11}$, $OC_{1-6}$alkyleneR$^{14}$, $C_{1-6}$alkyleneNR$^{12}R^{13}$ and $C(O)NR^{12}R^{13}$. In some embodiments, $R^{10}$ is selected from $C_{1-6}$alkyleneNR$^{12}R^{13}$ and $C(O)NR^{12}R^{13}$.

In some embodiments, $R^{11}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl. In some embodiments, $R^{11}$ is selected from H, $C_{1-6}$alkyl, $C_{1-6}$fluoroalkyl, $C_{3-10}$cycloalkyl, heterocycloalkyl, $C_{6-10}$aryl and heteroaryl. In some embodiments, $R^{11}$ is selected from H, $C_{1-6}$alkyl, $C_{1-6}$fluoroalkyl and heterocycloalkyl. In some embodiments, $R^{11}$ is heterocycloalkyl. In some embodiments, $R^{11}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl. In some embodiments $R^{11}$ is morpholinyl optionally substituted with one or two $C_{1-6}$alkyl, suitably methyl.

In some embodiments, $R^{12}$ and $R^{13}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{12}$ and $R^{13}$ are other than H they are each independently unsubstituted or substituted with one, two or three substituents selected from halo and $C_{1-6}$alkyl. In some embodiments, $R^{12}$ and $R^{13}$ are each independently selected from H, $C_{1-10}$alkyl, $C_{1-10}$fluoroalkyl, $C_{3-10}$cycloalkyl, heterocycloalkyl, heteroaryl and $C_{6-10}$aryl, and when $R^{12}$ and $R^{13}$ are other than H they are each independently unsubstituted or substituted with one, two or three substituents selected from halo and $C_{1-6}$alkyl. In some embodiments, $R^{12}$ and $R^{13}$ are each independently selected from H, $C_{1-10}$alkyl, $C_{3-10}$cycloalkyl and heterocycloalkyl, and when $R^{12}$ and $R^{13}$ are other than H they are each independently unsubstituted or substituted with one or two substituents selected from halo and $C_{1-6}$alkyl. In some embodiments, $R^{12}$ and $R^{13}$ are each independently selected from H, $C_{1-10}$alkyl, $C_{3-10}$cycloalkyl and heterocycloalkyl, and each of $R^{12}$ and $R^{13}$ (other than H) is unsubstituted. In some embodiments, $R^{12}$ and $R^{13}$ are each independently selected from H, $C_{1-10}$alkyl, $C_{3-10}$cycloalkyl and heterocycloalkyl, and when $R^{12}$ and $R^{13}$ are other than H they are each are independently substituted with halo. In some embodiments, $R^{12}$ and $R^{13}$ are each independently selected from H, $C_{1-10}$alkyl, $C_{3-10}$cycloalkyl and heterocycloalkyl. In some embodiments, $R^{12}$ and $R^{13}$ are each independently selected from H and $C_{3-10}$cycloalkyl.

In some embodiments, $R^{12}$ and $R^{13}$ together with the nitrogen atom to which they are attached form a 3-10 membered heterocycle that is unsubstituted or substituted with one, two or three substituents independently selected from halo, $OR^{15}$, $SR^{15}$, $NR^{16}R^{17}$, $C_{1-6}$alkyl, $C(O)R^{15}$, $C(O)OR^{15}$, $C(O)NR^{16}R^{17}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{15}$, $C_{1-6}$alkyleneOR$^{15}$, $C_{1-6}$alkyleneSR$^{15}$ and $C_{1-6}$alkyleneNR$^{16}R^{17}$. In some embodiments, $R^{12}$ and $R^{13}$ together with the nitrogen atom to which they are attached form a 3-10 membered heterocycle that is unsubstituted or substituted with one or two substituents independently selected from halo, $OR^{15}$, $NR^{16}R^{17}$, $C_{1-6}$alkyl, $SO_2C_{1-6}$alkyl, heterocycloalkyl, $C_{1-6}$alkylene$C_{3-10}$cycloalkyl and $C_{1-6}$alkyleneR$^{15}$. In some embodiments, $R^{12}$ and $R^{13}$ together with the nitrogen atom to which they are attached form a 3-10 membered heterocycle that is unsubstituted. In some embodiments, $R^{12}$ and $R^{13}$ together with the nitrogen atom to which they are attached form an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{14}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl. In some embodiments, $R^{14}$ is selected from $C_{3-10}$cycloalkyl and heterocycloalkyl. In some embodiments, $R^{14}$ is $C_{3-10}$cycloalkyl or heterocycloalkyl. In some embodiments $R^{14}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-TH-azepinyl, homopiperazinyl, 1,3-dioxepanyl, 4,7-dihydro-1,3-dioxepinyl, and hexamethylene oxidyl. In some embodiments $R^{14}$ is morpholinyl optionally substituted with one or two $C_{1-6}$alkyl, suitably methyl.

In some embodiments, $R^{15}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and when $R^{15}$ is other than H it is unsubstituted or substituted with one, two or three substituents selected from halo, $C_{1-6}$alkyl and $C_{1-6}$fluoroalkyl. In some embodiments, $R^{15}$ is selected from H, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and when $R^{15}$ is other than H it is unsubstituted or substituted with one, two or three substituents selected from halo, $C_{1-6}$alkyl and $C_{1-6}$fluoroalkyl. In some embodiments, $R^{15}$ is selected from H, $C_{6-10}$aryl and $C_{1-6}$alkylene$C_{6-10}$aryl, and when $R^{15}$ is other than H it is unsubstituted or substituted with one or two substituents selected from halo and $C_{1-6}$alkyl. In some embodiments, $R^{15}$ is selected from H and $C_{6-10}$aryl, and when $R^{15}$ is other than H it is unsubstituted or substituted with halo.

In some embodiments, $R^{16}$ and $R^{17}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl, and when $R^{16}$ and $R^{17}$ are other than H they are unsubstituted or substituted with one, two or three substituents independently selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)OH$, $C(O)OC_{1-6}$alkyl, $C(O)C_{1-6}$fluoroalkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl). In some embodiments, $R^{16}$ and $R^{17}$ are each independently selected from H, $C_{1-6}$alkyl, $C_{1-6}$fluoroalkyl, $C_{3-10}$cycloalkyl, heterocycloalkyl, $C_{6-10}$aryl, $C_{1-6}$alkylene$C_{6-10}$aryl, $C_{1-6}$alkylene$C_{3-10}$cycloalkyl and $C_{1-6}$alkyleneheterocycloalkyl. In some embodiments, $R^{16}$ and $R^{17}$ are each independently selected from H, $C_{1-6}$alkyl and $C_{1-6}$fluoroalkyl. In some embodiments, $R^{16}$ and $R^{17}$ are $C_{1-6}$alkyl.

In some embodiments, the compound of Formula I is selected from:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-6-(oxan-4-yloxy)pyridin-3-yl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridazine-3-carboxamide;

N-[5-[2-fluoro-5-(morpholin-4-ylmethyl)phenyl]-2-(4-methylpiperazin-1-yl)phenyl]-3-methoxybenzamide;

4-fluoro-N-[5-[2-fluoro-5-(morpholin-4-ylmethyl)phenyl]-2-(4-methylpiperazin-1-yl)phenyl]-3,5-dimethylbenzamide;

2-chloro-4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl] benzoate;

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[5-[6-(cyclopropylmethoxy)-2-fluoropyridin-3-yl]-2-(4-methylpiperazin-1-yl)phenyl]-6-oxo-4-(trifluoromethyl)-1H-pyridine-3-carboxamide;

N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

4-fluoro-N-[5-[2-fluoro-6-(oxan-4-yloxy)pyridin-3-yl]-2-(4-methylpiperazin-1-yl)phenyl]-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-(2-fluoro-6-pyrrolidin-1-ylpyridin-3-yl)-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-3-methylbenzamide;

N-[5-(2-fluorophenyl)-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-methyl-6-oxo-1H-pyridine-3-carboxamide;

N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-(3-fluoro-2-morpholin-4-ylpyridin-4-yl)-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide;

N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide;

N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide;

(R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide;
N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide;
N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;
N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;
N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide;
N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide;
[4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate;
N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;
N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;
N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;
N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;
(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;
N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;
(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;
N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;
N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;
N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;
N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;
(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;
N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;
N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;
N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;
N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide;
N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide;
N-[5-[6-(cyclopropylmethoxy)-2-fluoropyridin-3-yl]-2-[(3S,5R)-3,4,5-trimethylpiperazin-1-yl]phenyl]-6-oxo-4-(trifluoromethyl)-1H-pyridine-3-carboxamide;
N-[5-[3-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;
N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide;
N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide;
N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide;
N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide;
N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide;
N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;
N-[2-[3-(dimethylamino)pyrrolidin-1-yl]-5-[2-fluoro-5-(morpholin-4-ylmethyl)phenyl]phenyl]-4-fluoro-3,5-dimethylbenzamide;
4-fluoro-N-[5-[2-fluoro-5-(morpholin-4-ylmethyl)phenyl]-2-(4-methyl-1,4-diazepan-1-yl)phenyl]-3,5-dimethylbenzamide;
N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;
4-fluoro-N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-3,5-dimethylbenzamide;
4-fluoro-N-[5-[2-fluoro-5-(morpholin-4-ylmethyl)phenyl]-2-[4-(2,2,2-trifluoroethyl)piperazin-1-yl]phenyl]-3,5-dimethylbenzamide;
(S)—N-(2-(3,4-dimethylpiperazin-1-yl)-5-(3-fluoropyridin-2-yl)phenyl)-6-oxo-4-(trifluoromethyl)-1,6-dihydropyridine-3-carboxamide;
N-[5-[2-fluoro-5-(morpholin-4-ylmethyl)phenyl]-2-[4-(2,2,2-trifluoroethyl)piperazin-1-yl]phenyl]-6-oxo-4-(trifluoromethyl)-1H-pyridine-3-carboxamide;
N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;
N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;
N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-6-oxo-4-(trifluoromethyl)-1H-pyridine-3-carboxamide;
N-[2-[3-(dimethylamino)pyrrolidin-1-yl]-5-[2-fluoro-5-(morpholin-4-ylmethyl)phenyl]phenyl]-1-methyl-6-oxo-4-(trifluoromethyl)pyridine-3-carboxamide;

6-fluoro-N-[5-[2-fluoro-5-(morpholin-4-ylmethyl)phenyl]-2-(4-methylpiperazin-1-yl)phenyl]-1H-benzimidazole-4-carboxamide;

N-[5-[2-fluoro-5-(morpholin-4-ylmethyl)phenyl]-2-(4-methylpiperazin-1-yl)phenyl]-1H-benzimidazole-2-carboxamide;

N-[5-[2-fluoro-5-(morpholin-4-ylmethyl)phenyl]-2-[(2R)-2,4-dimethylpiperazin-1-yl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridine-3-carboxamide;

6-acetamido-N-[5-[2-fluoro-5-(morpholin-4-ylmethyl)phenyl]-2-(4-methylpiperazin-1-yl)phenyl]-4-methylpyridine-3-carboxamide;

N-[5-[5-[[4-(cyclopropylmethyl)piperazin-1-yl]methyl]-2-fluorophenyl]-2-(4-methylpiperazin-1-yl)phenyl]-6-methoxy-4-(trifluoromethyl)pyridine-3-carboxamide;

N-[5-[2-fluoro-5-(morpholin-4-ylmethyl)phenyl]-2-(4-methylpiperazin-1-yl)phenyl]-6-(methylamino)-4-(trifluoromethyl)pyridine-3-carboxamide;

6-amino-N-[5-[2-fluoro-5-(morpholin-4-ylmethyl)phenyl]-2-(4-methylpiperazin-1-yl)phenyl]-4-(trifluoromethyl)pyridine-3-carboxamide;

N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide;

N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[3-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;

N-[5-[4-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;

N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(4'-carbamoyl-2',3'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide;

N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide;

N-(5'-(cyclohexylcarbamoyl)-2'-fluoro-4-(4-methyl-3-oxopiperazin-1-yl)-[1,1'-biphenyl]-3-yl)-6-oxo-4-(trifluoromethyl)-1,6-dihydropyridine-3-carboxamide;

N-(4-((2-(dimethylamino)ethyl)(methyl)amino)-2'-fluoro-5'-(morpholinomethyl)-[1,1'-biphenyl]-3-yl)-6-oxo-4-(trifluoromethyl)-1,6-dihydropyridine-3-carboxamide; and N-(5'-((cyclohexylamino)methyl)-4-((2-(dimethylamino)ethyl)(methyl)amino)-2'-fluoro-[1,1'-biphenyl]-3-yl)-6-oxo-4-(trifluoromethyl)-1,6-dihydropyridine-3-carboxamide, or a pharmaceutically acceptable salt and/or solvate thereof.

In some embodiments, the compound of Formula I is selected from:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-6-(oxan-4-yloxy)pyridin-3-yl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridazine-3-carboxamide;

N-[5-[2-fluoro-5-(morpholin-4-ylmethyl)phenyl]-2-(4-methylpiperazin-1-yl)phenyl]-3-methoxybenzamide;

4-fluoro-N-[5-[2-fluoro-5-(morpholin-4-ylmethyl)phenyl]-2-(4-methylpiperazin-1-yl)phenyl]-3,5-dimethylbenzamide;

2-chloro-4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl]benzoate;

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[5-[6-(cyclopropylmethoxy)-2-fluoropyridin-3-yl]-2-(4-methylpiperazin-1-yl)phenyl]-6-oxo-(trifluoromethyl)-1H-pyridine-3-carboxamide;

N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

4-fluoro-N-[5-[2-fluoro-6-(oxan-4-yloxy)pyridin-3-yl]-2-(4-methylpiperazin-1-yl)phenyl]-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-(2-fluoro-6-pyrrolidin-1-ylpyridin-3-yl)-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-3-methylbenzamide;

N-[5-(2-fluorophenyl)-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-methyl-6-oxo-1H-pyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-(3-fluoro-2-morpholin-4-ylpyridin-4-yl)-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide;

N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide;

N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide;

(R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide;

N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;

N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide;

N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide;

[4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate;

N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-[5-[6-(cyclopropylmethoxy)-2-fluoropyridin-3-yl]-2-[(3S,5R)-3,4,5-trimethylpiperazin-1-yl]phenyl]-6-oxo-4-(trifluoromethyl)-1H-pyridine-3-carboxamide;

N-[5-[3-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide; and N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide, or a pharmaceutically acceptable salt and/or solvate thereof.

In some embodiments, the compound of Formula (I) is selected from:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-6-(oxan-4-yloxy)pyridin-3-yl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3,5-dimethylbenzamide;

2-chloro-4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl]benzoate;

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[5-[6-(cyclopropylmethoxy)-2-fluoropyridin-3-yl]-2-(4-methylpiperazin-1-yl)phenyl]-6-oxo-4-(trifluoromethyl)-1H-pyridine-3-carboxamide;

N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

4-fluoro-N-[5-[2-fluoro-6-(oxan-4-yloxy)pyridin-3-yl]-2-(4-methylpiperazin-1-yl)phenyl]-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-(2-fluoro-6-pyrrolidin-1-ylpyridin-3-yl)-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-(3-fluoro-2-morpholin-4-ylpyridin-4-yl)-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide;
N-[5-[6-(cyclopropylmethoxy)-2-fluoropyridin-3-yl]-2-[(3S,5R)-3,4,5-trimethylpiperazin-1-yl]phenyl]-6-oxo-4-(trifluoromethyl)-1H-pyridine-3-carboxamide;
N-[5-[3-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;
N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide;
N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide;
N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide;
N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide;
N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide;
N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;
N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;
(S)—N-(2-(3,4-dimethylpiperazin-1-yl)-5-(3-fluoropyridin-2-yl)phenyl)-6-oxo-4-(trifluoromethyl)-1,6-dihydropyridine-3-carboxamide;
N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;
N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;
N-[5-[2-fluoro-5-(morpholin-4-ylmethyl)phenyl]-2-[(2R)-2,4-dimethylpiperazin-1-yl]phenyl]-6-oxo-4-(trifluoromethyl)-1H-pyridine-3-carboxamide;
6-acetamido-N-[5-[2-fluoro-5-(morpholin-4-ylmethyl)phenyl]-2-(4-methylpiperazin-1-yl)phenyl]-4-methylpyridine-3-carboxamide;
N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide;
N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide;
N-[5-[2,4-difluoro-3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;
N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;
N-[5-[3-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;
N-[5-[4-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;
N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(4'-carbamoyl-2',3'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide; and
N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide, or a pharmaceutically acceptable salt and/or solvate thereof.

In some embodiments, the compound of Formula (I) is selected from, and pharmaceutically acceptable salts and/or solvates thereof:

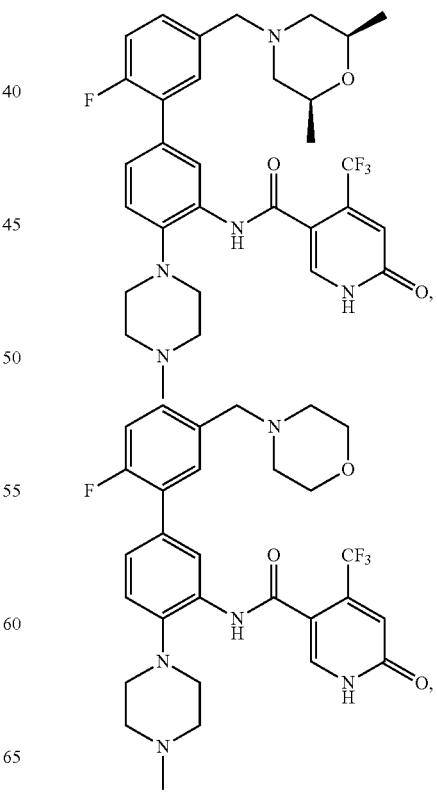

-continued
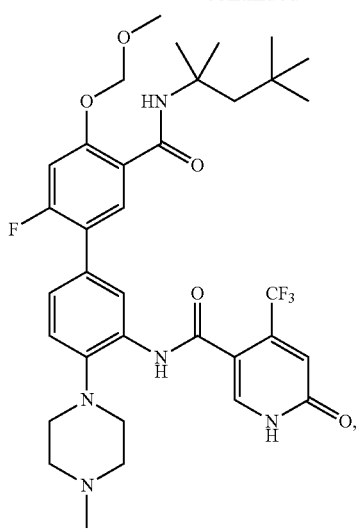
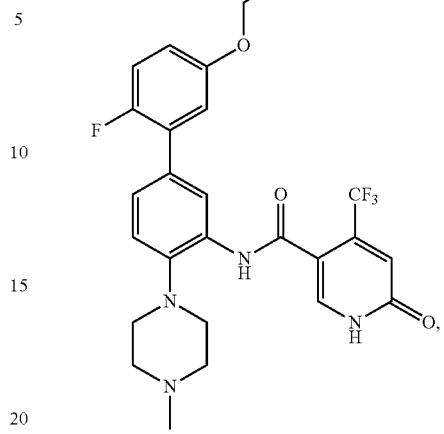
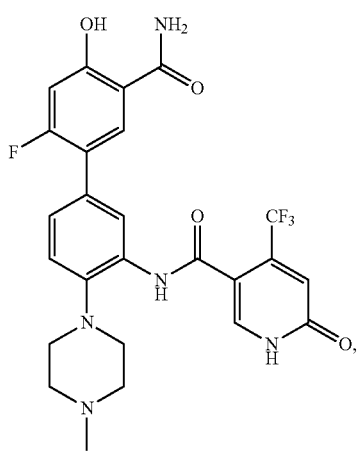
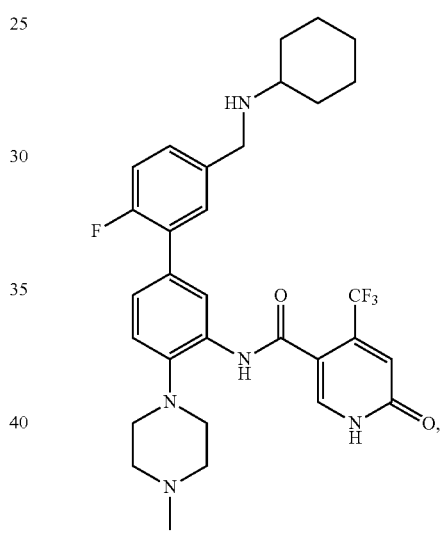
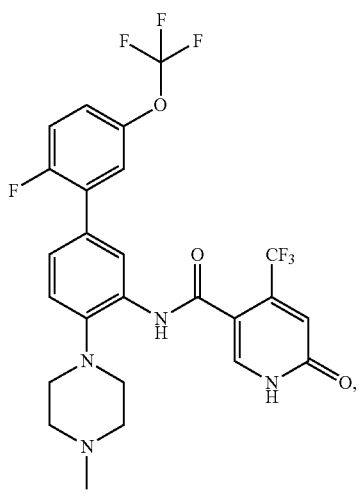
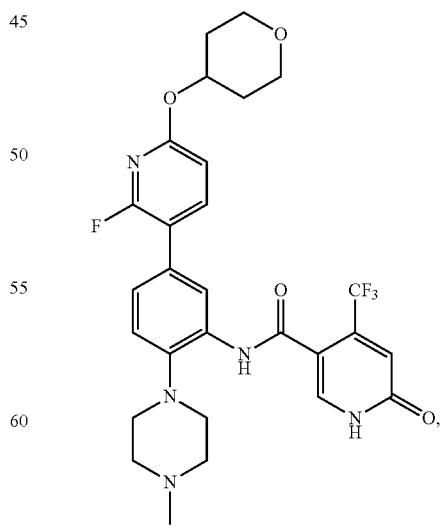

49
-continued
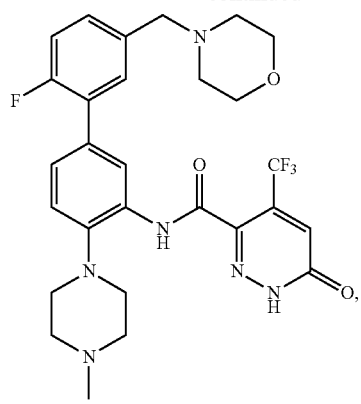
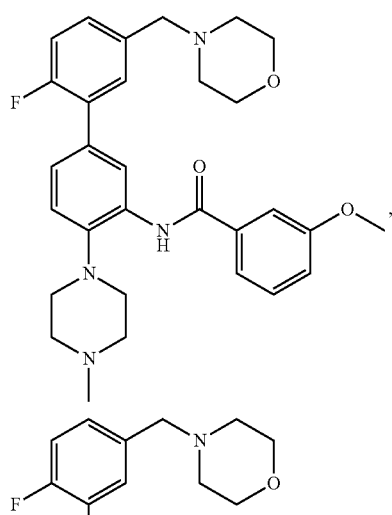
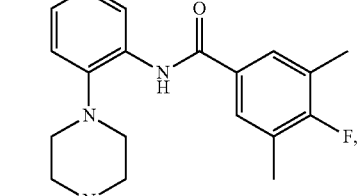
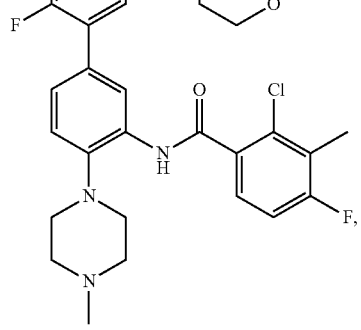
50
-continued
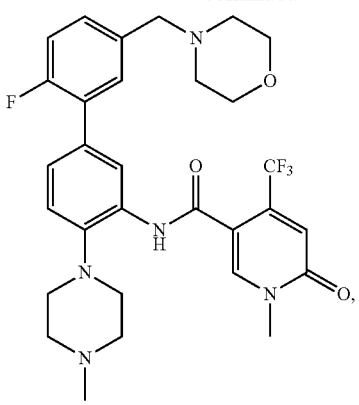
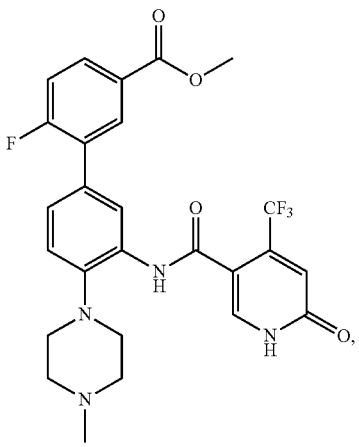
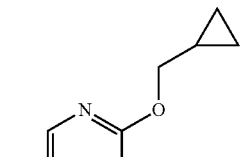
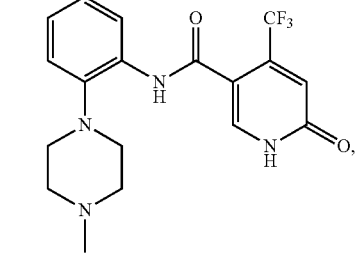

51
-continued
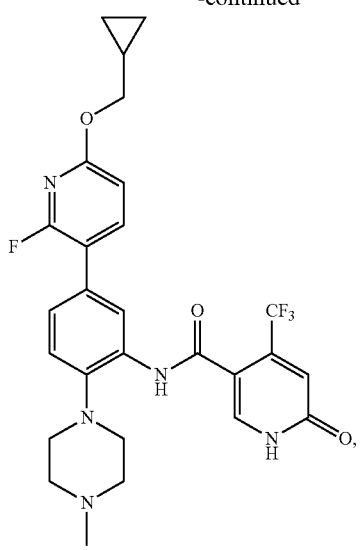
52
-continued
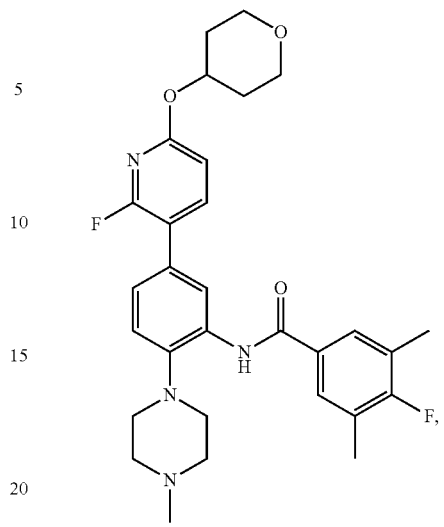
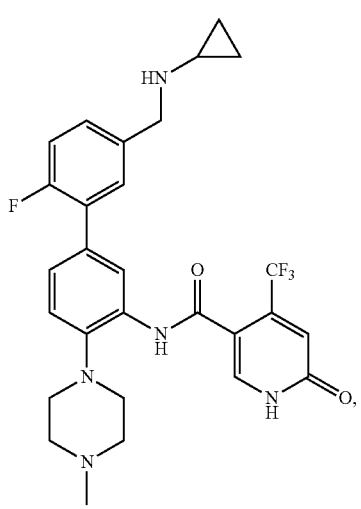
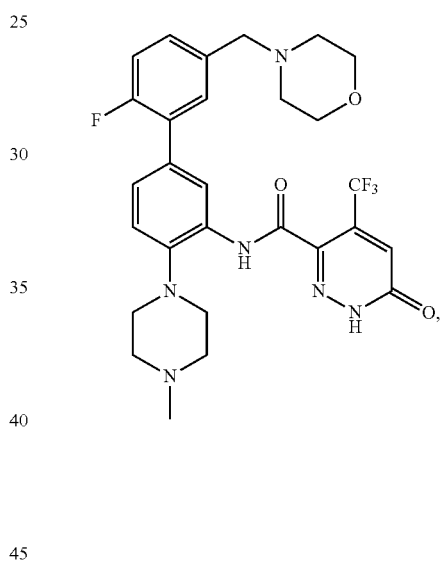
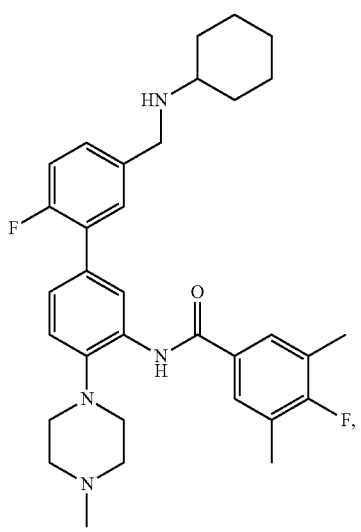
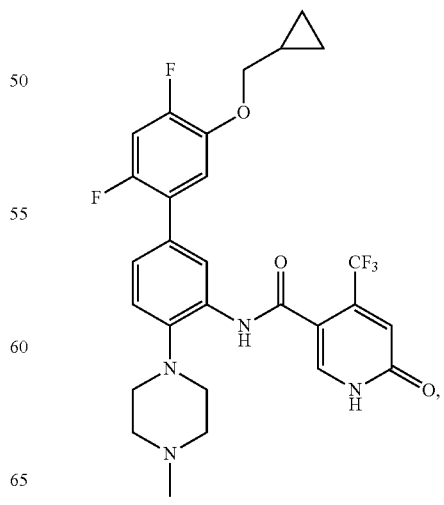

53
-continued
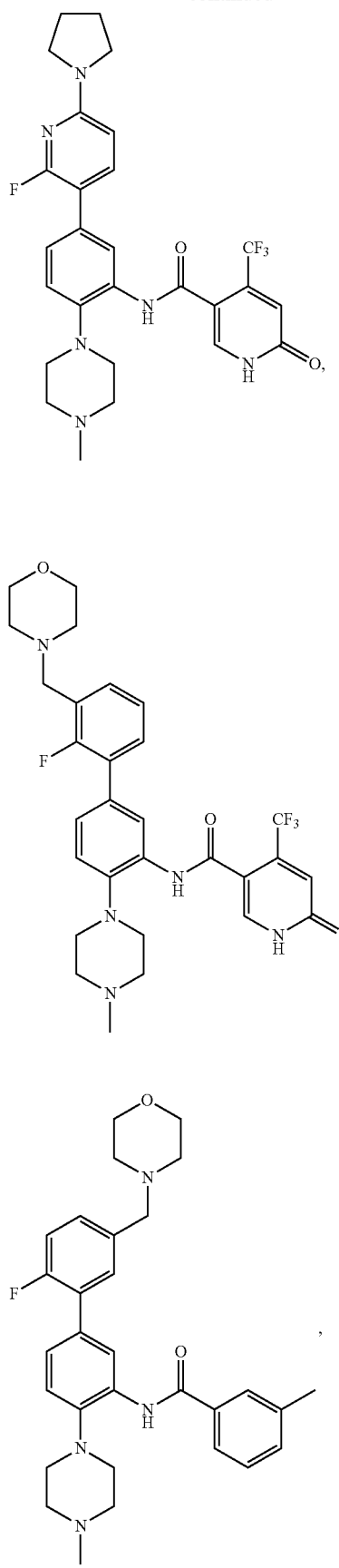
54
-continued
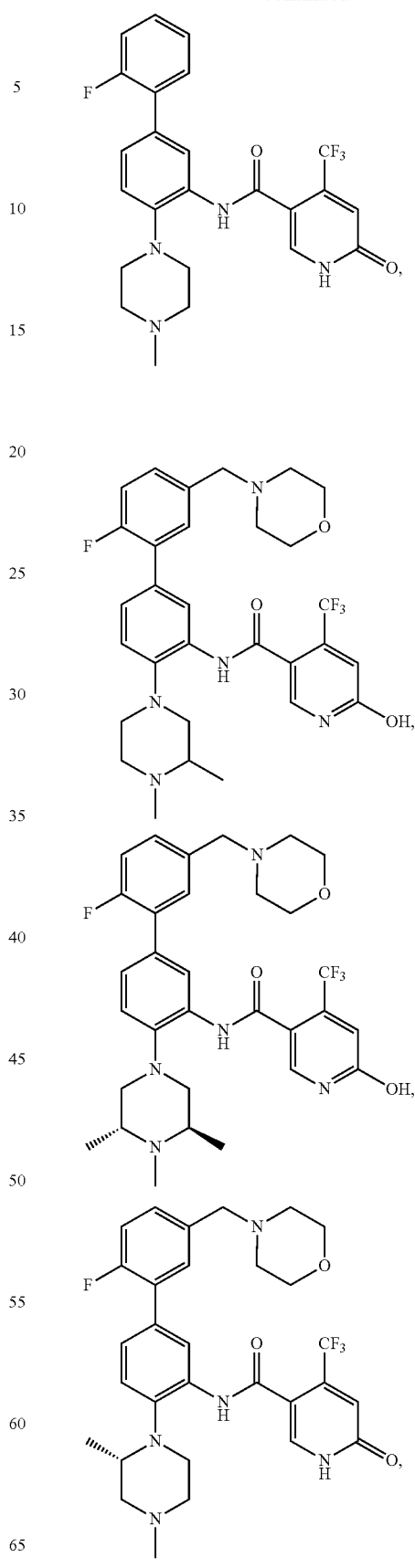

55
-continued
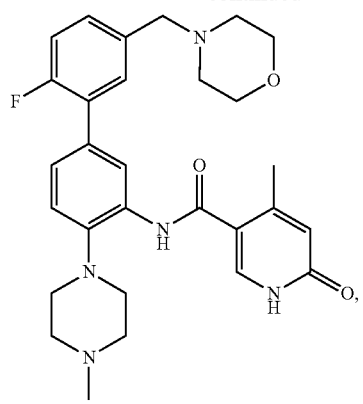
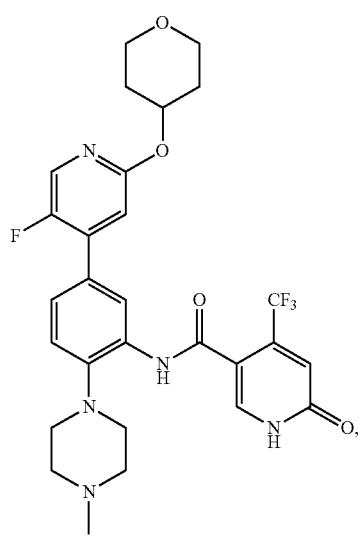
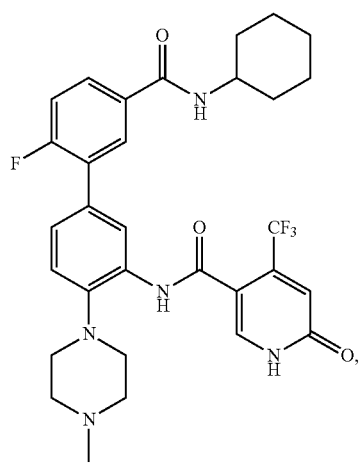
56
-continued
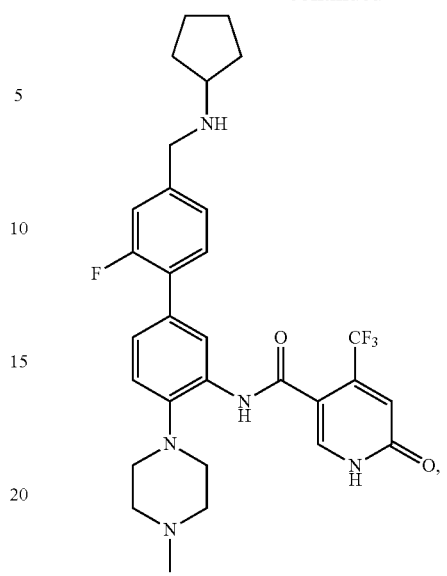
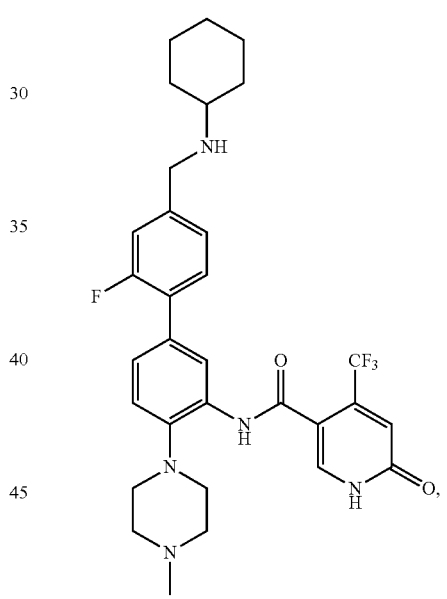
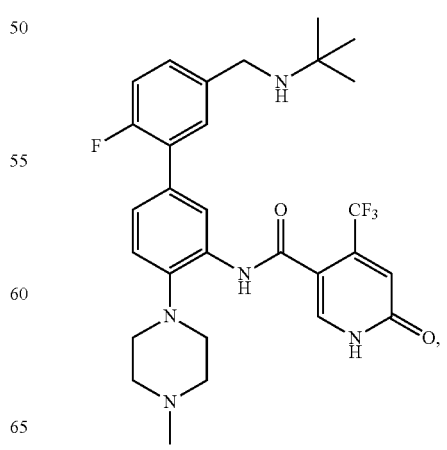

57
-continued
58
-continued
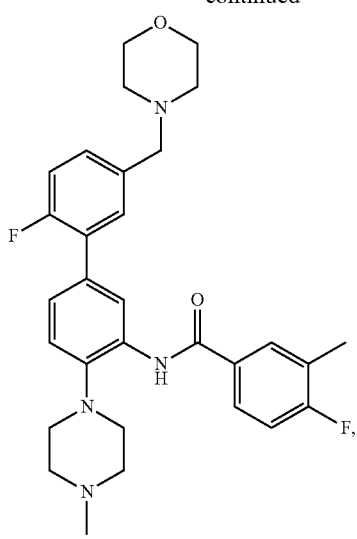
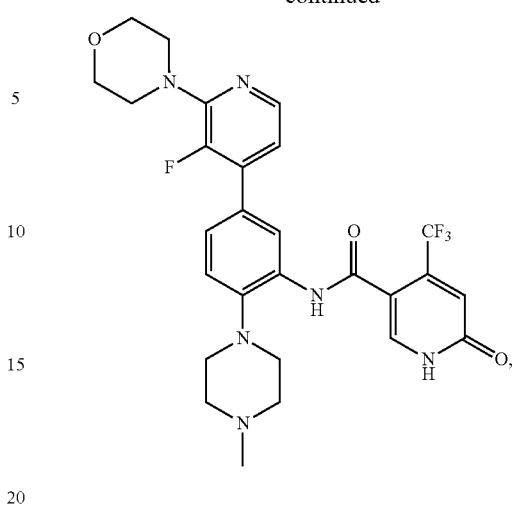
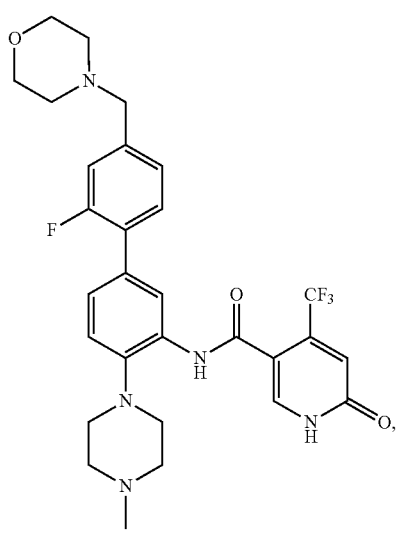

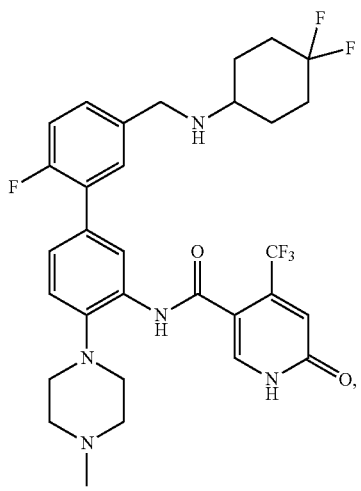
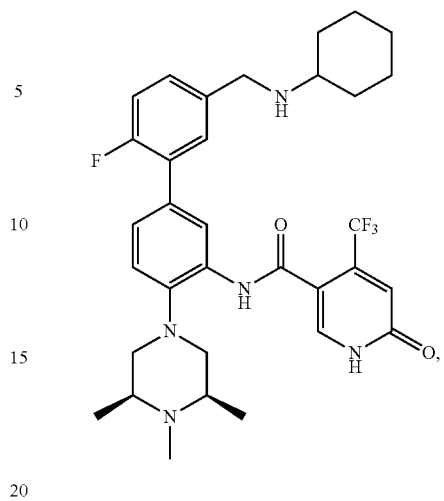
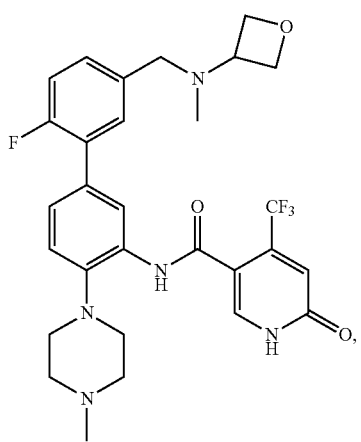
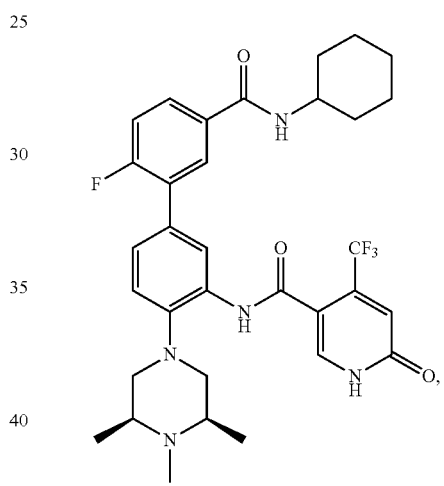
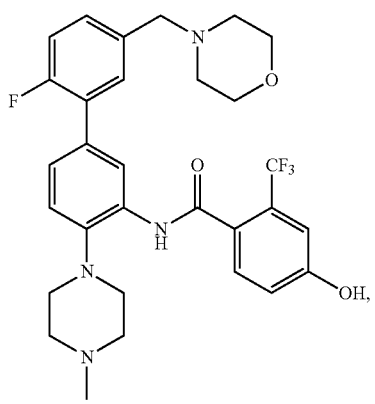
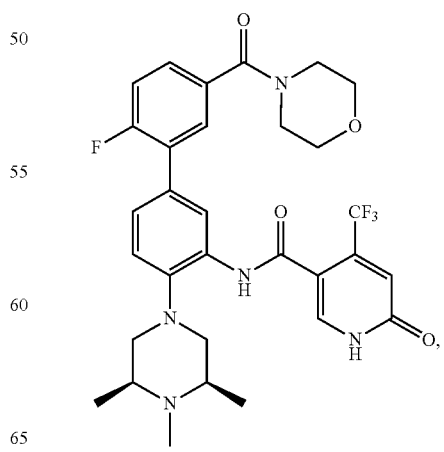

61
-continued
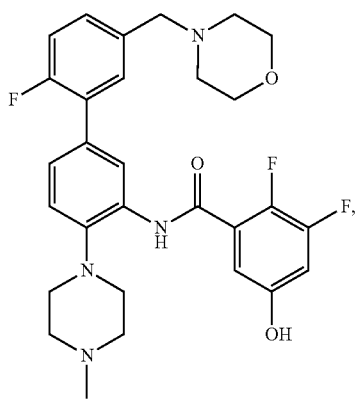
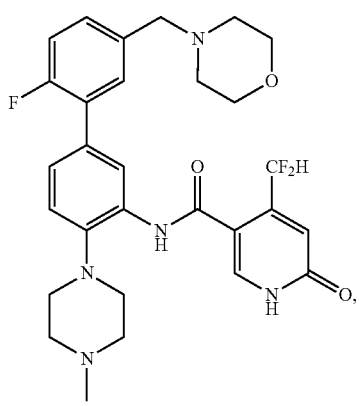
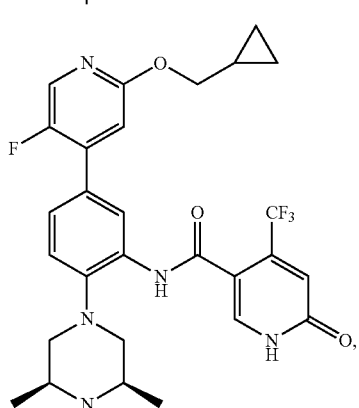
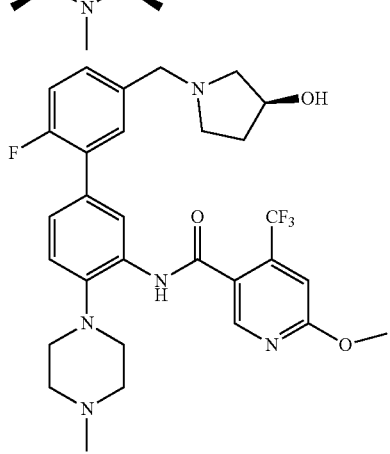,
62
-continued
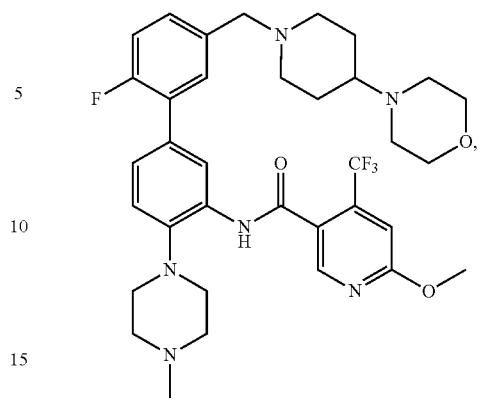,
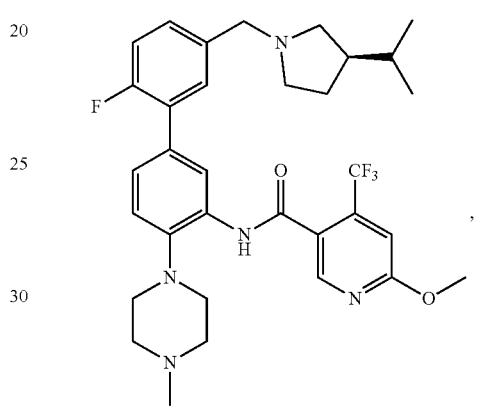,
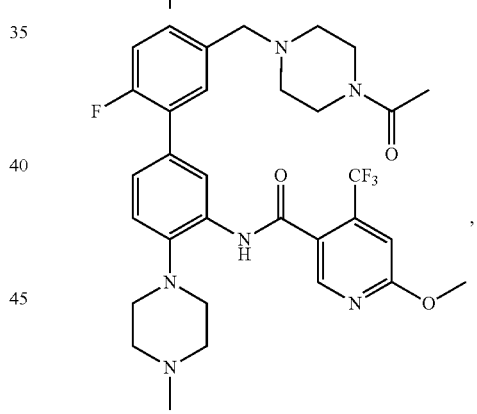,
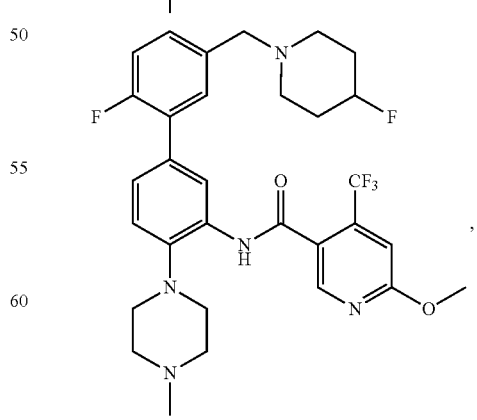, 63
-continued
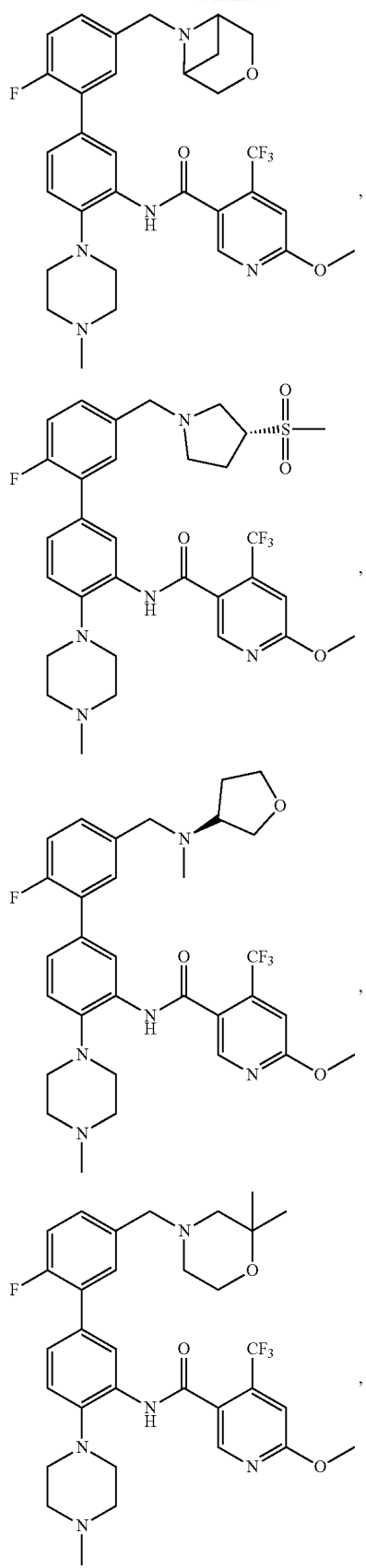
64
-continued
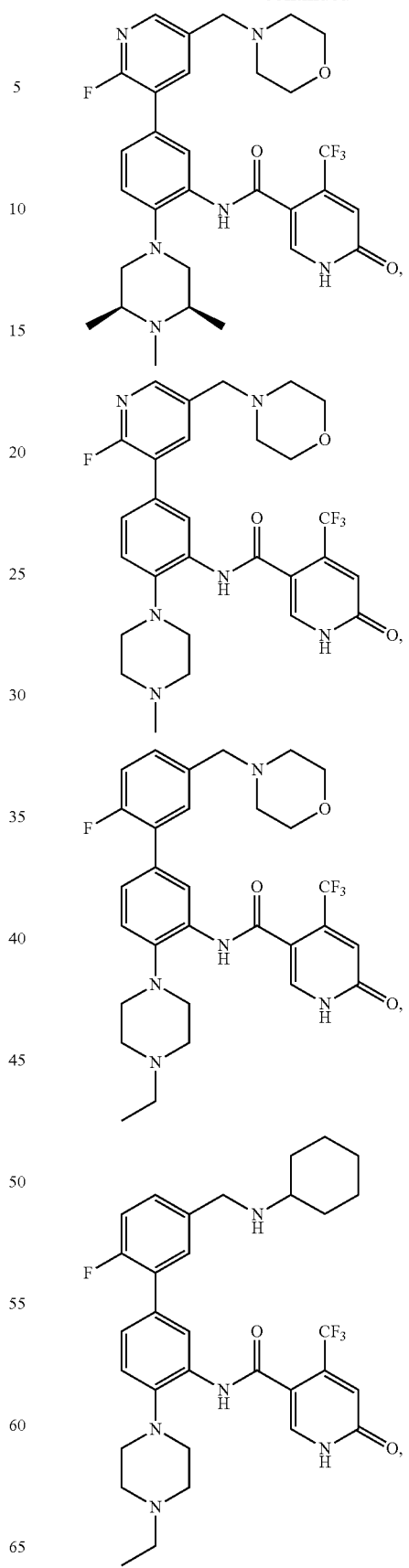

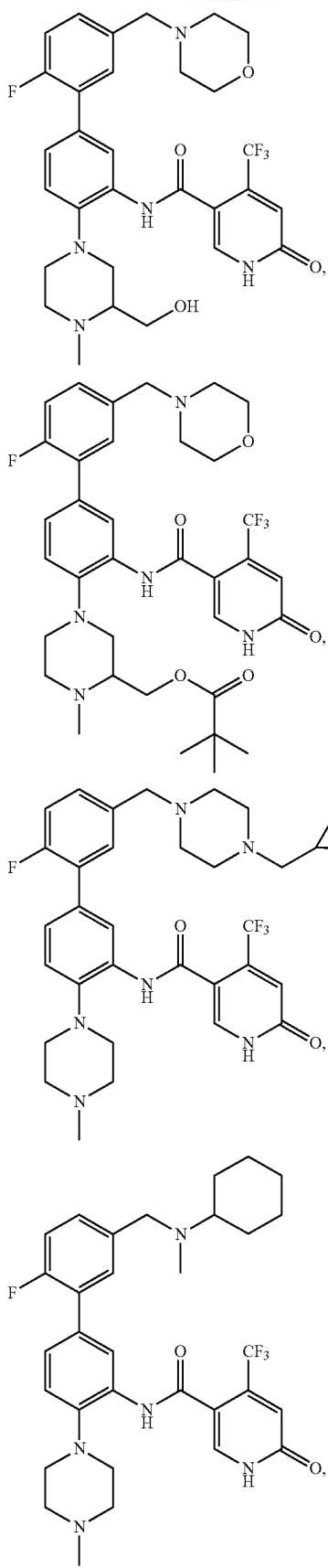
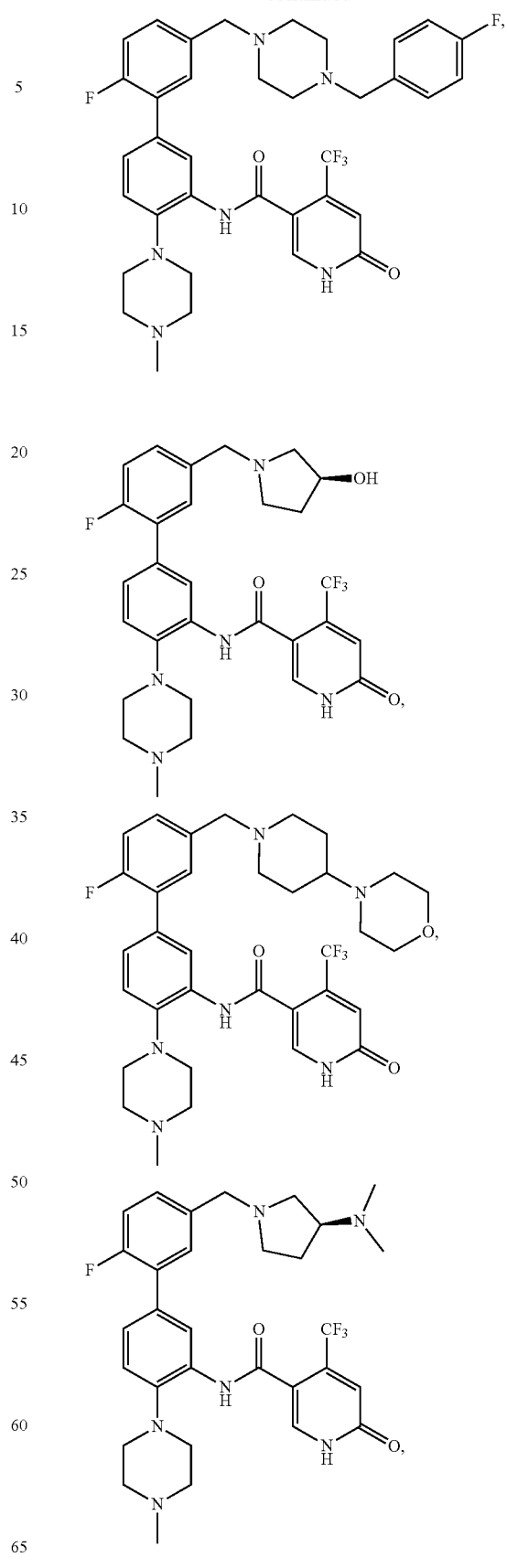

67
-continued
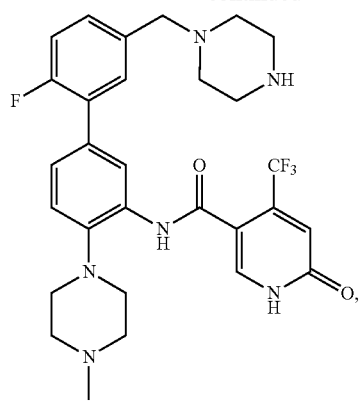
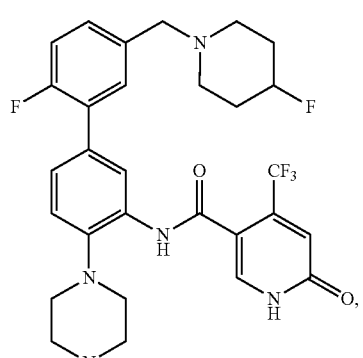
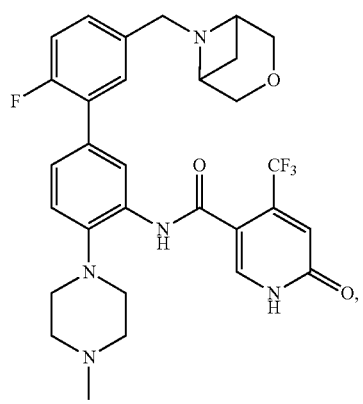
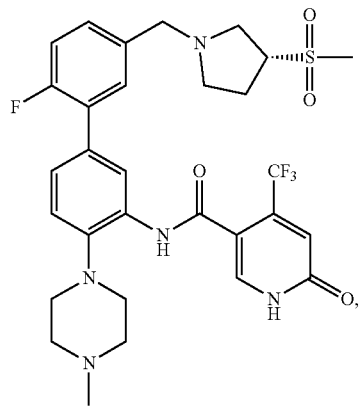
68
-continued
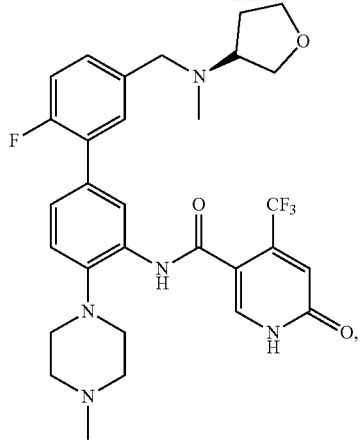
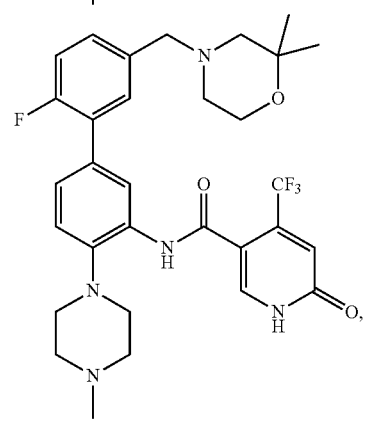
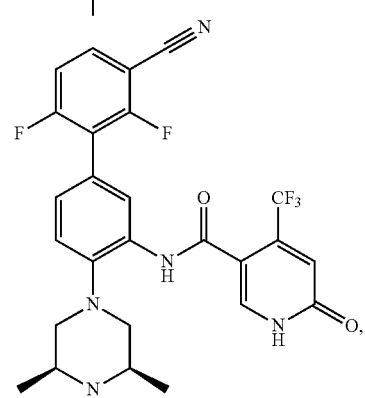
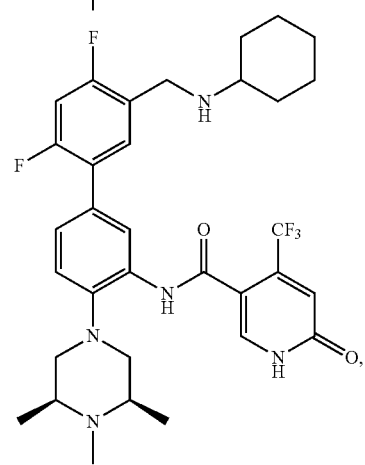

69
-continued
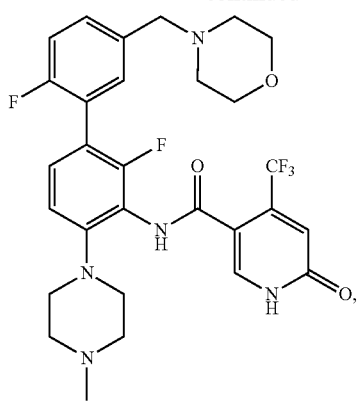
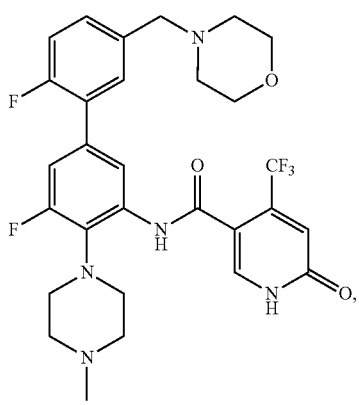
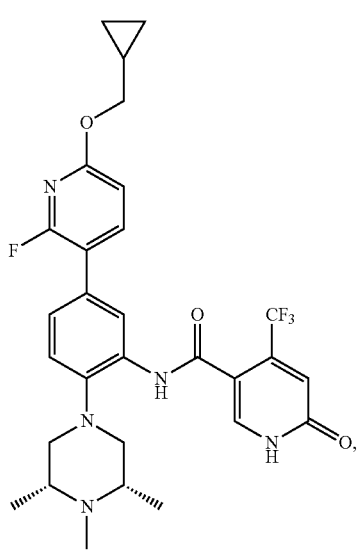
70
-continued
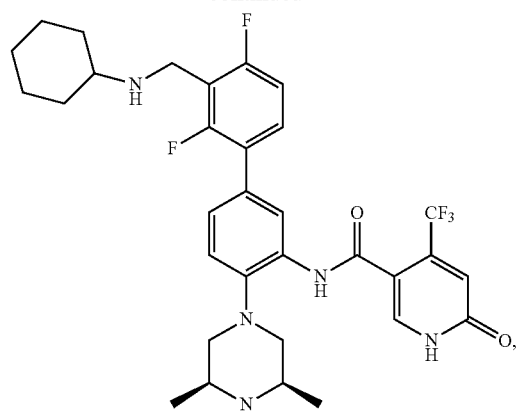
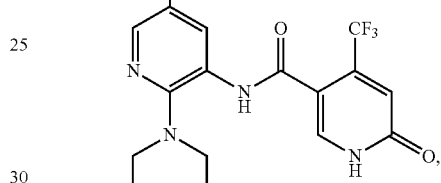
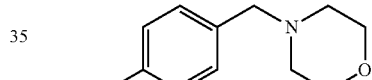
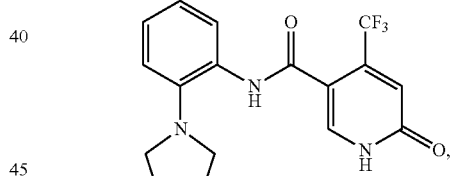

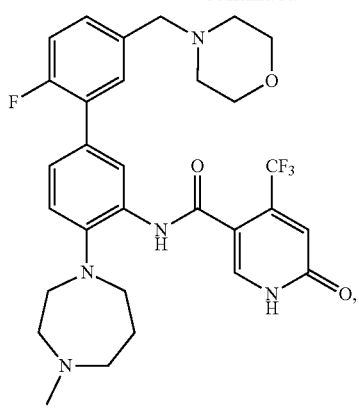

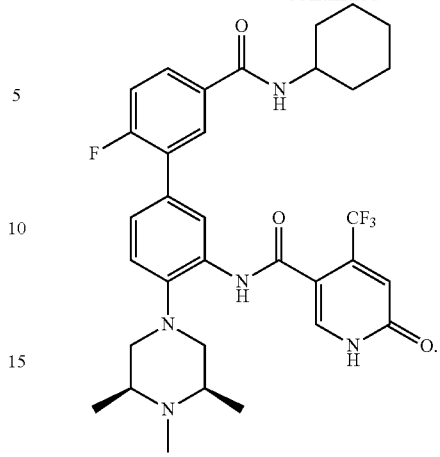

In some embodiments, the compound of Formula (I) is selected from, and pharmaceutically acceptable salts and/or solvates thereof:

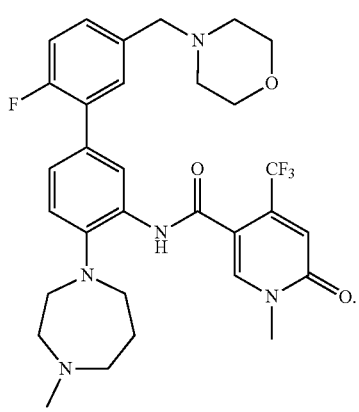

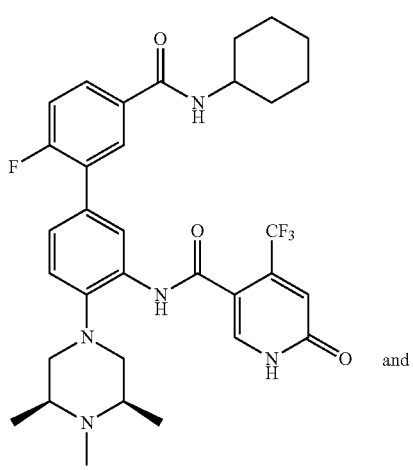

The present application also includes a compound of Formula (Ia) or a pharmaceutically acceptable salt and/or solvate thereof:

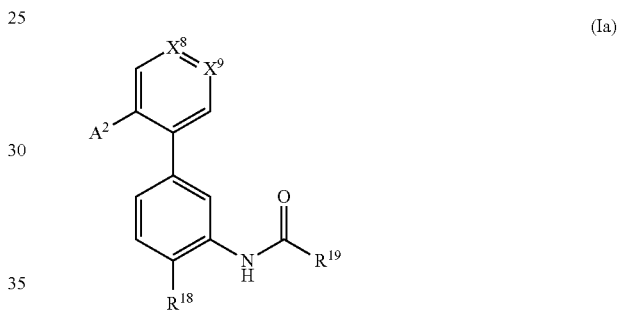

(Ia)

wherein:
$R^{18}$ is a heterocycloalkyl that is unsubstituted or substituted with one or more substituents selected from halo, $C_{1-6}$alkyl, $C_{1-6}$fluoroalkyl, $OR^{20}$, $SR^{20}$, $NR^{21}R^{22}$, $C_{1-6}$alkyleneOR$^{20}$, $C_{1-6}$alkyleneSR$^{20}$ and $C_{1-6}$alkyleneNR$^{21}R^{22}$, provided that $R^{18}$ comprises at least one basic nitrogen atom;
$R^{19}$ is selected from $C_{6-10}$aryl and heteroaryl, and $R^{19}$ is unsubstituted or substituted with one or more substituents selected from halo, $C_{1-6}$alkyl, $C_{1-6}$fluoroalkyl, =O, =S, $OR^{23}$, $SR^{23}$ and $NR^{24}R^{25}$;
$R^{20}$ and $R^{23}$ are independently selected from H, $C_{1-6}$alkyl, $C_{1-6}$fluoroalkyl, $C(O)C_{1-6}$alkyl and $C(O)C_{1-6}$fluoroalkyl;
$R^{21}$ and $R^{22}$ are independently selected from H, $C_{1-6}$alkyl, $C_{1-6}$fluoroalkyl, heterocycloalkyl, $C(O)C_{1-6}$alkyl and $C(O)C_{1-6}$fluoroalkyl, or $R^{21}$ and $R^{22}$ together with the nitrogen atom to which they are attached form a 3-10 membered heterocycle that is unsubstituted or substituted with one or more substituents selected from halo, OH, $C_{1-6}$alkyl, $OC_{1-6}$alkyl, $C_{1-6}$fluoroalkyl, $OC_{1-6}$fluoroalkyl, $C(O)C_{1-6}$alkyl and $C(O)C_{1-6}$fluoroalkyl;
$R^{24}$ and $R^{25}$ are independently selected from H, $C_{1-6}$alkyl, $C_{1-6}$fluoroalkyl, $C(O)C_{1-6}$alkyl and $C(O)C_{1-6}$fluoroalkyl, or $R^{24}$ and $R^{25}$ together with the nitrogen atom to which they are attached form a 3-10 membered heterocycle that is unsubstituted or substituted with one or more substituents selected from halo, OH, $C_{1-6}$alkyl, $OC_{1-6}$alkyl, $C_{1-6}$fluoroalkyl and $OC_{1-6}$fluoroalkyl;
$X^8$ and $X^9$ are each independently selected from $CR^{26}$ and N;
$R^{26}$ is selected from H, halo, CN, $C_{1-6}$alkyl, $C_{1-6}$fluoroalkyl, $OR^{27}$, $SR^{27}$, $NR^{28}R^{29}$, $R^{30}$, $C_{1-6}$alkyleneR$^{30}$, $OC_{1-6}$alkyleneR$^{30}$, SC$_{1-6}$alkyleneR$^{30}$, C$_{1-6}$alkyleneNR$^{28}$R$^{29}$, C$_{1-6}$alkyleneOR$^{27}$, C$_{1-6}$alkyleneSR$^{27}$, OC$_{1-6}$alkyleneNR$^{28}$R$^{29}$, SC$_{1-6}$alkyleneNR$^{28}$R$^{29}$, OC$_{1-6}$alkyleneOR$^{27}$, SC$_{1-6}$alkyleneOR$^{27}$, OC$_{1-6}$alkyleneSR$^{27}$, SC$_{1-6}$alkyleneSR$^{27}$, C(O)OR$^{27}$, C(S)OR$^{27}$, C(S)NR$^{28}$R$^{29}$ and C(O)NR$^{28}$R$^{29}$;

R$^{27}$ is selected from H, C$_{1-6}$alkyl, C$_{1-6}$fluoroalkyl, C(O)C$_{1-6}$alkyl, C(O)C$_{1-6}$fluoroalkyl, C$_{3-10}$cycloalkyl, heterocycloalkyl, C$_{6-10}$aryl, heteroaryl, C$_{1-6}$alkyleneC$_{3-10}$cycloalkyl, C$_{1-6}$alkyleneC$_{6-10}$aryl, C$_{1-6}$alkyleneheteroaryl and C$_{1-6}$alkyleneheterocycloalkyl, and when R$^{27}$ is other than H it is unsubstituted or substituted with one or more substituents selected from halo, OR$^{31}$, SR$^{31}$, NR$^{32}$R$^{33}$, C$_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{31}$, C$_{1-6}$alkyleneOR$^{31}$, C$_{1-6}$alkyleneSR$^{31}$ and C$_{1-6}$alkyleneNR$^{32}$R$^{33}$;

R$^{28}$ and R$^{29}$ are each independently selected from H, C$_{1-10}$alkyl, C$_{1-10}$fluoroalkyl, C(O)C$_{1-6}$alkyl, C(O)C$_{1-6}$fluoroalkyl, C$_{3-10}$cycloalkyl, heterocycloalkyl, heteroaryl, C$_{6-10}$aryl, C$_{1-6}$alkyleneC$_{3-10}$cycloalkyl, C$_{1-6}$alkyleneC$_{6-10}$aryl, C$_{1-6}$alkyleneheteroaryl and C$_{1-6}$alkyleneheterocycloalkyl, and when R$^{28}$ and R$^{29}$ are other than H they are each independently unsubstituted or substituted with one or more substituents selected from halo, OR$^{31}$, SR$^{31}$, NR$^{32}$R$^{33}$, C$_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{31}$, C$_{1-6}$alkyleneOR$^{31}$, C$_{1-6}$alkyleneSR$^{31}$ and C$_{1-6}$alkyleneNR$^{32}$R$^{33}$, or R$^{28}$ and R$^{29}$ together with the nitrogen atom to which they are attached form a 3-10 membered heterocycle that is unsubstituted or substituted with one or more substituents independently selected from halo, OR$^{31}$, SR$^{31}$, NR$^{32}$R$^{33}$, C$_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{31}$, C$_{1-6}$alkyleneOR$^{31}$, C$_{1-6}$alkyleneSR$^{31}$ and C$_{1-6}$alkyleneNR$^{32}$R$^{33}$;

R$^{30}$ is selected from C(O)C$_{1-6}$alkyl, C(O)C$_{1-6}$fluoroalkyl, C$_{3-10}$cycloalkyl, heterocycloalkyl, heteroaryl and C$_{6-10}$aryl, and when R$^{30}$ is other than H it is unsubstituted or substituted with one or more substituents independently selected from halo, OR$^{31}$, SR$^{31}$, NR$^{32}$R$^{33}$, C$_{1-6}$alkyl, C(O)R$^{31}$, C(O)OR$^{31}$, C(O)NR$^{32}$R$^{33}$, S(O)C$_{1-6}$alkyl, SO$_2$C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneR$^{31}$, C$_{1-6}$alkyleneOR$^{31}$, C$_{1-6}$alkyleneSR$^{31}$ and C$_{1-6}$alkyleneNR$^{32}$R$^{33}$;

R$^{31}$ is selected from H, C$_{1-6}$alkyl, C$_{1-6}$fluoroalkyl, C(O)C$_{1-6}$alkyl, C(O)C$_{1-6}$fluoroalkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl, and when R$^{31}$ is other than H it is unsubstituted or substituted with one or more substituents selected from halo, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl);

R$^{32}$ and R$^{33}$ are each independently selected from H, C$_{1-6}$alkyl, C$_{1-6}$fluoroalkyl, C(O)C$_{1-6}$alkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl and when R$^{32}$ and R$^{33}$ are other than H they are each unsubstituted or substituted with one or more substituents independently selected from halo, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)OH, C(O)OC$_{1-6}$alkyl, C(O)C$_{1-6}$fluoroalkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl), or R$^{32}$ and R$^{33}$ together with the nitrogen atom to which they are attached form a 3-10 membered heterocycle that is unsubstituted or substituted with one or more substituents selected from halo, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)C$_{1-6}$fluoroalkyl, C(O)OH, C(O)OC$_{1-6}$alkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl);

A$^2$ is F; and all alkyl and alkylene groups are optionally fluorosubstituted.

In some embodiments, R$^{18}$ is a heterocycloalkyl that is unsubstituted or substituted with one, two or three substituents selected from halo, C$_{1-6}$alkyl, C$_{1-6}$fluoroalkyl, C$_{1-6}$alkyleneOR$^{20}$, NR$^{21}$R$^{22}$ and C$_{1-6}$alkyleneNR$^{21}$R$^{22}$, provided that R$^{18}$ comprises at least one basic nitrogen atom. In some embodiments, R$^{18}$ is a heterocycloalkyl that is substituted with one, two or three substituents selected from halo, C$_{1-6}$alkyl, C$_{1-6}$alkyleneOR$^{20}$ and NR$^{21}$R$^{22}$, provided that R$^{18}$ comprises at least one basic nitrogen atom. In some embodiments, R$^{18}$ is a heterocycloalkyl that is substituted with one or two substituents selected from C$_{1-6}$alkyl, C$_{1-6}$alkyleneOR$^{20}$ and NR$^{21}$R$^{22}$, provided that R$^{18}$ comprises at least one basic nitrogen atom.

In some embodiments, R$^{18}$ is selected from:

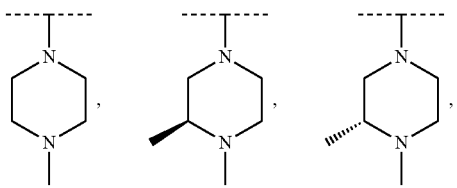

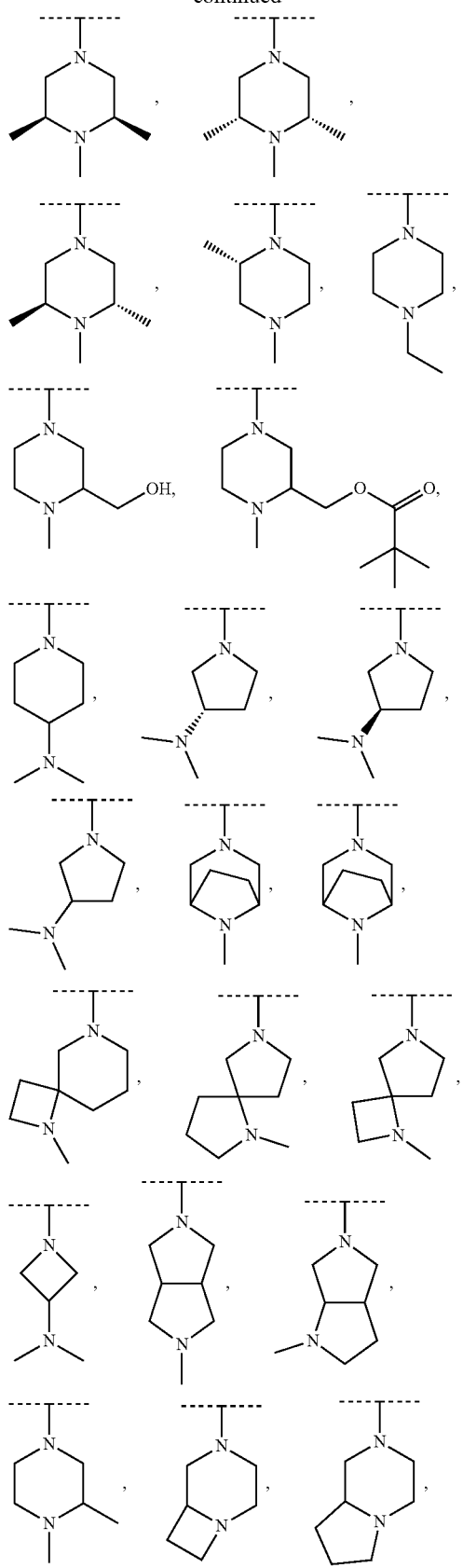
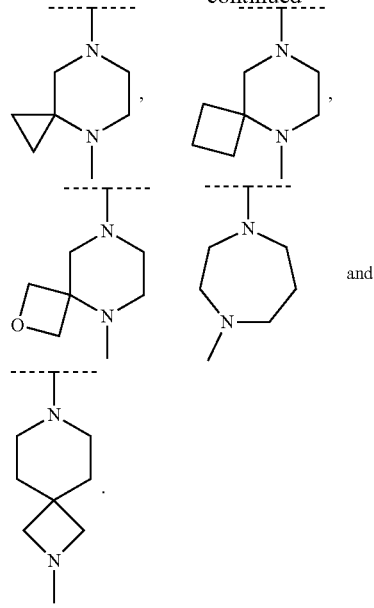
In some embodiments, $R^{18}$ is selected from:
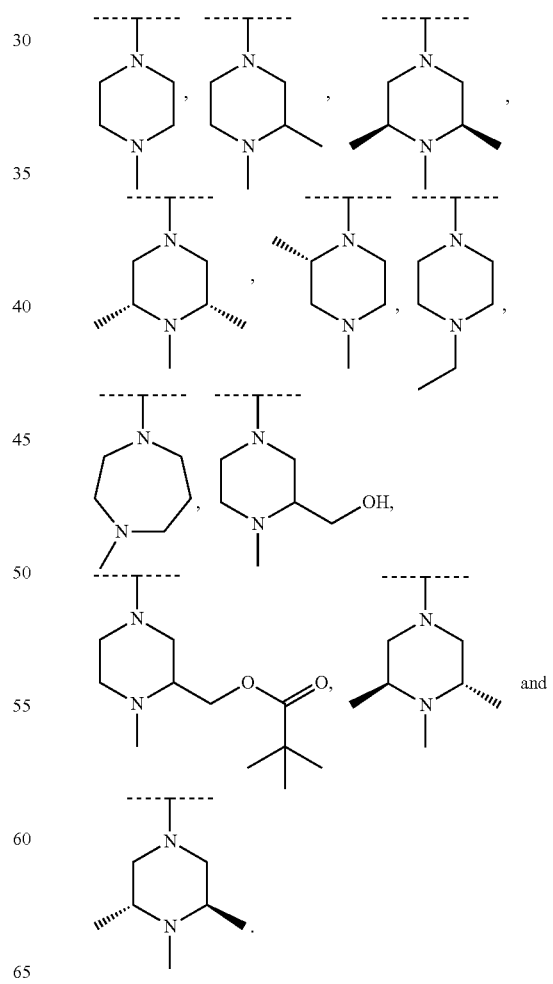

In some embodiments, R$^{18}$ is selected from:

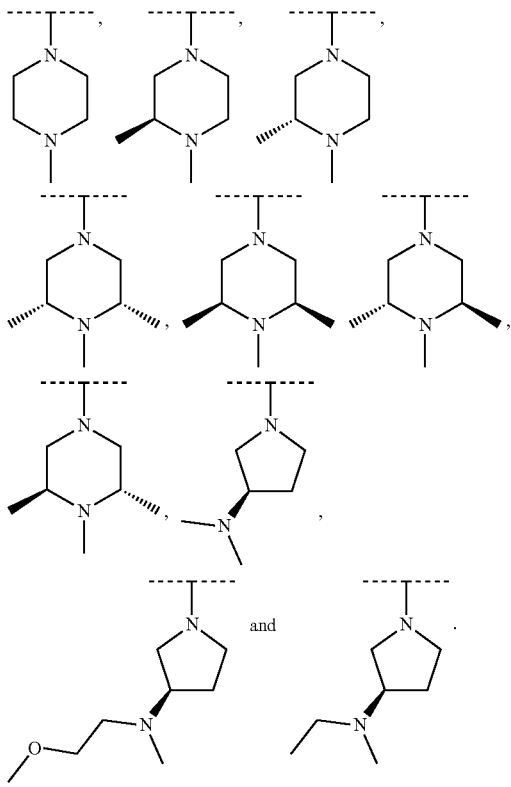

In some embodiments, R$^{18}$ is selected from:

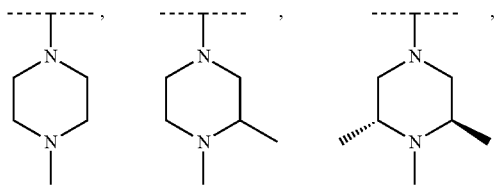

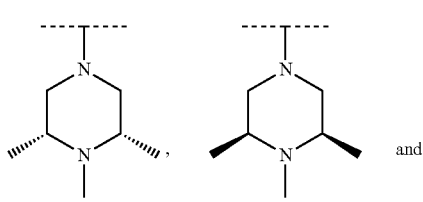

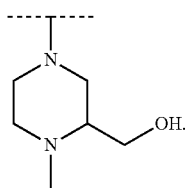

In some embodiments, R$^{18}$ is selected from:

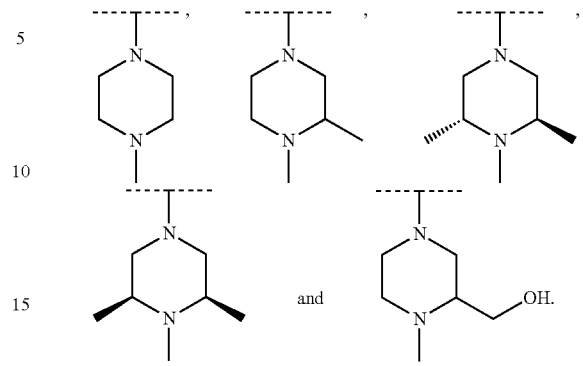

In some embodiments, R$^{18}$ is selected from:

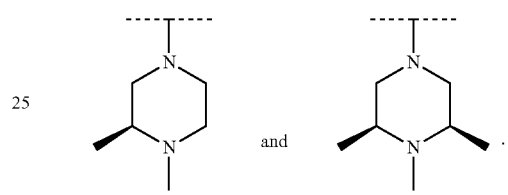

In some embodiments, R$^{19}$ is selected from C$_{6-10}$aryl and heteroaryl, and R$^{19}$ is unsubstituted or substituted with one, two or three substituents selected from halo, C$_{1-6}$alkyl, C$_{1-6}$fluoroalkyl, =O, OR$^{23}$, SR$^{23}$ and NR$^{24}$R$^{25}$. In some embodiments, R$^{19}$ is selected from C$_{6-10}$aryl and heteroaryl, and R$^{19}$ is unsubstituted or substituted with one, two or three substituents selected from halo, C$_{1-6}$alkyl, C$_{1-6}$fluoroalkyl, =O, OR$^{23}$ and NR$^{24}$R$^{25}$. In some embodiments, R$^{19}$ is selected from C$_{6-10}$aryl and heteroaryl, and R$^{19}$ is unsubstituted or substituted with one or two substituents selected from halo, C$_{1-6}$alkyl, C$_{1-6}$fluoroalkyl, =O and OR$^{23}$. In some embodiments, R$^2$ is selected from phenyl and C$_6$-heteroaryl, and R$^{19}$ is substituted with one to three substituents selected from F, CF$_2$H, CF$_3$ and =O.

In some embodiments, R$^{19}$ is selected from:

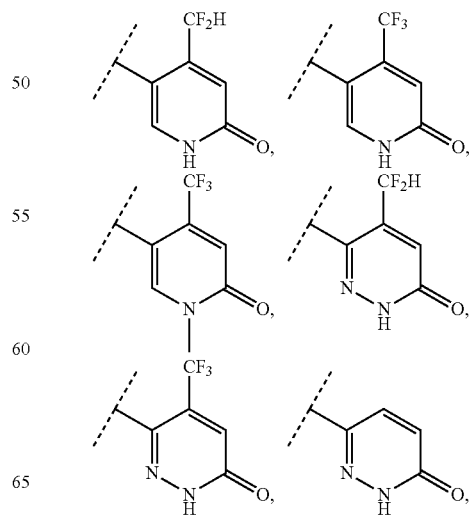

-continued
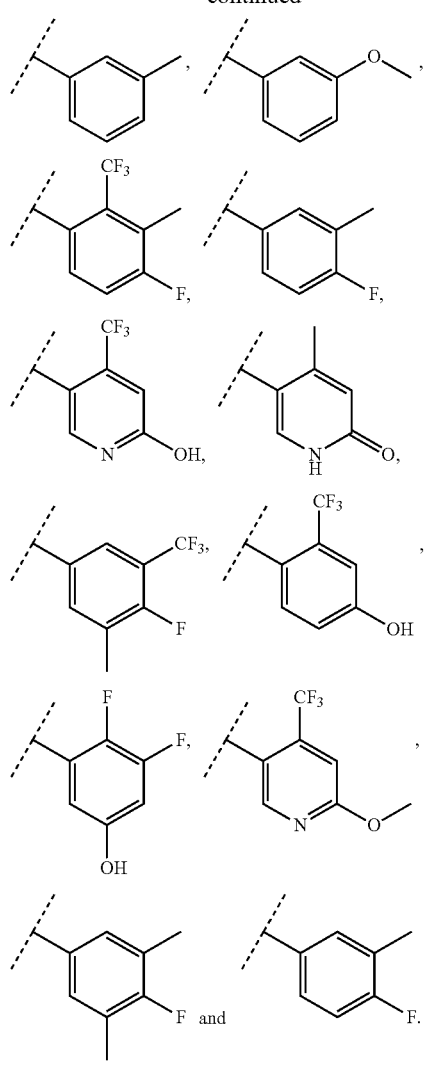
In some embodiments, $R^{19}$ is selected from:
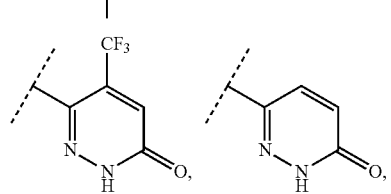
-continued
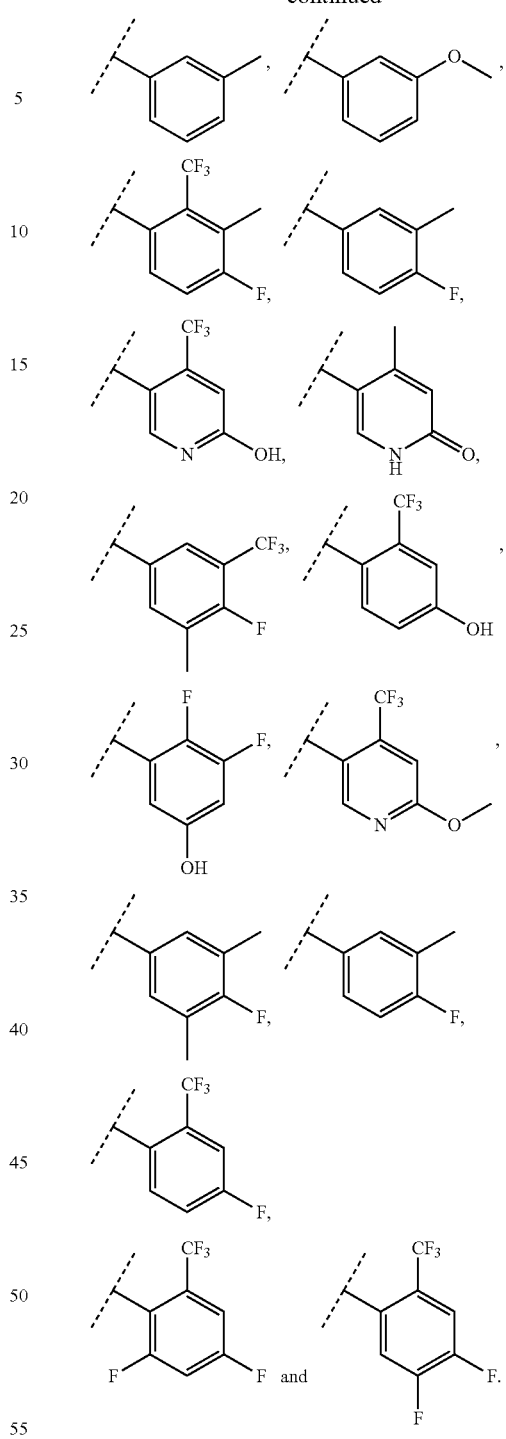
In some embodiments, $R^9$ is selected from:

-continued
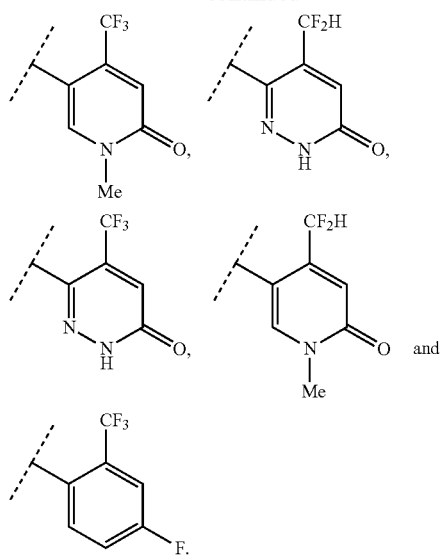
In some embodiments, $R^{19}$ is selected from:
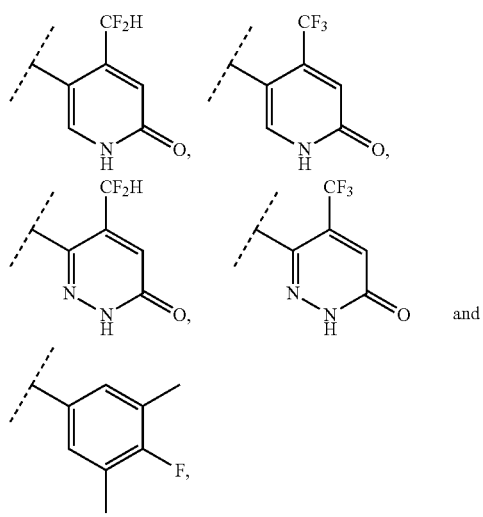
and tautomers thereof.
In some embodiments, $R^{19}$ is selected from:
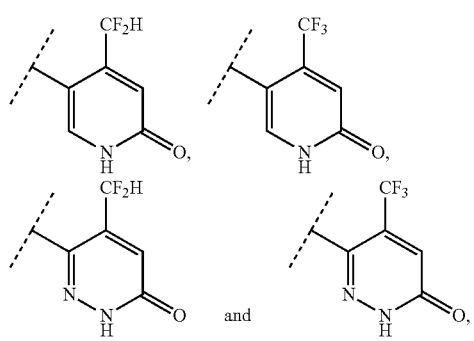
or a tautomer thereof.
In some embodiments, $R^{19}$ is selected from:
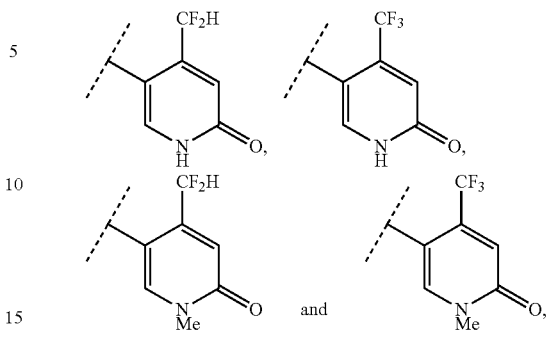
or a tautomer thereof.
In some embodiments, $R^{19}$ is selected from: F,
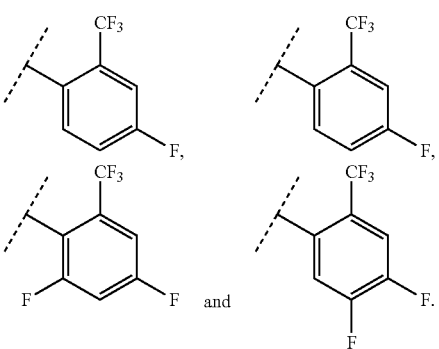
In some embodiments, $R^{19}$ is
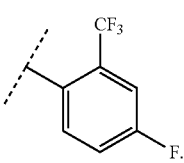
In an embodiment, $R^{19}$ is
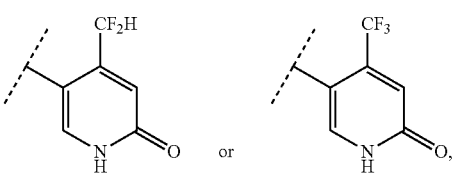
and the corresponding tautomers are
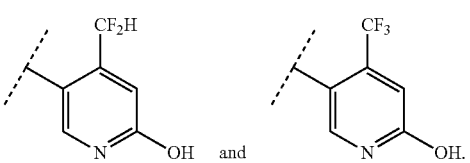

In some embodiments, $R^{20}$ is selected from H, $C_{1-6}$alkyl, $C_{1-6}$fluoroalkyl and $C(O)C_{1-6}$alkyl. In some embodiments, $R^{20}$ is selected from H, $C_{1-6}$alkyl and $C(O)C_{1-6}$alkyl.

In some embodiments, $R^{21}$ and $R^{22}$ are independently selected from H, $C_{1-6}$alkyl and heterocycloalkyl. In some embodiments, $R^{21}$ and $R^{22}$ are independently selected from H and $C_{1-6}$alkyl. In some embodiments, $R^{21}$ and $R^{22}$ together with the nitrogen atom to which they are attached form a 3-10 membered heterocycle that is unsubstituted or substituted with one, two or three substituents selected from halo and $C_{1-6}$alkyl. In some embodiments, $R^{21}$ and $R^{22}$ together with the nitrogen atom to which they are attached form a 3-10 membered heterocycle that is unsubstituted. In some embodiments, $R^{21}$ and $R^{22}$ together with the nitrogen atom to which they are attached form an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{23}$ is selected from H, $C_{1-6}$alkyl, $C_{1-6}$fluoroalkyl and $C(O)C_{1-6}$alkyl. In some embodiments, $R^{23}$ is selected from H and $C_{1-6}$alkyl.

In some embodiments, one of $X^8$ and $X^9$ is N and the other of $X^8$ and $X^9$ is $CR^{26}$. In some embodiments, $X^8$ and $X^9$ are $CR^{26}$.

In some embodiments, $R^{26}$ is selected from H, halo, CN, $C_{1-6}$alkyl, $C_{1-6}$fluoroalkyl, $OR^{27}$, $NR^{28}R^{29}$, $R^{30}$, $C_{1-6}$alkylene$R^{30}$, $OC_{1-6}$alkylene$R^{30}$, $C_{1-6}$alkyleneNR$^{28}$R$^{29}$, $C_{1-6}$alkyleneOR$^{27}$, $OC_{1-6}$alkyleneNR$^{28}$R$^{29}$, $OC_{1-6}$alkyleneOR$^{27}$, $C(O)OR^{27}$ and $C(O)NR^{28}R^{29}$. In some embodiments, $R^{26}$ is selected from H, halo, CN, $OR^{27}$, $NR^{28}R^{29}$, $R^{30}$, $C_{1-6}$alkylene$R^{30}$, $OC_{1-6}$alkylene$R^{30}$, $C_{1-6}$alkyleneNR$^{28}$R$^{29}$, $C_{1-6}$alkyleneOR$^{27}$, $OC_{1-6}$alkyleneNR$^{28}$R$^{29}$, $OC_{1-6}$alkyleneOR$^{27}$, $C(O)OR^{27}$ and $C(O)NR^{28}R^{29}$. In some embodiments, $R^{26}$ is selected from H, halo, CN, $OR^{27}$, $OC_{1-6}$alkylene$R^{30}$, $C_{1-6}$alkyleneNR$^{28}$R$^{29}$, $OC_{1-6}$alkyleneOR$^{27}$, $C(O)OR^{27}$ and $C(O)NR^{28}R^{29}$. In some embodiments, $R^{26}$ is selected from $OR^{27}$, $OC_{1-6}$alkylene$R^{30}$, $C_{1-6}$alkyleneNR$^{28}$R$^{29}$ and $C(O)NR^{28}R^{29}$. In some embodiments, $R^{26}$ is selected from $C_{1-6}$alkyleneNR$^{28}$R$^{29}$ and $C(O)NR^{28}R^{29}$.

In some embodiments, $R^{27}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl. In some embodiments, $R^{27}$ is selected from H, $C_{1-6}$alkyl, $C_{1-6}$fluoroalkyl, $C_{3-10}$cycloalkyl, heterocycloalkyl, $C_{6-10}$aryl and heteroaryl. In some embodiments, $R^{27}$ is selected from H, $C_{1-6}$alkyl, $C_{1-6}$fluoroalkyl and heterocycloalkyl. In some embodiments, $R^{27}$ is heterocycloalkyl. In some embodiments, $R^{27}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{28}$ and $R^{29}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{28}$ and $R^{29}$ are other than H they are each independently unsubstituted or substituted with one, two or three substituents selected from halo and $C_{1-6}$alkyl. In some embodiments, $R^{28}$ and $R^{29}$ are each independently selected from H, $C_{1-10}$alkyl, $C_{1-10}$fluoroalkyl, $C_{3-10}$cycloalkyl, heterocycloalkyl, heteroaryl and $C_{6-10}$aryl, and when $R^{28}$ and $R^{29}$ are other than H they are each independently unsubstituted or substituted with one, two or three substituents selected from halo and $C_{1-6}$alkyl. In some embodiments, $R^{28}$ and $R^{29}$ are each independently selected from H, $C_{1-10}$alkyl, $C_{3-10}$cycloalkyl and heterocycloalkyl, and when $R^{28}$ and $R^{29}$ are other than H they are each independently unsubstituted or substituted with one or two substituents selected from halo and $C_{1-6}$alkyl. In some embodiments, $R^{28}$ and $R^{29}$ are each independently selected from H, $C_{1-10}$alkyl, $C_{3-10}$cycloalkyl and heterocycloalkyl, and each of $R^{28}$ and $R^{29}$ is unsubstituted. In some embodiments, $R^{28}$ and $R^{29}$ are each independently selected from H, $C_{1-10}$alkyl, $C_{3-10}$cycloalkyl and heterocycloalkyl, and when $R^{28}$ and $R^{29}$ are other than H they are each independently substituted with halo. In some embodiments, $R^{28}$ and $R^{29}$ are each independently selected from H, $C_{1-10}$alkyl, $C_{3-10}$cycloalkyl and heterocycloalkyl. In some embodiments, $R^{28}$ and $R^{29}$ are each independently selected from H and $C_{3-10}$cycloalkyl.

In some embodiments, $R^{28}$ and $R^{29}$ together with the nitrogen atom to which they are attached form a 3-10 membered heterocycle that is unsubstituted or substituted with one, two or three substituents independently selected from halo, $OR^{31}$, $SR^{31}$, $NR^{32}R^{33}$, $C_{1-6}$alkyl, $C(O)R^{31}$, $C(O)OR^{31}$, $C(O)NR^{32}R^{33}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkylene$R^{31}$, $C_{1-6}$alkyleneOR$^{31}$, $C_{1-6}$alkyleneSR$^{31}$ and $C_{1-6}$alkyleneNR$^{32}$R$^{33}$. In some embodiments, $R^{28}$ and $R^{29}$ together with the nitrogen atom to which they are attached form a 3-10 membered heterocycle that is unsubstituted or substituted with one or two substituents independently selected from halo, $OR^{31}$, $NR^{32}R^{33}$, $C_{1-6}$alkyl, $SO_2C_{1-6}$alkyl, heterocycloalkyl, $C_{1-6}$alkyleneC$_{3-10}$cycloalkyl and $C_{1-6}$alkylene$R^{31}$. In some embodiments, $R^{28}$ and $R^{29}$ together with the nitrogen atom to which they are attached form a 3-10 membered heterocycle that is unsubstituted. In some embodiments, $R^{28}$ and $R^{29}$ together with the nitrogen atom to which they are attached form an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1, 3-dioxepinyl, and hexamethylene oxidyl.

In some embodiments, $R^{30}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl. In some embodiments, $R^{30}$ is selected from $C_{3-10}$cycloalkyl and heterocycloalkyl. In some embodiments, $R^{30}$ is $C_{3-10}$cycloalkyl. In some embodiments, $R^{30}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{31}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and when $R^{31}$ is other than H it is unsubstituted or substituted with one, two or three substituents selected from halo, $C_{1-6}$alkyl and $C_{1-6}$fluoroalkyl. In some embodiments, $R^{31}$ is selected from H, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and when $R^{31}$ is other than H it is unsubstituted or substituted with one, two or three substituents selected from halo, $C_{1-6}$alkyl and $C_{1-6}$fluoroalkyl. In some embodiments, $R^{31}$ is selected from H, $C_{6-10}$aryl and $C_{1-6}$alkyleneC$_{6-10}$aryl, and when $R^{31}$ is other than H it is unsubstituted or substituted with one or two substituents selected from halo and $C_{1-6}$alkyl. In some embodiments, $R^{31}$ is selected from H and $C_{6-10}$aryl, and when $R^{31}$ is other than H it is unsubstituted or substituted with one or two substituents selected from halo and $C_{1-6}$alkyl. In some embodiments, $R^{31}$ is selected from H and $C_{6-10}$aryl, and when $R^{31}$ is other than H it is unsubstituted or substituted with halo.

In some embodiments, $R^{32}$ and $R^{33}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl and when $R^{32}$ and $R^{33}$ are other than H they are unsubstituted or substituted with one two or three substituents independently selected from halo, $C_{1-6}$alkyl, $C_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)OH, C(O)OC$_{1-6}$alkyl, C(O)C$_{1-6}$fluoroalkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl). In some embodiments, $R^{32}$ and $R^{33}$ are each independently selected from H, $C_{1-6}$alkyl, $C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl. In some embodiments, $R^{32}$ and $R^{33}$ are each independently selected from H, $C_{1-6}$alkyl and $C_{1-6}$fluoroalkyl. In some embodiments, $R^{32}$ and $R^{33}$ are $C_{1-6}$alkyl.

In some embodiments, the compound of Formula I(a) is selected from:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridazine-3-carboxamide;

N-[5-[2-fluoro-5-(morpholin-4-ylmethyl)phenyl]-2-(4-methylpiperazin-1-yl)phenyl]-3-methoxybenzamide;

4-fluoro-N-[5-[2-fluoro-5-(morpholin-4-ylmethyl)phenyl]-2-(4-methylpiperazin-1-yl)phenyl]-3,5-dimethylbenzamide;

2-chloro-4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl]benzoate;

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[5-[6-(cyclopropylmethoxy)-2-fluoropyridin-3-yl]-2-(4-methylpiperazin-1-yl)phenyl]-6-oxo-4-(trifluoromethyl)-1H-pyridine-3-carboxamide;

N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-3-methylbenzamide;

N-[5-(2-fluorophenyl)-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-methyl-6-oxo-1H-pyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide;

N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide;

N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide;

(R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide;

N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;

N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide;

N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide;

[4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate;

N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide;

N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide;

N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide;

N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide;

N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide;

N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide;

N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-[2-[3-(dimethylamino)pyrrolidin-1-yl]-5-[2-fluoro-5-(morpholin-4-ylmethyl)phenyl]phenyl]-4-fluoro-3,5-dimethylbenzamide;

4-fluoro-N-[5-[2-fluoro-5-(morpholin-4-ylmethyl)phenyl]-2-(4-methyl-1,4-diazepan-1-yl)phenyl]-3,5-dimethylbenzamide;

N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

4-fluoro-N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-3,5-dimethylbenzamide;

4-fluoro-N-[5-[2-fluoro-5-(morpholin-4-ylmethyl)phenyl]-2-[4-(2,2,2-trifluoroethyl)piperazin-1-yl]phenyl]-3,5-dimethylbenzamide;

N-[5-[2-fluoro-5-(morpholin-4-ylmethyl)phenyl]-2-[4-(2,2,2-trifluoroethyl)piperazin-1-yl]phenyl]-6-oxo-4-(trifluoromethyl)-1H-pyridine-3-carboxamide;

N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-6-oxo-4-(trifluoromethyl)-1H-pyridine-3-carboxamide;

N-[2-[3-(dimethylamino)pyrrolidin-1-yl]-5-[2-fluoro-5-(morpholin-4-ylmethyl)phenyl]phenyl]-1-methyl-6-oxo-4-(trifluoromethyl)pyridine-3-carboxamide;

6-fluoro-N-[5-[2-fluoro-5-(morpholin-4-ylmethyl)phenyl]-2-(4-methylpiperazin-1-yl)phenyl]-1H-benzimidazole-4-carboxamide;

N-[5-[2-fluoro-5-(morpholin-4-ylmethyl)phenyl]-2-(4-methylpiperazin-1-yl)phenyl]-1H-benzimidazole-2-carboxamide;

N-[5-[2-fluoro-5-(morpholin-4-ylmethyl)phenyl]-2-[(2R)-2,4-dimethylpiperazin-1-yl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridine-3-carboxamide;

6-acetamido-N-[5-[2-fluoro-5-(morpholin-4-ylmethyl)phenyl]-2-(4-methylpiperazin-1-yl)phenyl]-4-methylpyridine-3-carboxamide;

N-[5-[5-[[4-(cyclopropylmethyl)piperazin-1-yl]methyl]-2-fluorophenyl]-2-(4-methylpiperazin-1-yl)phenyl]-6-methoxy-4-(trifluoromethyl)pyridine-3-carboxamide;

N-[5-[2-fluoro-5-(morpholin-4-ylmethyl)phenyl]-2-(4-methylpiperazin-1-yl)phenyl]-6-(methylamino)-4-(trifluoromethyl)pyridine-3-carboxamide;

6-amino-N-[5-[2-fluoro-5-(morpholin-4-ylmethyl)phenyl]-2-(4-methylpiperazin-1-yl)phenyl]-4-(trifluoromethyl)pyridine-3-carboxamide;

N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide;

N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide;

N-(5'-(cyclohexylcarbamoyl)-2'-fluoro-4-(4-methyl-3-oxopiperazin-1-yl)-[1,1'-biphenyl]-3-yl)-6-oxo-4-(trifluoromethyl)-1,6-dihydropyridine-3-carboxamide;

N-(4-((2-(dimethylamino)ethyl)(methyl)amino)-2'-fluoro-5'-(morpholinomethyl)-[1,1'-biphenyl]-3-yl)-6-oxo-4-(trifluoromethyl)-1,6-dihydropyridine-3-carboxamide; and N-(5'-((cyclohexylamino)methyl)-4-((2-(dimethylamino)ethyl)(methyl)amino)-2'-fluoro-[1,1'-biphenyl]-3-yl)-6-oxo-4-(trifluoromethyl)-1,6-dihydropyridine-3-carboxamide, or or a pharmaceutically acceptable salt and/or solvate thereof.

In some embodiments, the compound of Formula I(a) is selected from:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridazine-3-carboxamide;

N-[5-[2-fluoro-5-(morpholin-4-ylmethyl)phenyl]-2-(4-methylpiperazin-1-yl)phenyl]-3-methoxybenzamide;

4-fluoro-N-[5-[2-fluoro-5-(morpholin-4-ylmethyl)phenyl]-2-(4-methylpiperazin-1-yl)phenyl]-3,5-dimethylbenzamide;

2-chloro-4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl]benzoate;

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[5-[6-(cyclopropylmethoxy)-2-fluoropyridin-3-yl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-3-methylbenzamide;

N-[5-(2-fluorophenyl)-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide;

N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide;

N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide;

(R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide;

N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;

N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide;

N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide;

[4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate;

N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide;

N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide;

N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide;

N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide; and N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide, or or a pharmaceutically acceptable salt and/or solvate thereof.

In some embodiments, the compound of Formula (Ia) is selected from:

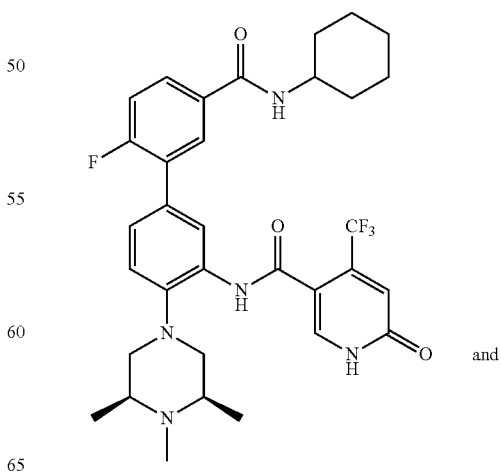 and

-continued

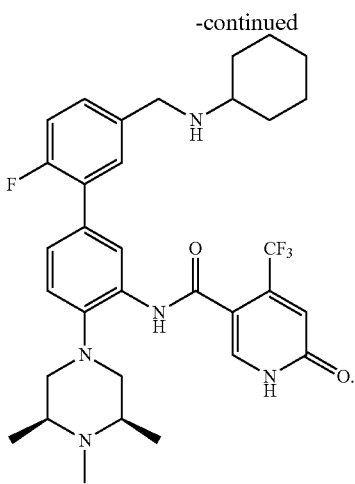

The present application also includes a compound of Formula (Ib) or a pharmaceutically acceptable salt and/or solvate thereof:

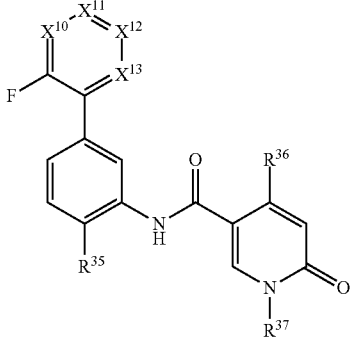

(Ib)

wherein
$X^{10}$, $X^{11}$ and $X^{13}$ are independently selected from CH and N;
$X^{12}$ is $CR^{38}$;
$R^{35}$ is selected from

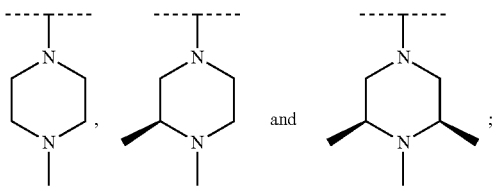

$R^{36}$ is selected from $CF_3$ and $CHF_2$;
$R^{37}$ is selected from H and $CH_3$; and
$R^{38}$ is from H, halo, CN, $C_{1-6}$alkyl, $C_{1-6}$fluoroalkyl, $OR^{39}$, $SR^{39}$, $NR^{40}R^{41}$, $R^{42}$, $C_{1-6}$alkylene$R^{42}$, $OC_{1-6}$alkylene$R^{42}$, $SC_{1-6}$alkylene$R^{42}$, $C_{1-6}$alkyleneNR$^{40}R^{41}$, $C_{1-6}$alkyleneOR$^{39}$, $C_{1-6}$alkyleneSR$^{39}$, $OC_{1-6}$alkyleneNR$^{40}R^{41}$, $SC_{1-6}$alkyleneNR$^{40}R^{41}$, $OC_{1-6}$alkyleneOR$^{39}$, $SC_{1-6}$alkyleneOR$^{39}$, $OC_{1-6}$alkyleneSR$^{39}$, $SC_{1-6}$alkyleneSR$^{39}$, $C(O)OR^{39}$, $C(S)OR^{39}$, $C(S)NR^{40}R^{41}$ and $C(O)NR^{40}R^{41}$;
$R^{39}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{39}$ is other than H it is unsubstituted or substituted with one or more substituents selected from halo, $OR^{43}$, $SR^{43}$, $NR^{44}R^{45}$, $C_{1-6}$alkyl, $C(O)R^{43}$, $C(O)OR^{43}$, $C(O)NR^{44}R^{45}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{43}$, $C_{1-6}$alkyleneOR$^{43}$, $C_{1-6}$alkyleneSR$^{43}$ and $C_{1-6}$alkyleneNR$^{44}R^{45}$;
$R^{40}$ and $R^{41}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkyleneC$_{3-10}$cycloalkyl, $C_{1-6}$alkyleneC$_{6-10}$aryl, $C_{1-6}$alkyleneheteroaryl and $C_{1-6}$alkyleneheterocycloalkyl, and when $R^{40}$ and $R^{41}$ are other than H they are each independently unsubstituted or substituted with one or more substituents selected from halo, $OR^{43}$, $SR^{43}$, $NR^{44}R^{45}$, $C_{1-6}$alkyl, $C(O)R^{43}$, $C(O)OR^{43}$, $C(O)NR^{44}R^{45}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{43}$, $C_{1-6}$alkyleneOR$^{43}$, $C_{1-6}$alkyleneSR$^{43}$ and $C_{1-6}$alkyleneNR$^{44}R^{45}$, or
$R^{40}$ and $R^{41}$ together with the nitrogen atom to which they are attached form a 3-10 membered heterocycle that is unsubstituted or substituted with one or more substituents independently selected from halo, $OR^{43}$, $SR^{43}$, $NR^{44}R^{45}$, $C_{1-6}$alkyl, $C(O)R^{43}$, $C(O)OR^{43}$, $C(O)NR^{44}R^{45}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{43}$, $C_{1-6}$alkyleneOR$^{43}$, $C_{1-6}$alkyleneSR$^{43}$ and $C_{1-6}$alkyleneNR$^{44}R^{45}$;
$R^{42}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl, and when $R^{42}$ is other than H it is unsubstituted or substituted with one or more substituents independently selected from halo, $OR^{43}$, $SR^{43}$, $NR^{44}R^{45}$, $C_{1-6}$alkyl, $C(O)R^{43}$, $C(O)OR^{43}$, $C(O)NR^{44}R^{45}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneR$^{43}$, $C_{1-6}$alkyleneOR$^{43}$, $C_{1-6}$alkyleneSR$^{43}$ and $C_{1-6}$alkyleneNR$^{44}R^{45}$;
$R^{43}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl, and when $R^{43}$ is other than H it is unsubstituted or substituted with one or more substituents selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl)($C_{1-6}$alkyl), $C(O)C_{1-6}$alkyl, $C(O)C_{1-6}$fluoroalkyl, $C(O)OH$, $C(O)OC_{1-6}$alkyl, $C(O)NH_2$, $C(O)NHC_{1-6}$alkyl, $C(O)N(C_{1-6}$alkyl)($C_{1-6}$alkyl), $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkyleneC$_{6-10}$aryl, $C_{1-6}$alkyleneC$_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$ alkyl, $C_{1-6}$alkyleneNH$_2$, $C_{1-6}$alkyleneNHC$_{1-6}$alkyl and $C_{1-6}$alkyleneN(C$_{1-6}$alkyl)(C$_{1-6}$alkyl);
$R^{44}$ and $R^{45}$ are each independently selected from H, $C_{1-6}$alkyl, $C_{1-6}$fluoroalkyl, $C(O)C_{1-6}$alkyl, $C_{3-10}$cycloalkyl, heterocycloalkyl, $C_{6-10}$aryl, $C_{1-6}$alkyleneC$_{6-10}$aryl, $C_{1-6}$alkyleneC$_{3-10}$cycloalkyl and $C_{1-6}$alkyleneheterocycloalkyl and when $R^{44}$ and $R^{45}$ are other than H they are each unsubstituted or substituted with one or more substituents independently selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, C(O)OH, $C(O)OC_{1-6}$alkyl, $C(O)C_{1-6}$fluoroalkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl$)(C_{1-6}$alkyl$)$, or $R^{44}$ and $R^{45}$ together with the nitrogen atom to which they are attached form a 3-10 membered heterocycle that is unsubstituted or substituted with one or more substituents selected from halo, $C_{1-6}$alkyl, $C_{1-6}$fluoroalkyl, OH, SH, $OC_{1-6}$alkyl, $OC_{1-6}$fluoroalkyl, $SC_{1-6}$alkyl, $SC_{1-6}$fluoroalkyl, $NH_2$, $NHC_{1-6}$alkyl, $N(C_{1-6}$alkyl$)(C_{1-6}$alkyl$)$, $C(O)C_{1-6}$alkyl, $C(O)C_{1-6}$fluoroalkyl, C(O)OH, $C(O)OC_{1-6}$alkyl, $C(O)NH_2$, $C(O)NHC_{1-6}$alkyl, $C(O)N(C_{1-6}$alkyl$)(C_{1-6}$alkyl$)$, $SO_2C_{1-6}$alkyl, $S(O)C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkyleneOH, $C_{1-6}$alkyleneOC$_{1-6}$alkyl, $C_{1-6}$alkyleneSH, $C_{1-6}$alkyleneSC$_{1-6}$alkyl, $C_{1-6}$alkyleneNH$_2$, $C_{1-6}$alkyleneNHC$_{1-6}$alkyl and $C_{1-6}$alkyleneN(C$_{1-6}$alkyl$)(C_{1-6}$alkyl$)$; and all alkyl and alkylene groups are optionally fluorosubstituted.

In some embodiments, $X^{10}$, $X^{11}$ and $X^{13}$ are each CH.

In some embodiments, $R^{39}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, heteroaryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl. In some embodiments, $R^{39}$ is selected from H, $C_{1-6}$alkyl, $C_{1-6}$fluoroalkyl, $C_{3-10}$cycloalkyl, heterocycloalkyl, $C_{6-10}$aryl and heteroaryl. In some embodiments, $R^{39}$ is selected from H, $C_{1-6}$alkyl, $C_{1-6}$fluoroalkyl and heterocycloalkyl. In some embodiments, $R^{39}$ is heterocycloalkyl.

In some embodiments, $R^{39}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{40}$ and $R^{41}$ are each independently selected from H, $C_{1-10}$alkyl, $C_{1-10}$fluoroalkyl, $C(O)C_{1-6}$alkyl, $C(O)C_{1-6}$fluoroalkyl, $C_{3-10}$cycloalkyl, heterocycloalkyl, heteroaryl, $C_{6-10}$aryl, $C_{1-6}$alkylene$C_{3-10}$cycloalkyl, $C_{1-6}$alkylene$C_{6-10}$aryl, $C_{1-6}$alkyleneheteroaryl and $C_{1-6}$alkyleneheterocycloalkyl, and when $R^{40}$ and $R^{41}$ are other than H they are each independently unsubstituted or substituted with one, two or three substituents selected from halo and $C_{1-6}$alkyl. In some embodiments, $R^{40}$ and $R^{41}$ are each independently selected from H, $C_{1-10}$alkyl, $C_{1-10}$fluoroalkyl, $C_{3-10}$cycloalkyl, heterocycloalkyl, heteroaryl and $C_{6-10}$aryl, and when $R^{40}$ and $R^{41}$ are other than H they are each independently unsubstituted or substituted with one, two or three substituents selected from halo and $C_{1-6}$alkyl. In some embodiments, $R^{40}$ and $R^{41}$ are each independently selected from H, $C_{1-10}$alkyl, $C_{3-10}$cycloalkyl and heterocycloalkyl, and when $R^{40}$ and $R^{41}$ are other than H they are each independently unsubstituted or substituted with one or two substituents selected from halo and $C_{1-6}$alkyl. In some embodiments, $R^{40}$ and $R^{41}$ are each independently selected from H, $C_{1-10}$alkyl, $C_{3-10}$cycloalkyl and heterocycloalkyl, and each of $R^{40}$ and $R^{41}$ is unsubstituted. In some embodiments, $R^{40}$ and $R^{41}$ are each independently selected from H, $C_{1-10}$alkyl, $C_{3-10}$cycloalkyl and heterocycloalkyl, and when $R^{40}$ and $R^{41}$ are other than H they are each independently substituted with halo. In some embodiments, $R^{40}$ and $R^{41}$ are each independently selected from H, $C_{1-10}$alkyl, $C_{3-10}$cycloalkyl and heterocycloalkyl. In some embodiments, $R^{40}$ and $R^{41}$ are each independently selected from H and $C_{3-10}$cycloalkyl.

In some embodiments, $R^{40}$ and $R^{41}$ together with the nitrogen atom to which they are attached form a 3-10 membered heterocycle that is unsubstituted or substituted with one, two or three substituents independently selected from halo, $OR^{43}$, $SR^{43}$, $NR^{44}R^{45}$, $C_{1-6}$alkyl, $C(O)R^{43}$, $C(O)OR^{43}$, $C(O)NR^{44}R^{45}$, $S(O)C_{1-6}$alkyl, $SO_2C_{1-6}$alkyl, $C_{6-10}$aryl, heteroaryl, $C_{3-10}$cycloalkyl, heterocycloalkyl, $C_{1-6}$alkylene$C_{6-10}$aryl, $C_{1-6}$alkylene$C_{3-10}$cycloalkyl, $C_{1-6}$alkyleneheteroaryl, $C_{1-6}$alkyleneheterocycloalkyl, $C_{1-6}$alkylene$R^{43}$, $C_{1-6}$alkyleneOR$^{43}$, $C_{1-6}$alkyleneSR$^{43}$ and $C_{1-6}$alkyleneNR$^{44}R^{45}$. In some embodiments, $R^{40}$ and $R^{41}$ together with the nitrogen atom to which they are attached form a 3-10 membered heterocycle that is unsubstituted or substituted with one or two substituents independently selected from halo, $OR^{43}$, 45 $C_{1-6}$alkyl, $SO_2C_{1-6}$alkyl, heterocycloalkyl, $C_{1-6}$alkylene$C_{3-10}$cycloalkyl and $C_{1-6}$alkylene$R^{43}$. In some embodiments, $R^{40}$ and $R^{41}$ together with the nitrogen atom to which they are attached form a 3-10 membered heterocycle that is unsubstituted. In some embodiments, $R^{40}$ and $R^{41}$ together with the nitrogen atom to which they are attached form an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-1H-azepinyl, homopiperazinyl, 1,3-dioxepanyl, 4,7-dihydro-1,3-dioxepinyl, and hexamethylene oxidyl.

In some embodiments, $R^{42}$ is selected from $C(O)C_{1-6}$alkyl, $C(O)C_{1-6}$fluoroalkyl, $C_{3-10}$cycloalkyl, heterocycloalkyl, heteroaryl and $C_{6-10}$aryl. In some embodiments, $R^{42}$ is selected from $C_{3-10}$cycloalkyl and heterocycloalkyl. In some embodiments, $R^{42}$ is $C_{3-10}$cycloalkyl. In some embodiments, $R^{42}$ is an unsubstituted or substituted monocyclic heterocycloalkyl selected from aziridinyl, oxiranyl, thiiranyl, azetidinyl, oxetanyl, thietanyl, pyrrolidinyl, pyrrolinyl, imidazolidinyl, pyrazolidinyl, pyrazolinyl, dioxolanyl, sulfolanyl, 2,3-dihydrofuranyl, 2,5-dihydrofuranyl, tetrahydrofuranyl, thiophanyl, piperidinyl, 1,2,3,6-tetrahydropyridinyl, piperazinyl, morpholinyl, thiomorpholinyl, pyranyl, thiopyranyl, 2,3-dihydropyranyl, tetrahydropyranyl, 1,4-dihydropyridinyl, 1,4-dioxanyl, 1,3-dioxanyl, dioxanyl, homopiperidinyl, 2,3,4,7-tetrahydro-TH-azepinyl, homopiperazinyl, 1,3-dioxepanyl, 4,7-dihydro-1,3-dioxepinyl, and hexamethylene oxidyl.

In some embodiments, $R^{43}$ is selected from H, $C_{1-6}$alkyl, $C_{1-6}$fluoroalkyl, $C(O)C_{1-6}$alkyl, $C(O)C_{1-6}$fluoroalkyl, $C_{3-10}$cycloalkyl, heterocycloalkyl, $C_{6-10}$aryl, $C_{1-6}$alkyleneC$_{6-10}$aryl, C$_{1-6}$alkyleneC$_{3-10}$cycloalkyl and C$_{1-6}$alkyleneheterocycloalkyl, and when R$^{43}$ is other than H it is unsubstituted or substituted with one, two or three substituents selected from halo, C$_{1-6}$alkyl and C$_{1-6}$fluoroalkyl. In some embodiments, R$^{43}$ is selected from H, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl, and when R$^{43}$ is other than H it is unsubstituted or substituted with one, two or three substituents selected from halo, C$_{1-6}$alkyl and C$_{1-6}$fluoroalkyl. In some embodiments, R$^{43}$ is selected from H, C$_{6-10}$aryl and C$_{1-6}$alkyleneC$_{6-10}$aryl, and when R$^{43}$ is other than H it is unsubstituted or substituted with one or two substituents selected from halo and C$_{1-6}$alkyl. In some embodiments, R$^{43}$ is selected from H and C$_{6-10}$aryl, and when R$^{43}$ is other than H it is unsubstituted or substituted with one or two substituents selected from halo and C$_{1-6}$alkyl. In some embodiments, R$^{43}$ is selected from H and C$_{6-10}$aryl, and when R$^{43}$ is other than H it is unsubstituted or substituted with halo.

In some embodiments, R$^{44}$ and R$^{45}$ are each independently selected from H, C$_{1-6}$alkyl, C$_{1-6}$fluoroalkyl, C(O)C$_{1-6}$alkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl and when R$^{44}$ and R$^{45}$ are other than H they are unsubstituted or substituted with one two or three substituents independently selected from halo, C$_{1-6}$alkyl, C$_{1-6}$fluoroalkyl, OH, SH, OC$_{1-6}$alkyl, OC$_{1-6}$fluoroalkyl, SC$_{1-6}$alkyl, SC$_{1-6}$fluoroalkyl, NH$_2$, NHC$_{1-6}$alkyl, N(C$_{1-6}$alkyl)(C$_{1-6}$alkyl), C(O)C$_{1-6}$alkyl, C(O)OH, C(O)OC$_{1-6}$alkyl, C(O)C$_{1-6}$fluoroalkyl, C(O)NH$_2$, C(O)NHC$_{1-6}$alkyl, C(O)N(C$_{1-6}$alkyl)(C$_{1-6}$alkyl), SO$_2$C$_{1-6}$alkyl, S(O)C$_{1-6}$alkyl, C$_{6-10}$aryl, heteroaryl, C$_{3-10}$cycloalkyl, heterocycloalkyl, C$_{1-6}$alkyleneC$_{6-10}$aryl, C$_{1-6}$alkyleneC$_{3-10}$cycloalkyl, C$_{1-6}$alkyleneheteroaryl, C$_{1-6}$alkyleneheterocycloalkyl, C$_{1-6}$alkyleneOH, C$_{1-6}$alkyleneOC$_{1-6}$alkyl, C$_{1-6}$alkyleneSH, C$_{1-6}$alkyleneSC$_{1-6}$alkyl, C$_{1-6}$alkyleneNH$_2$, C$_{1-6}$alkyleneNHC$_{1-6}$alkyl and C$_{1-6}$alkyleneN(C$_{1-6}$alkyl)(C$_{1-6}$alkyl). In some embodiments R$^{44}$ and R$^{45}$ are each independently selected from H, C$_{1-6}$alkyl, C$_{1-6}$fluoroalkyl, C$_{3-10}$cycloalkyl, heterocycloalkyl, C$_{6-10}$aryl, C$_{1-6}$alkyleneC$_{6-10}$aryl, C$_{1-6}$alkyleneC$_{3-10}$cycloalkyl and C$_{1-6}$alkyleneheterocycloalkyl. In some embodiments, R$^{44}$ and R$^{45}$ are each independently selected from H, C$_{1-6}$alkyl and C$_{1-6}$fluoroalkyl. In some embodiments, R$^{44}$ and R$^{45}$ are C$_{1-6}$alkyl.

In some embodiments, the compounds of Formula Ib are selected from:

N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

N-5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide;

N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide;

N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[3-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;

N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide; and N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide, or a pharmaceutically acceptable salt and/or solvate thereof.

The compounds of the present application are suitably formulated in a conventional manner into compositions using one or more carriers. Accordingly, the present application also includes a composition comprising one or more compounds of the application and a carrier. The compounds of the application are suitably formulated into pharmaceutical compositions for administration to subjects in a biologically compatible form suitable for administration in vivo. Accordingly, the present application further includes a pharmaceutical composition comprising one or more compounds of the application and a pharmaceutically acceptable carrier. In embodiments of the application the pharmaceutical compositions are used in the treatment of any of the diseases, disorders or conditions described herein.

The compounds of the application are administered to a subject in a variety of forms depending on the selected route of administration, as will be understood by those skilled in the art. For example, a compound of the application is administered by oral, inhalation, parenteral, buccal, sublingual, nasal, rectal, vaginal, patch, pump, topical or transdermal administration and the pharmaceutical compositions formulated accordingly. In some embodiments, administration is by means of a pump for periodic or continuous delivery. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

Parenteral administration includes systemic delivery routes other than the gastrointestinal (GI) tract, and includes, for example intravenous, intra-arterial, intraperitoneal, subcutaneous, intramuscular, transepithelial, nasal, intrapulmonary (for example, by use of an aerosol), intrathecal, rectal and topical (including the use of a patch or other transdermal delivery device) modes of administration. Parenteral administration may be by continuous infusion over a selected period of time.

In some embodiments, a compound of the application is orally administered, for example, with an inert diluent or with an assimilable edible carrier, or it is enclosed in hard or soft shell gelatin capsules, or it is compressed into tablets, or it is incorporated directly with the food of the diet. In some embodiments, the compound is incorporated with excipient and used in the form of ingestible tablets, buccal tablets, troches, capsules, caplets, pellets, granules, lozenges, chewing gum, powders, syrups, elixirs, wafers, aqueous solutions and suspensions, and the like. In the case of tablets, carriers that are used include lactose, corn starch, sodium citrate and salts of phosphoric acid. Pharmaceutically acceptable excipients include binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). In embodiments, the tablets are coated by methods well known in the art. In the case of tablets, capsules, caplets, pellets or granules for oral administration, pH sensitive enteric coatings, such as Eudragits™ designed to control the release of active ingredients are optionally used. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. Timed-release compositions are formulated, for example as liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In some embodiments, liposomes are formed from a variety of phospholipids, such as cholesterol, stearylamine or phosphatidylcholines. For oral administration in a capsule form, useful carriers or diluents include lactose and dried corn starch.

In some embodiments, liquid preparations for oral administration take the form of, for example, solutions, syrups or suspensions, or they are suitably presented as a dry product for constitution with water or other suitable vehicle before use. When aqueous suspensions and/or emulsions are administered orally, the compound of the application is suitably suspended or dissolved in an oily phase that is combined with emulsifying and/or suspending agents. If desired, certain sweetening and/or flavoring and/or coloring agents are added. Such liquid preparations for oral administration are prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid). Useful diluents include lactose and high molecular weight polyethylene glycols.

It is also possible to freeze-dry the compounds of the application and use the lyophilizates obtained, for example, for the preparation of products for injection.

In some embodiments, a compound of the application is administered parenterally. For example, solutions of a compound of the application are prepared in water suitably mixed with a surfactant such as hydroxypropylcellulose. In some embodiments, dispersions are prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations. For parenteral administration, sterile solutions of the compounds of the application are usually prepared, and the pH's of the solutions are suitably adjusted and buffered. For intravenous use, the total concentration of solutes should be controlled to render the preparation isotonic. For ocular administration, ointments or droppable liquids are delivered, for example, by ocular delivery systems known to the art such as applicators or eye droppers. In some embodiment, such compositions include mucomimetics such as hyaluronic acid, chondroitin sulfate, hydroxypropyl methylcellulose or polyvinyl alcohol, preservatives such as sorbic acid, EDTA or benzyl chromium chloride, and the usual quantities of diluents or carriers. For pulmonary administration, diluents or carriers will be selected to be appropriate to allow the formation of an aerosol.

In some embodiments, a compound of the application is formulated for parenteral administration by injection, including using conventional catheterization techniques or infusion. Formulations for injection are, for example, presented in unit dosage form, e.g., in ampoules or in multi-dose containers, with an added preservative. In some embodiments, the compositions take such forms as sterile suspensions, solutions or emulsions in oily or aqueous vehicles, and contain formulating agents such as suspending, stabilizing and/or dispersing agents. In all cases, the form must be sterile and must be fluid to the extent that easy syringability exists. Alternatively, the compounds of the application are suitably in a sterile powder form for reconstitution with a suitable vehicle, e.g., sterile pyrogen-free water, before use.

In some embodiments, compositions for nasal administration are conveniently formulated as aerosols, drops, gels and powders. For intranasal administration or administration by inhalation, the compounds of the application are conveniently delivered in the form of a solution, dry powder formulation or suspension from a pump spray container that is squeezed or pumped by the patient or as an aerosol spray presentation from a pressurized container or a nebulizer. Aerosol formulations typically comprise a solution or fine suspension of the active substance in a physiologically acceptable aqueous or non-aqueous solvent and are usually presented in single or multidose quantities in sterile form in a sealed container, which, for example, take the form of a cartridge or refill for use with an atomising device. Alternatively, the sealed container is a unitary dispensing device such as a single dose nasal inhaler or an aerosol dispenser fitted with a metering valve which is intended for disposal after use. Where the dosage form comprises an aerosol dispenser, it will contain a propellant which is, for example, a compressed gas such as compressed air or an organic propellant such as fluorochlorohydrocarbon. Suitable propellants include but are not limited to dichlorodifluoromethane, trichlorofluoromethane, dichlorotetrafluoroethane, heptafluoroalkanes, carbon dioxide or another suitable gas. In the case of a pressurized aerosol, the dosage unit is suitably determined by providing a valve to deliver a metered amount. In some embodiments, the pressurized container or nebulizer contains a solution or suspension of the active compound. Capsules and cartridges (made, for example, from gelatin) for use in an inhaler or insufflator are, for example, formulated containing a powder mix of a compound of the application and a suitable powder base such as lactose or starch. The aerosol dosage forms can also take the form of a pump-atomizer.

Compositions suitable for buccal or sublingual administration include tablets, lozenges, and pastilles, wherein a compound of the application is formulated with a carrier such as sugar, acacia, tragacanth, or gelatin and glycerine. Compositions for rectal administration are conveniently in the form of suppositories containing a conventional suppository base such as cocoa butter.

Suppository forms of the compounds of the application are useful for vaginal, urethral and rectal administrations. Such suppositories will generally be constructed of a mixture of substances that is solid at room temperature but melts at body temperature. The substances commonly used to create such vehicles include but are not limited to *theobroma* oil (also known as cocoa butter), glycerinated gelatin, other glycerides, hydrogenated vegetable oils, mixtures of polyethylene glycols of various molecular weights and fatty acid esters of polyethylene glycol. See, for example: *Remington's Pharmaceutical Sciences,* 16th Ed., Mack Publishing, Easton, Pa., 1980, pp. 1530-1533 for further discussion of suppository dosage forms.

In some embodiments a compound of the application is coupled with soluble polymers as targetable drug carriers. Such polymers include, for example, polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, in some embodiments, a compound of the application is coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

A compound of the application including pharmaceutically acceptable salts and/or solvates thereof is suitably used on their own but will generally be administered in the form of a pharmaceutical composition in which the one or more compounds of the application (the active ingredient) is in association with a pharmaceutically acceptable carrier. Depending on the mode of administration, the pharmaceutical composition will comprise from about 0.05 wt % to about 99 wt % or about 0.10 wt % to about 70 wt %, of the active ingredient, and from about 1 wt % to about 99.95 wt % or about 30 wt % to about 99.90 wt % of a pharmaceutically acceptable carrier, all percentages by weight being based on the total composition.

A compound of the application is either used alone or in combination with other known agents useful for treating diseases, disorders or conditions that are mediated or treatable by inhibition of binding between WDR5 protein and its binding partners, and those that are treatable with a WDR5 inhibitor, such as the compounds disclosed herein. When used in combination with other agents useful in treating diseases, disorders or conditions mediated or treatable by inhibition of binding between WDR5 protein and its binding partners, it is an embodiment that a compound of the application is administered contemporaneously with those agents. As used herein, "contemporaneous administration" of two substances to a subject means providing each of the two substances so that they are both active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion. In an embodiment, a compound of the present application is administered with another therapeutic agent simultaneously or sequentially in separate unit dosage forms or together in a single unit dosage form. Accordingly, the present application provides a single unit dosage form comprising one or more compounds of the application, an additional therapeutic agent, and a pharmaceutically acceptable carrier.

The dosage of a compound of the application varies depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. In some embodiments, a compound of the application is administered initially in a suitable dosage that is adjusted as required, depending on the clinical response. Dosages will generally be selected to maintain a serum level of the compound of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. For administration in suppository form, a representative amount is from about 0.1 mg/kg to about 10 mg/kg or about 0.1 mg/kg to about 1 mg/kg. In an embodiment of the application, compositions are formulated for oral administration and the one or more compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. In embodiments of the application the one or more compounds of the application are administered in a single daily, weekly or monthly dose or the total daily dose is divided into two, three or four daily doses.

In the above, the term "a compound" also includes embodiments wherein one or more compounds are referenced.

(c) Methods and Uses of the Application
(i) Therapeutic Methods and Uses

The compounds of the application have been shown to be inhibitors of the binding of WDR5 to MLL1.

Accordingly, the present application includes a method for inhibition of binding of WDR5 to its binding partners in a cell, either in a biological sample or in a patient, comprising administering an effective amount of one or more compounds of the application to the cell. The application also includes a use of one or more compounds of the application for inhibition of binding of WDR5 to its binding partners in a cell as well as a use of one or more compounds of the application for the preparation of a medicament for inhibition of binding of WDR5 to its binding partners in a cell. The application further includes one or more compounds of the application for use to inhibit binding of WDR5 to its binding partners in a cell.

It is an embodiment of the present application, in all aspects, that the binding partner for WDR5 is MLL1, or a portion thereof. In some embodiments, the binding partner for WDR5 is the WDR5 interacting (WIN) motif, consisting of amino acid residues 3762-3773 next to the SET domain in the MLL1 protein, [*J. Biol. Chem.*, 2008, 283(47):32158-32161; *J. Biol. Chem.*, 2008, 283(50):35258-35264].

As the compounds of the application have been shown to be capable of inhibiting the binding of WDR5 to its binding partners, the compounds of the application are useful for treating diseases, disorders or conditions mediated or treatable by inhibition of binding between WDR5 protein and its binding partners. Therefore the compounds of the present application are useful as medicaments. Accordingly, the present application includes a compound of the application for use as a medicament.

The present application also includes a method of treating a disease, disorder or condition that is mediated or treatable by inhibition of binding between WDR5 protein and its binding partners comprising administering a therapeutically effective amount of one or more compounds of the application to a subject in need thereof. The present application also includes a use of one or more compounds of the application for treating a disease, disorder or condition mediated or treatable by inhibition of binding between WDR5 protein and its binding partners as well as a use of one or more compounds of the application for the preparation of a medicament for treating a disease, disorder or condition mediated or treatable by inhibition of binding between WDR5 protein and its binding partners. The application further includes one or more compounds of the application for use in treating a disease, disorder or condition mediated or treatable by inhibition of binding between WDR5 protein and its binding partners.

In an embodiment, the disease, disorder or condition mediated or treatable by inhibition of binding between WDR5 protein and its binding partners is a neoplastic disorder. Accordingly, the present application also includes a method of treating a neoplastic disorder comprising administering a therapeutically effective amount of one or more compounds of the application to a subject in need thereof. The present application also includes a use of one or more compounds of the application for treatment of a neoplastic disorder as well as a use of one or more compounds of the application for the preparation of a medicament for treatment of a neoplastic disorder. The application further includes one or more compounds of the application for use in treating a neoplastic disorder. In an embodiment, the treatment is in an amount effective to ameliorate at least one symptom of the neoplastic disorder, for example, reduced cell proliferation or reduced tumor mass, among others, in a subject in need of such treatment.

In another embodiment of the present application, the disease, disorder or condition mediated or treatable by inhibition of binding between WDR5 protein and its binding partners is cancer. Accordingly, the present application also includes a method of treating cancer comprising administering a therapeutically effective amount of one or more compounds of the application to a subject in need thereof. The present application also includes a use of one or more compounds of the application for treatment of cancer as well as a use of one or more compounds of the application for the preparation of a medicament for treatment of cancer. The application further includes one or more compounds of the application for use in treating cancer. In an embodiment, the compound is administered for the prevention of cancer in a subject such as a mammal having a predisposition for cancer.

In an embodiment, the cancer is selected from, but not limited to: Acute Lymphoblastic Leukemia, Adult; Acute Lymphoblastic Leukemia, Childhood; Acute Myeloid Leukemia, Adult; Adrenocortical Carcinoma; Adrenocortical Carcinoma, Childhood; AIDS-Related Lymphoma; AIDS-Related Malignancies; Anal Cancer; Astrocytoma, Childhood Cerebellar; Astrocytoma, Childhood Cerebral; Bile Duct Cancer, Extrahepatic; Bladder Cancer; Bladder Cancer, Childhood; Bone Cancer, Osteosarcoma/Malignant Fibrous Histiocytoma; Brain Stem Glioma, Childhood; Brain Tumor, Adult; Brain Tumor, Brain Stem Glioma, Childhood; Brain Tumor, Cerebellar Astrocytoma, Childhood; Brain Tumor, Cerebral Astrocytoma/Malignant Glioma, Childhood; Brain Tumor, Ependymoma, Childhood; Brain Tumor, Medulloblastoma, Childhood; Brain Tumor, Supratentorial Primitive Neuroectodermal Tumors, Childhood; Brain Tumor, Visual Pathway and Hypothalamic Glioma, Childhood; Brain Tumor, Childhood (Other); Breast Cancer; Breast Cancer and Pregnancy; Breast Cancer, Childhood; Breast Cancer, Male; Bronchial Adenomas/Carcinoids, Childhood; Carcinoid Tumor, Childhood; Carcinoid Tumor, Gastrointestinal; Carcinoma, Adrenocortical; Carcinoma, Islet Cell; Carcinoma of Unknown Primary; Central Nervous System Lymphoma, Primary; Cerebellar Astrocytoma, Childhood; Cerebral Astrocytoma/Malignant Glioma, Childhood; Cervical Cancer; Childhood Cancers; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer, Childhood; Cutaneous T-Cell Lymphoma; Endometrial Cancer; Ependymoma, Childhood; Epithelial Cancer, Ovarian; Esophageal Cancer; Esophageal Cancer, Childhood; Ewing's Family of Tumors; Extracranial Germ Cell Tumor, Childhood; Extragonadal Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastric (Stomach) Cancer, Childhood; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer, Adult (Primary); Hepatocellular (Liver) Cancer, Childhood (Primary); Hodgkin's Lymphoma, Adult; Hodgkin's Lymphoma, Childhood; Hodgkin's Lymphoma During Pregnancy; Hypopharyngeal Cancer; Hypothalamic and Visual Pathway Glioma, Childhood; Intraocular Melanoma; Islet Cell Carcinoma (Endocrine Pancreas); Kaposi's Sarcoma; Kidney Cancer; Laryngeal Cancer; Laryngeal Cancer, Childhood; Leukemia, Acute Lymphoblastic, Adult; Leukemia, Acute Lymphoblastic, Childhood; Leukemia, Acute Myeloid, Adult; Leukemia, Acute Myeloid, Childhood; Leukemia, Chronic Lymphocytic; Leukemia, Chronic Myelogenous; Leukemia, Hairy Cell; Lip and Oral Cavity Cancer; Liver Cancer, Adult (Primary); Liver Cancer, Childhood (Primary); Lung Cancer, Non-Small Cell; Lung Cancer, Small Cell; Lymphoblastic Leukemia, Adult Acute; Lymphoblastic Leukemia, Childhood Acute; Lymphocytic Leukemia, Chronic; Lymphoma, AIDS-Related; Lymphoma, Central Nervous System (Primary); Lymphoma, Cutaneous T-Cell; Lymphoma, Hodgkin's, Adult; Lymphoma, Hodgkin's, Childhood; Lymphoma, Hodgkin's During Pregnancy; Lymphoma, Non-Hodgkin's, Adult; Lymphoma, Non-Hodgkin's, Childhood; Lymphoma, Non-Hodgkin's During Pregnancy; Lymphoma, Primary Central Nervous System; Macroglobulinemia, Waldenstrom's; Male Breast Cancer; Malignant Mesothelioma, Adult; Malignant Mesothelioma, Childhood; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia, Childhood Acute; Myeloma, Multiple; Myeloproliferative Disorders, Chronic; Nasal Cavity and Paranasal Sinus Cancer; Nasopharyngeal Cancer; Nasopharyngeal Cancer, Childhood; Neuroblastoma; Non-Hodgkin's Lymphoma, Adult; Non-Hodgkin's Lymphoma, Childhood; Non-Hodgkin's Lymphoma During Pregnancy; Non-Small Cell Lung Cancer; Oral Cancer, Childhood; Oral Cavity and Lip Cancer; Oropharyngeal Cancer; Osteosarcoma/Malignant Fibrous Histiocytoma of Bone; Ovarian Cancer, Childhood; Ovarian Epithelial Cancer; Ovarian Germ Cell Tumor; Ovarian Low Malignant Potential Tumor; Pancreatic Cancer; Pancreatic Cancer, Childhood; Pancreatic Cancer, Islet Cell; Paranasal Sinus and Nasal Cavity Cancer; Parathyroid Cancer; Penile Cancer; Pheochromocytoma; Pineal and Supratentorial Primitive Neuroectodermal Tumors, Childhood; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer, Adult; Primary Liver Cancer, Childhood; Prostate Cancer; Rectal Cancer; Renal Cell (Kidney) Cancer; Renal Cell Cancer, Childhood; Renal Pelvis and Ureter, Transitional Cell Cancer; Retinoblastoma; Rhabdomyosarcoma, Childhood; Salivary Gland Cancer; Salivary Gland Cancer, Childhood; Sarcoma, Ewing's Family of Tumors; Sarcoma, Kaposi's; Sarcoma (Osteosarcoma)/Malignant Fibrous Histiocytoma of Bone; Sarcoma, Rhabdomyosarcoma, Childhood; Sarcoma, Soft Tissue, Adult; Sarcoma, Soft Tissue, Childhood; Sezary Syndrome; Skin Cancer; Skin Cancer, Childhood; Skin Cancer (Melanoma); Skin Carcinoma, Merkel Cell; Small Cell Lung Cancer; Small Intestine Cancer; Soft Tissue Sarcoma, Adult; Soft Tissue Sarcoma, Childhood; Squamous Neck Cancer with Occult Primary, Metastatic; Stomach (Gastric) Cancer; Stomach (Gastric) Cancer, Childhood; Supratentorial Primitive Neuroectodermal Tumors, Childhood; T-Cell Lymphoma, Cutaneous; Testicular Cancer; Thymoma, Childhood; Thymoma, Malignant; Thyroid Cancer; Thyroid Cancer, Childhood; Transitional Cell Cancer of the Renal Pelvis and Ureter; Trophoblastic Tumor, Gestational; Unknown Primary Site, Cancer of, Childhood; Unusual Cancers of Childhood; Ureter and Renal Pelvis, Transitional Cell Cancer; Urethral Cancer; Uterine Sarcoma; Vaginal Cancer; Visual Pathway and Hypothalamic Glioma, Childhood; Vulvar Cancer; Waldenstrom's Macro globulinemia; and Wilms' Tumor. Metastases of the aforementioned cancers can also be treated in accordance with the methods described herein.

In an embodiment, the cancer is selected from solid cancer and leukemias. In another embodiment, the cancer is selected from leukaemia, lymphoma, non-Hodgkin's lymphoma, Burkitt lymphoma, MLL-fusion lymphoma, primary effusion leukemia and multiple myeloma. In a further embodiment of the present application, the cancer is selected from leukemia, melanoma, lung cancer, bladder cancer, colon cancer, brain cancer, ovarian cancer, breast cancer, prostate cancer, neuroblastoma and kidney cancer. In a further embodiment of the present application, the cancer is selected from leukemia, bladder cancer, brain cancer, prostate cancer and neuroblastoma. In a further embodiment, the cancer is selected from bladder cancer, gliomas, glioblastomas, acute myeloid leukemia (AML) and MYCN-amplified neuroblastoma.

In an embodiment, the disease, disorder or condition mediated or treatable by inhibition of binding between WDR5 protein and its binding partners is a disease, disorder or condition associated with an uncontrolled and/or abnormal cellular activity affected directly or indirectly by a binding of WDR5 to its binding partners. In another embodiment, the uncontrolled and/or abnormal cellular activity that is affected directly or indirectly by binding of WDR5 to its binding partners is proliferative activity in a cell. Accordingly, the application also includes a method of inhibiting proliferative activity in a cell, comprising administering an effective amount of one or more compounds of the application to the cell. The present application also includes a use of one or more compounds of the application for inhibition of proliferative activity in a cell as well as a use of one or more compounds of the application for the preparation of a medicament for inhibition of proliferative activity in a cell. The application further includes one or more compounds of the application for use in inhibiting proliferative activity in a cell.

The present application also includes a method of inhibiting uncontrolled and/or abnormal cellular activities mediated directly or indirectly by binding of WDR5 to its binding partners in a cell, either in a biological sample or in a subject, comprising administering an effective amount of one or more compounds of the application to the cell. The application also includes a use of one or more compounds of the application for inhibition of uncontrolled and/or abnormal cellular activities mediated directly or indirectly by binding of WDR5 to its binding partners in a cell as well as a use of one or more compounds of the application for the preparation of a medicament for inhibition of uncontrolled and/or abnormal cellular activities mediated directly or indirectly binding of WDR5 to its binding partners in a cell. The application further includes one or more compounds of the application for use in inhibiting uncontrolled and/or abnormal cellular activities mediated directly or indirectly by binding of WDR5 to its binding partners in a cell.

In further embodiments, the present application also includes a method of treating a disease, disorder or condition that is mediated or treatable by inhibition of binding between WDR5 protein and its binding partners comprising administering a therapeutically effective amount of one or more compounds of the application in combination with another known agent useful for treatment of a disease, disorder or condition mediated or treatable by inhibition of binding between WDR5 protein and its binding partners to a subject in need thereof. The present application also includes a use of one or more compounds of the application in combination with a known agent useful for treatment of a disease, disorder or condition mediated or treatable by inhibition of binding between WDR5 protein and its binding partners, for treatment of a disease, disorder or condition mediated or treatable by inhibition of binding between WDR5 protein and its binding partners.

In a further embodiment, the disease, disorder or condition mediated or treatable by inhibition of binding between WDR5 protein and its binding partners is cancer and the one or more compounds of the application are administered in combination with one or more additional cancer treatments. In another embodiment, the additional cancer treatment is selected from radiotherapy, chemotherapy, targeted therapies such as antibody therapies and small molecule therapies such as tyrosine-kinase inhibitors, immunotherapy, hormonal therapy and anti-angiogenic therapies.

(II) Methods of Preparing the Compounds of the Application

Scheme 1 illustrates one embodiment of a route to compounds of the application in which Suzuki or related coupling is performed on commercially available compounds A to afford intermediates B. Subsequent coupling of B with a carboxylic acid or appropriate or acid halide provides compounds of the application.

Scheme 1:

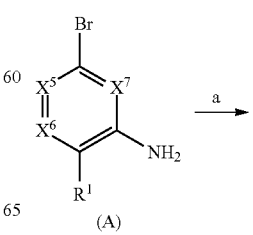

(A)

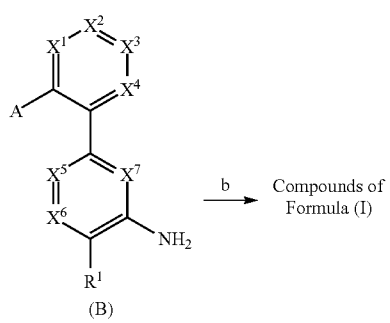

a) R$^a$B(OH)$_2$ or boronate ester, Pd(Amphos)Cl$_2$, K$_3$PO$_4$, dioxane/H$_2$O, μwave, 110° C.; b) R$^2$C(O)OH, coupling agent or R$^2$C(O)X, where X is a halide, amine;

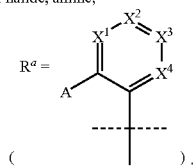

In an alternate embodiment, compounds of Formula (I) are prepared by first coupling with the carboxylic acid or acyl halides with aniline A followed by Suzuki or related coupling (scheme 2).

Scheme 2:

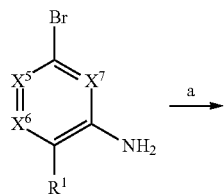

a) R$^a$C(O)OH, coupling agent or R$^2$C(O)X, wherein X is a halide amine;
b) R$^a$B(OH)$_2$ or boronate ester, Pd(Amphos)Cl$_2$, K$_3$PO$_4$, dioxane/H$_2$O, μwave, 110° C.;

In some embodiments of the application, compounds of Formula (I) are prepared from the commercially available nitrobenzene D (L=Cl or Br; M=F or Br). Nucleophilic aromatic substitution with, for example, various piperazines provide intermediate E. In some embodiments, reduction of E under reductive conditions by various means including catalytic hydrogenation and dissolving metal reductions both in their various forms [see House, H. O., *Modern Synthetic Reactions*, Second Edition, W. A. Benjamin, Inc., Menlo Park, Calif., publication (1972)] affords aniline F. Coupling of F with boronic acids or esters, for example under the Suzuki conditions [*Tetrahedron* 2002, 58:9633-9695; *Organic Letters* 2006, 8(9), 1787-1789] affords intermediate G. Related coupling reactions for the conversion of F to G or H to Formula (I) as described in Scheme 3 include the Heck (olefin) [*J. Am. Chem. Soc.* 1974 96(4):1133-1136]; Stille (organostannane) [*Synthesis* 1992 803-815]; Sonogashira (acetylene) [*Tetrahedron Lett* 1975 16(50): 4467-4470] and Negishi (organozinc) [*Aldrichimica Acta.*, 2005, 38(3):71-78] coupling reactions.

Scheme 3:

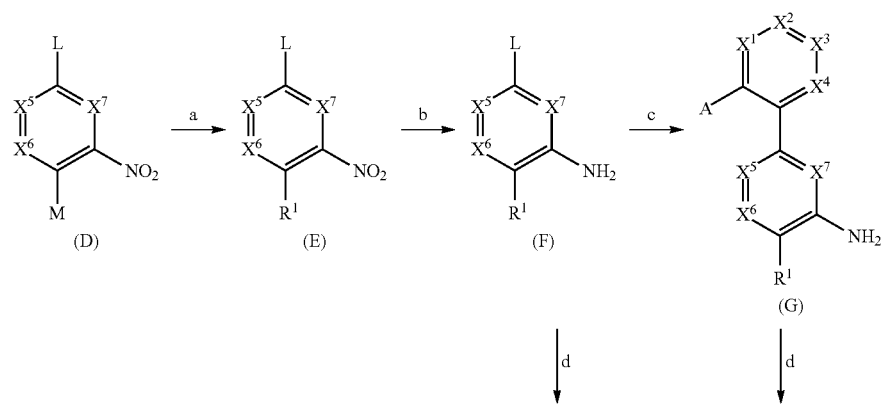

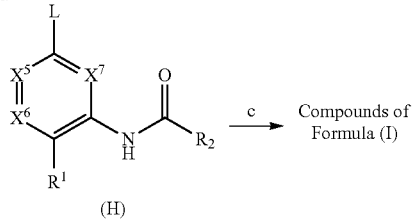

(H) → c → Compounds of Formula (I)

a) piperazine, base; b) Zn or Fe, alcohol solvent; c) $R^aB(OH)_2$ or boronate ester, Pd(Amphos)Cl$_2$, K$_3$PO$_4$, dioxane/H$_2$O, μwave, 110° C.; d) $R^2C(O)OH$, coupling agent or $R^2C(O)X$, wherein X is a halide, amine;

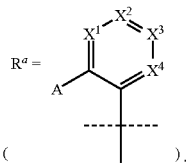

$R^a = $ ( ).

In some embodiments, compounds of Formula (I) are prepared by treatment of intermediate I with piperazines to afford the intermediate J (Scheme 4). In some embodiments, bromination of J with N-bromosuccinimide provides the versatile intermediate K which is transformed into compounds of Formula (I) according to Scheme 3.

-continued

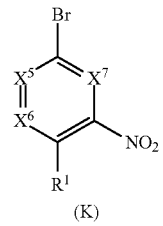

(K)

a) piperazine, base; b) N-bromosuccinimide

In some embodiments of the application, compounds of Formula (I) wherein $R^2$=trifluoromethylpyridone are prepared as shown in Scheme 5. Therefore, in some embodiments, acylation of compound F (prepared, for example, via Scheme 3) with the 6-chloro-4-(trifluoromethyl)nicotinic acid chloride (generated in situ from the corresponding acid and SOCl$_2$] gives amide L. Hydroylsis of L with sodium acetate in acetic acid under microwave conditions provides pyridone M. Coupling of M with boronic acids or esters, for example, under the Suzuki conditions delivers compounds of Formula (Ic). Alternatively, in some embodiments, the Suzuki coupled intermediate N is acylated with the 6-chloro-4-(trifluoromethyl)nicotinic acid chloride to give Id which is subsequently hydrolysed to compounds Ic (Scheme 5).

Scheme 4:

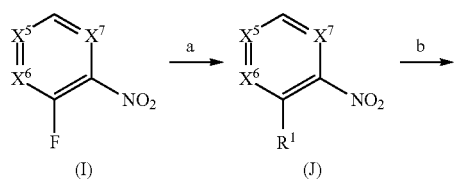

Scheme 5:

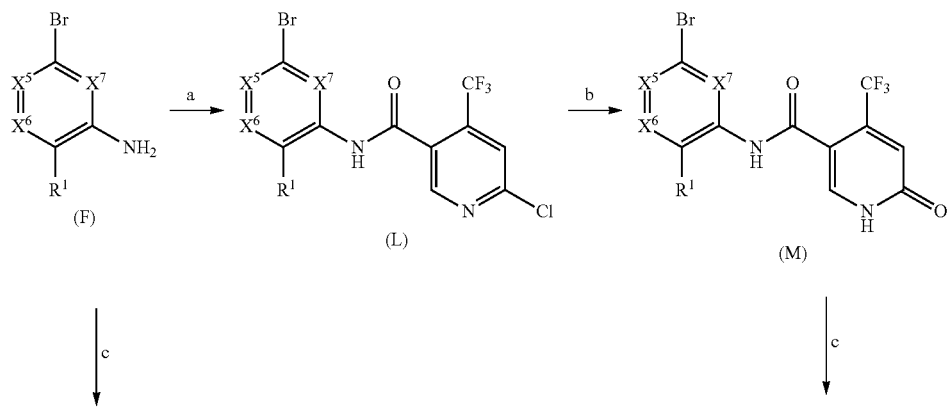

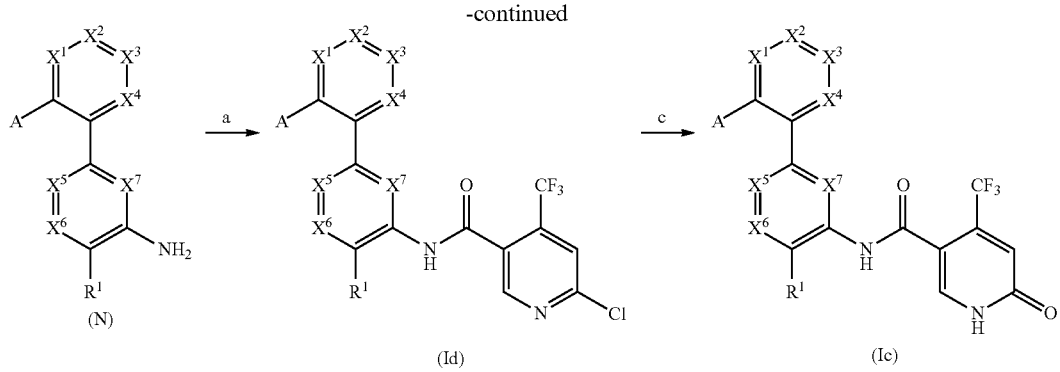

a) R²C(O)OH, coupling agent or R²C(O)X, wherein X is halide amine b) NaOAc, AcOH, μwave, 160° C.;
c) RᵃB(OH)₂ or boronate ester, Pd(Amphos)Cl₂,

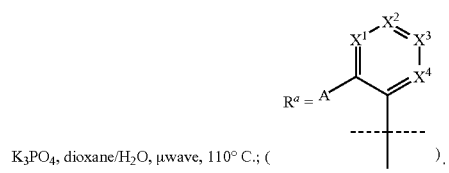

K₃PO₄, dioxane/H₂O, μwave, 110° C.; ( ).

Scheme 6 illustrates another embodiment for the preparation of compounds of Formula (Ic) wherein $R^2$ in the compounds of Formula (I) is trifluoromethylpyridone. In some embodiments, acylation of aniline F with the 6-methoxy-4-(trifluoromethyl)nicotinic acid [$R^a$=Me] or 4-(trifluoromethyl)-6-(2-(trimethylsilyl)ethoxy)nicotinic acid [$R^a$=—CH₂CH₂TMS] (generated from the corresponding acid and the alcohol as in scheme 7) give amide O. In some embodiments, the amide O is then transformed into the boronate ester P. The Suzuki coupling of P to a variety halides affords intermediates Q. In some embodiments, subsequent deprotection of Q provides compounds of the present application (Formula Ie). In some embodiments, compounds of Formula Id are prepared by via Suzuki coupling to Q followed by deprotection (scheme 6).

Scheme 6:

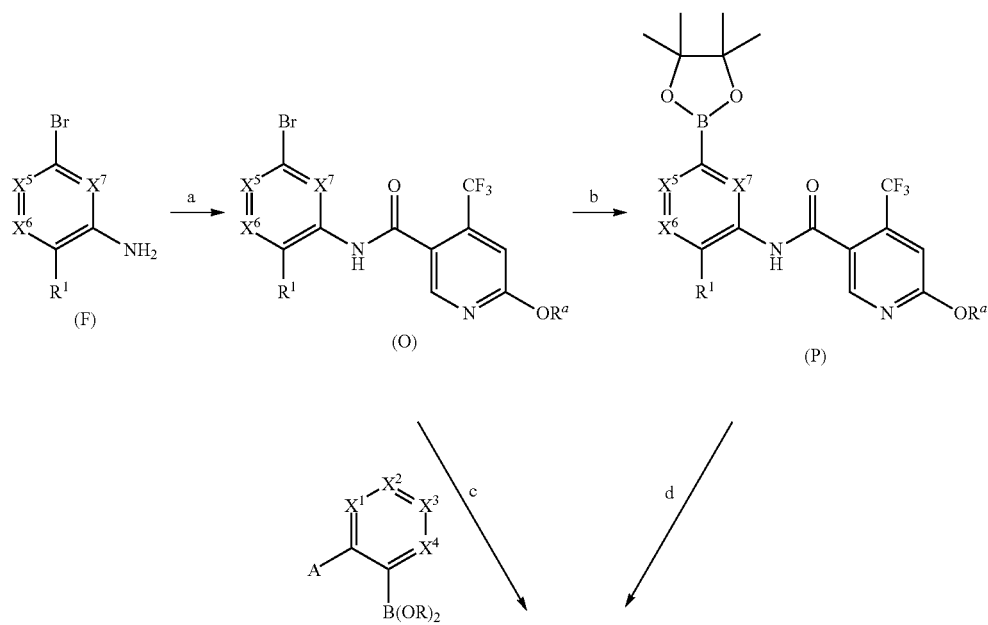

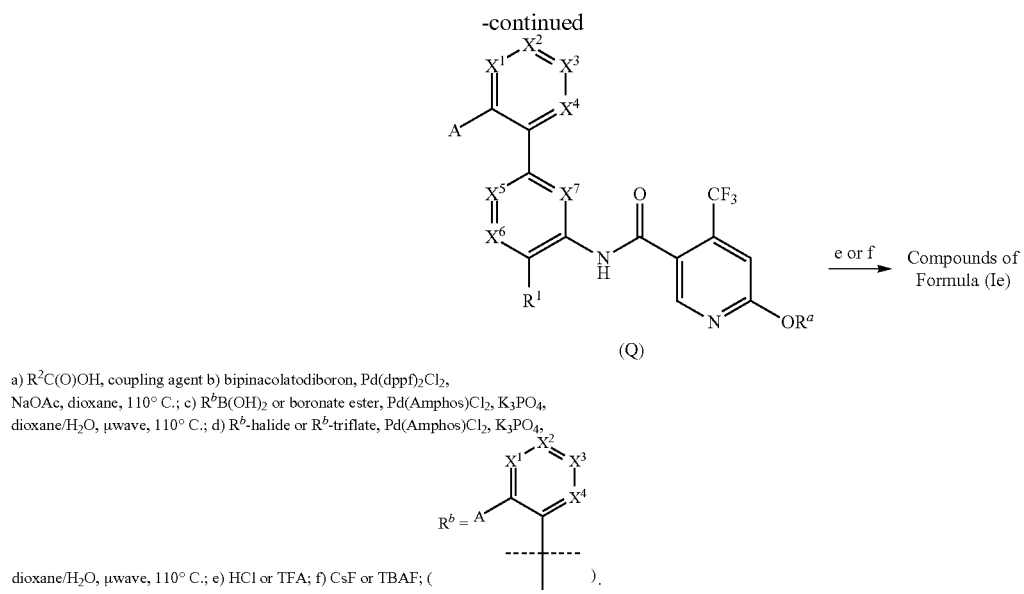

a) R²C(O)OH, coupling agent b) bipinacolatodiboron, Pd(dppf)₂Cl₂, NaOAc, dioxane, 110° C.; c) R^b B(OH)₂ or boronate ester, Pd(Amphos)Cl₂, K₃PO₄, dioxane/H₂O, μwave, 110° C.; d) R^b-halide or R^b-triflate, Pd(Amphos)Cl₂, K₃PO₄, dioxane/H₂O, μwave, 110° C.; e) HCl or TFA; f) CsF or TBAF; ( [structure] ).

Scheme 7:

a) NaOMe, MeOH; b) NaH, TMS—EtOH

Throughout the synthetic methods and processes described herein it is to be understood that, where appropriate, suitable protecting groups will be added to, and subsequently removed from, the various reactants and intermediates in a manner that will be readily understood by one skilled in the art. Conventional procedures for using such protecting groups as well as examples of suitable protecting groups are described, for example, in "*Protective Groups in Organic Synthesis*", T. W. Green, P. G. M. Wuts, Wiley-Interscience, New York, (1999). It is also to be understood that a transformation of a group or substituent into another group or substituent by chemical manipulation can be conducted on any intermediate or final product on the synthetic path toward the final product, in which the possible type of transformation is limited only by inherent incompatibility of other functionalities carried by the molecule at that stage to the conditions or reagents employed in the transformation. Such inherent incompatibilities, and ways to circumvent them by carrying out appropriate transformations and synthetic steps in a suitable order, will be readily understood to one skilled in the art. Examples of transformations are given herein, and it is to be understood that the described transformations are not limited only to the generic groups or substituents for which the transformations are exemplified. References and descriptions of other suitable transformations are given in "Comprehensive Organic Transformations—A Guide to Functional Group Preparations" R. C. Larock, VHC Publishers, Inc. (1989). References and descriptions of other suitable reactions are described in textbooks of organic chemistry, for example, "*Advanced Organic Chemistry*", March, 4th ed. McGraw Hill (1992) or, "*Organic Synthesis*", Smith, McGraw Hill, (1994). Techniques for purification of intermediates and final products include, for example, straight and reversed phase chromatography on column or rotating plate, recrystallisation, distillation and liquid-liquid or solid-liquid extraction, which will be readily understood by one skilled in the art.

EXAMPLES

The following non-limiting examples are illustrative of the present application:

(A) General Methods

Exemplary compounds were synthesized using the methods described herein, or other methods, which are known in the art. Unless otherwise noted, reagents and solvents were obtained from commercial suppliers (e.g. Aldrich, Enamine, Combiblock, Bepharm, J&W PharmLab,).

The compounds and/or intermediates were characterized by high performance liquid chromatography (HPLC) using a Waters ACQUITY UPLC system with a SQ (single quadrupole) MS and a photodiode array (PDA) detector (Milford, Mass.). The analytical columns were reversed phase Acquity UPLC BEH C18 (2.1×50 mm, 1.7 μm). A gradient elution was used (flow 0.4 mL/min), typically starting with mobile phase 0.1% formic acid in water (solvent A) and 0.1% formic acid in acetonitrile (solvent B). A gradient starting at 95% solvent A going to 5% in 1.8 min., holding for 0.5 min., going back to 95% in 0.5 min. and equilibrating the column for 0.5 min. Compounds were detected by ultraviolet light (UV) absorption at either 220 or 254 nm. HPLC solvents were from Burdick and Jackson (Muskegan, Mich.), or Fisher Scientific (Pittsburgh, Pa.).

In some instances, purity was assessed by thin layer chromatography (TLC) using glass or plastic backed silica gel plates, such as, for example, Baker-Flex Silica Gel 1B2-F flexible sheets. TLC results were readily detected visually under ultraviolet light, or by employing well-known iodine vapor and other various staining techniques.

The compounds and/or intermediates were characterized by LCMS. General conditions are as follows. Low and High resolution Mass spectra were acquired on LC/MS systems using electrospray ionization methods from a range of instruments of the following configurations: Low resolution—Waters ACQUITY UPLC system with a SQ (single quadrupole) MS; Waters ACQUITY UPLC H-Class system with a 3100 (single quadrupole) MS. High resolution—Waters ACQUITY UPLC II system equipped with a Synapt Xevo QTof and Waters ACQUITY UPLC II system equipped with a Synapt G2S QTof mass spectrometer with an atmospheric pressure ionization source. [M+H] refers to the protonated molecular ion of the chemical species.

Nuclear magnetic resonance (NMR) analysis was performed on a Bruker 500 MHz NMR spectrometer using ICON-NMR, under TopSpin program control. Spectra were measured at 298K, unless indicated otherwise and were referenced relative to the solvent chemical shift. The compounds of the application were prepared by conventional methods for chemical synthesis according to the procedures outlined in the schemes below. The starting materials for the processes described in the present application are known or may readily be prepared by conventional methods from commercially available chemicals.

(b) Synthesis of Compounds

The following compounds were prepared using one or more of the synthetic methods disclosed in Schemes 1 to 7:

Example 1: Synthesis of N-(5'-(((2S,6R)-2,6-dimethylmorpholino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

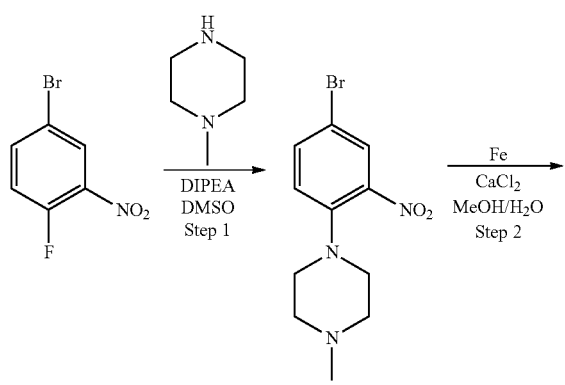

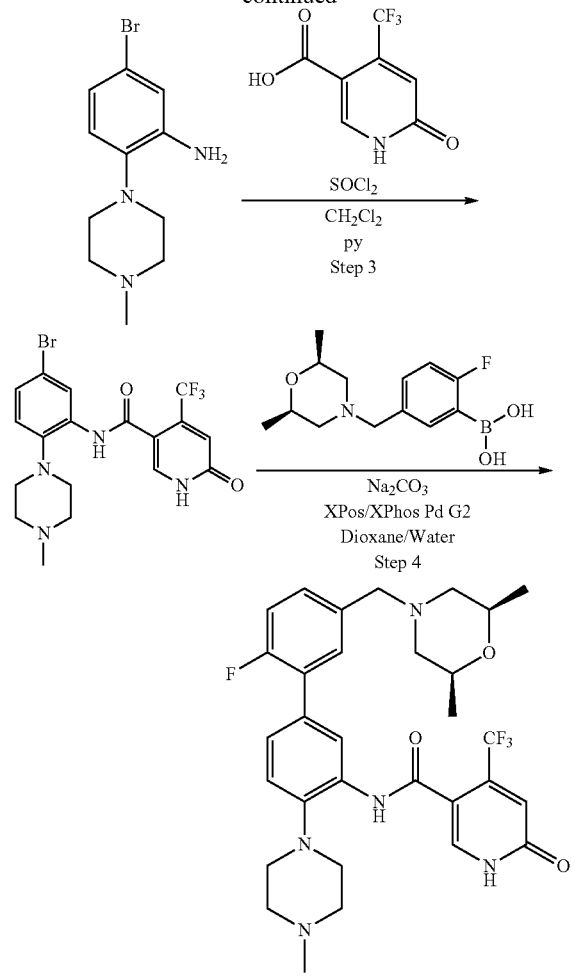

Step 1:
1-(4-Bromo-2-nitrophenyl)-4-methylpiperazine

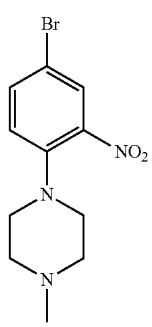 [SMILES: CN1CCN(c2ccc(Br)cc2[N+](=O)[O-])CC1]

A 100 mL round bottom flask was charged with 4-bromo-1-fluoro-2-nitrobenzene (3.4 mL, 27 mmol), 1-methylpiperazine (3.3 mL, 29 mmol), and N,N-diisopropylethylamine (9.2 mL, 54 mmol) in DMSO (20 mL). After 2 hours at 80° C. the reaction mixture was diluted with water (50 mL) and EtOAc (50 mL), and the aqueous layer was extracted with EtOAc (3×50 mL). The combined organic layers were dried over MgSO$_4$, filtered, and concentrated under reduced pressure. The residue was purified by flash column chromatography [5-30% MeOH/EtOAc] to afford the title compound (7.94 g, quantitative yield) as an orange oil. $^1$H NMR (500 MHz, DMSO-$d_6$) δ 8.00 (d, J=2.4 Hz, 1H), 7.72 (dd, J=2.4, 8.9 Hz, 1H), 7.26 (d, J=8.9 Hz, 1H), 2.97 (t, J=5.0 Hz, 4H), 2.40 (t, J=4.8 Hz, 4H), 2.20 (s, 3H); HRMS (ESI) m z calcd for $C_{11}H_{15}BrN_3O_2$ [M+H]$^+$=300.0348, found: 300.0353 g/mol.

Step 2: 5-Bromo-2-(4-methylpiperazin-1-yl)aniline

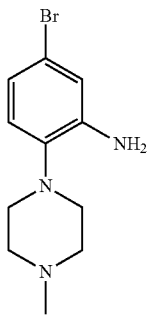

1-(4-Bromo-2-nitrophenyl)-4-methylpiperazine (7.94 g, 27 mmol), iron powder (7.39 g, 132 mmol), and calcium chloride (3.52 g, 32 mmol) were dissolved in a mixture of MeOH (50 mL) and water (50 mL), and refluxed at 100° C. for 3 h. The solution was then basified with 1M NaOH, diluted with brine, and extracted with EtOAc (5×50 mL). The combined organic layers were dried over MgSO$_4$, filtered, and concentrated under reduced pressure. The crude product was purified by flash column chromatography [5-30% MeOH/EtOAc] to afford the title compound (2.75 g, 39% yield). $^1$H NMR (500 MHz, DMSO-$d_6$) δ 6.83 (d, J=2.4 Hz, 1H), 6.80 (d, J=8.3 Hz, 1H), 6.65 (dd, J=2.4, 8.3 Hz, 1H), 4.97 (s, 2H), 2.76 (br s, 4H), 2.47 (br s, 4H), 2.22 (s, 3H); HRMS (ESI) m z calcd for $C_{11}H_{17}BrN_3$ [M+H]$^+$=270.0606, found: 270.0612 g/mol Step 3: N-(5-Bromo-2-(4-methylpiperazin-1-yl)phenyl)-6-oxo-4-(trifluoromethyl)-1,6-dihydropyridine-3-carboxamide

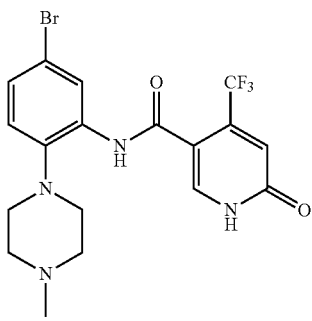 [SMILES: CN1CCN(c2ccc(Br)cc2NC(=O)c2c[nH]c(=O)cc2C(F)(F)F)CC1]

The 6-hydroxy-4-(trifluoromethyl)nicotinic acid (1.890 g, 8.94 mmol) was suspended in SOCl$_2$ (24.33 mL, 335 mmol) and stirred at 80° C. for 2 h. The solution become clear, and was then cooled to 23° C. The excess SOCl$_2$ was removed under reduced pressure, and the resulting solid was dried under vacuum for 2 h. The dry residue was dissolved in CH$_2$Cl$_2$ (10 mL) and added over a 30 min period to a solution of 5-bromo-2-(4-methylpiperazin-1-yl)aniline (2.013 g, 7.45 mmol) and pyridine (1.801 mL, 22.36 mmol) in CH$_2$Cl$_2$ (20 mL). The resulting mixture was then stirred for 12 h. The reaction was diluted with saturated aqueous sodium bicarbonate solution (100 mL), sonicated to dissolve any solid particles, and extracted with CH$_2$Cl$_2$ (4×50 mL). The combined organic extracts were dried (Na$_2$SO$_4$), filtered, and concentrated under reduced pressure. The residue was purified by flash column chromatography on silica gel [0-100%, 89% CH$_2$Cl$_2$, 10% MeOH, 1% NH$_4$Ac/CH$_2$Cl$_2$] to afford the title compound (366 mg, 10% yield) as a yellow solid. $^1$H NMR (500 MHz, MeOD) δ 8.20 (d, J=2.3 Hz, 1H), 7.95 (s, 1H), 7.32 (dd, J=8.6, 2.3 Hz, 1H), 7.18 (d, J=8.6 Hz, 1H), 6.91 (s, 1H), 2.95 (t, J=4.8 Hz, 4H), 2.69 (s, 4H), 2.40 (s, 3H); HRMS (ESI) m z calcd for $C_{18}H_{19}BrF_3N_4O_2$ [M+H]$^+$=459.0643, found: 459.0647 g/mol.

Step 4: N-(5'-(((2S,6R)-2,6-dimethylmorpholino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

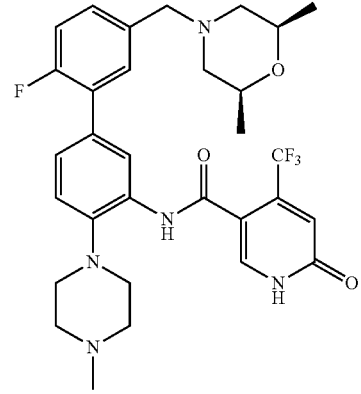 [SMILES: C[C@@H]1CN(Cc2ccc(F)c(-c3ccc(N4CCN(C)CC4)c(NC(=O)c4c[nH]c(=O)cc4C(F)(F)F)c3)c2)C[C@H](C)O1]

In a 5 mL microwave vial N-(5-bromo-2-(4-methylpiperazin-1-yl)phenyl)-6-oxo-4-(trifluoromethyl)-1,6-dihydropyridine-3-carboxamide (0.109 g, 0.228 mmol), (5-(((2S,6R)-2,6-dimethylmorpholino)methyl)-2-fluorophenyl) boronic acid (0.183 g, 0.684 mmol), sodium carbonate, anhydrous (0.241 g, 2.278 mmol), XPhos (0.022 g, 0.046 mmol) and XPhos Pd G2 (0.036 g, 0.046 mmol) were suspended in 5:3 mixture of 1,4-Dioxane (7.12 mL)/water (4.27 mL) to give a white suspension. The suspension was stirred for 5 min, degassed, purged with N$_2$, and microwaved for 60 min at 120° C. After cooling to 23° C., all solvents were removed under reduced pressure, and the crude material purified using by flash column chromatography on silica gel [1-10% MeOH/DCM+0.5% NH$_4$OH] to afford the title compound (74.9%, 103.3 mg). $^1$H NMR (500 MHz, MeOD) δ 8.16 (s, 1H), 7.98 (s, 1H), 7.47 (dd, J=7.6, 2.2 Hz, 1H), 7.40 (dt, J=8.3, 1.9 Hz, 1H), 7.32 (d, J=8.3 Hz, 1H), 7.30 (dd, J=6.2, 3.7 Hz, 1H), 7.14 (dd, J=10.6, 8.4 Hz, 1H), 6.91 (s, 1H), 3.68 (dqd, J=12.3, 6.3, 1.9 Hz, 2H), 3.53 (s, 2H), 3.01 (t, J=4.8 Hz, 4H), 2.76 (d, J=10.8 Hz, 2H), 2.68 (s, 4H), 2.38 (s, 3H), 1.77 (t, J=10.8 Hz, 2H), 1.11 (d, J=6.3 Hz, 6H); LCMS [M+1]$^+$=602.5 g/mol.

In a like manner, the following additional compounds of the application were prepared using schemes 1-7:

Example 2: N-(2'-fluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

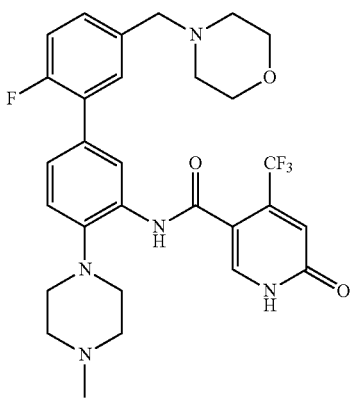 [SMILES: CN1CCN(c2ccc(-c3cc(CN4CCOCC4)ccc3F)cc2NC(=O)c2c[nH]c(=O)cc2C(F)(F)F)CC1]

The title compound (white solid, 71 mg, 59%) was prepared according to the sequence described above for the preparation of example 1 using (2-fluoro-5-(morpholinomethyl)phenyl)boronic acid (192 mg) in place of (5-(((2S,6R)-2,6-dimethylmorpholino)methyl)-2-fluorophenyl)boronic acid. $^1$H NMR (500 MHz, MeOD) δ 8.15 (s, 1H), 7.98 (s, 1H), 7.48 (dd, J=7.6, 2.4 Hz, 1H), 7.40 (dt, J=8.3, 2.1 Hz, 1H), 7.35-7.30 (m, 2H), 7.14 (dd, J=10.8, 8.1 Hz, 1H), 6.91 (s, 1H), 3.71-3.67 (m, 4H), 3.55 (s, 2H), 3.02 (t, J=4.9 Hz, 4H), 2.68 (s, 4H), 2.48 (s, J=11.9, 7.2 Hz, 4H), 2.38 (s, 3H); LCMS [M+H]$^+$=574.4 g/mol.

Example 3: N-(2'-fluoro-4'-(methoxymethoxy)-4-(4-methylpiperazin-1-yl)-5'-((2,4,4-trimethylpentan-2-yl)carbamoyl)-[1,1'-biphenyl]-3-yl)-6-oxo-4-(trifluoromethyl)-1,6-dihydropyridine-3-carboxamide

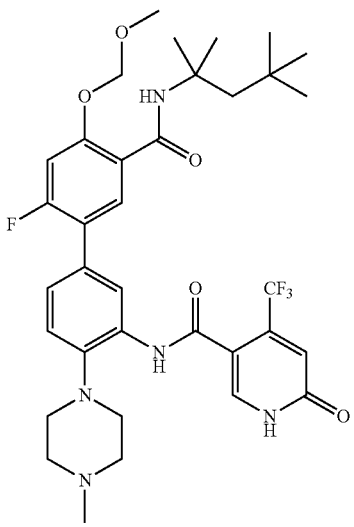 [SMILES: COCOc1cc(F)c(-c2ccc(N3CCN(C)CC3)c(NC(=O)c3c[nH]c(=O)cc3C(F)(F)F)c2)cc1C(=O)NC(C)(C)CC(C)(C)C]

The title compound (white solid, 36 mg, 33%) was prepared according to the sequence described above for the preparation of example 1 using: 4-fluoro-2-(methoxymethoxy)-5-(4,4,5,5-tetramethyl-1,3,2-dioxaborolan-2-yl)-N-(2,4,4-trimethylpentan-2-yl)benzamide (93 mg) in place of (5-(((2S,6R)-2,6-dimethylmorpholino)methyl)-2-fluorophenyl)boronic acid. $^1$H NMR (500 MHz, DMSO) δ 9.46 (s, 1H), 7.81 (s, 1H), 7.78 (d, J=9.4 Hz, 1H), 7.32 (d, J=8.3 Hz, 1H), 7.27 (d, J=8.3 Hz, 1H), 7.17 (d, J=12.7 Hz, 1H), 6.83 (s, 1H), 5.41 (s, 2H), 3.46 (s, 4H), 2.93 (s, 3H), 2.28 (s, 3H), 1.84 (s, 2H), 1.43 (s, 6H), 1.00 (s, 9H); LCMS [M+1]+=690.8 g/mol.

Example 4: N-(5'-carbamoyl-2'-fluoro-4'-hydroxy-4-(4-methylpiperazin-1-yl)-[1,1'-biphenyl]-3-yl)-6-oxo-4-(trifluoromethyl)-1,6-dihydropyridine-3-carboxamide

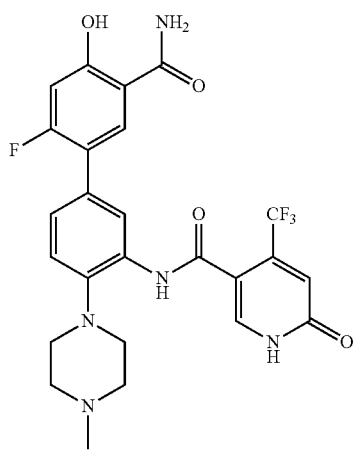 [SMILES: CN1CCN(c2ccc(-c3cc(C(N)=O)c(O)cc3F)cc2NC(=O)c2c[nH]c(=O)cc2C(F)(F)F)CC1]

30 mg of N-(2'-fluoro-4'-(methoxymethoxy)-4-(4-methylpiperazin-1-yl)-5'-((2,4,4-trimethylpentan-2-yl)carbamoyl)-[1,1'-biphenyl]-3-yl)-6-oxo-4-(trifluoromethyl)-1,6-dihydropyridine-3-carboxamide (from example 3; 36 mg, 0.048 mmol, 45.0% yield) were dissolved in DCM (3 mL). TFA was added (1 mL) and the suspension was heated at 40° C. for 1 hour. The volatiles were removed and the crude was purified using preparative HPLC to obtain the title compound (white solid, 12 mg, 17%). $^1$H NMR (500 MHz, DMSO) δ 9.94 (s, 1H), 9.56 (s, 1H), 8.52 (s, 1H), 8.07-8.03 (m, 2H), 8.01 (t, J=7.2 Hz, 2H), 7.33 (q, J=8.6 Hz, 2H), 6.85 (d, J=12.1 Hz, 1H), 6.83 (s, 1H), 3.52 (d, J=11.5 Hz, 2H), 3.24 (dd, J=19.7, 10.4 Hz, 4H), 3.03 (t, J=11.8 Hz, 2H), 2.87 (s, 3H); LCMS [M+1]$^+$=534.7 g/mol.

Example 5: N-(2'-fluoro-4-(4-methylpiperazin-1-yl)-5'-(trifluoromethoxy)-[1,1'-biphenyl]-3-yl)-6-oxo-4-(trifluoromethyl)-1,6-dihydropyridine-3-carboxamide

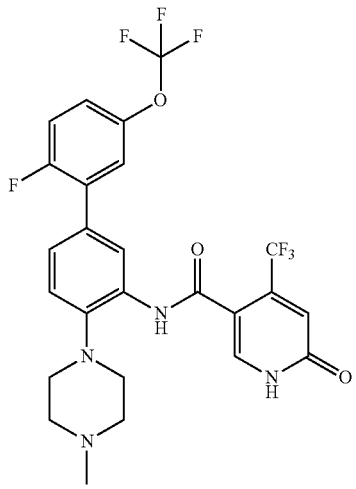 [SMILES: CN1CCN(c2ccc(-c3cc(OC(F)(F)F)ccc3F)cc2NC(=O)c2c[nH]c(=O)cc2C(F)(F)F)CC1]

The title compound (white solid, 46 mg, 86%) was prepared according to the sequence described above for the preparation of example 1 using 2-fluoro-5-(trifluoromethoxy)benzeneboronic acid (64 mg) in place of (5-(((2S,6R)-2,6-dimethylmorpholino)methyl)-2-fluorophenyl)boronic acid. $^1$H NMR (500 MHz, DMSO) δ 9.50 (s, 1H), 7.99 (s, 1H), 7.95 (s, 1H), 7.49-7.43 (m, 3H), 7.38 (d, J=8.3 Hz, 1H), 7.28 (d, J=8.4 Hz, 1H), 6.82 (s, 1H), 2.93 (s, 4H), 2.26 (s, 3H); LCMS [M+1]+=559.6 g/mol.

Example 6: N-(2'-fluoro-5'-isobutoxy-4-(4-methylpiperazin-1-yl)-[1,1'-biphenyl]-3-yl)-6-oxo-4-(trifluoromethyl)-1,6-dihydropyridine-3-carboxamide

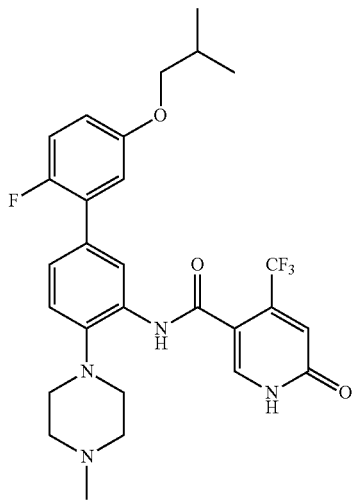 [SMILES: CC(C)COc1ccc(F)c(-c2ccc(N3CCN(C)CC3)c(NC(=O)c3c[nH]c(=O)cc3C(F)(F)F)c2)c1]

The title compound (white solid, 39 mg, 73%) was prepared according to the sequence described above for the preparation of example 1 using 2-fluoro-5-isobutoxyphenylboronic acid (61 mg) in place of (5-(((2S,6R)-2,6-dimethylmorpholino)methyl)-2-fluorophenyl)boronic acid. $^1$H NMR (500 MHz, MeOD) δ 8.11 (s, 1H), 7.98 (s, 1H), 7.39 (d, J=8.3 Hz, 1H), 7.32 (d, J=8.3 Hz, 1H), 7.10-7.05 (m, 1H), 6.98 (dd, J=6.3, 3.1 Hz, 1H), 6.92 (s, 1H), 6.88 (dt, J=8.8, 3.4 Hz, 1H), 3.76 (d, J=6.4 Hz, 2H), 3.02 (t, J=4.6 Hz, 4H), 2.68 (s, 4H), 2.38 (s, 3H), 2.11-2.02 (m, 1H), 1.04 (d, J=6.7 Hz, 6H); LCMS [M+1]+=547.8 g/mol.

Example 7: N-(5'-((cyclohexylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

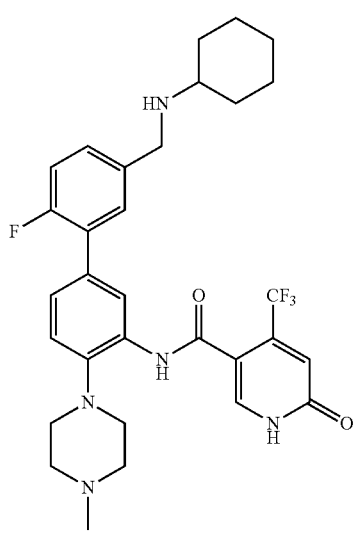 [SMILES: CN1CCN(c2ccc(-c3cc(CNC4CCCCC4)ccc3F)cc2NC(=O)c2c[nH]c(=O)cc2C(F)(F)F)CC1]

The title compound (white solid, 30 mg, 55%) was prepared according to the sequence described above for the preparation of example 1 using 5-(N-cyclohexylaminomethyl)-2-fluorophenylboronic acid, pinacol ester (91 mg) in place of (5-(((2S,6R)-2,6-dimethylmorpholino)methyl)-2-fluorophenyl)boronic acid. $^1$H NMR (500 MHz, DMSO) δ 9.43 (s, 1H), 8.00 (s, 1H), 7.97 (s, 1H), 7.48-7.43 (m, 1H), 7.38-7.30 (m, 2H), 7.29-7.20 (m, 2H), 6.79 (s, 1H), 3.80 (s, 2H), 2.90 (d, J=4.3 Hz, 4H), 2.49-2.40 (m, 4H), 2.23 (s, 3H), 1.86 (d, J=11.8 Hz, 2H), 1.67 (dd, J=9.0, 3.5 Hz, 2H), 1.53 (d, J=11.0 Hz, 1H), 1.25-0.98 (m, 6H); LCMS [M+1]+= 586.9 g/mol.

127

Example 8: N-(5-(2-fluoro-6-((tetrahydro-2H-pyran-4-yl)oxy)pyridin-3-yl)-2-(4-methylpiperazin-1-yl)phenyl)-6-oxo-4-(trifluoromethyl)-1,6-dihydropyridine-3-carboxamide

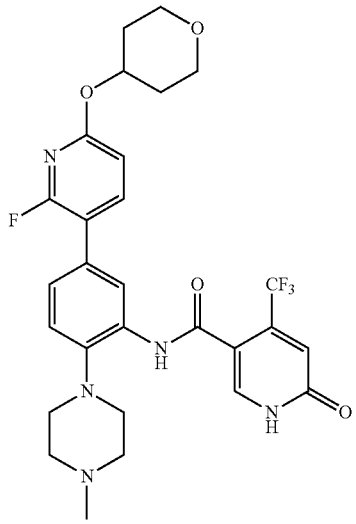 [SMILES: CN1CCN(c2ccc(-c3ccc(OC4CCOCC4)nc3F)cc2NC(=O)c2c[nH]c(=O)cc2C(F)(F)F)CC1]

The title compound (white solid, 37 mg, 84%) was prepared according to the sequence described above for the preparation of example 1 using 2-fluoro-6-(tetrahydropyran-4-yloxy)pyridine-3-boronic acid (54 mg) in place of (5-(((2S,6R)-2,6-dimethylmorpholino)methyl)-2-fluorophenyl)boronic acid. $^1$H NMR (500 MHz, DMSO) δ 9.46 (s, 1H), 7.99-7.93 (m, 3H), 7.33 (d, J=8.3 Hz, 1H), 7.26 (d, J=8.4 Hz, 1H), 6.87 (d, J=8.2 Hz, 1H), 6.82 (s, 1H), 5.13-5.07 (m, 1H), 3.86 (dt, J=11.2, 4.2 Hz, 2H), 3.51 (t, J=9.4 Hz, 2H), 2.91 (s, 4H), 2.53 (s, 4H), 2.26 (s, 3H), 2.03 (dd, J=9.0, 3.8 Hz, 2H), 1.69-1.61 (m, 2H); LCMS [M+1]$^+$= 576.8 g/mol.

Example 9: N-(2'-fluoro-4-(4-methylpiperazin-1-yl)-5'-(morpholinomethyl)-[1,1'-biphenyl]-3-yl)-6-oxo-1,6-dihydropyridazine-3-carboxamide

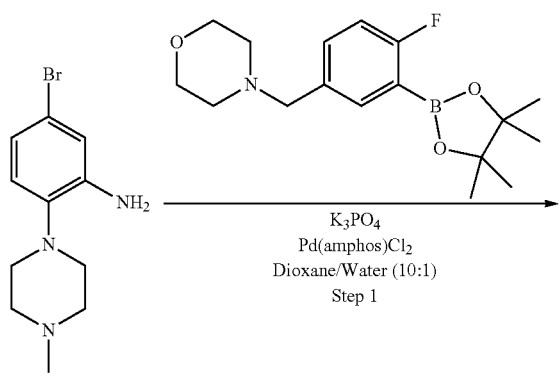

128

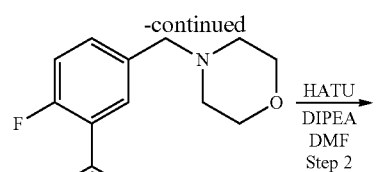

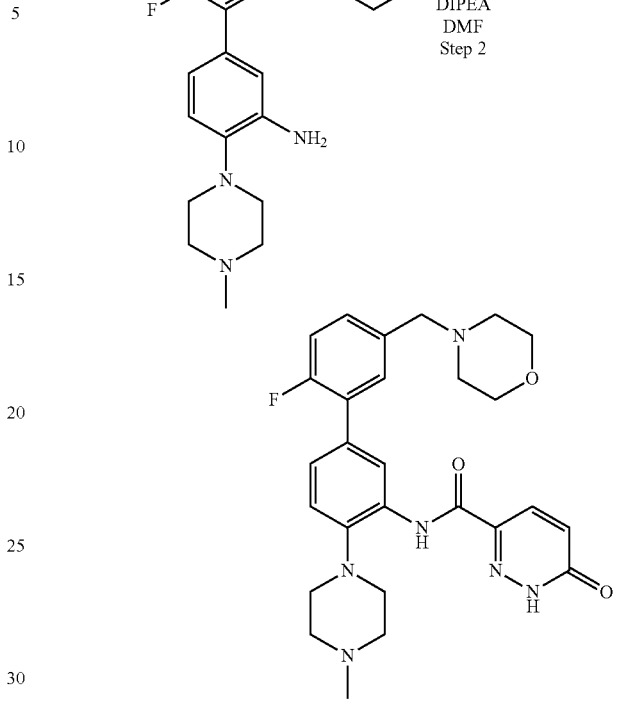

Step 1: 2'-fluoro-4-(4-methylpiperazin-1-yl)-5'-(morpholinomethyl)-[1,1'-biphenyl]-3-amine

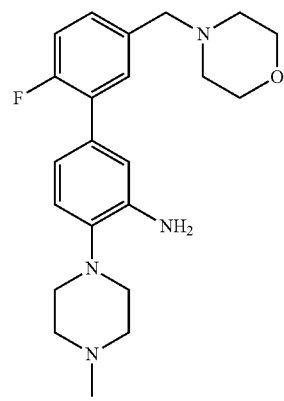 [SMILES: CN1CCN(c2ccc(-c3cc(CN4CCOCC4)ccc3F)cc2N)CC1]

In a 250 mL round bottom flask 5-bromo-2-(4-methylpiperazin-1-yl)aniline (760 mg, 2.81 mmol), 2-fluoro-5-(morpholinomethyl)phenylboronic acid, pinacol ester (1446 mg, 4.50 mmol) bis(di-tert-butyl(4-dimethylaminophenyl)phosphine)dichloropalladium(II) (199 mg, 0.281 mmol) and potassium phosphate tribasic reagent grade (1194 mg, 5.63 mmol) were dissolved in water 1,4-dioxane (40 μl)/(4 μl) (10:1 mixture) to give a white suspension. The suspension was stirred for 5 min, degassed, purged with N$_2$, and microwaved for 60 min at 120° C. The solvent was evaporated and 15 mL of CH$_2$Cl$_2$ were added. The suspension was sonicated and extracted from water (15 mL). The solvent was evaporated in vacuo yielding the crude product by flash column chromatography on silica gel (0-100%, 89% $CH_2Cl_2$, 10% MeOH, 1% $NH_4Ac/CH_2Cl_2$) to afford the title compound. $^1H$ NMR (500 MHz, DMSO-d6) δ=7.37-7.32 (m, 1H), 7.25 (dd, J=2.1, 4.9 Hz, 1H), 7.23-7.16 (m, 1H), 6.97 (d, J=8.2 Hz, 1H), 6.87 (s, 1H), 6.73 (d, J=8.1 Hz, 1H), 4.81 (s, 2H), 3.58 (t, J=4.4 Hz, 4H), 3.48 (s, 2H), 2.85 (br. s., 4H), 2.37 (br. s., 4H), 2.25 (s, 3H); LCMS $[M+H]^+$=385.7 g/mol Step 2: 2'-fluoro-4-(4-methylpiperazin-1-yl)-5'-(morpholinomethyl)-[1,1'-biphenyl]-3-amine

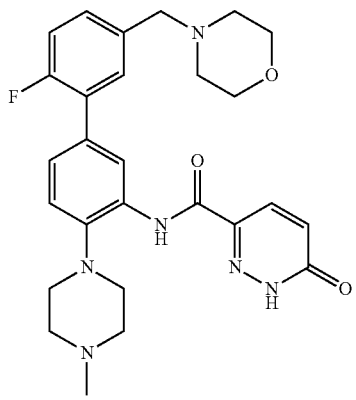 [SMILES: CN1CCN(c2ccc(-c3cc(CN4CCOCC4)ccc3F)cc2NC(=O)c2ccc(=O)[nH]n2)CC1]

A mixture of 2'-fluoro-4-(4-methylpiperazin-1-yl)-5'-(morpholinomethyl)-[1,1'-biphenyl]-3-amine (46 mg, 0.120 mmol), 6-oxo-1,6-dihydropyridazine-3-carboxylic acid (18.44 mg, 0.132 mmol) and HATU (68.2 mg, 0.179 mmol) was suspended in N,N-dimethylformamide (2 mL). After 5 min agitation, N,N-diisopropylethylamine (46.4 mg, 0.359 mmol) was added. The suspension was stirred at 23° C. for 90 min. The reaction was diluted with saturated aqueous sodium chloride solution (5 mL) and extracted with EtOAc (4×10 mL). The combined organic extracts were dried ($Na_2SO_4$), filtered, and concentrated under reduced pressure. The residue was purified by flash column chromatography on silica gel [0-100%, 89% $CH_2Cl_2$, 10% MeOH, 1% $NH_4Ac/CH_2Cl_2$] to afford the title compound (36 mg, 56% yield) as a yellow solid. $^1H$ NMR (500 MHz, DMSO-$d_6$) δ=10.13 (s, 1H), 8.56 (s, 1H), 7.98 (d, J=9.9 Hz, 1H), 7.44-7.40 (m, 1H), 7.38 (d, J=8.2 Hz, 1H), 7.36-7.32 (m, 1H), 7.31-7.25 (m, 2H), 7.08 (s, 1H), 3.63-3.55 (m, 4H), 3.54-3.49 (m, 2H), 2.94-2.87 (m, 4H), 2.73-2.55 (m, 4H), 2.44-2.36 (m, 4H), 2.33 (s, 3H); LCMS $[M+H]^+$=507.8 g/mol.

Example 10: N-(2'-fluoro-4-(4-methylpiperazin-1-yl)-5'-(morpholinomethyl)-[1,1'-biphenyl]-3-yl)-3-methoxybenzamide

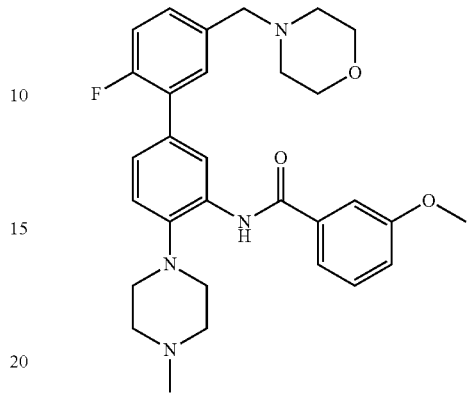

To a solution of 2'-fluoro-4-(4-methylpiperazin-1-yl)-5'-(morpholinomethyl)-[1,1'-biphenyl]-3-amine (37 mg, 0.096 mmol) and 3-methoxybenzoyl chloride (19.70 mg, 0.115 mmol) in dichloromethane (3 mL), N,N-diisopropylethylamine (37.3 mg, 0.289 mmol) was added. The solution was stirred for 30 min. The reaction was diluted with saturated aqueous sodium chloride solution (5 mL) and extracted with EtOAc (4×10 mL). The combined organic extracts were dried ($Na_2SO_4$), filtered, and concentrated under reduced pressure. The residue was purified by flash column chromatography on silica gel [0-100%, 89% $CH_2Cl_2$, 10% MeOH, 1% $NH_4Ac/CH_2Cl_2$] to afford the title compound (40 mg, 76%) as a yellow solid. $^1H$ NMR (500 MHz, DMSO-$d_6$) δ=9.62 (s, 1H), 8.33 (s, 1H), 7.56-7.47 (m, 3H), 7.43 (s, 1H), 7.40-7.31 (m, 3H), 7.28 (d, J=10.6 Hz, 1H), 7.23-7.17 (m, 1H), 3.88 (s, 3H), 3.64-3.54 (m, 4H), 3.54-3.49 (m, 2H), 2.99-2.86 (m, 4H), 2.58-2.52 (m, 4H), 2.44-2.33 (m, 4H), 2.25 (s, 3H); LCMS $[M+H]^+$=519.8 g/mol.

Example 11: 4-fluoro-N-(2'-fluoro-4-(4-methylpiperazin-1-yl)-5'-(morpholinomethyl)-[1,1'-biphenyl]-3-yl)-3,5-dimethylbenzamide

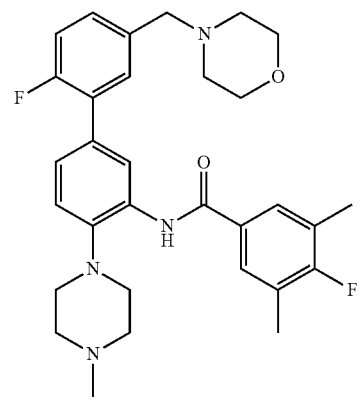 [SMILES: Cc1cc(C(=O)Nc2cc(-c3cc(CN4CCOCC4)ccc3F)ccc2N2CCN(C)CC2)cc(C)c1F]

The title compound (white solid, 58 mg, 79%) was prepared according to the sequence described above for the preparation of example 9 using 4-fluoro-3,5-dimethylbenzoic acid (32.8 mg) in place of 6-oxo-1,6-dihydropyridazine-3-carboxylic acid. ¹H NMR (500 MHz, DMSO-d₆) δ=9.58 (s, 1H), 8.30 (s, 1H), 7.72 (d, J=6.7 Hz, 2H), 7.35 (d, J=17.2 Hz, 5H), 3.58 (t, J=4.2 Hz, 4H), 3.51 (s, 2H), 2.94 (t, J=4.5 Hz, 4H), 2.62-2.52 (m, 4H), 2.41-2.35 (m, 4H), 2.33 (s, 6H), 2.26 (s, 3H); LCMS [M+H]+=535.7 g/mol.

Example 12: 2-chloro-4-fluoro-N-(2'-fluoro-4-(4-methylpiperazin-1-yl)-5'-(morpholinomethyl)-[1,1'-biphenyl]-3-yl)-3-methylbenzamide

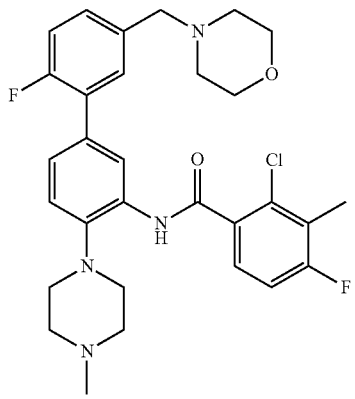 [SMILES: Cc1c(F)ccc(C(=O)Nc2cc(-c3cc(CN4CCOCC4)ccc3F)ccc2N2CCN(C)CC2)c1Cl]

The title compound (white solid, 45 mg, 59%) was prepared according to the sequence described above for the preparation of example 9 using 2-chloro-4-fluoro-3-methylbenzoic acid (36.8 mg) in place of 6-oxo-1,6-dihydropyridazine-3-carboxylic acid. ¹H NMR (500 MHz, DMSO-d₆) δ=9.50 (s, 1H), 8.18 (s, 1H), 7.60-7.49 (m, 1H), 7.55 (d, J=6.5 Hz, 1H), 7.42 (d, J=7.0 Hz, 1H), 7.39-7.22 (m, 6H), 3.58 (t, J=4.2 Hz, 4H), 3.52 (s, 2H), 2.94 (br. s., 4H), 2.38 (br. s., 5H), 2.34 (s, 3H), 2.23 (s, 3H); LCMS [M+H]+=555.7 g/mol.

Example 13: N-(2'-fluoro-4-(4-methylpiperazin-1-yl)-5'-(morpholinomethyl)-[1,1'-biphenyl]-3-yl)-1-methyl-6-oxo-4-(trifluoromethyl)-1,6-dihydropyridine-3-carboxamide

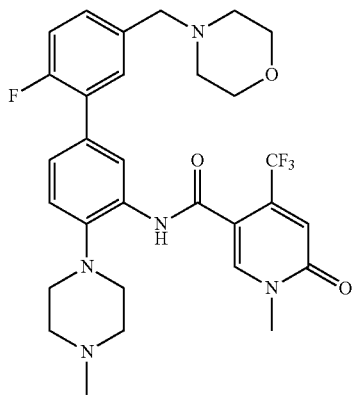 [SMILES: CN1CCN(c2ccc(-c3cc(CN4CCOCC4)ccc3F)cc2NC(=O)c2cn(C)c(=O)cc2C(F)(F)F)CC1]

To a solution of 2'-fluoro-4-(4-methylpiperazin-1-yl)-5'-(morpholinomethyl)-[1,1'-biphenyl]-3-amine (196 mg, 0.510 mmol) in 1,4-dioxane (5 mL), methylmagnesium chloride, 3 M (0.077 ml, 0.230 mmol) was added and stirred at 60° C. for 30 min. Then a dilute solution of methyl 1-methyl-6-oxo-4-(trifluoromethyl)-1,6-dihydropyridine-3-carboxylate (30 mg, 0.128 mmol) in 1,4-dioxane (5 mL) was added. The suspension was stirred at 65° C. for 30 min. The reaction was diluted with saturated aqueous sodium chloride solution (5 mL) and extracted with EtOAc (4×10 mL). The combined organic extracts were dried (Na₂SO₄), filtered, and concentrated under reduced pressure. The residue was purified by flash column chromatography on silica gel [0-100%, 89% CH₂Cl₂, 10% MeOH, 1% NH₄Ac/CH₂Cl₂] followed by preparative HPLC to afford the title compound (6.5 mg, 8%) as a white solid. ¹H NMR (500 MHz, MeOD-d₄) δ=8.28 (s, 1H), 8.16 (s, 1H), 7.50 (dd, J=2.0, 7.6 Hz, 1H), 7.46-7.40 (m, 1H), 7.36 (d, J=8.3 Hz, 2H), 7.23-7.11 (m, 1H), 6.96 (s, 1H), 3.72 (t, J=4.6 Hz, 4H), 3.68 (s, 3H), 3.58 (s, 2H), 3.03 (s, 4H), 2.75-2.57 (m, 4H), 2.51 (br. s., 4H), 2.38 (s, 3H); LCMS [M+H]+=588.8 g/mol.

Example 14: methyl 6-fluoro-4'-(4-methylpiperazin-1-yl)-3'-(6-oxo-4-(trifluoromethyl)-1,6-dihydropyridine-3-carboxamido)-[1,1'-biphenyl]-3-carboxylate

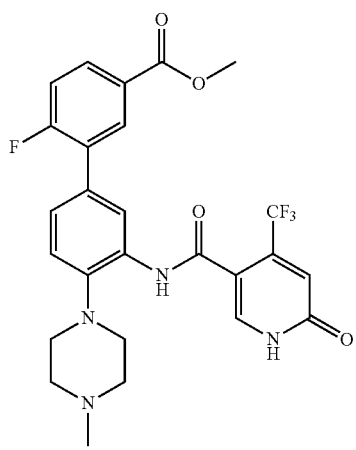 [SMILES: COC(=O)c1ccc(F)c(-c2ccc(N3CCN(C)CC3)c(NC(=O)c3c[nH]c(=O)cc3C(F)(F)F)c2)c1]

The title compound (white solid, 2 mg, 4%) was prepared according to the sequence described above for the preparation of example 1 using (2-fluoro-5-methoxycarbonylphenyl)boronic acid (57 mg) in place of (5-(((2S,6R)-2,6-dimethylmorpholino)methyl)-2-fluorophenyl)boronic acid. ¹H NMR (500 MHz, MeOD) δ 8.16 (dd, J=7.7, 2.2 Hz, 2H), 8.05 (ddd, J=8.4, 4.7, 2.2 Hz, 1H), 8.01 (s, 1H), 7.45 (d, J=8.3 Hz, 1H), 7.39 (d, J=8.3 Hz, 1H), 7.32 (dd, J=10.2, 8.7 Hz, 1H), 6.93 (s, 1H), 3.93 (s, 3H), 3.14 (s, 4H), 3.08 (s, 4H), 2.68 (s, 3H); LCMS [M+H]+=533.7 g/mol.

Example 15: N-(5-(2-(cyclopropylmethoxy)-5-fluoropyridin-4-yl)-2-(4-methylpiperazin-1-yl)phenyl)-6-oxo-4-(trifluoromethyl)-1,6-dihydropyridine-3-carboxamide

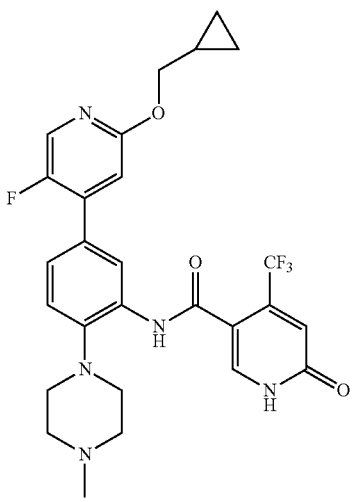

The title compound (white solid, 14 mg, 43%) was prepared according to the sequence described above for the preparation of example 1 using 2-(cyclopropylmethoxy)-5-fluoropyridine-4-boronic acid (12 equiv. 146 mg) in place of (5-(((2S,6R)-2,6-dimethylmorpholino)methyl)-2-fluorophenyl)boronic acid. $^1$H NMR (500 MHz, MeOD) δ 8.22 (s, 1H), 8.05 (d, J=2.4 Hz, 1H), 8.00 (s, 1H), 7.51 (d, J=8.4 Hz, 1H), 7.38 (d, J=8.4 Hz, 1H), 6.95 (s, 1H), 6.92 (d, J=5.4 Hz, 1H), 4.14 (d, J=7.1 Hz, 2H), 3.07 (t, J=4.5 Hz, 4H), 2.76 (s, 4H), 2.45 (s, 3H), 1.33-1.27 (m, 1H), 0.64-0.60 (m, 2H), 0.39-0.35 (m, 2H); LCMS [M+1]$^+$=546.8 g/mol.

Example 16: N-(5-(6-(cyclopropylmethoxy)-2-fluoropyridin-3-yl)-2-(4-methylpiperazin-1-yl)phenyl)-6-oxo-4-(trifluoromethyl)-1,6-dihydropyridine-3-carboxamide

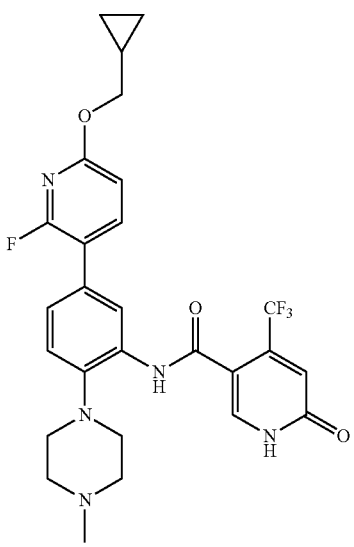

The title compound (white solid, 36 mg, 93%) was prepared according to the sequence described above for the preparation of example 1 using 6-(cyclopropylmethoxy)-2-fluoropyridine-3-boronic acid (34 mg) in place of (5-(((2S,6R)-2,6-dimethylmorpholino)methyl)-2-fluorophenyl)boronic acid. $^1$H NMR (500 MHz, MeOD) δ 8.12 (s, 1H), 7.98 (s, 1H), 7.91 (dd, J=9.8, 8.6 Hz, 1H), 7.39 (d, J=8.3 Hz, 1H), 7.33 (d, J=8.4 Hz, 1H), 6.93 (s, 1H), 6.77 (d, J=8.2 Hz, 1H), 4.13 (d, J=7.1 Hz, 2H), 3.04 (s, 4H), 2.79 (s, 4H), 2.47 (s, 3H), 1.28 (d, J=7.9 Hz, 1H), 0.63-0.59 (m, 2H), 0.37 (q, J=4.7 Hz, 2H); LCMS [M+1]$^+$=546.8 g/mol.

Example 17: N-(5'-(((cyclopropylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

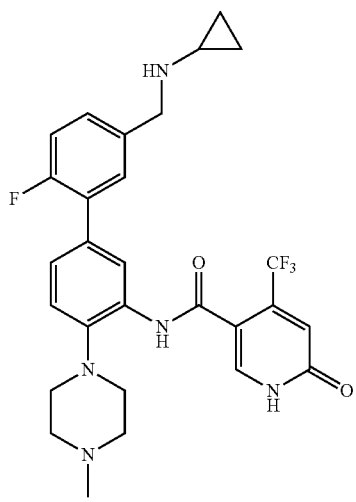 [SMILES: CN1CCN(c2ccc(-c3cc(OCC4CC4)ncc3F)cc2NC(=O)c2c[nH]c(=O)cc2C(F)(F)F)CC1]

The title compound (white solid, bicarbonate salt 3 mg, 6%) was prepared according to the sequence described above for the preparation of example 1 using 5-(cyclopropylaminomethyl)-2-fluorophenylboronic acid pinacol ester (66 mg) in place of (5-(((2S,6R)-2,6-dimethylmorpholino)methyl)-2-fluorophenyl)boronic acid. $^1$H NMR (500 MHz, MeOD) δ 8.16 (s, 1H), 7.98 (s, 1H), 7.62-7.58 (m, 1H), 7.43 (d, J=8.3 Hz, 2H), 7.35 (d, J=8.3 Hz, 1H), 7.23 (dd, J=10.4, 8.5 Hz, 1H), 6.93 (s, 1H), 4.13 (s, 2H), 3.06 (s, 4H), 2.81 (s, 4H), 2.51 (d, J=3.6 Hz, 1H), 2.48 (s, 3H), 0.77-0.70 (m, 2H), 0.70-0.62 (m, 2H); LCMS [M+1]$^+$=576.8 g/mol.

Example 18: N-(5'-((cyclohexylamino)methyl)-2'-fluoro-4-(4-methylpiperazin-1-yl)-[1,1'-biphenyl]-3-yl)-4-fluoro-3,5-dimethylbenzamide

Step 1: N-(5-bromo-2-(4-methylpiperazin-1-yl)phenyl)-4-fluoro-3,5-dimethylbenzamide

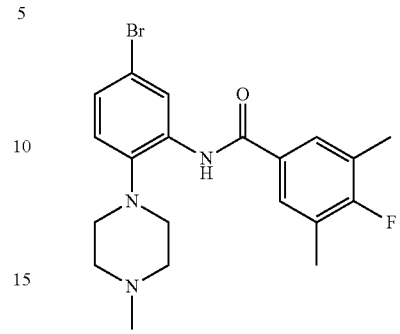

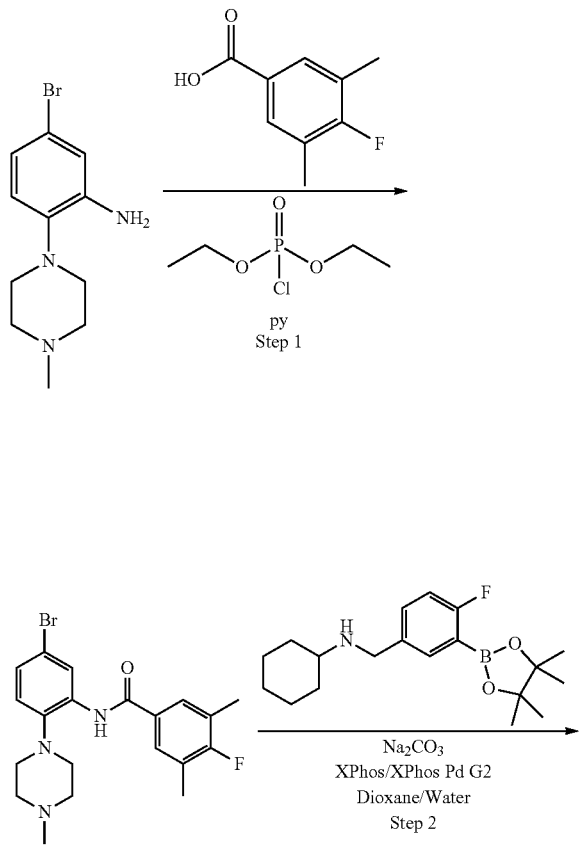

In a 5 mL MW vial a suspension of 4-fluoro-3,5-dimethylbenzoic acid (498 mg, 2.96 mmol) in pyridine, anhydrous (2.4 mL, 29.6 mmol) was added slowly diethyl chlorophosphate (428 µL, 2.96 mmol) at RT in an atmosphere of nitrogen. The reaction mixture was stirred at rt for 2 h. The suspension turned solution and then suspension again. To this 5-bromo-2-(4-methylpiperazin-1-yl)aniline (see example 1, step 2. 200 mg, 0.740 mmol) was added and the reaction was heated at 70° C. for 3 h. After completion, pyridine was removed in vacuo and the residue partitioned between dichloromethane (3 mL) and saturated sodium bicarbonate solution (3 mL). The suspension was stirred for 10 min. The organic layer was separated, dried over anhydrous $Na_2SO_4$. The solvent was evaporated in vacuo yielding the crude product. The solvent was evaporated in vacuo yielding the crude product was purified by flash column chromatography on silica gel (0-100%, 89% $CH_2Cl_2$, 10% MeOH, 1% $NH_4Ac/CH_2Cl_2$) to afford the title compound (232 mg, 75%). $^1$H NMR (500 MHz, CDCl3) δ 9.15 (s, 1H), 8.72 (d, J=2.2 Hz, 1H), 7.57 (d, J=6.6 Hz, 2H), 7.25 (dd, J=8.5, 2.2 Hz, 1H), 7.16 (d, J=8.5 Hz, 1H), 3.18 (s, 4H), 3.00 (s, 4H), 2.65 (s, 3H), 2.37 (d, J=1.8 Hz, 6H); LCMS [M+H]$^+$=422.5 g/mol.

Step 2: N-(5'-((cyclohexylamino)methyl)-2'-fluoro-4-(4-methylpiperazin-1-yl)-[1,1'-biphenyl]-3-yl)-4-fluoro-3,5-dimethylbenzamide

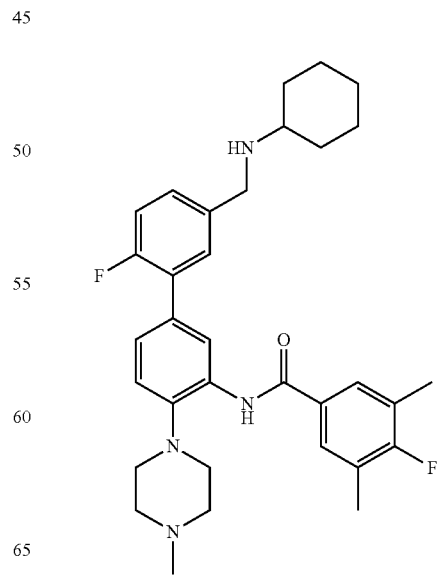

In a 5 mL microwave vial N-(5-bromo-2-(4-methylpiperazin-1-yl)phenyl)-4-fluoro-3,5-dimethylbenzamide (0.030 g, 0.072 mmol), 5-(N-cyclohexylaminomethyl)-2-fluorophenylboronic acid, pinacol ester (0.072 g, 0.217 mmol), sodium carbonate, anhydrous (0.077 g, 0.724 mmol) XPhos (6.91 mg, 0.014 mmol) and XPhos Pd G2 (0.011 g, 0.014 mmol) were suspended in 5:3 mixture of 1,4-Dioxane (2.3 mL)/water (1.4 mL) to give a white suspension. The suspension was stirred for 5 min, degassed, purged with $N_2$, and microwaved for 60 min at 120° C. After cooling to 23° C., all solvents were removed under reduced pressure, and the crude material purified using by flash column chromatography on silica gel [1-10% MeOH/DCM+0.5% $NH_4OH$] to afford the title compound (36 mg, 87%). $^1$H NMR (500 MHz, MeOD) δ 8.39 (s, 1H), 7.71 (s, 1H), 7.70 (s, 1H), 7.52 (dd, J=7.5, 2.1 Hz, 1H), 7.38 (s, 2H), 7.36-7.33 (m, 1H), 7.16 (dd, J=10.6, 8.4 Hz, 1H), 3.85 (s, 2H), 3.04 (t, J=4.7 Hz, 4H), 2.69 (s, 4H), 2.54 (tt, J=10.4, 3.5 Hz, 1H), 2.39 (s, 3H), 2.36 (d, J=1.9 Hz, 6H), 2.00 (d, J=10.5 Hz, 2H), 1.77 (d, J=13.0 Hz, 2H), 1.66 (d, J=12.4 Hz, 1H), 1.31-1.15 (m, 5H); LCMS $[M+H]^+$=547.8 g/mol.

Example 19: 4-fluoro-N-(5-(2-fluoro-6-((tetrahydro-2H-pyran-4-yl)oxy)pyridin-3-yl)-2-(4-methylpiperazin-1-yl)phenyl)-3,5-dimethylbenzamide The title compound (white solid, 17 mg, 38%) was prepared according to the sequence described above for the preparation of example 18 using 2-fluoro-6-(tetrahydropyran-4-yloxy)pyridine-3-boronic acid (52 mg) in place of 5-(N-cyclohexylaminomethyl)-2-fluorophenylboronic acid, pinacol ester. $^1$H NMR (500 MHz, MeOD) δ 8.28 (s, 1H), 7.84 (dd, J=10.3, 8.1 Hz, 1H), 7.60 (d, J=6.8 Hz, 2H), 7.28-7.23 (m, 2H), 6.68 (d, J=8.1 Hz, 1H), 5.09 (ddd, J=12.5, 8.3, 4.0 Hz, 1H), 4.48 (s, 4H), 3.88 (dt, J=9.3, 4.4 Hz, 2H), 3.54 (ddd, J=12.0, 9.0, 3.2 Hz, 2H), 2.93 (t, J=4.9 Hz, 4H), 2.70-2.48 (m, 4H), 2.29 (s, 3H), 2.26 (d, J=2.2 Hz, 6H), 2.01 (ddd, J=13.0, 7.5, 4.3 Hz, 2H), 1.72-1.65 (m, 2H); LCMS $[M+H]^+$=537.6 g/mol.

Example 20: N-(2'-fluoro-4-(4-methylpiperazin-1-yl)-5'-(morpholinomethyl)-[1,1'-biphenyl]-3-yl)-6-oxo-4-(trifluoromethyl)-1,6-dihydropyridazine-3-carboxamide

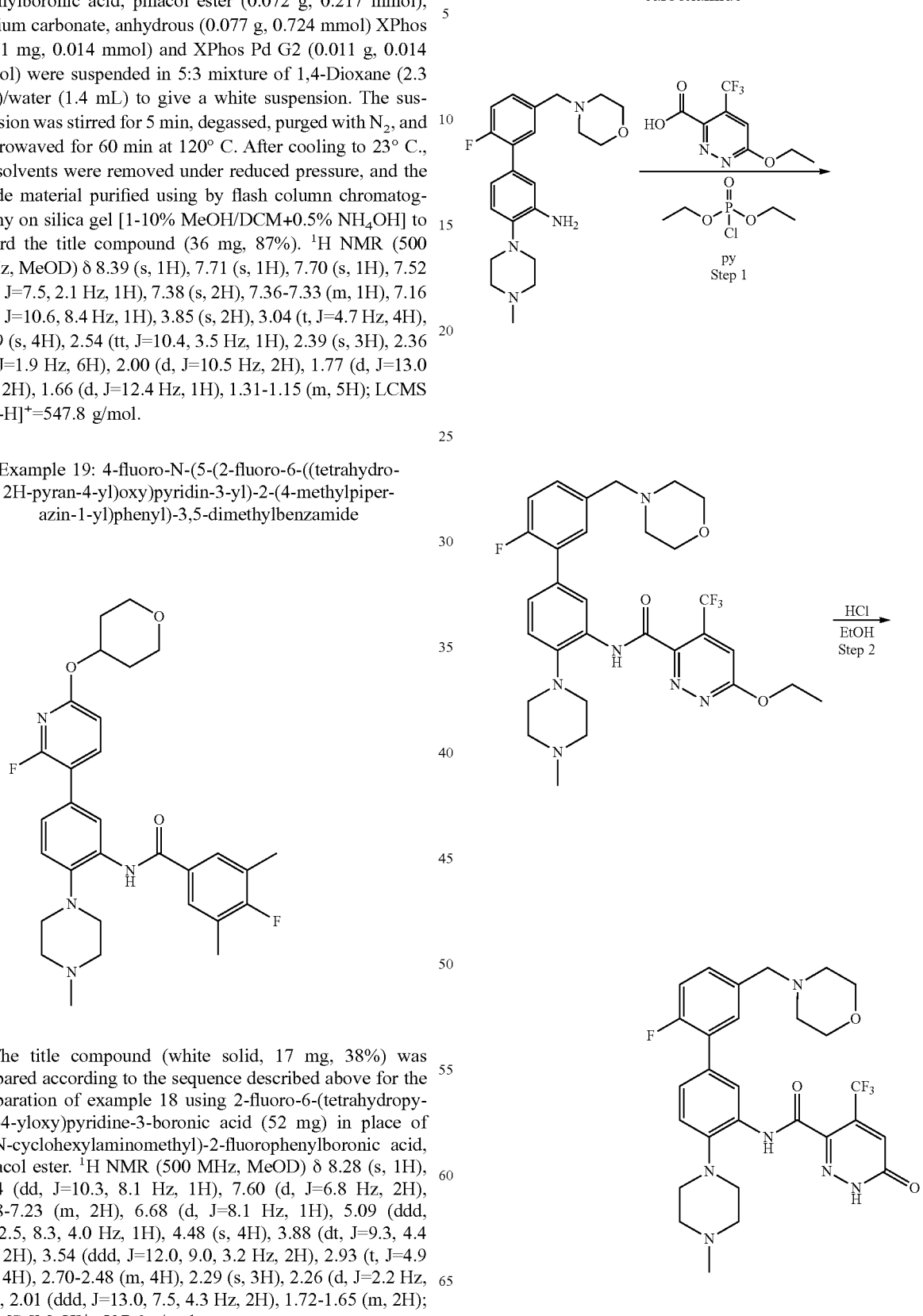

Step 1: 6-ethoxy-N-(2'-fluoro-4-(4-methylpiperazin-1-yl)-5'-(morpholinomethyl)-[1,1'-biphenyl]-3-yl)-4-(trifluoromethyl)pyridazine-3-carboxamide

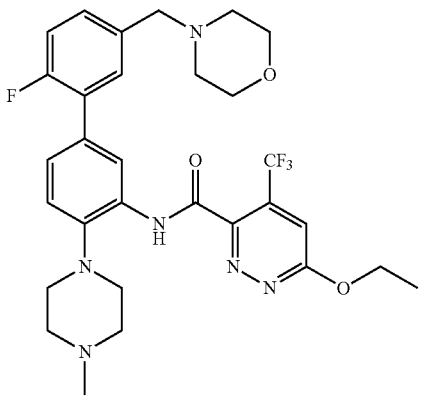 [SMILES: CCOc1cc(C(F)(F)F)c(C(=O)Nc2cc(-c3cc(CN4CCOCC4)ccc3F)ccc2N2CCN(C)CC2)nn1]

In a 10 mL MW vial a suspension of 6-ethoxy-4-(trifluoromethyl)pyridazine-3-carboxylic acid (0.138 g, 0.585 mmol) in pyridine, anhydrous (2 mL) was added slowly diethyl chlorophosphate (0.085 mL, 0.585 mmol) at RT in an atmosphere of nitrogen. The reaction mixture was stirred at RT for 45 min. The suspension turned solution and then suspension again. To this 2'-fluoro-4-(4-methylpiperazin-1-yl)-5'-(morpholinomethyl)-[1,1'-biphenyl]-3-amine (0.075 g, 0.195 mmol) was added and the reaction was heated at 90° C. for 5 hours. After completion, pyridine was removed in vacuo and the residue partitioned between ethyl acetate (15 mL) and saturated sodium bicarbonate solution (15 mL). The suspension was stirred for 10 min. The organic layer was separated, dried over anhydrous Na$_2$SO$_4$. The solvent was evaporated in vacuo yielding the crude product by flash column chromatography on silica gel (0-100%, 89% CH$_2$Cl$_2$, 10% MeOH, 1% NH$_4$Ac/CH$_2$Cl$_2$) to afford the desired compound (30 mg, 26%). LCMS [M+H]$^+$=603.7 g/mol.

Step 2: N-(2'-fluoro-4-(4-methylpiperazin-1-yl)-5'-(morpholinomethyl)-[1,1'-biphenyl]-3-yl)-6-oxo-4-(trifluoromethyl)-1,6-dihydropyridazine-3-carboxamide

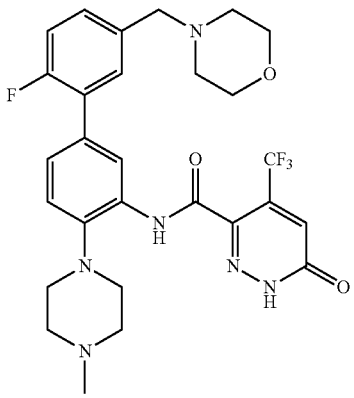

A solution of 6-ethoxy-N-(2'-fluoro-4-(4-methylpiperazin-1-yl)-5'-(morpholinomethyl)-[1,1'-biphenyl]-3-yl)-4-(trifluoromethyl)pyridazine-3-carboxamide (8.5 mg, 0.014 mmol) in ethanol (0.2 mL) and conc. HCl (0.4 mL) was heated to 80° C. for 15 minutes. The mixture was cooled, concentrated in vacuo and triturated with ether to afford hydrochloride salt of the title compound as a tan solid (6 mg, 62%). $^1$H NMR (500 MHz, DMSO-d$_6$) δ=11.35 (br. s., 1H), 11.19 (br. s., 1H), 10.90 (br. s., 1H), 10.71 (br. s., 1H), 10.15 (s, 1H), 8.37 (s, 1H), 7.82 (d, J=5.9 Hz, 1H), 7.66 (br. s., 1H), 7.57 (s, 1H), 7.48-7.37 (m, 2H), 4.40 (d, J=4.0 Hz, 2H), 4.07-3.87 (m, 8H), 3.87-3.70 (m, 4H), 2.93 (d, J=4.5 Hz, 3H); LCMS [M+H]$^+$=575.7 g/mol.

Example 21: N-(5'-(cyclopropylmethoxy)-2',4'-difluoro-4-(4-methylpiperazin-1-yl)-[1,1'-biphenyl]-3-yl)-6-oxo-4-(trifluoromethyl)-1,6-dihydropyridine-3-carboxamide

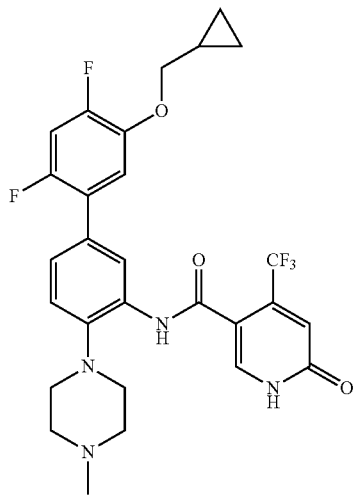

The title compound (white solid, 7.36 mg, 20%) was prepared according to the sequence described above for the preparation of example 1 using 5-(cyclopropylmethoxy)-2,4-difluorophenylboronic acid (58.9 mg) in place of (5-(((2S,6R)-2,6-dimethylmorpholino)methyl)-2-fluorophenyl)boronic acid. $^1$H NMR (500 MHz, MeOD) δ 8.06 (s, 1H), 7.99 (s, 1H), 7.39 (d, J=8.4 Hz, 1H), 7.33 (d, J=8.3 Hz, 1H), 7.16 (dd, J=8.9, 7.8 Hz, 1H), 7.06 (t, J=10.6 Hz, 1H), 6.93 (s, 1H), 3.93 (d, J=6.9 Hz, 2H), 3.09 (s, 4H), 2.94 (s, 4H), 2.59 (s, 3H), 1.29-1.26 (m, 1H), 0.65-0.60 (m, 2H), 0.36 (q, J=4.8 Hz, 2H); LCMS [M+1]$^+$=563.6 g/mol.

Example 22: N-(5-(2-fluoro-6-(pyrrolidin-1-yl)pyridin-3-yl)-2-(4-methylpiperazin-1-yl)phenyl)-6-oxo-4-(trifluoromethyl)-1,6-dihydropyridine-3-carboxamide

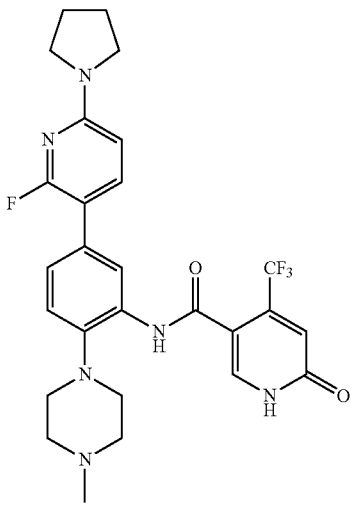 [SMILES: CN1CCN(c2ccc(-c3ccc(N4CCCC4)nc3F)cc2NC(=O)c2c[nH]c(=O)cc2C(F)(F)F)CC1]

The title compound (white solid, 34.9 mg, 91%) was prepared according to the sequence described above for the preparation of example 1 using 2-fluoro-6-(pyrrolidin-1-yl)-3-(4,4,5,5-tetramethyl-1,3,2-dioxaborolan-2-yl)pyridine (4 equiv, 74.9 mg) in place of (5-(((2S,6R)-2,6-dimethylmorpholino)methyl)-2-fluorophenyl)boronic acid. $^1$H NMR (500 MHz, MeOD) δ 8.09 (s, 1H), 7.97 (s, 1H), 7.74 (dd, J=10.3, 8.5 Hz, 1H), 7.35 (d, J=8.4 Hz, 1H), 7.29 (d, J=8.4 Hz, 1H), 6.92 (s, 1H), 6.41 (dd, J=8.4, 1.1 Hz, 1H), 3.46 (t, J=6.6 Hz, 4H), 3.00 (t, J=4.6 Hz, 4H), 2.67 (s, 4H), 2.38 (s, 3H), 2.06-2.02 (m, 4H); LCMS [M+H]$^+$=545.7 g/mol.

Example 23: N-(2'-fluoro-4-(4-methylpiperazin-1-yl)-3'-(morpholinomethyl)-[1,1'-biphenyl]-3-yl)-6-oxo-4-(trifluoromethyl)-1,6-dihydropyridine-3-carboxamide

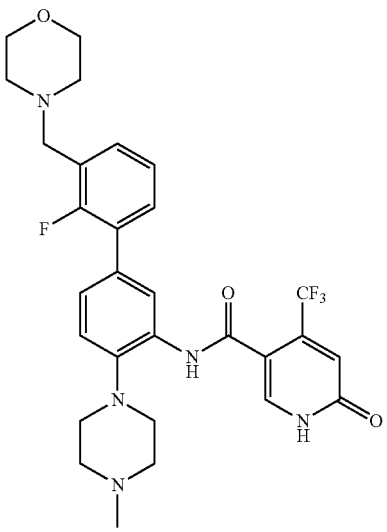 [SMILES: CN1CCN(c2ccc(-c3cccc(CN4CCOCC4)c3F)cc2NC(=O)c2c[nH]c(=O)cc2C(F)(F)F)CC1]

The title compound (white solid, 30.2 mg, 78%) was prepared according to the sequence described above for the preparation of example 1 using 4-(2-fluoro-3-(4,4,5,5-tetramethyl-1,3,2-dioxaborolan-2-yl)benzyl)morpholine (4 equiv. 127 mg) in place of (5-(((2S,6R)-2,6-dimethylmorpholino)methyl)-2-fluorophenyl)boronic acid. $^1$H NMR (500 MHz, MeOD) δ 8.13 (s, 1H), 7.97 (s, 1H), 7.44-7.38 (m, 3H), 7.33 (d, J=8.3 Hz, 1H), 7.23 (t, J=7.6 Hz, 1H), 6.92 (s, 1H), 3.72-3.68 (m, 4H), 3.66 (s, 2H), 3.02 (t, J=4.4 Hz, 4H), 2.68 (s, 4H), 2.54 (s, 4H), 2.39 (s, 3H); LCMS [M+H]$^+$=574.7 g/mol.

Example 24: N-(2'-fluoro-4-(4-methylpiperazin-1-yl)-5'-(morpholinomethyl)-[1,1'-biphenyl]-3-yl)-3-methylbenzamide

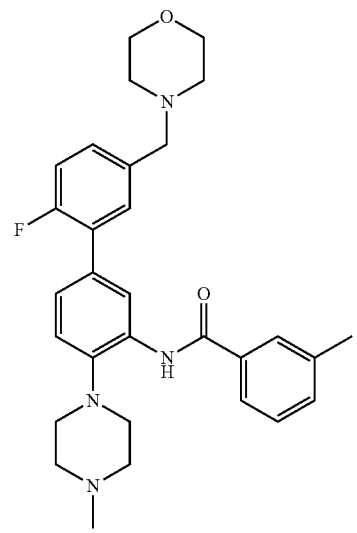 [SMILES: Cc1cccc(C(=O)Nc2cc(-c3cc(CN4CCOCC4)ccc3F)ccc2N2CCN(C)CC2)c1]

The title compound (white solid, 33.9 mg, 80%) was prepared a modified procedure of example 1 using 4-(4-fluoro-3-(4,4,5,5-tetramethyl-1,3,2-dioxaborolan-2-yl)benzyl)morpholine (4 equiv, 108 mg) in place of (5-(((2S,6R)-2,6-dimethylmorpholino)methyl)-2-fluorophenyl)boronic acid in the final step. $^1$H NMR (500 MHz, MeOD) δ 8.46 (s, 1H), 7.80 (s, 1H), 7.76 (dd, J=5.7, 2.9 Hz, 1H), 7.50 (dd, J=7.6, 2.0 Hz, 1H), 7.46 (d, J=4.8 Hz, 2H), 7.37 (s, 2H), 7.36-7.32 (m, 1H), 7.16 (dd, J=10.6, 8.4 Hz, 1H), 3.71-3.69 (m, 4H), 3.56 (s, 2H), 3.04 (t, J=4.7 Hz, 4H), 2.69 (s, 4H), 2.49 (s, 4H), 2.47 (s, 3H), 2.39 (s, 3H); LCMS [M+H]$^+$=503.7 g/mol.

Example 25: N-(2'-fluoro-4-(4-methylpiperazin-1-yl)-[1,1'-biphenyl]-3-yl)-6-oxo-4-(trifluoromethyl)-1,6-dihydropyridine-3-carboxamide

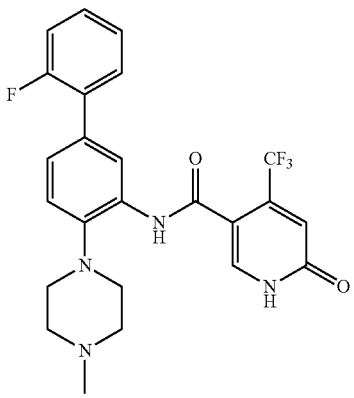 [SMILES: CN1CCN(c2ccc(-c3ccccc3F)cc2NC(=O)c2c[nH]c(=O)cc2C(F)(F)F)CC1]

The title compound (white solid, 28.9 mg, 93%) was prepared according to the sequence described above for the preparation of example 1 using 2-(2-fluorophenyl)-4,4,5,5-tetramethyl-1,3,2-dioxaborolane (4 equiv. 57.9 mg) in place of (5-(((2S,6R)-2,6-dimethylmorpholino)methyl)-2-fluorophenyl)boronic acid. $^1$H NMR (500 MHz, MeOD) δ 8.14 (s, 1H), 7.97 (s, 1H), 7.49 (td, J=7.8, 2.2 Hz, 1H), 7.40 (dt, J=8.3, 2.2 Hz, 1H), 7.38-7.31 (m, 2H), 7.25 (t, J=7.5 Hz, 1H), 7.18 (dd, J=11.2, 8.1 Hz, 1H), 6.92 (s, 1H), 3.04 (t, J=4.9 Hz, 4H), 2.73 (s, 4H), 2.42 (s, 3H); LCMS [M+H]$^+$= 475.7 g/mol.

Example 26: N-(4-(3,4-dimethylpiperazin-1-yl)-2'-fluoro-5'-(morpholinomethyl)-[1,1'-biphenyl]-3-yl)-6-hydroxy-4-(trifluoromethyl)nicotinamide

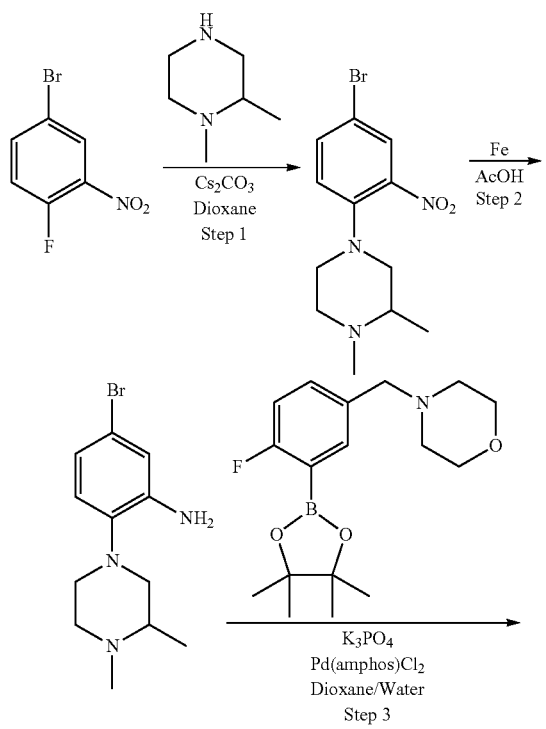

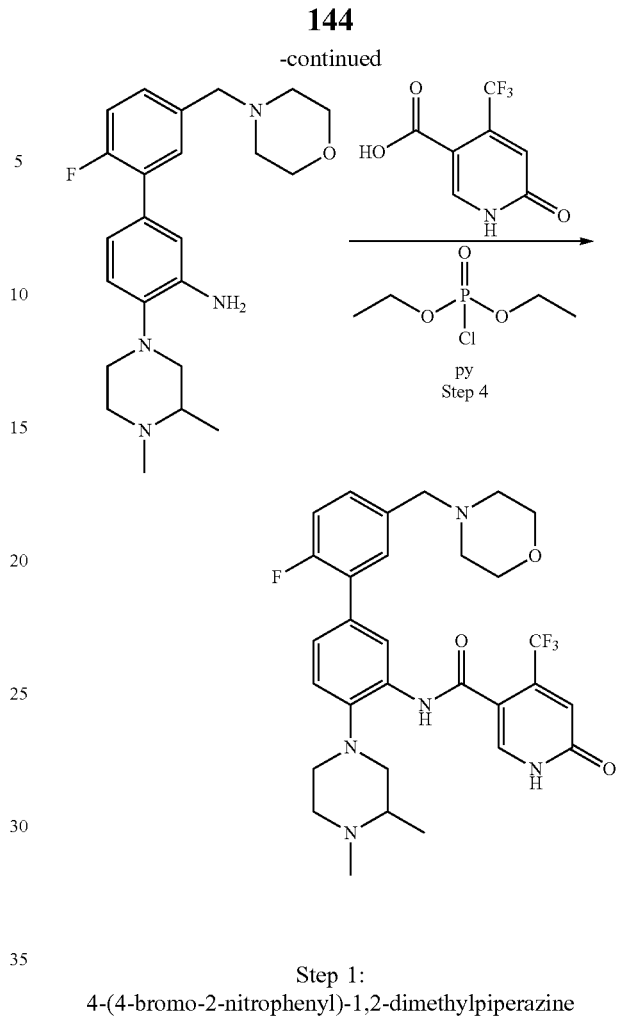

Step 1:
4-(4-bromo-2-nitrophenyl)-1,2-dimethylpiperazine

To a solution of 1,2-dimethyl-piperazine dichloride hydrate (104 mg, 0.909 mmol) and cesium carbonate (889 mg, 2.73 mmol) in dioxane (5 ml), 4-bromo-1-fluoro-2-nitrobenzene (200 mg, 0.909 mmol) was charged in one portion. The mixture was stirred for 30 min at 23° C. The mixture was concentrated to dryness followed by worked up with saturated NaCl solution and EtOAc. The organic extract was separated and concentrated to get the title compound (264 mg, 88% yield), as a dark red oil. $^1$H NMR (500 MHz, DMSO-d$_6$) δ=8.02 (d, J=2.4 Hz, 1H), 7.73 (dd, J=2.4, 8.9 Hz, 1H), 7.27 (d, J=8.9 Hz, 1H), 3.10-2.87 (m, 3H), 2.75 (d, J=11.4 Hz, 1H), 2.66-2.58 (m, 1H), 2.20 (s, 5H), 0.98 (d, J=6.2 Hz, 3H); LCMS [M+H]$^+$=314.5.

Step 2: 5-bromo-2-(3,4-dimethylpiperazin-1-yl)aniline

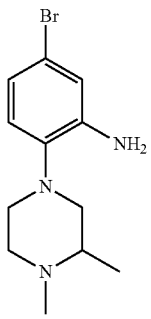

4-(4-Bromo-2-nitrophenyl)-1,2-dimethylpiperazine (264 mg, 0.798 mmol) and iron powder (508 mg, 9.09 mmol) were suspended in acetic acid (5 ml) and agitated at 80° C. for 2 h. The suspension was cooled to RT, filtered through celite, washed with DCM and concentrated to dryness. The residue was purified by flash column chromatography on silica gel [0-100%, 89% CH$_2$Cl$_2$, 10% MeOH, 1% NH$_4$Ac/CH$_2$Cl$_2$] to afford the title compound (198 mg, 69% yield) as a yellow solid. $^1$H NMR (500 MHz, DMSO-d$_6$) δ=7.12 (br. s., 1H), 6.91-6.76 (m, 3H), 6.74-6.58 (m, 1H), 6.08-5.89 (m, 1H), 5.12-4.86 (m, 1H), 5.02 (br. s., 2H), 4.72 (br. s., 1H), 2.90 (br. s., 3H), 2.75-2.61 (m, 2H), 2.31 (br. s., 6H), 1.92 (s, 5H), 1.04 (br. s., 4H). LCMS (M+H)+284.4.

Step 3: 4-(3,4-dimethylpiperazin-1-yl)-2'-fluoro-5'-(morpholinomethyl)-[1,1'-biphenyl]-3-amine

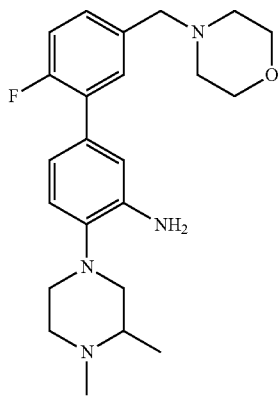

A mixture of 5-bromo-2-(3,4-dimethylpiperazin-1-yl)aniline (194 mg, 0.683 mmol), 2-fluoro-5-(morpholinomethyl)phenyl boronic acid, pinacol ester (351 mg, 1.092 mmol), potassium phosphate tribasic reagent grade (48.3 mg, 0.068 mmol) and bis(di-tert-butyl(4-dimethylaminophenyl)phosphine)dichloropalladium(II) (48.3 mg, 0.068 mmol) were suspended in dioxane (40 mL) and water (4 mL) (10:1 mixture). The mixture was agitated at 65-70° C. for 90 min. The mixture was quenched using saturated NaCl solution and EtOAc. The phases were separated, the organic extract was concentrated and the residue was purified by flash column chromatography on silica gel [0-100%, 89% CH$_2$Cl$_2$, 10% MeOH, 1% NH$_4$Ac/CH$_2$Cl$_2$] to afford the title compound (220 mg, 77%) as a brown solid.

Step 4: N-(4-(3,4-dimethylpiperazin-1-yl)-2'-fluoro-5'-(morpholinomethyl)-[1,1'-biphenyl]-3-yl)-6-hydroxy-4-(trifluoromethyl)nicotinamide

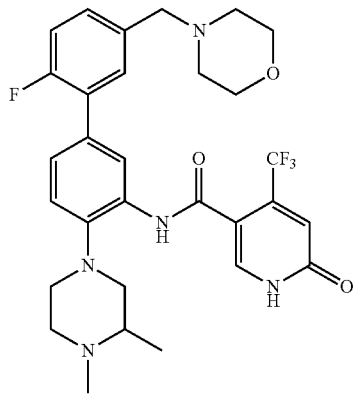

In a 10 mL MW vial a suspension of 6-hydroxy-4-(trifluoromethyl)nicotinic acid (52.0 mg, 0.251 mmol) in pyridine (1.0 mL) and N,N-diisopropylethylamine (32.4 mg, 0.251 mmol) was added slowly diethyl chlorophosphate (43.3 mg, 0.251 mmol) at RT in an atmosphere of nitrogen. The reaction mixture was stirred at RT for 2 hours. The suspension turned solution and then suspension again. To this, 4-(3,4-dimethylpiperazin-1-yl)-2'-fluoro-5'-(morpholinomethyl)-[1,1'-biphenyl]-3-amine (25 mg, 0.063 mmol) in dichloromethane (2 mL) was added and the reaction was heated at 80° C. for 16 hours. After completion, pyridine was removed in vacuo and the residue partitioned between dichloromethane (3 mL) and saturated sodium bicarbonate solution (3 mL). The suspension was stirred for 10 min. The organic layer was separated, dried over anhydrous Na$_2$SO$_4$. The solvent was evaporated in vacuo yielding the crude product by flash column chromatography on silica gel (0-100%, 89% CH$_2$Cl$_2$, 10% MeOH, 1% NH$_4$Ac/CH$_2$Cl$_2$) to afford the title compound (0.025 mmol, 40.5% yield) as a yellow powder. $^1$H NMR (500 MHz, DMSO-d$_6$) δ=9.35 (s, 1H), 7.88 (d, J=4.9 Hz, 2H), 7.32-7.28 (m, 1H), 7.26-7.20 (m, 2H), 7.19-7.14 (m, 2H), 6.72 (s, 1H), 3.48 (t, J=4.3 Hz, 4H), 3.41 (s, 2H), 2.96-2.85 (m, 2H), 2.81-2.67 (m, 2H), 2.38-2.32 (m, 1H), 2.28 (br. s., 6H), 2.19-2.16 (m, 1H), 2.14 (s, 3H), 0.91 (d, J=6.2 Hz, 3H); LCMS [M+H]$^+$=588.7 g/mol.

Example 27: N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

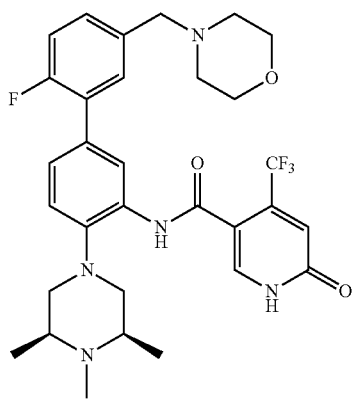 [SMILES: C[C@@H]1CN(c2ccc(-c3cc(CN4CCOCC4)ccc3F)cc2NC(=O)c2c[nH]c(=O)cc2C(F)(F)F)C[C@H](C)N1C]

The title compound (yellow solid, 9.6 mg, 25%) was prepared according to the sequence described above for the preparation of example 26 using (2R,6S)-1,2,6-trimethylpiperazine (117 mg, 0.909 mmol) in place of 1,2-dimethylpiperazine dichloride hydrate. $^1$H NMR (500 MHz, MeOD-$d_4$) δ=8.15 (br. s., 1H), 7.99 (s, 1H), 7.50 (dd, J=1.8, 7.6 Hz, 1H), 7.42 (d, J=8.2 Hz, 1H), 7.38-7.26 (m, 3H), 7.17 (dd, J=8.5, 10.5 Hz, 1H), 6.92 (s, 1H), 3.72 (t, J=4.4 Hz, 4H), 3.58 (s, 2H), 3.04 (d, J=11.2 Hz, 2H), 2.69 (t, J=11.2 Hz, 2H), 2.61-2.55 (m, 2H), 2.54-2.48 (m, 4H), 2.40 (s, 3H), 1.19 (d, J=6.2 Hz, 6H); LCMS [M+H]$^+$=602.7 g/mol.

Example 28: (S)—N-(4-(2,4-dimethylpiperazin-1-yl)-2'-fluoro-5'-(morpholinomethyl)-[1,1'-biphenyl]-3-yl)-6-oxo-4-(trifluoromethyl)-1,6-dihydropyridine-3-carboxamide

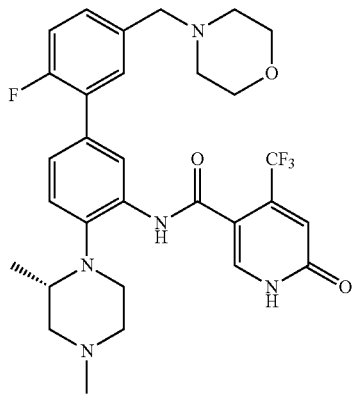

The title compound (yellow solid, 9.2 mg, 24%) was prepared according to the sequence described above for the preparation of example 26 using (R)-1,3-dimethylpiperazine dihydrochloride (106 mg, 0.568 mmol) in place of 1,2-dimethyl-piperazine dichloride hydrate. $^1$H NMR (500 MHz, MeOD-$d_4$) δ=8.45 (s, 1H), 8.01 (s, 1H), 7.53 (dd, J=2.0, 7.7 Hz, 1H), 7.48-7.45 (m, 1H), 7.44-7.40 (m, 1H), 7.37 (dt, J=2.3, 5.4 Hz, 1H), 7.18 (dd, J=8.4, 10.5 Hz, 1H), 6.94 (s, 1H), 6.97-6.92 (m, 1H), 3.72 (t, J=4.5 Hz, 4H), 3.59 (s, 2H), 2.95 (d, J=6.8 Hz, 4H), 2.52 (br. s., 4H), 2.42-2.40 (m, 1H), 2.39 (s, 3H), 2.12 (s, 1H), 1.95 (s, 1H), 1.31 (br. s., 1H), 0.89 (d, J=6.2 Hz, 3H); LCMS [M+H]$^+$=588.7 g/mol.

Example 29: N-(2'-fluoro-4-(4-methylpiperazin-1-yl)-5'-(morpholinomethyl)-[1,1'-biphenyl]-3-yl)-4-methyl-6-oxo-1,6-dihydropyridine-3-carboxamide

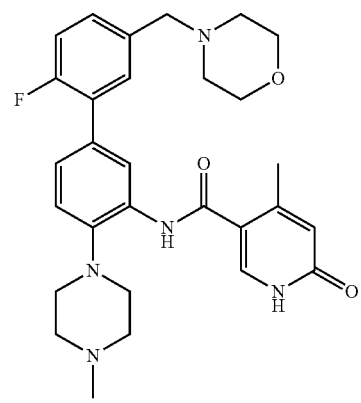

In a 10 mL MW vial a suspension of 4-Methyl-6-oxo-1,6-dihydropyridine-3-carboxylic acid (0.080 g, 0.520 mmol) in pyridine (4.0 mL) was added slowly diethyl chlorophosphate (0.075 mL, 0.520 mmol) at RT in an atmosphere of nitrogen. The reaction mixture was stirred at RT for 2 hours. The suspension turned solution and then suspension again. To this 2'-fluoro-4-(4-methylpiperazin-1-yl)-5'-(morpholinomethyl)-[1,1'-biphenyl]-3-amine (0.040 g, 0.104 mmol) was added and the reaction was heated at 90° C. for 5 hours. After completion, pyridine was removed in vacuo and the residue partitioned between dichloromethane (3 mL) and saturated sodium bicarbonate solution (3 mL). The suspension was stirred for 10 min. The organic layer was separated, dried over anhydrous $Na_2SO_4$. The solvent was evaporated in vacuo yielding the crude product by flash column chromatography on silica gel (0-100%, 89% $CH_2Cl_2$, 10% MeOH, 1% $NH_4Ac/CH_2Cl_2$) to afford the desired compound (11 mg, 20%). $^1$H NMR (500 MHz, MeOD-$d_4$) δ=8.15 (s, 1H), 7.74 (s, 1H), 7.39 (dd, J=2.0, 7.6 Hz, 1H), 7.31-7.19 (m, 3H), 7.05 (dd, J=8.4, 10.5 Hz, 1H), 6.35 (s, 1H), 3.60 (t, J=4.6 Hz, 4H), 3.46 (s, 2H), 2.93 (t, J=4.7 Hz, 4H), 2.58 (br. s., 3H), 2.39 (br. s., 4H), 2.35 (s, 3H), 2.28 (s, 3H); LCMS [M+H]$^+$=520.7 g/mol.

Example 30: N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

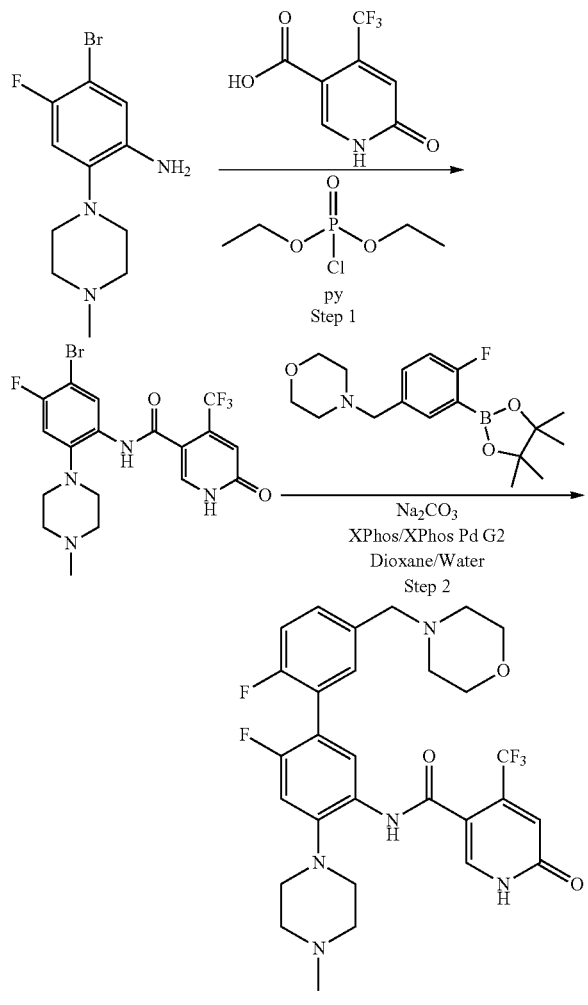

Step 1: N-(5-bromo-4-fluoro-2-(4-methylpiperazin-1-yl)phenyl)-6-oxo-4-(trifluoromethyl)-1,6-dihydropyridine-3-carboxamide

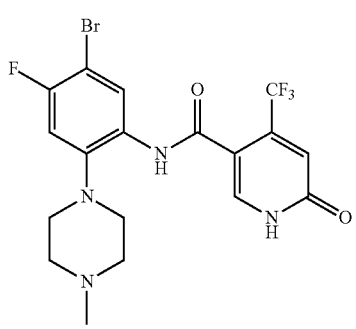 [SMILES: CN1CCN(c2cc(F)c(Br)cc2NC(=O)c2c[nH]c(=O)cc2C(F)(F)F)CC1]

In a 10 mL MW vial a suspension of 6-hydroxy-4-(trifluoromethyl)nicotinic acid (719 mg, 3.47 mmol) in pyridine, anhydrous (4210 µl, 52.1 mmol) was added slowly diethyl chlorophosphate (514 µl, 3.56 mmol) at RT in an atmosphere of nitrogen. The reaction mixture was stirred at RT for 2 h. The suspension turned solution and then suspension again. To this 5-bromo-4-fluoro-2-(4-methylpiperazin-1-yl)aniline (250 mg, 0.868 mmol) was added and the reaction was heated at 70° C. for 3 h. After completion, pyridine was removed in vacuo and the residue partitioned between ethyl acetate (3 mL) and saturated sodium bicarbonate solution (3 mL). The suspension was stirred for 10 min. The organic layer was separated, dried over anhydrous $Na_2SO_4$. The solvent was evaporated in vacuo yielding the crude product by flash column chromatography on silica gel (0-100%, 89% $CH_2Cl_2$, 10% MeOH, 1% $NH_4Ac/CH_2Cl_2$) to afford the desired compound. $^1$H NMR (500 MHz, MeOD) δ 8.12 (d, J=7.4 Hz, 1H), 7.93 (s, 1H), 7.12 (d, J=10.1 Hz, 1H), 6.91 (s, 1H), 2.96 (t, J=4.6 Hz, 4H), 2.64 (s, 4H), 2.36 (s, 3H); LCMS [M+1]$^+$=459.4 g/mol.

Step 2: N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide In a 5 mL microwave vial N-(5-bromo-4-fluoro-2-(4-methylpiperazin-1-yl)phenyl)-6-oxo-4-(trifluoromethyl)-1,6-dihydropyridine-3-carboxamide (29.41 mg, 0.062 mmol), 4-(4-fluoro-3-(4,4,5,5-tetramethyl-1,3,2-dioxaborolan-2-yl)benzyl)morpholine (59.4 mg, 0.185 mmol), sodium carbonate, anhydrous (65.3 mg, 0.616 mmol), XPhos (5.88 mg, 0.012 mmol) and XPhos Pd G2 (9.70 mg, 0.012 mmol) were suspended in 2:1 mixture of 1,4-Dioxane (2 mL)/water (1 mL) to give a white suspension. The suspension was stirred for 5 min, degassed, purged with $N_2$, and microwaved for 60 min at 120° C. After cooling to 23° C., all solvents were removed under reduced pressure. The crude material was purified using by flash column chromatography on silica gel [1-10% MeOH/DCM+0.5% $NH_4OH$] to afford the title compound (30.6 mg, 81%). $^1$H NMR (500 MHz, MeOD) δ 7.95 (s, 1H), 7.85 (d, J=7.6 Hz, 1H), 7.40 (dd, J=9.2, 6.1 Hz, 2H), 7.18-7.14 (m, 1H), 7.09 (d, J=11.2 Hz, 1H), 6.92 (s, 1H), 3.74-3.66 (m, 4H), 3.57 (s, 2H), 3.04 (s, 4H), 2.68 (s, 4H), 2.49 (s, 4H), 2.39 (s, 3H); LCMS [M+1]$^+$=592.7 g/mol.

Example 31: N-(5-(5-fluoro-2-((tetrahydro-2H-pyran-4-yl)oxy)pyridin-4-yl)-2-(4-methylpiperazin-1-yl)phenyl)-6-oxo-4-(trifluoromethyl)-1,6-dihydropyridine-3-carboxamide

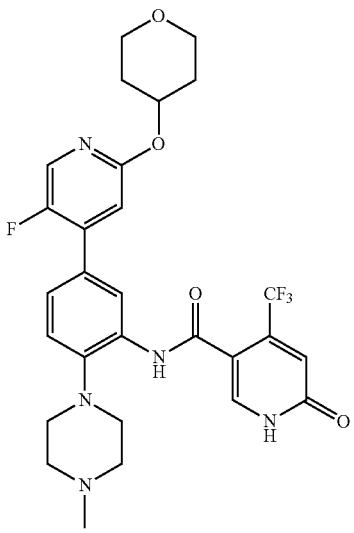 [SMILES: CN1CCN(c2ccc(-c3cc(OC4CCOCC4)ncc3F)cc2NC(=O)c2c[nH]c(=O)cc2C(F)(F)F)CC1]

The title compound (white solid, 28.5 mg, 66%) was prepared according to the sequence described above for the preparation of example 1 using [5-Fluoro-2-(oxan-4-yloxy)pyridin-4-yl]boronic acid (48.3 mg) in place of (5-(((2S,6R)-2,6-dimethylmorpholino)methyl)-2-fluorophenyl)boronic acid. $^1$H NMR (500 MHz, MeOD) δ 8.20 (s, 1H), 8.04 (d, J=2.7 Hz, 1H), 7.98 (s, 1H), 7.49 (dt, J=8.3, 2.2 Hz, 1H), 7.36 (d, J=8.3 Hz, 1H), 6.93 (s, 1H), 6.91 (d, J=5.6 Hz, 1H), 5.22-5.17 (m, 1H), 3.97 (dt, J=9.3, 4.4 Hz, 2H), 3.61 (ddd, J=12.2, 7.7, 3.3 Hz, 2H), 3.04 (t, J=4.9 Hz, 4H), 2.70 (s, 4H), 2.39 (d, J=11.7 Hz, 3H), 2.12-2.04 (m, 2H), 1.81-1.72 (m, 2H); LCMS [M+H]$^+$=576.7 g/mol.

Example 32: N-(5'-(cyclohexylcarbamoyl)-2'-fluoro-4-(4-methylpiperazin-1-yl)-[1,1'-biphenyl]-3-yl)-6-oxo-4-(trifluoromethyl)-1,6-dihydropyridine-3-carboxamide

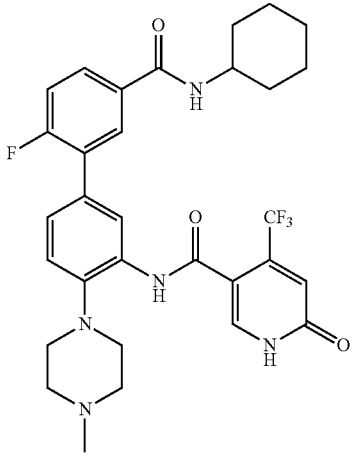 [SMILES: CN1CCN(c2ccc(-c3cc(C(=O)NC4CCCCC4)ccc3F)cc2NC(=O)c2c[nH]c(=O)cc2C(F)(F)F)CC1]

The title compound (white solid, 33.9 mg, 89%) was prepared according to the sequence described above for the preparation of example 1 using [5-fluoro-2-(oxan-4-yloxy)pyridin-4-yl]boronic acid (50.7 mg) in place of (5-(((2S,6R)-2,6-dimethylmorpholino)methyl)-2-fluorophenyl)boronic acid. (89% yield): $^1$H NMR (500 MHz, MeOD) δ 8.18 (s, 1H), 7.98 (s, 1H), 7.97 (dd, J=7.3, 2.7 Hz, 1H), 7.85-7.80 (m, 1H), 7.47-7.42 (m, 1H), 7.36 (d, J=8.6 Hz, 1H), 7.27 (dd, J=10.4, 8.4 Hz, 1H), 6.92 (s, 1H), 3.86 (ddd, J=10.5, 9.3, 3.9 Hz, 1H), 3.03 (t, J=4.9 Hz, 4H), 2.70 (s, 4H), 2.44-2.37 (m, 3H), 2.00-1.93 (m, 2H), 1.85-1.79 (m, 2H), 1.71-1.66 (m, 1H), 1.46-1.32 (m, 4H), 1.23 (dddd, J=16.1, 12.5, 9.9, 6.1 Hz, 1H); LCMS [M+H]$^+$=600.7 g/mol.

Example 33: N-(4'-((cyclopentylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

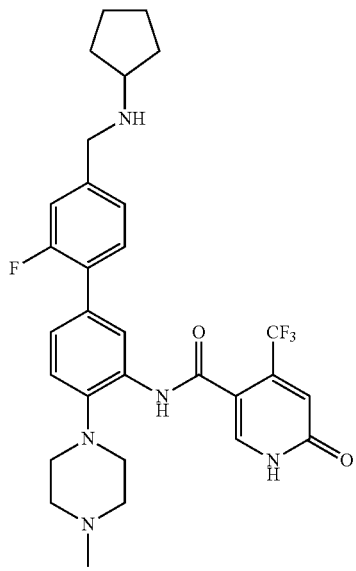

The title compound (white solid, 27.6 mg, 69%) was prepared according to the sequence described above for the preparation of example 1 using 4-(N-cyclopentylaminomethyl)-2-fluorophenylboronic acid, pinacol ester (63.5 mg) in place of (5-(((2S,6R)-2,6-dimethylmorpholino)methyl)-2-fluorophenyl)boronic acid. $^1$H NMR (500 MHz, MeOD) δ 8.18 (s, 1H), 8.03 (s, 1H), 7.53 (t, J=8.2 Hz, 1H), 7.39 (dt, J=8.6, 2.1 Hz, 1H), 7.33 (d, J=8.3 Hz, 1H), 7.32-7.25 (m, 2H), 6.85 (s, 1H), 3.98 (s, 2H), 3.01 (t, J=4.8 Hz, 4H), 2.66 (s, 4H), 2.37 (s, 3H), 2.03 (dt, J=12.5, 7.0 Hz, 2H), 1.82-1.74 (m, 2H), 1.66-1.60 (m, 2H), 1.53 (dt, J=15.4, 7.3 Hz, 2H); LCMS [M+H]$^+$=572.7 g/mol.

Example 34: N-(4'-((cyclohexylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

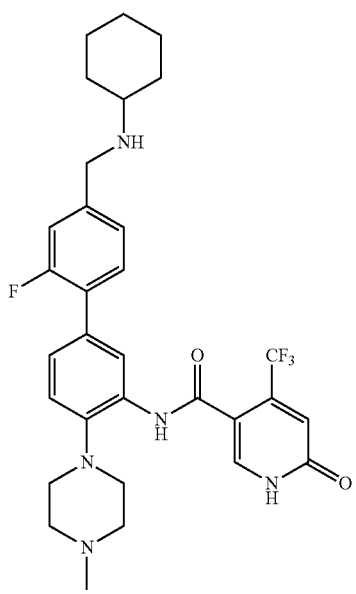 [SMILES: CN1CCN(c2ccc(-c3ccc(CNC4CCCCC4)cc3F)cc2NC(=O)c2c[nH]c(=O)cc2C(F)(F)F)CC1]

The title compound (white solid, 26.8 mg, 66%) was prepared according to the sequence described above for the preparation of example 1 using 4-(N-cyclohexylaminomethyl)-2-fluorophenylboronic acid, pinacol ester (65 mg) in place of (5-(((2S,6R)-2,6-dimethylmorpholino)methyl)-2-fluorophenyl)boronic acid. $^1$H NMR (500 MHz, MeOD) δ 8.18 (s, 1H), 8.04 (s, 1H), 7.52 (t, J=8.2 Hz, 1H), 7.39 (dt, J=8.3, 2.1 Hz, 1H), 7.33 (d, J=8.6 Hz, 1H), 7.30-7.25 (m, 2H), 6.84 (s, 1H), 3.99 (s, 2H), 3.01 (t, J=4.8 Hz, 4H), 2.76-2.71 (m, 1H), 2.66 (d, J=1.7 Hz, 4H), 2.36 (s, 3H), 2.07 (dd, J=12.7, 2.4 Hz, 2H), 1.85-1.80 (m, 2H), 1.68 (dd, J=9.8, 6.8 Hz, 1H), 1.38-1.17 (m, 6H); LCMS [M+H]$^+$=586.6 g/mol.

Example 35: N-(5'-((tert-butylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

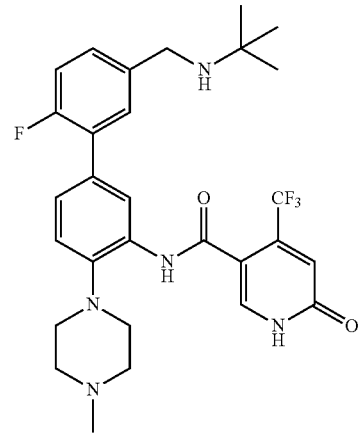 [SMILES: CN1CCN(c2ccc(-c3cc(CNC(C)(C)C)ccc3F)cc2NC(=O)c2c[nH]c(=O)cc2C(F)(F)F)CC1]

The title compound (white solid, 27.4 mg, 71%) was prepared according to the sequence described above for the preparation of example 1 using 5-(t-butylaminomethyl)-2-fluorophenylboronic acid pinacol ester (61.8 mg) in place of (5-(((2S,6R)-2,6-dimethylmorpholino)methyl)-2-fluorophenyl)boronic acid. $^1$H NMR (500 MHz, MeOD) δ 8.23 (s, 1H), 8.12 (s, 1H), 7.61 (dd, J=7.2, 1.8 Hz, 1H), 7.46-7.42 (m, 1H), 7.42-7.39 (m, 1H), 7.34 (d, J=8.3 Hz, 1H), 7.25 (dd, J=10.4, 8.6 Hz, 1H), 6.77 (s, 1H), 4.05 (s, 2H), 3.01 (t, J=4.6 Hz, 4H), 2.66 (s, 4H), 2.36 (s, 3H), 1.37 (s, 9H); LCMS [M+H]$^+$=560.6 g/mol.

Example 36: 4-fluoro-N-(2'-fluoro-4-(4-methylpiperazin-1-yl)-5'-(morpholinomethyl)-[1,1'-biphenyl]-3-yl)-3-methylbenzamide

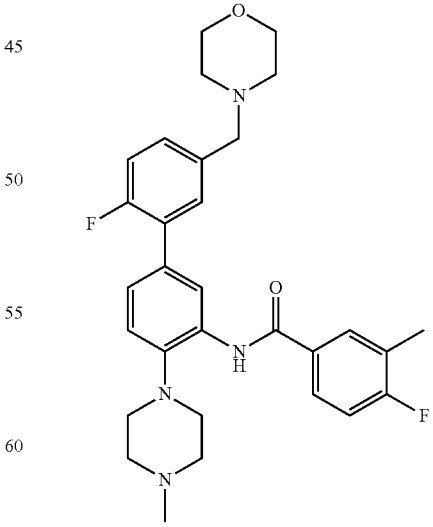

A mixture of 4-fluoro-3-methylbenzoic acid (30.8 mg, 0.2 mmol) in thionyl chloride (0.73 mL) was heated at 60° C. for 10 min, cooled to RT and concentrated to dryness (white solid). 2'-fluoro-4-(4-methylpiperazin-1-yl)-5'-(morpholinomethyl)-[1,1'-biphenyl]-3-amine (38.4 mg, 0.1 mmol) was added, followed by DCM (10 mL) and Et₃N (0.056 mL, 0.4 mmol). The resulting mixture was stirred at RT for 1 hour and heated at 40° C. for 30 min. Additional 4-fluoro-3-methylbenzoic acid (30.8 mg, 0.2 mmol) in thionyl chloride (0.73 mL) was heated at 80° C. for 30 min. After evaporation, a colorless oil was obtained and transferred to the above reaction mixture using 5 mL of DCM. The resulting mixture was stirred overnight at RT. The reaction was then quenched with H₂O (10 mL), basified with sat. NaHCO₃ (pH=8) and extracted with DCM (20 mL×3). The combined extracts were concentrated, purified by flash chromatography (0-20% MeOH/CH₂Cl₂) and triturated with MeOH to give the title compound as a white solid (19.0 mg, 36%). $^1$H NMR (500 MHz, DMSO-d6) δ=9.59 (s, 1H), 8.26 (s, 1H), 7.91 (d, J=6.7 Hz, 1H), 7.85 (br. s., 1H), 7.44-7.24 (m, 6H), 3.58 (br. s., 4H), 3.51 (s, 2H), 2.93 (br. s., 4H), 2.51 (br. s., 4H), 2.42-2.32 (m, 7H), 2.26 (s, 3H); LCMS [M+H]$^+$=521.5 g/mol.

Example 37: N-(2'-fluoro-4-(4-methylpiperazin-1-yl)-5'-(((tetrahydro-2H-pyran-4-yl)amino)methyl)-[,1'-biphenyl]-3-yl)-6-oxo-4-(trifluoromethyl)-1,6-dihydropyridine-3-carboxamide

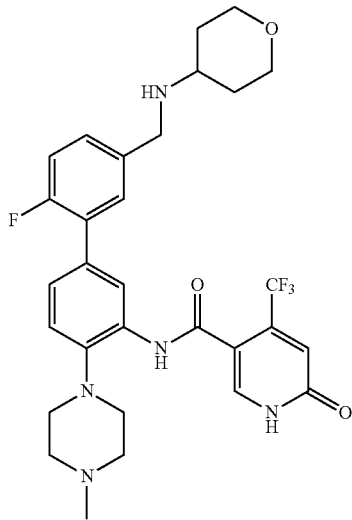

The title compound (white solid, 9.13 mg, 35.6%) was prepared according to the sequence described above for the preparation of example 1 using (2-fluoro-5-(((tetrahydro-2H-pyran-4-yl)amino)methyl)phenyl)boronic acid (32.7 mg) in place of (5-(((2S,6R)-2,6-dimethylmorpholino)methyl)-2-fluorophenyl)boronic acid. 1H NMR (500 MHz, MeOD) δ 8.18 (s, 1H), 8.02 (s, 1H), 7.54 (dd, J=7.5, 2.1 Hz, 1H), 7.41 (dt, J=8.1, 1.7 Hz, 1H), 7.37 (ddd, J=7.8, 4.5, 2.2 Hz, 1H), 7.34 (d, J=8.3 Hz, 1H), 7.18 (dd, J=10.6, 8.4 Hz, 1H), 6.87 (s, 1H), 3.96 (dd, J=11.5, 3.5 Hz, 2H), 3.91 (s, 2H), 3.41 (td, J=11.9, 1.6 Hz, 2H), 3.01 (t, J=4.7 Hz, 4H), 2.90-2.82 (m, 1H), 2.66 (s, 4H), 2.37 (s, 3H), 1.94 (dd, J=12.6, 2.0 Hz, 2H), 1.50 (qd, J=12.4, 4.5 Hz, 2H); LCMS [M+H]$^+$=588.4 g/mol.

Example 38: N-(2'-fluoro-4-(4-methylpiperazin-1-yl)-4'-(morpholinomethyl)-[1,1'-biphenyl]-3-yl)-6-oxo-4-(trifluoromethyl)-1,6-dihydropyridine-3-carboxamide

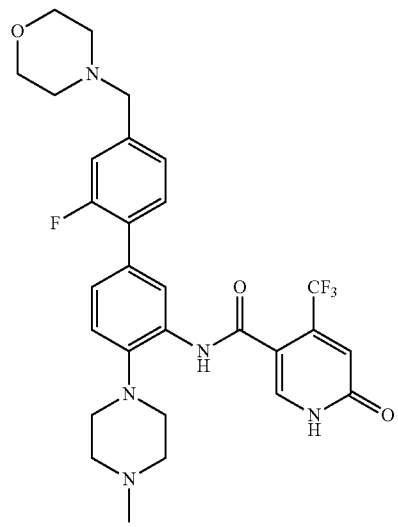 [SMILES: CN1CCN(c2ccc(-c3ccc(CN4CCOCC4)cc3F)cc2NC(=O)c2c[nH]c(=O)cc2C(F)(F)F)CC1]

The title compound (white solid, 30.3 mg, 79%) was prepared according to the sequence described above for the preparation of example 1 using 2-fluoro-4-(morpholinomethyl)phenylboronic acid pinacol ester (63.8 mg) in place of (5-(((2S,6R)-2,6-dimethylmorpholino)methyl)-2-fluorophenyl)boronic acid. $^1$H NMR (500 MHz, MeOD) δ 8.13 (s, 1H), 7.97 (s, 1H), 7.46 (t, J=7.9 Hz, 1H), 7.40 (dt, J=8.3, 2.1 Hz, 1H), 7.33 (d, J=8.3 Hz, 1H), 7.26-7.19 (m, J=14.9, 6.8 Hz, 2H), 6.92 (s, 1H), 3.73-3.70 (m, 4H), 3.57 (s, 2H), 3.03 (t, J=4.9 Hz, 4H), 2.72 (s, 4H), 2.52-2.47 (m, 4H), 2.42 (s, 3H); LCMS [M+H]$^+$=574.4 g/mol.

Example 39: N-(5-(3-fluoro-2-morpholinopyridin-4-yl)-2-(4-methylpiperazin-1-yl)phenyl)-6-oxo-4-(trifluoromethyl)-1,6-dihydropyridine-3-carboxamide

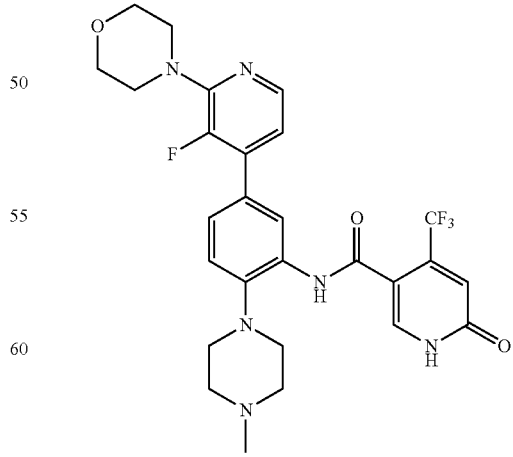

The title compound (white solid, 20.8 mg, 56%) was prepared according to the sequence described above for the preparation of example 1 using 3-fluoro-2-(4-morpholino)pyridine-4-boronic acid pinacol ester (60.0 mg) in place of (5-(((2S,6R)-2,6-dimethylmorpholino)methyl)-2-fluorophenyl)boronic acid. $^1$H NMR (500 MHz, MeOD) δ 8.18 (s, 1H), 8.02 (d, J=5.1 Hz, 1H), 7.98 (s, 1H), 7.46 (dt, J=8.3, 2.1 Hz, 1H), 7.36 (d, J=8.4 Hz, 1H), 7.01 (t, J=5.1 Hz, 1H), 6.93 (s, 1H), 3.86-3.82 (m, 4H), 3.47-3.43 (m, 4H), 3.05 (t, J=4.9 Hz, 4H), 2.75 (s, 4H), 2.44 (s, J=6.8 Hz, 3H); LCMS [M+H]$^+$=561.2 g/mol.

Example 40: N-(5'-((dimethylamino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

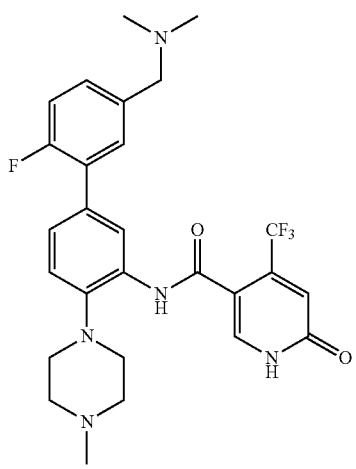 [SMILES: CN(C)Cc1ccc(F)c(-c2ccc(N3CCN(C)CC3)c(NC(=O)c3c[nH]c(=O)cc3C(F)(F)F)c2)c1]

The title compound (white solid, 27.3 mg, 75%) was prepared according to the sequence described above for the preparation of example 1 using 2-fluoro-5-(dimethylaminomethyl)phenylboronic acid pinacol ester (55.7 mg) in place of (5-(((2S,6R)-2,6-dimethylmorpholino)methyl)-2-fluorophenyl)boronic acid. $^1$H NMR (500 MHz, MeOD) δ 8.16 (s, 1H), 7.98 (s, 1H), 7.60 (dd, J=7.4, 2.1 Hz, 1H), 7.45-7.41 (m, 2H), 7.36 (d, J=8.3 Hz, 1H), 7.27 (dd, J=10.4, 8.5 Hz, 1H), 6.93 (s, 1H), 4.03 (s, 2H), 3.05 (t, J=4.6 Hz, 4H), 2.77 (s, 4H), 2.64 (s, 6H), 2.45 (s, 3H); LCMS [M+H]$^+$=532.3 g/mol.

Example 41: 4-fluoro-N-(2'-fluoro-4-(4-methylpiperazin-1-yl)-5'-(morpholinomethyl)-[1,1'-biphenyl]-3-yl)-3-methyl-5-(trifluoromethyl)benzamide

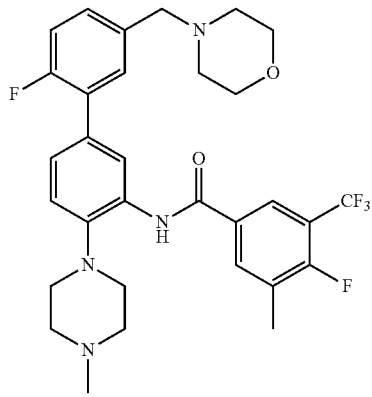 [SMILES: Cc1cc(C(=O)Nc2cc(-c3cc(CN4CCOCC4)ccc3F)ccc2N2CCN(C)CC2)cc(C(F)(F)F)c1F]

To a 50 mL of RBF charged with 4-fluoro-3-methyl-5-(trifluoromethyl)benzoic acid (44.4 mg, 0.2 mmol) was added thionyl chloride (0.73 mL, 10 mmol). The resulting solution was heated at 80° C. for 1 hour. Evaporation of thionyl chloride gave the corresponding benzoyl chloride as a colorless oil. The chloride was redissolved in DCM (10 mL) and Et$_3$N (0.056 mL, 0.4 mmol) was added, followed by 2'-fluoro-4-(4-methylpiperazin-1-yl)-5'-(morpholinomethyl)-[1,1'-biphenyl]-3-amine (38.4 mg, 0.1 mmol). The resulting mixture was stirred overnight at RT. After quenching with 1 M NaHCO$_3$ (10 mL) the suspension was extracted with DCM (20 mL×3). The combined extracts were dried over Na$_2$SO$_4$, evaporated and purified flash chromatography columns (0-100% EtOAc/hex) followed by a secondary purification (0-10% MeOH/DCM) and a cation exchange column eluting with MeOH:NH$_4$OH to give the title compound as a white solid (39.5 mg, 67%). $^1$H NMR (500 MHz, MeOH-d4) δ=8.39 (s, 1H), 8.16 (d, J=6.0 Hz, 1H), 8.11 (d, J=5.7 Hz, 1H), 7.48 (dd, J=2.0, 7.6 Hz, 1H), 7.40-7.32 (m, 3H), 7.15 (dd, J=8.4, 10.6 Hz, 1H), 3.70 (t, J=4.6 Hz, 4H), 3.55 (s, 2H), 3.02 (t, J=4.7 Hz, 4H), 2.68 (br. s., 3H), 2.49 (br. s., 4H), 2.47-2.43 (m, 3H), 2.38 (s, 3H); LCMS [M+H]$^+$=589.3 g/mol.

Example 42: N-(5'-(((4,4-difluorocyclohexyl)amino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

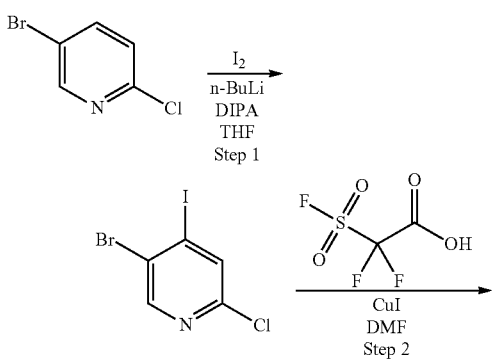

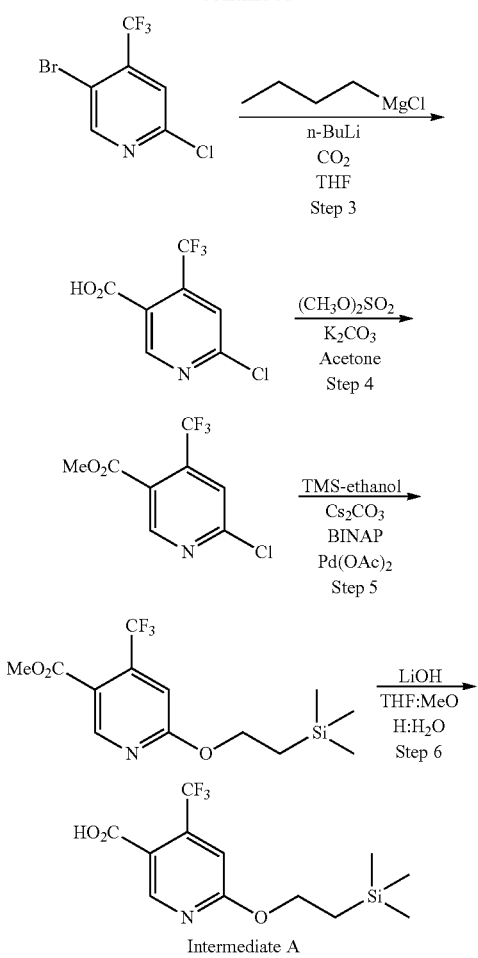

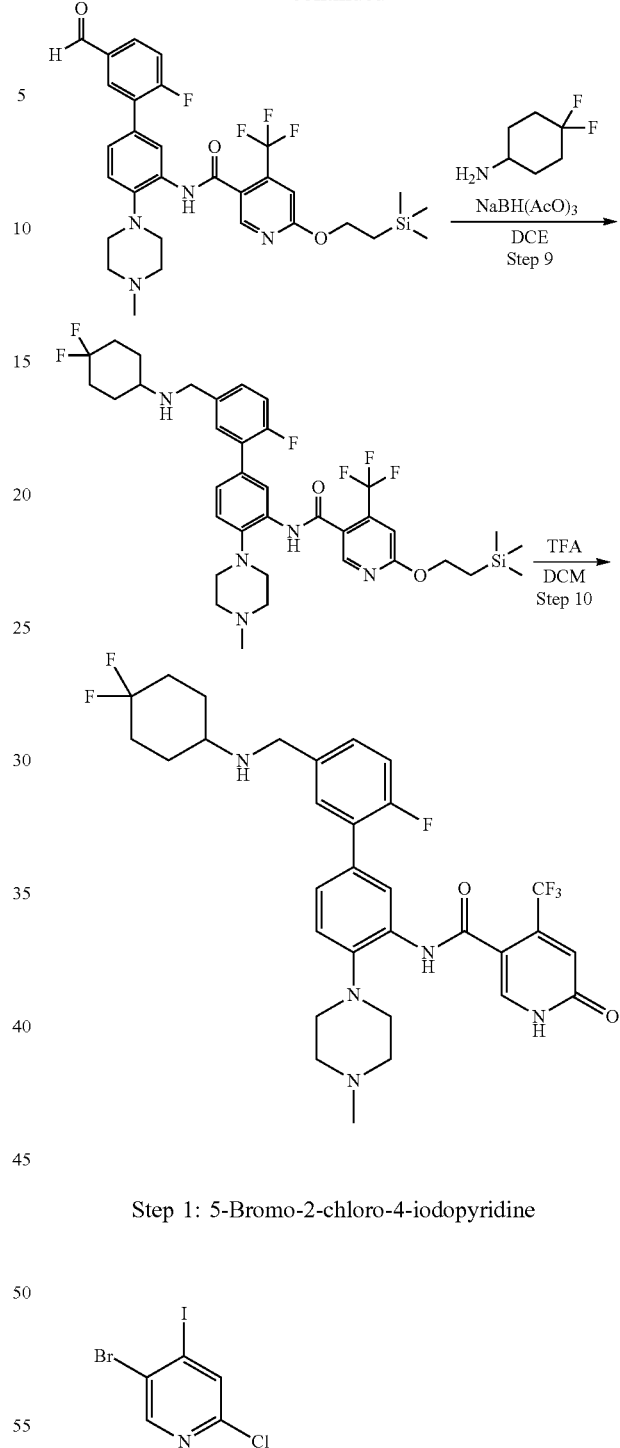

Step 1: 5-Bromo-2-chloro-4-iodopyridine

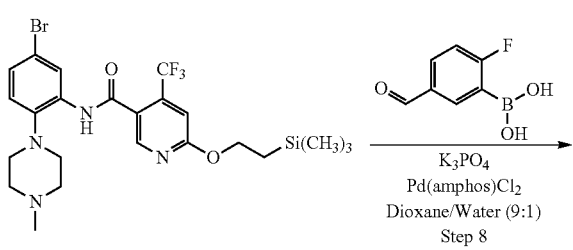

To a stirred solution of DIPA (18 mL, 105.2 mmol) in dry THF (150 mL) was cooled to −78° C. and n-BuLi (42 mL, 105.2 mmol, 2.5 M in THF) was drop wise added under Argon atm. Then, the reaction mixture was stirred for 30 min. at the same temp. Followed by the addition of a solution of 2-chloro-5-bromopyridine (20 g, 105.2 mmol) in dry THF (50 mL) and stirred for 1 hour at the same temp. Then, a solution of iodine (26 g, 105.2 mmol) in THF (80 mL) was added drop wise at −78° C., after completion of addition the reaction mixture was allowed to RT over 16 hours. The reaction mixture was quenched with saturated aqueous solution of sodium thiosulfate (500 mL), extracted with EtOAc (2×500 mL). The combined organic layer was dried over Na₂SO₄ and concentrated under reduced pressure to get crude compound. The crude compound was recrystallized from ethanol (120 mL) to give the title compound (17 g, 51.5%) as an off white solid. LCMS [M+H]⁺=319.9 g/mol.

Step 2: 5-Bromo-2-chloro-4-(trifluoromethyl)pyridine

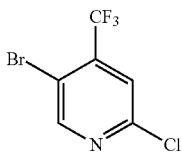 [SMILES: FC(F)(F)c1cc(Cl)ncc1Br]

To a stirred solution of 5-bromo-2-chloro-4-iodopyridine (20.0 g, 63.09 mmol) in DMF (200 mL), methyl 2,2-difluoro-2-(fluorosulfonyl)acetate (16.15 mL, 126.18 mmol) and CuI (24.02 g, 126.18 mmol) were added at RT under argon atmosphere. The reaction mixture was heated to 100° C. for 6 hours. The reaction mixture was diluted with water (200 mL) filtered off and washed with n-pentane (2×500 mL) and cold water (3×1000 mL). The separated organic layer dried over with sodium sulfate and concentrated under reduced pressure at 30° C. to give the crude compound. That was purified by column chromatography (5% pet ether: EtOAc) that resulted in the title compound (9.0 g, 44%) as a liquid compound. TLC: 5% EtOAc in pet ether. LCMS [M+H]⁺=261.0 g/mol.

Step 3: 6-Chloro-4-(trifluoromethyl)nicotinic acid

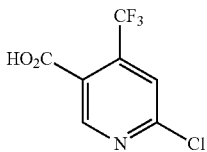 [SMILES: O=C(O)c1cnc(Cl)cc1C(F)(F)F]

To a solution of butyl magnesium chloride (27.8 mL, 47.2 mmol, 1.7 M in THF) in THF was added to n-butyl lithium (30.0 mL, 74.3 mmol, 2.5 M in hexane) at 0° C. and the reaction mixture was stirred for 10 min, then diluted with THF (80 mL) and cooled to −78° C. Then 5-bromo-2-chloro-4-(trifluoromethyl)pyridine (17.5 g, 67.5 mmol) in THF (30 mL) was added and the reaction mixture was stirred for 1 hour at same temperature, before being poured onto crushed dry ice then slowly allowed to RT for 16 hours. The reaction mixture was concentrated, acidified with 2N HCl (80 mL) and extracted with EtOAc (2×500 mL). The organic layer was separated, dried over with sodium sulfate and concentrated under reduced pressure to gave the crude residue. The crude compound was recrystallized from n-pentane (30 mL) and dried on high vacuum to gave the title compound (10 g, 66.6%) as an off white solid compound. LCMS [M+H]⁺=225.9 g/mol.

Step 4: Methyl 6-chloro-4-(trifluoromethyl)nicotinate

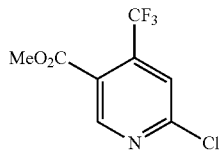 [SMILES: COC(=O)c1cnc(Cl)cc1C(F)(F)F]

To a solution of 6-chloro-4-(trifluoromethyl)nicotinic acid (16.6 g, 75.1 mmol) in acetone (160 mL), potassium carbonate (15.55 g, 112.6 mmol) and dimethylsulphate (8.21 mL, 97.6 mmol) were added at 0° C. The reaction mixture was allowed to warm at RT and was stirred for 2 hours. The reaction mixture was concentrated under reduced pressure to give crude residue. The crude compound was dissolved in EtOAc (500 mL) washed with brine (2×200 mL) and water (2×200 mL). The separated organic layer was dried over Na₂SO₄ and concentrated under reduced pressure. The crude product was purified by column chromatography (0-2% EtOAc/petroleum ether) to afford the title compound (13 g, 72.22%) as a liquid. LCMS [M+H]⁺=240.1 g/mol.

Step 5: Methyl 4-(trifluoromethyl)-6-(2-(trimethylsilyl)ethoxy)nicotinate

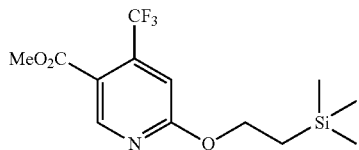 [SMILES: COC(=O)c1cnc(OCC[Si](C)(C)C)cc1C(F)(F)F]

To a suspension of methyl 6-chloro-4-(trifluoromethyl)nicotinate (12.7 g, 53.1 mmol) in toluene (120 mL), TMS-ethanol (4.71 mL, 53.1 mmol), cesium carbonate (51.8 g, 159.4 mmol) and BINAP (3.571 g, 5.3 mmol) were added and the suspension was degassed for 15 min. Pd(OAc)₂ (0.95 g, 4.2 mmol) was added. The reaction mixture was heated to 120° C. for 2 hours. The reaction mixture was diluted with EtOAc (500 mL) filtered through a celite pad and concentrated under reduced pressure. The crude product was purified by column chromatography silica gel (5% EtOAc in pet ether) to afford the title compound (9.0 g, 65%) as a pale yellow color liquid. LCMS [M+H]⁺=294.15 g/mol, as the major fragment.

Step 4-(Trifluoromethyl)-6-(2-(trimethylsilyl)ethoxy)nicotinic acid

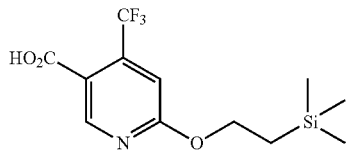 [SMILES: C[Si](C)(C)CCOc1cc(C(F)(F)F)c(C(=O)O)cn1]

To a solution of methyl 4-(trifluoromethyl)-6-(2-(trimethylsilyl)ethoxy)nicotinate (20 g, 62.3 mmol) in THF:MeOH: H₂O (60 mL:40 mL:20 mL), lithium hydroxide mono hydrate (10 g, 249.2 mmol) was added. The reaction mixture was stirred at RT for 16 h. The reaction was concentrated under reduced pressure and the crude was acidified with 2N HCl (20 mL) to obtain a precipitate that was filtered off, washed with diethyl ether (50 mL) and dried on high vacuum to give the title compound (9.2 g, 48.40%) as an off white solid. LCMS [M−H]⁻=306.2 g/mol.

Step 7: N-(5-bromo-2-(4-methylpiperazin-1-yl)phenyl)-4-(trifluoromethyl)-6-(2-(trimethylsilyl)ethoxy)nicotinamide

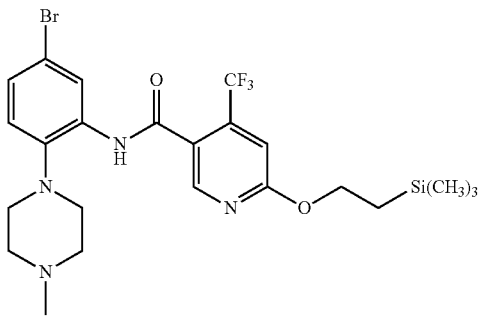

Propylphosphonic anhydride solution (0.881 mL, 1.481 mmol) was added dropwise to a mix of 4-(trifluoromethyl)-6-(2-(trimethylsilyl)ethoxy)nicotinic acid (0.427 mg, 1.388 mmol) and pyridine (0.298 ml, 3.70 mmol) in dry tetrahydrofuran (THF) (9.25 mL) under $N_2$ at RT. After 1.5 hours of stirring a pale yellow solution was obtained. Then 5-bromo-2-(4-methylpiperazin-1-yl)aniline (see example 1, step 2, 0.250 g, 0.925 mmol) was added as a solid and the reaction mixture was heated at 50° C. The crude product was allowed to cool to RT. THF was removed and the residue was partitioned between ethyl acetate (25 mL) and sodium bicarbonate sat solution (25 mL). The organic phase was separated and the aqueous phase was extracted with additional ethyl acetate (25 mL). The organic phase was evaporated in vacuo yielding the crude product that was purified by flash column chromatography on silica gel (0-100%, 89% $CH_2Cl_2$, 10% MeOH, 1% $NH_4Ac/CH_2Cl_2$) to afford the desired compound (283 mg, yield 53%); ¹H NMR (500 MHz, MeOD) δ 8.54 (s, 1H), 8.27 (s, 1H), 7.35 (dd, J=8.6, 2.3 Hz, 1H), 7.20 (d, J=8.6 Hz, 1H), 7.13 (s, 1H), 4.59-4.54 (m, 2H), 2.99 (t, J=4.7 Hz, 4H), 2.75 (s, 4H), 2.43 (s, 3H), 1.22-1.17 (m, 2H), 0.10 (s, 9H); LCMS [M+1]⁺=559.0 g/mol.

Step 8: N-(2'-fluoro-5'-formyl-4-(4-methylpiperazin-1-yl)-[1,1'-biphenyl]-3-yl)-4-(trifluoromethyl)-6-(2-(trimethylsilyl)ethoxy)nicotinamide

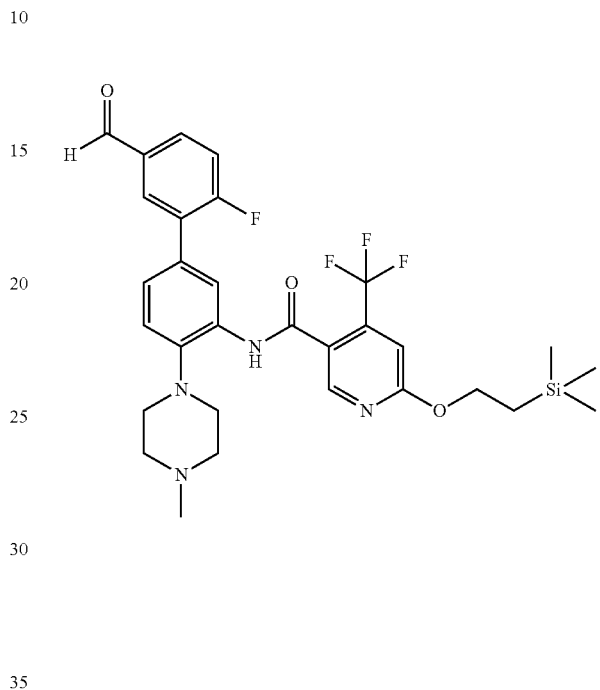

In a 5 mL MW vial N-(5-bromo-2-(4-methylpiperazin-1-yl)phenyl)-4-(trifluoromethyl)-6-(2-(trimethylsilyl)ethoxy) nicotinamide (145 mg, 0.259 mmol), 2-fluoro-5-formylphenylboronic acid (60.9 mg, 0.363 mmol), bis(di-tert-butyl(4-dimethylaminophenyl)phosphine)dichloropalladium(II) (18.35 mg, 0.026 mmol) and potassium phosphate tribasic reagent grade (110 mg, 0.518 mmol) were dissolved in 1,4-dioxane (3 mL)/water (0.4 mL) (9:1 mixture) to give a white suspension. The suspension was stirred for 5 min, degassed, purged with $N_2$, and microwaved for 60 min at 110° C. The solvent was evaporated and 15 mL of $CH_2Cl_2$ were added. The suspension was sonicated and extracted from water (15 mL). The solvent was evaporated in vacuo yielding the crude product that was purified by flash column chromatography on silica gel (0-100%, 89% $CH_2Cl_2$, 10% MeOH, 1% $NH_4Ac/CH_2Cl_2$) to afford the title compound (126 mg, 81%). ¹H NMR (500 MHz, DMSO-d6) δ=9.97 (s, 1H), 9.63 (s, 1H), 8.52 (s, 1H), 8.02 (br. s., 1H), 7.98 (d, J=6.4 Hz, 1H), 7.90 (dt, J=2.4, 5.3 Hz, 1H), 7.53-7.46 (m, 1H), 7.36 (d, J=8.3 Hz, 1H), 7.25 (d, J=8.3 Hz, 1H), 7.15 (s, 1H), 4.43 (t, J=8.2 Hz, 2H), 3.32-3.28 (m, 4H), 2.87 (br. s., 4H), 2.18-2.11 (m, 3H), 1.09-1.05 (m, 2H), 0.04--0.02 (m, 9H); LCMS [M+1]⁺=603.8 g/mol.

165

Step 9: N-(5'-(((4,4-difluorocyclohexyl)amino)methyl)-2'-fluoro-4-(4-methylpiperazin-1-yl)-[1,1'-biphenyl]-3-yl)-4-(trifluoromethyl)-6-(2-(trimethylsilyl)ethoxy)nicotinamide

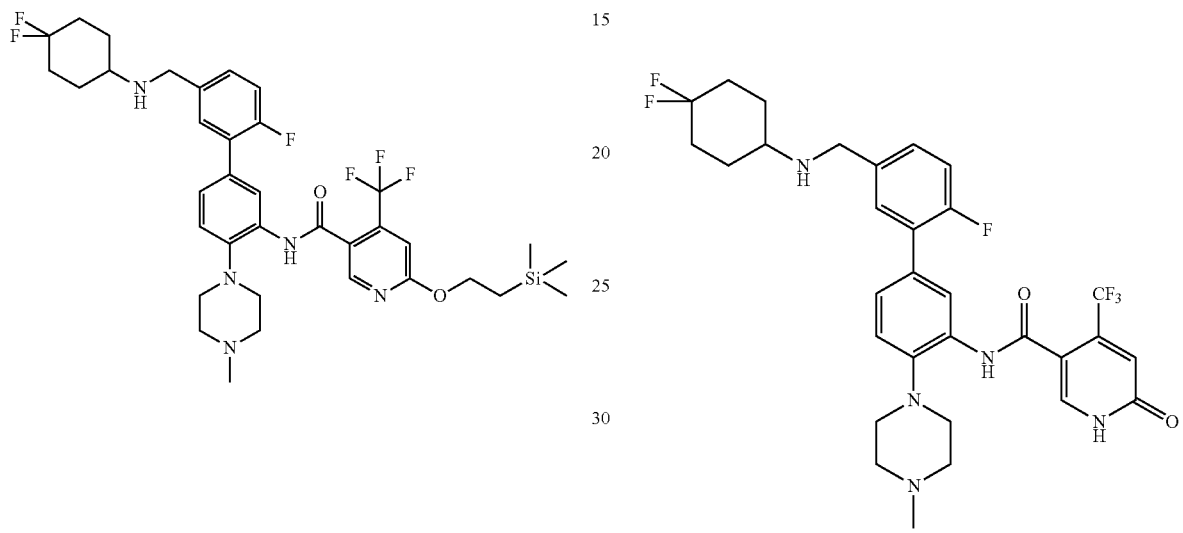

N-(2'-fluoro-5'-formyl-4-(4-methylpiperazin-1-yl)-[1,1'-biphenyl]-3-yl)-4-(trifluoromethyl)-6-(2-(trimethylsilyl)ethoxy)nicotinamide (40 mg, 0.066 mmol), 4,4-difluorocyclohexylamine hydrochloride (11.39 mg, 0.066 mmol) and sodium triacetoxyborohydride (21.10 mg, 0.100 mmol) were mixed in anhydrous DCE (3 mL). The reaction mixture was stirred for 16 hours at RT. Triethylamine (0.019 mL, 0.133 mmol) then was added and stirred at RT for an extra 5 more hours. The reaction mixture was quenched with saturated NH$_4$Cl solution. The organic phase was separated and the aqueous phase was extracted with DCM (2×10 mL), the combined organic phases were washed with NaCl solution, dried over Na$_2$SO$_4$ and concentrated to get the crude product that was purified by flash column chromatography on silica gel (0-100%, 89% CH$_2$Cl$_2$, 10% MeOH, 1% NH$_4$Ac/CH$_2$Cl$_2$) to afford the title compound (35 mg, 78%). $^1$H NMR (500 MHz, MeOD-d4) δ=8.25-8.16 (m, 1H), 8.25-8.16 (m, 1H), 8.21 (s, 1H), 8.03 (s, 1H), 7.71 (dd, J=1.9, 7.2 Hz, 1H), 7.58-7.53 (m, 1H), 7.50 (d, J=8.3 Hz, 1H), 7.42 (d, J=8.3 Hz, 1H), 7.38-7.32 (m, 1H), 6.96 (s, 1H), 4.34 (s, 2H), 3.64 (d, J=10.1 Hz, 2H), 3.44-3.34 (m, 5H), 3.20 (d, J=11.9 Hz, 2H), 2.99 (s, 3H), 2.36-2.28 (m, 2H), 2.31 (d, J=11.7 Hz, 2H), 2.23 (br. s., 2H), 2.07-1.89 (m, 2H), 1.84-1.72 (m, 2H); LCMS [M+1]$^+$=620.3 g/mol.

166

Step 10: N-(5'-(((4,4-difluorocyclohexyl)amino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide N-(5'-(((4,4-difluorocyclohexyl)amino)methyl)-2'-fluoro-4-(4-methylpiperazin-1-yl)-[1,1'-biphenyl]-3-yl)-4-(trifluoromethyl)-6-(2-(trimethylsilyl)ethoxy)nicotinamide (36 mg, 0.050 mmol) was dissolved in 2 mL of dichloromethane and trifluoroacetic acid (104 µL, 1.355 mmol) was added. The purple solution was stirred for 1 hour and the solvent was evaporated. The residue was purified using a cation exchange column eluting with MeOH:NH$_4$OH and freeze dried for 2 days to afford the title compound (35 mg, 78%). $^1$H NMR (500 MHz, MeOD-d$_4$) δ=8.25-8.16 (m, 1H), 8.25-8.16 (m, 1H), 8.21 (s, 1H), 8.03 (s, 1H), 7.71 (dd, J=1.9, 7.2 Hz, 1H), 7.58-7.53 (m, 1H), 7.50 (d, J=8.3 Hz, 1H), 7.42 (d, J=8.3 Hz, 1H), 7.38-7.32 (m, 1H), 6.96 (s, 1H), 4.34 (s, 2H), 3.64 (d, J=10.1 Hz, 2H), 3.44-3.34 (m, 5H), 3.20 (d, J=11.9 Hz, 2H), 2.99 (s, 3H), 2.36-2.28 (m, 2H), 2.31 (d, J=11.7 Hz, 2H), 2.23 (br. s., 2H), 2.07-1.89 (m, 2H), 1.84-1.72 (m, 2H); LCMS [M+H]$^+$=622.1 g/mol.

Example 43: N-(2'-fluoro-5'-((methyl(oxetan-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide

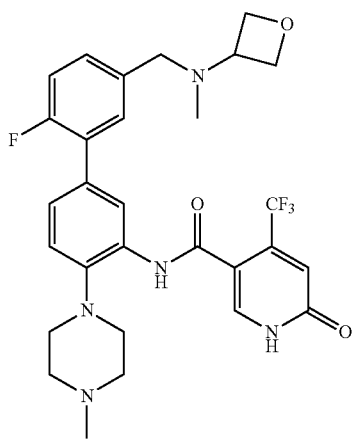 [SMILES: CN1CCN(c2ccc(-c3cc(CN(C)C4COC4)ccc3F)cc2NC(=O)c2c[nH]c(=O)cc2C(F)(F)F)CC1]

The title compound (white solid, 39 mg, 89%) was prepared according to the sequence described above for the preparation of example 42 using N-Methyl-3-oxetanamine (8.24 mg, 0.095 mmol) in place of 4,4-difluorocyclohexylamine hydrochloride. $^1$H NMR (500 MHz, MeOD-d$_4$) δ=8.11 (s, 1H), 7.95 (s, 1H), 7.63 (dd, J=2.0, 7.1 Hz, 1H), 7.51-7.45 (m, 1H), 7.43 (d, J=8.3 Hz, 1H), 7.34 (d, J=8.3 Hz, 1H), 7.29 (dd, J=8.7, 10.1 Hz, 1H), 6.87 (s, 1H), 4.75-4.64 (m, 4H), 4.55-4.47 (m, 1H), 4.29 (s, 2H), 3.56 (d, J=11.1 Hz, 2H), 3.27 (br. s., 2H), 3.24-3.20 (m, 2H), 3.12 (d, J=12.2 Hz, 2H), 2.90 (s, 3H), 2.73 (s, 3H); LCMS [M+H]$^+$=574.3 g/mol.

Example 44: N-(2'-fluoro-4-(4-methylpiperazin-1-yl)-5'-(morpholinomethyl)-[1,1'-biphenyl]-3-yl)-4-hydroxy-2-(trifluoromethyl)benzamide

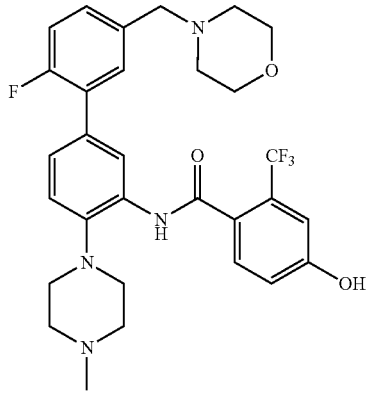 [SMILES: CN1CCN(c2ccc(-c3cc(CN4CCOCC4)ccc3F)cc2NC(=O)c2ccc(O)cc2C(F)(F)F)CC1]

In a 20 mL microwave vial, a mixture of 2'-fluoro-4-(4-methylpiperazin-1-yl)-5'-(morpholinomethyl)-[1,1'-biphenyl]-3-amine (77 mg, 0.2 mmol), 4-hydroxy-2-(trifluoromethyl)benzoic acid (82 mg, 0.4 mmol) and DCC (103 mg, 0.5 mmol) in DCM (5 mL) was heated at 45° C. for 16 hours. Additional 4-hydroxy-2-(trifluoromethyl)benzoic acid (62 mg, 0.3 mmol) and DCC (83 mg, 0.4 mmol) were added and the resulting mixture was stirred at 45° C. for 3 hours. The mixture was evaporated and the crude was purified by flash chromatography (gradient: EtOAc/hex 0-100% then MeOH/DCM 0-20%), and a cation exchange column eluting with MeOH:NH$_4$OH to give the title compound as a white solid (33.9 mg, 29%). $^1$H NMR (500 MHz, CD$_3$OD) δ 8.34 (br. s., 1H), 7.60 (d, J=8.3 Hz, 1H), 7.51 (d, J=7.3 Hz, 1H), 7.42-7.33 (m, 3H), 7.23-7.11 (m, 3H), 3.72 (br. s., 4H), 3.58 (br. s., 2H), 3.02 (br. s., 4H), 2.74-2.44 (m, 8H), 2.35 (s, 3H); LCMS [M+H]$^+$=573.3 g/mol.

Example 45: N-(5'-(((cyclohexylamino)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

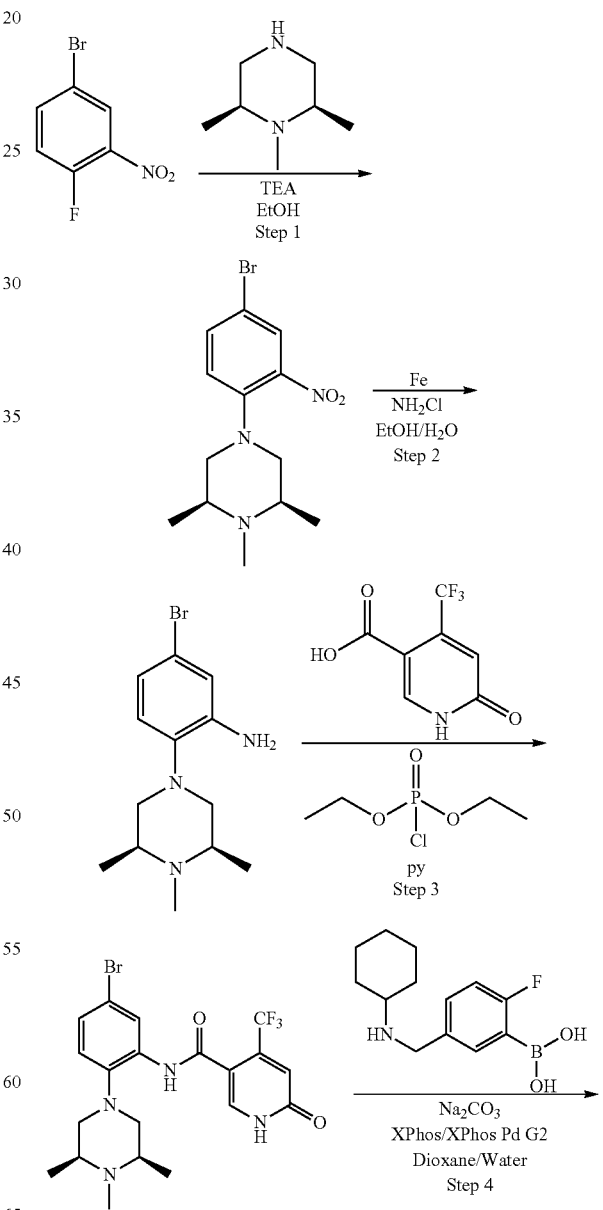

169

-continued

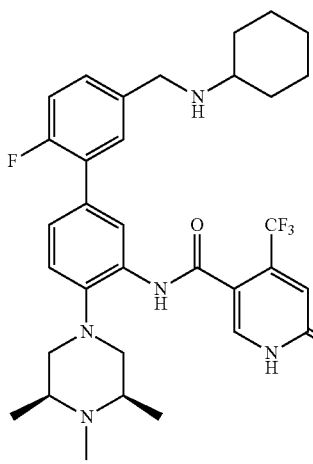

Step 1: (2R,6S)-4-(4-bromo-2-nitrophenyl)-1,2,6-trimethylpiperazine

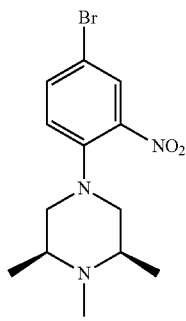 [SMILES: C[C@@H]1CN(c2ccc(Br)cc2[N+](=O)[O-])C[C@H](C)N1C]

To a solution of (2R,6S)-1,2,6-trimethylpiperazine (5.87 g, 45.8 mmol) in ethanol (200 mL) was added TEA (7.65 mL, 54.5 mmol) under argon for 20 mins then followed by addition of compound 4-bromo-1-fluoro-2-nitrobenzene (10 g, 45.8 mmol) at RT under argon atm and heated to 85° C. for 16 hours. Then, the reaction mixture was cooled to RT, the solvent was evaporated under reduced pressure, the crude product was poured on ice-water (300 mL), extracted with EtOAc (2×100 mL). The combined organic layers were dried over Na$_2$SO$_4$ and concentrated under reduced pressure gave crude product. Which was purified by flash column chromatography on silica gel (0-100%, 89% CH$_2$Cl$_2$, 10% MeOH, 1% NH$_4$Ac/CH$_2$Cl$_2$) to afford the title compound (2.5 g, 37.31%) as a pale yellow color liquid.

170

Step 2: 5-bromo-2-((3R,5S)-3,4,5-trimethylpiperazin-1-yl)aniline

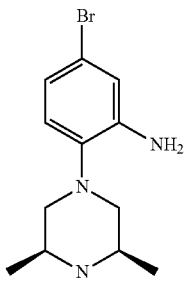

To a solution of (2R,6S)-4-(4-bromo-2-nitrophenyl)-1,2,6-trimethylpiperazine (7 g, 21.4 mmol) in ethanol/water (70:20 mL) was added NH$_4$Cl (9.24 g, 171.2 mmol) followed by iron powder (9.59 g, 171.2 mmol) at RT under argon atm and heated to 80° C. for 16 hours. Then, the reaction mixture was cooled to RT filtered through celite bed washed with methanol, the filtrated was concentrated under reduced pressure to give the crude product. Which was purified by neutral alumina column chromatography using 100% CH$_2$C$_2$ as an eluent to afford the title compound (4.6 g, 72.4%) as an off white solid. LCMS [M+H]$^+$=300.09 g/mol.

Step 3: N-(5-bromo-2-((3S,5R)-3,4,5-trimethylpiperazin-1-yl)phenyl)-6-oxo-4-(trifluoromethyl)-1,6-dihydropyridine-3-carboxamide

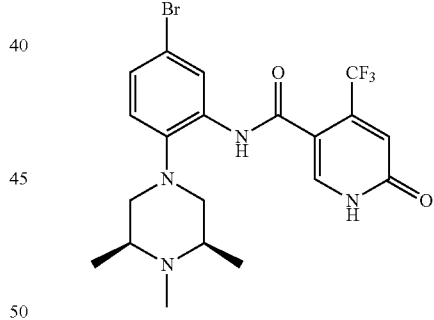

In a 10 mL MW vial a suspension of 6-hydroxy-4-(trifluoromethyl)nicotinic acid (1111 mg, 5.37 mmol) in pyridine, anhydrous (6509 µl, 80 mmol) was added slowly diethyl chlorophosphate (795 µl, 5.50 mmol) at RT in an atmosphere of nitrogen. The reaction mixture was stirred at RT for 2 h. The suspension turned solution and then suspension again. To this 5-bromo-2-((3S,5R)-3,4,5-trimethylpiperazin-1-yl)aniline (400 mg, 1.341 mmol) was added and the reaction was heated at 70° C. for 3 h. After completion, pyridine was removed in vacuo and the residue partitioned between ethyl acetate (3 mL) and saturated sodium bicarbonate solution (3 mL). The suspension was stirred for 10 min. The organic layer was separated, dried over anhydrous Na$_2$SO$_4$. The solvent was evaporated in vacuo yielding the crude product by flash column chromatography on silica gel (0-100%, 89% CH$_2$Cl$_2$, 10% MeOH, 1% NH₄Ac/CH₂Cl₂) to afford the desired compound (537 mg, 80%). ¹H NMR (500 MHz, MeOD) δ 8.19 (d, J=2.3 Hz, 1H), 7.93 (s, 1H), 7.32 (dd, J=8.6, 2.3 Hz, 1H), 7.15 (d, J=8.6 Hz, 1H), 6.90 (s, 1H), 2.93 (d, J=11.3 Hz, 2H), 2.61 (t, J=11.1 Hz, 2H), 2.53 (ddd, J=10.3, 6.2, 3.2 Hz, 2H), 2.37 (s, 3H), 1.15 (d, J=6.2 Hz, 6H); LCMS [M+1]⁺=486.0 g/mol.

Step 4: N-(5'-((cyclohexylamino)methyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

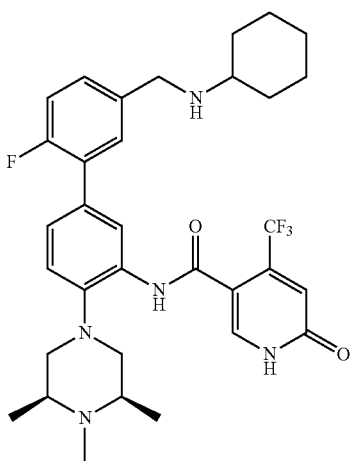 [SMILES: C[C@@H]1CN(c2ccc(-c3cc(CNC4CCCCC4)ccc3F)cc2NC(=O)c2c[nH]c(=O)cc2C(F)(F)F)C[C@H](C)N1C]

In a 5 mL MW vial N-(5-bromo-2-((3S,5R)-3,4,5-trimethylpiperazin-1-yl)phenyl)-6-oxo-4-(trifluoromethyl)-1,6-dihydropyridine-3-carboxamide (30.75 mg, 0.063 mmol), 5-(N-cyclohexylaminomethyl)-2-fluorophenylboronic acid, pinacol ester (63.1 mg, 0.189 mmol), sodium carbonate, anhydrous (66.9 mg, 0.631 mmol), XPhos (6.02 mg, 0.013 mmol) and XPhos Pd G2 (9.93 mg, 0.013 mmol) were dissolved in water (1183 µL) and 1,4-dioxane (1972 µL) to give a white suspension. The suspension was stirred for 5 min, degassed, purged with N₂, and microwaved for 60 min at 120° C. The solvent was evaporated and 15 mL of CH₂Cl₂ were added. The suspension was sonicated and extracted from water. The solvent was evaporated in vacuo yielding the product that was purified by flash column chromatography on silica gel (0-100%, 89% CH₂Cl₂, 10% MeOH, 1% NH₄Ac/CH₂Cl₂) to afford the desired compound (34.6 mg, 88%). ¹H NMR (500 MHz, MeOD) δ 8.17 (s, 1H), 8.06 (s, 1H), 7.59 (dd, J=7.3, 1.9 Hz, 1H), 7.41 (d, J=8.2 Hz, 2H), 7.30 (d, J=8.3 Hz, 1H), 7.22 (dd, J=10.4, 8.5 Hz, 1H), 6.81 (s, 1H), 4.05 (s, 2H), 3.01 (d, J=11.2 Hz, 2H), 2.88-2.80 (m, 1H), 2.66 (t, J=11.2 Hz, 2H), 2.55-2.49 (m, 2H), 2.36 (s, 3H), 2.10 (d, J=11.6 Hz, 2H), 1.84 (d, J=12.9 Hz, 2H), 1.70 (d, J=12.9 Hz, 1H), 1.36-1.25 (m, 5H), 1.16 (d, J=6.2 Hz, 6H); LCMS [M+1]⁺=614.4 g/mol.

Example 46: N-(5'-(cyclohexylcarbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

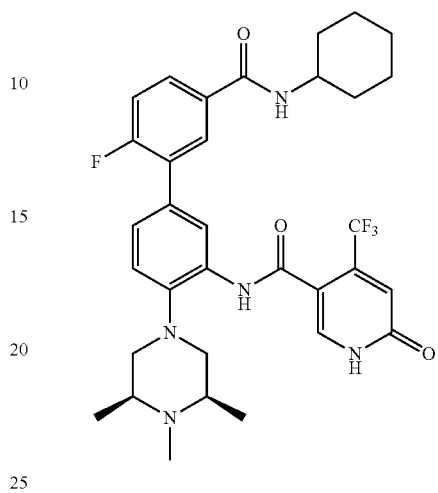

The title compound (white solid, 35.2 mg, 89%) was prepared according to the sequence described above for the preparation of example 45 using 5-(cyclohexylcarbamoyl)-2-fluorophenylboronic acid (49.2 mg) in place of 5-(N-cyclohexylaminomethyl)-2-fluorophenylboronic acid, pinacol ester. ¹H NMR (500 MHz, MeOD) δ 8.16 (s, 1H), 7.97 (s, 1H), 7.96 (dd, J=7.3, 2.7 Hz, 1H), 7.82 (ddd, J=8.6, 4.6, 2.4 Hz, 1H), 7.44 (dt, J=8.3, 2.1 Hz, 1H), 7.33 (d, J=8.3 Hz, 1H), 7.27 (dd, J=10.6, 8.4 Hz, 1H), 6.92 (s, 1H), 3.86 (tt, J=7.8, 4.2 Hz, 1H), 3.05 (dd, J=8.8, 2.4 Hz, 2H), 2.70 (t, J=11.1 Hz, 2H), 2.67-2.60 (m, 2H), 2.43 (s, 3H), 1.96 (dd, J=10.4, 5.5 Hz, 2H), 1.82 (dt, J=13.0, 3.3 Hz, 2H), 1.69 (dt, J=14.2, 3.7 Hz, 1H), 1.48-1.31 (m, 5H), 1.19 (d, J=6.1 Hz, 6H); LCMS [M+H]⁺=628.0 g/mol.

Example 47: N-(2'-fluoro-5'-(morpholine-4-carbonyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

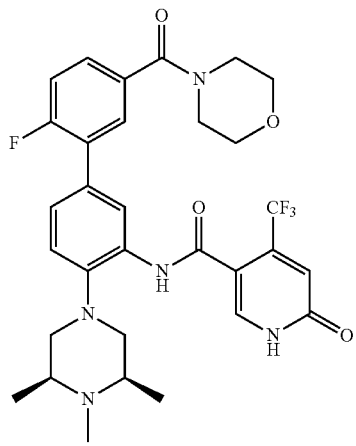 [SMILES: C[C@@H]1CN(c2ccc(-c3cc(C(=O)N4CCOCC4)ccc3F)cc2NC(=O)c2c[nH]c(=O)cc2C(F)(F)F)C[C@H](C)N1C]

The title compound (white solid, 27.4 mg, 66%) was prepared according to the sequence described above for the preparation of example 45 using 2-fluoro-5-(morpholine-4-carbonyl)phenylboronic acid (47.5 mg) in place of 5-(N-cyclohexylaminomethyl)-2-fluorophenylboronic acid, pinacol ester. $^1$H NMR (500 MHz, MeOD) δ 8.14 (s, 1H), 7.96 (s, 1H), 7.60 (dd, J=7.3, 2.4 Hz, 1H), 7.46 (ddd, J=8.6, 4.5, 2.2 Hz, 1H), 7.44-7.41 (m, 1H), 7.33-7.28 (m, 2H), 6.92 (s, 1H), 3.75 (s, 7H), 3.54 (s, 2H), 3.05 (d, J=11.2 Hz, 2H), 2.69 (t, J=11.1 Hz, 2H), 2.63 (d, J=8.8 Hz, 2H), 2.42 (s, 3H), 1.19 (d, J=6.1 Hz, 6H); LCMS [M+H]$^+$ 616.3 g/mol.

Example 48: 2,3-difluoro-N-(2'-fluoro-4-(4-methylpiperazin-1-yl)-5'-(morpholinomethyl)-[1,1'-biphenyl]-3-yl)-5-hydroxybenzamide

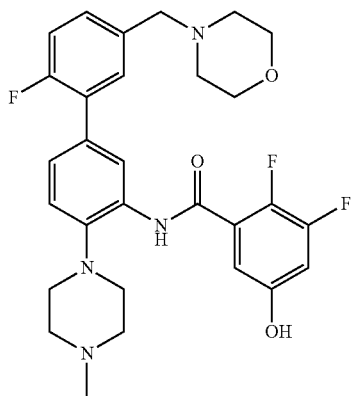 [SMILES: CN1CCN(c2ccc(-c3cc(CN4CCOCC4)ccc3F)cc2NC(=O)c2cc(O)cc(F)c2F)CC1]

A mixture of 2'-fluoro-4-(4-methylpiperazin-1-yl)-5'-(morpholinomethyl)-[1,1'-biphenyl]-3-amine (77 mg, 0.2 mmol), 2,3-difluoro-5-hydroxybenzoic acid (70 mg, 0.4 mmol) and DCC (124 mg, 0.6 mmol) in DCM (5 mL) in a 20 mL microwave vial was sealed and heated at 45° C. overnight (18 hours). Additional 2,3-Difluoro-5-hydroxybenzoic acid (70 mg, 0.4 mmol) and DCC (124 mg, 0.6 mmol) were added and the resulting mixture was heated at 45° C. for another 8 hours. The volatiles were evaporated and the crude was purified by flash column chromatography on silica gel (0-100%, 89% CH$_2$Cl$_2$, 10% MeOH, 1% NH$_4$Ac/CH$_2$Cl$_2$) to give the title compound as a white solid (15.4 mg, 14%). $^1$H NMR (500 MHz, MeOD-d4) δ=8.65 (s, 1H), 7.52 (dd, J=1.9, 7.6 Hz, 1H), 7.46-7.35 (m, 4H), 7.18 (dd, J=8.4, 10.5 Hz, 1H), 6.81 (d, J=8.8 Hz, 1H), 3.73 (t, J=4.6 Hz, 4H), 3.59 (s, 2H), 3.05 (t, J=4.7 Hz, 4H), 2.77 (br. s., 4H), 2.52 (br. s., 4H), 2.45 (s, 3H); LCMS [M+H]$^+$=541.4.

Example 49: 4-(difluoromethyl)-N-(2'-fluoro-4-(4-methylpiperazin-1-yl)-5'-(morpholinomethyl)-[1,1'-biphenyl]-3-yl)-6-oxo-1,6-dihydropyridine-3-carboxamide

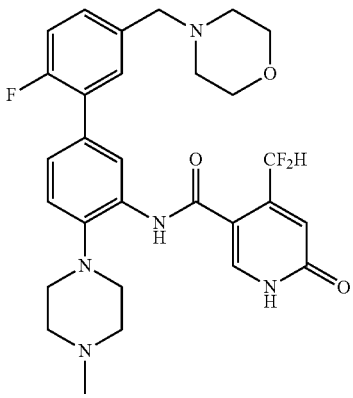 [SMILES: CN1CCN(c2ccc(-c3cc(CN4CCOCC4)ccc3F)cc2NC(=O)c2c[nH]c(=O)cc2C(F)F)CC1]

In a 10 mL MW vial a suspension of 4-(difluoromethyl)-6-hydroxynicotinic acid (59.0 mg, 0.312 mmol) in pyridine, anhydrous (379 μl, 4.68 mmol) was added slowly diethyl chlorophosphate (46.2 μl, 0.320 mmol) at RT in an atmosphere of nitrogen. The reaction mixture was stirred at RT for 2 hours. The suspension turned solution and then suspension again. To this 2'-fluoro-4-(4-methylpiperazin-1-yl)-5'-(morpholinomethyl)-[1,1'-biphenyl]-3-amine (30 mg, 0.078 mmol) was added and the reaction was heated at 70° C. for 3 hours. After completion, pyridine was removed in vacuo and the residue partitioned between ethyl acetate (3 mL) and saturated sodium bicarbonate solution (3 mL). The suspension was stirred for 10 min. The organic layer was separated, dried over anhydrous Na$_2$SO$_4$. The solvent was evaporated in vacuo yielding the crude product by flash column chromatography on silica gel (0-100%, 89% CH$_2$Cl$_2$, 10% MeOH, 1% NH$_4$Ac/CH$_2$Cl$_2$) to afford the desired compound (33 mg, 74%). $^1$H NMR (500 MHz, MeOD) δ 8.08 (s, 1H), 8.04 (s, 1H), 7.48 (dd, J=7.6, 2.0 Hz, 1H), 7.41 (d, J=8.1 Hz, 1H), 7.33 (d, J=8.3 Hz, 1H), 7.33 (ddd, J=8.6, 4.5, 2.2 Hz, 1H), 7.31 (t, J=55.0 Hz, 1H), 7.15 (dd, J=10.6, 8.4 Hz, 1H), 6.82 (s, 1H), 3.71-3.68 (m, 4H), 3.56 (s, 2H), 3.03 (t, J=4.6 Hz, 4H), 2.69 (s, 4H), 2.49 (s, 4H), 2.39 (s, 3H); LCMS [M+H]$^+$ 556.54 g/mol.

Example 50: N-(5-(2-(cyclopropylmethoxy)-5-fluoropyridin-4-yl)-2-((3S,5R)-3,4,5-trimethylpiperazin-1-yl)phenyl)-6-oxo-4-(trifluoromethyl)-1,6-dihydropyridine-3-carboxamide

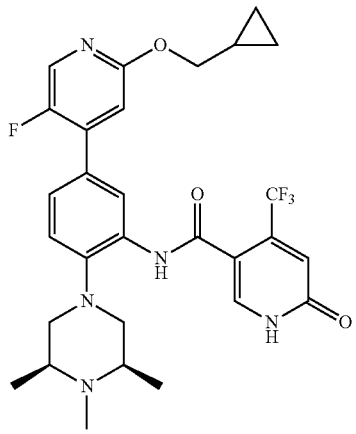 [SMILES: C[C@@H]1CN(c2ccc(-c3cc(OCC4CC4)ncc3F)cc2NC(=O)c2c[nH]c(=O)cc2C(F)(F)F)C[C@H](C)N1C]

The title compound (light brown solid, 25.7 mg, 57%) was prepared according to the sequence described above for the preparation of example 45 using 2-(cyclopropylmethoxy)-5-fluoropyridine-4-boronic acid (24.6 mg, 0.117 mmol) in place of 5-(N-cyclohexylaminomethyl)-2-fluorophenylboronic acid, pinacol ester. $^1$H NMR (500 MHz, MeOD-$d_4$) δ 8.20 (s, 1H), 8.05 (d, J=2.45 Hz, 1H), 7.99 (s, 1H), 7.51 (d, J=8.10 Hz, 1H), 7.35 (d, J=8.44 Hz, 1H), 6.93-6.95 (m, 1H), 6.92 (d, J=5.33 Hz, 1H), 4.14 (d, J=7.09 Hz, 2H), 3.10 (d, J=11.13 Hz, 2H), 2.62-2.75 (m, 4H), 2.45 (s, 3H), 1.26-1.34 (m, 1H), 1.21 (d, J=5.99 Hz, 6H), 0.57-0.67 (m, 2H), 0.35-0.40 (m, 2H); LCMS [M+H]$^+$=574.2 g/mol.

Example 51: (S)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide

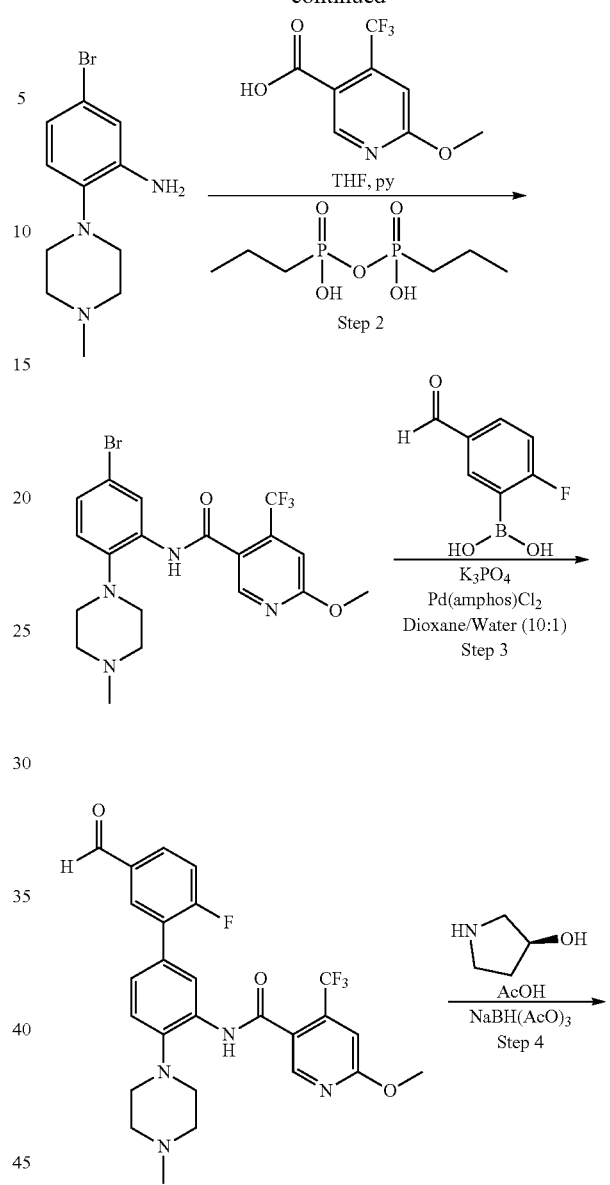

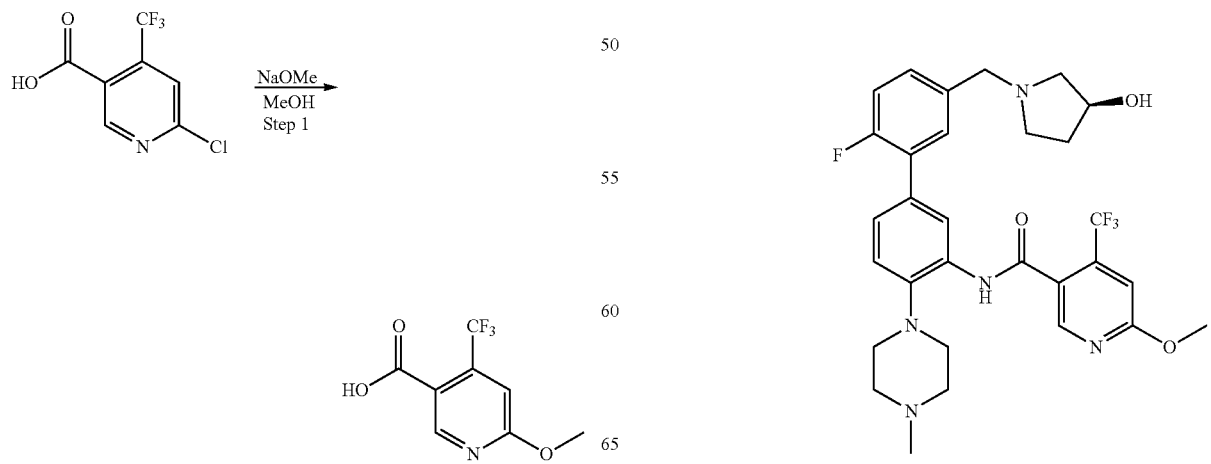

Step 1: 6-Methoxy-4-(trifluoromethyl)nicotinic acid

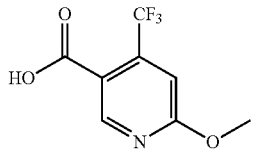

In an RBF a mixture of 6-chloro-4-(trifluoromethyl)nicotinic acid (1 g, 4.43 mmol), sodium methoxide (95%, powder) (3.78 g, 66.5 mmol) in methanol (10 mL) was refluxed (75° C.) under $N_2$. The reaction was cooled to RT after 5 hours, quenched with saturated citric acid solution and extracted with EtOAc (4×10 mL). The combined organic phases were dried over $Na_2SO_4$ and concentrated to get the title compound as a white solid. (1.003 g, 97%). $^1$H NMR (500 MHz, DMSO-d6) δ=8.48 (s, 1H), 7.02 (s, 1H), 3.96 (s, 3H); LCMS [M+H]$^+$=222.5 g/mol.

Step 2: N-(5-bromo-2-(4-methylpiperazin-1-yl)phenyl)-6-methoxy-4 (trifluoromethyl)nicotinamide

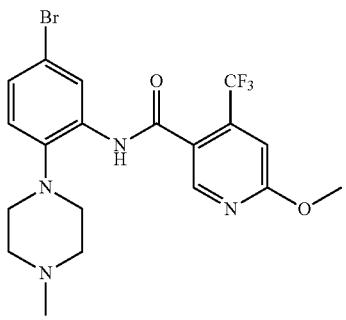 [SMILES: COc1cc(C(F)(F)F)c(C(=O)Nc2cc(Br)ccc2N2CCN(C)CC2)cn1]

Propylphosphonic anhydride solution (4.04 ml, 6.78 mmol) was added dropwise to a mixture of 5-bromo-2-(4-methylpiperazin-1-yl)aniline (764 mg, 2.83 mmol) and 6-methoxy-4-(trifluoromethyl)nicotinic acid (500 mg, 2.261 mmol) in dry THF (30 mL). Then pyridine (0.674 mL, 8.37 mmol) was added and the suspension was heated at 50° C. for 16 hours. The reaction mixture was allowed to cool to RT, the volatiles were evaporated and the residue was dissolved in dichloromethane (30 mL) and water (30 mL). The organic phase was separated, the aqueous phase was extracted with dichloromethane (3×10 mL) and the combined organic phases were washed with 1N NaOH solution (aq), dried over $Na_2SO_4$ and concentrated to get the desired product as a light brown solid (714 mg, 67%). $^1$H NMR (500 MHz, MeOD-d$_4$) δ=8.50-8.41 (m, 1H), 8.17 (d, J=1.6 Hz, 1H), 7.27-7.21 (m, 1H), 7.14-7.06 (m, 2H), 3.98-3.94 (m, 1H), 3.98-3.94 (m, 3H), 2.84 (t, J=4.7 Hz, 4H), 2.65-2.39 (m, 4H), 2.22 (s, 3H). LCMS [M+H]$^+$=473.6 g/mol.

Step 3: N-(2'-fluoro-5'-formyl-4-(4-methylpiperazin-1-yl)-[1,1'-biphenyl]-3-yl)-6-methoxy-4-(trifluoromethyl)nicotinamide

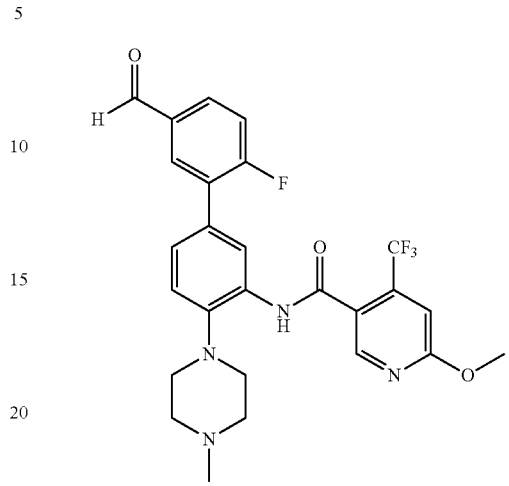

N-(5-bromo-2-(4-methylpiperazin-1-yl)phenyl)-6-methoxy-4-(trifluoromethyl)nicotinamide (400 mg, 0.845 mmol) and 2-fluoro-5-formylphenylboronic acid (199 mg, 1.183 mmol) were mixed in 1,4-doxane (9 mL). Potassium phosphate tribasic reagent grade (359 mg, 1.690 mmol) was added as a solution in water (3 mL). The vial was flushed with $N_2$, then bis(di-tert-butyl(4-dimethylaminophenyl)phosphine)dichloropalladium(II) (59.8 mg, 0.085 mmol) was added, the vial was sealed, and the mixture was heated in a microwave reactor to 110° C. for 30 minutes. The crude mixture was concentrated onto celite and purified by flash column chromatography on silica gel (0-100%, 89% $CH_2Cl_2$, 10% MeOH, 1% $NH_4Ac/CH_2Cl_2$) to afford the title compound (337 mg, 71%) as a pale yellow foam. $^1$H NMR (500 MHz, MeODL-d4) δ=10.08-9.99 (m, 1H), 8.65-8.56 (m, 1H), 8.34-8.23 (m, 1H), 8.18-8.10 (m, 1H), 7.98 (ddd, J=2.0, 4.8, 8.3 Hz, 1H), 7.50-7.40 (m, 3H), 7.24 (s, 1H), 4.08 (s, 3H), 3.07 (t, J=4.6 Hz, 4H), 2.68 (br. s., 4H), 2.38 (s, 3H); LCMS [M+H]$^+$=517.3 g/mol.

Step 4: (R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide

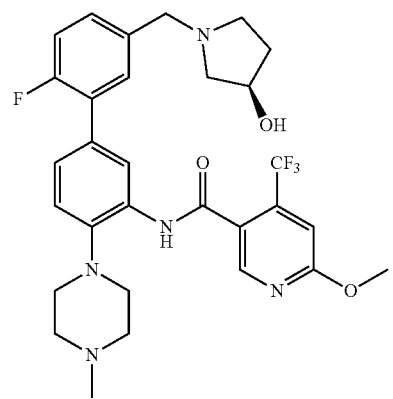 [SMILES: COc1cc(C(F)(F)F)c(C(=O)Nc2cc(-c3cc(CN4CC[C@@H](O)C4)ccc3F)ccc2N2CCN(C)CC2)cn1]

N-(2'-fluoro-5'-formyl-4-(4-methylpiperazin-1-yl)-[1,1'-biphenyl]-3-yl)-6-methoxy-4-(trifluoromethyl)nicotinamide (30 mg, 0.058 mmol), (R)-3-pyrrolidinol (10.12 mg, 0.116 mmol) and acetic acid, glacial, 99.8% (0.013 ml, 0.232 mmol) were mixed in anhydrous dichloroethane. A cloudy solution was obtained. After 10 min, sodium triacetoxyborohydride (36.9 mg, 0.174 mmol) was added and the reaction mixture was stirred at RT for 30 min. The reaction mixture was quenched with saturated aqueous NaHCO$_3$ solution. The organic phase was separated, the aqueous phase was extracted with dichloromethane (×2) and the combined organic phases were washed with brine, dried over Na$_2$SO$_4$ and concentrated to get the crude. It was purified on reverse phase column (0-50%, water/acetonitrile). The title compound was isolated as a pale yellow solid (28.5 mg, 79%). $^1$H NMR (500 MHz, MeOD-d4) δ 8.49 (s, 1H), 8.13 (br. s., 1H), 7.41 (d, J=7.09 Hz, 1H), 7.30-7.35 (m, 1H), 7.25 (d, J=8.19 Hz, 2H), 7.12 (s, 1H), 7.03-7.09 (m, 1H), 4.26 (d, J=6.85 Hz, 1H), 3.97 (s, 3H), 3.59-3.68 (m, 2H), 2.93 (t, J=4.28 Hz, 4H), 2.68-2.79 (m, 2H), 2.42-2.61 (m, 6H), 2.25 (s, 3H), 2.02-2.12 (m, 1H), 1.64 (dd, J=5.07, 8.25 Hz, 1H); LCMS [M+H]$^+$=588.44 g/mol.

Example 52: N-(2'-fluoro-4-(4-methylpiperazin-1-yl)-5'-((4-morpholinopiperidin-1-yl)methyl)-[,1'-biphenyl]-3-yl)-6-methoxy-4-(trifluoromethyl)nicotinamide

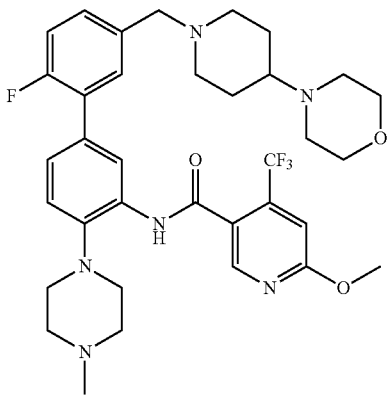 [SMILES: COc1cc(C(F)(F)F)c(C(=O)Nc2cc(-c3cc(CN4CCC(N5CCOCC5)CC4)ccc3F)ccc2N2CCN(C)CC2)cn1]

The title compound (white solid, 28.5 mg, 70%) was prepared according to the sequence described above for the preparation of example 51 using 4-Morpholinopiperidine 98% (19.78 mg, 0.116 mmol) in place of (R)-3-pyrrolidinol. $^1$H NMR (500 MHz, MeOD-d4) δ 8.49 (s, 1H), 8.13 (s, 1H), 7.39 (d, J=6.72 Hz, 1H), 7.30-7.34 (m, 1H), 7.25 (d, J=8.44 Hz, 1H), 7.21-7.21 (m, 1H), 7.20-7.23 (m, 1H), 7.12 (s, 1H), 7.03-7.09 (m, 1H), 6.99-6.99 (m, 1H), 3.96 (s, 3H), 3.58 (t, J=4.46 Hz, 4H), 3.47 (s, 2H), 2.89-2.95 (m, 6H), 2.54 (br. s., 4H), 2.47 (br. s., 4H), 2.25 (s, 3H), 2.08-2.14 (m, 1H), 1.98 (t, J=11.49 Hz, 2H), 1.81 (d, J=12.10 Hz, 2H), 1.42-1.50 (m, 2H); LCMS [M+H]$^+$ 671.4 g/mol.

Example 53: (R)—N-(2'-fluoro-5'-((3-isopropylpyrrolidin-1-yl)methyl)-4-(4-methylpiperazin-1-yl)-[1,1'-biphenyl]-3-yl)-6-methoxy-4-(trifluoromethyl)nicotinamide

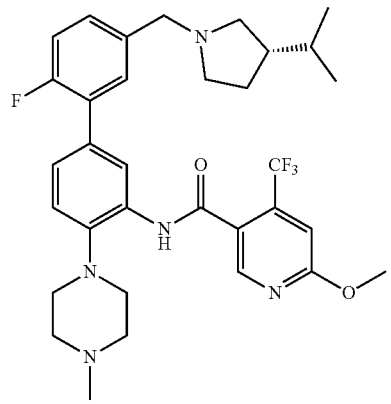 [SMILES: COc1cc(C(F)(F)F)c(C(=O)Nc2cc(-c3cc(CN4CC[C@@H](C(C)C)C4)ccc3F)ccc2N2CCN(C)CC2)cn1]

The title compound (white solid, 52%) was prepared according to the sequence described above for the preparation of example 51 using (3R)-(+)-3-(dimethylamino)pyrrolidine (13.27 mg, 0.116 mmol) in place of (R)-3-pyrrolidinol. $^1$H NMR (500 MHz, MeOD-d4) δ 8.48 (s, 1H), 8.13 (s, 1H), 7.37-7.43 (m, 1H), 7.32 (d, J=8.31 Hz, 1H), 7.21-7.27 (m, 2H), 7.10-7.13 (m, 1H), 7.05 (dd, J=8.62, 10.33 Hz, 1H), 3.96 (s, 3H), 3.54-3.65 (m, 2H), 2.83-3.03 (m, 6H), 2.76-2.81 (m, 1H), 2.47-2.71 (m, 6H), 2.36 (dd, J=7.15, 9.35 Hz, 1H), 2.25 (s, 3H), 2.17-2.24 (m, 6H), 1.92-2.02 (m, 1H), 1.65-1.74 (m, 1H); LCMS [M+H]$^+$=615.6 g/mol.

Example 54: N-(5'-((4-acetylpiperazin-1-yl)methyl)-2'-fluoro-4-(4-methylpiperazin-1-yl)-[1,1'-biphenyl]-3-yl)-6-methoxy-4-(trifluoromethyl)nicotinamide

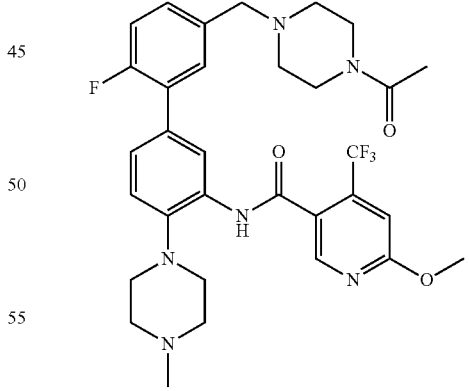

The title compound (white solid, 29 mg, 75%) was prepared according to the sequence described above for the preparation of example 51 using 1-Acetylpiperazine (14.89 mg, 0.116 mmol) in place of (R)-3-pyrrolidinol. $^1$H NMR (500 MHz, MeOD-d4) δ 8.45-8.50 (m, 1H), 8.10-8.18 (m, 1H), 7.41 (d, J=7.21 Hz, 1H), 7.29-7.34 (m, 1H), 7.21-7.27 (m, 2H), 7.10-7.13 (m, 1H), 7.03-7.08 (m, 1H), 3.96 (s, 3H), 3.48-3.52 (m, 4H), 3.43-3.47 (m, 2H), 2.93 (t, J=4.46 Hz, 4H), 2.55 (br. s., 4H), 2.39-2.43 (m, 2H), 2.36 (t, J=4.89 Hz, 2H), 2.26 (s, 3H), 1.98 (s, 3H); LCMS [M+H]+=629.45 g/mol.

Example 55: N-(2'-fluoro-5'-((4-fluoropiperidin-1-yl)methyl)-4-(4-methylpiperazin-1-yl)-[1,1'-biphenyl]-3-yl)-6-methoxy-4-(trifluoromethyl)nicotinamide

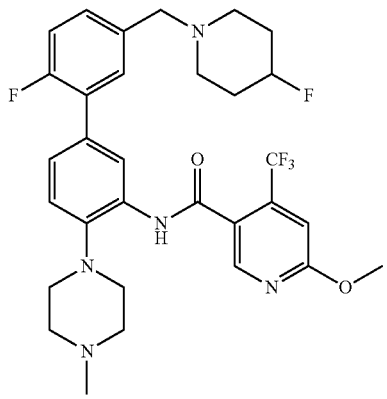 [SMILES: COc1cc(C(F)(F)F)c(C(=O)Nc2cc(-c3cc(CN4CCC(F)CC4)ccc3F)ccc2N2CCN(C)CC2)cn1]

The title compound (white solid, 23 mg, 62%) was prepared according to the sequence described above for the preparation of example 51 using 4-fluoropiperidine hydrochloride (16.22 mg, 0.116 mmol).in place of (R)-3-pyrrolidinol. $^1$H NMR (500 MHz, MeODL-d4) δ 8.48 (s, 1H), 8.13 (s, 1H), 7.40 (d, J=6.97 Hz, 1H), 7.30-7.35 (m, 1H), 7.21-7.27 (m, 2H), 7.12 (s, 1H), 7.06 (dd, J=8.56, 10.39 Hz, 1H), 4.48-4.65 (m, 1H), 3.96 (s, 3H), 3.49 (s, 2H), 2.93 (t, J=4.46 Hz, 4H), 2.55 (br. s., 6H), 2.36 (br. s., 2H), 2.26 (s, 3H), 1.72-1.88 (m, 4H); LCMS [M+H]+=604.4 g/mol.

Example 56: N-(5'-(3-oxa-6-azabicyclo[3.1.1]heptan-6-ylmethyl)-2'-fluoro-4-(4-methylpiperazin-1-yl)-[1,1'-biphenyl]-3-yl)-6-methoxy-4-(trifluoromethyl)nicotinamide

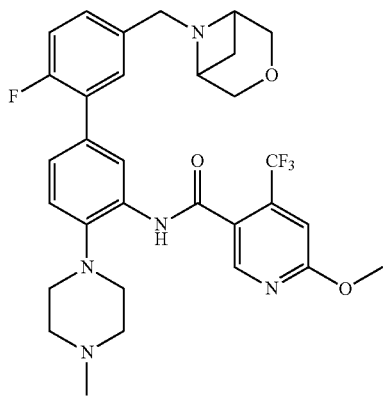 [SMILES: COc1cc(C(F)(F)F)c(C(=O)Nc2cc(-c3cc(CN4C5COCC4C5)ccc3F)ccc2N2CCN(C)CC2)cn1]

The title compound (white solid, 13 mg, 36%) was prepared according to the sequence described above for the preparation of example 51 using 3-oxa-6-aza-bicyclo[3.1.1] heptane (11.52 mg, 0.116 mmol) in place of (R)-3-pyrrolidinol. $^1$H NMR (500 MHz, MeOD-d4) δ 8.48 (s, 1H), 8.12 (br. s., 1H), 7.44 (d, J=6.97 Hz, 1H), 7.32 (d, J=8.07 Hz, 1H), 7.21-7.30 (m, 2H), 7.12 (s, 1H), 7.03-7.10 (m, 1H), 4.26 (d, J=11.13 Hz, 2H), 3.96 (s, 3H), 3.88 (br. s., 2H), 3.70 (d, J=11.00 Hz, 2H), 3.48 (d, J=5.62 Hz, 2H), 2.94 (d, J=4.28 Hz, 4H), 2.40-2.82 (m, 6H), 2.26 (s, 3H); LCMS [M+H]+ 600.5 g/mol.

Example 57: (R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide

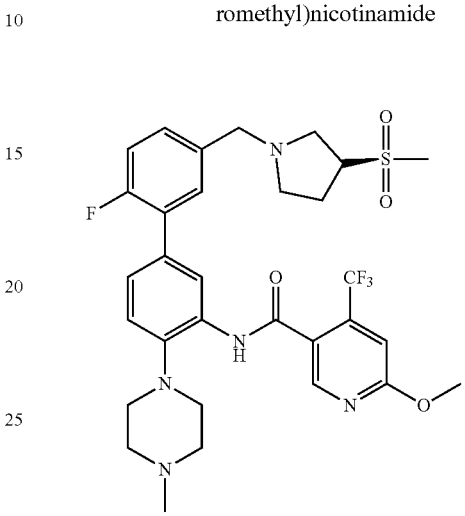

The title compound (white solid, 28 mg, 71%) was prepared according to the sequence described above for the preparation of example 51 using (R)-3-(methylsulfonyl) pyrrolidine (17.33 mg, 0.116 mmol) in place of (R)-3-pyrrolidinol. $^1$H NMR (500 MHz, MeOD-d4) δ 8.45-8.53 (m, 1H), 8.13 (s, 1H), 7.41 (d, J=7.09 Hz, 1H), 7.32 (d, J=8.31 Hz, 1H), 7.24 (d, J=8.19 Hz, 2H), 7.11 (s, 1H), 7.03-7.08 (m, 1H), 3.96 (s, 3H), 3.57-3.69 (m, 3H), 2.93 (t, J=4.28 Hz, 4H), 2.84-2.89 (m, 2H), 2.83 (s, 3H), 2.49-2.72 (m, 6H), 2.26 (s, 3H), 2.15 (q, J=6.85 Hz, 2H); LCMS [M+H]+=650.4 g/mol.

Example 58: (S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide

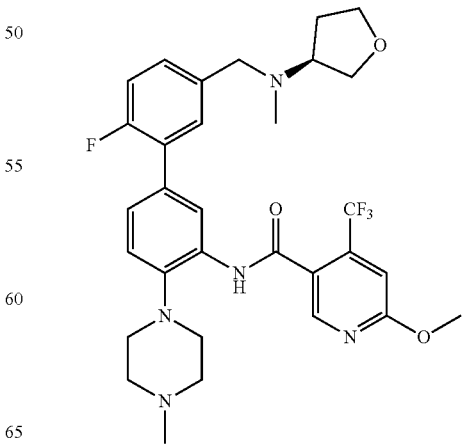

The title compound (white solid, 22 mg, 60%) was prepared according to the sequence described above for the preparation of example 51 using (S)-methyl-(tetrahydrofuran-3-yl)-amine hydrochloride (15.99 mg, 0.116 mmol) in place of (R)-3-pyrrolidinol. $^1$H NMR (500 MHz, MeOD-d4) δ 8.60 (s, 1H), 8.25 (br. s., 1H), 7.50 (d, J=6.97 Hz, 1H), 7.44 (d, J=8.31 Hz, 1H), 7.37 (d, J=8.44 Hz, 2H), 7.23 (s, 1H), 7.16-7.21 (m, 1H), 4.08 (s, 3H), 3.99 (dt, J=4.16, 8.50 Hz, 1H), 3.89 (t, J=7.89 Hz, 1H), 3.75-3.81 (m, 2H), 3.64-3.69 (m, 1H), 3.54-3.59 (m, 1H), 3.25-3.31 (m, 1H), 3.06 (br. s., 4H), 2.69 (br. s., 4H), 2.39 (s, 3H), 2.21 (s, 3H), 2.12-2.19 (m, 1H), 1.96-2.03 (m, 1H); LCMS [M+H]$^+$=602.5 g/mol.

Example 59: N-(5'-((2,2-dimethylmorpholino)methyl)-2'-fluoro-4-(4-methylpiperazin-1-yl)-[1,1'-biphenyl]-3-yl)-6-methoxy-4-(trifluoromethyl)nicotinamide

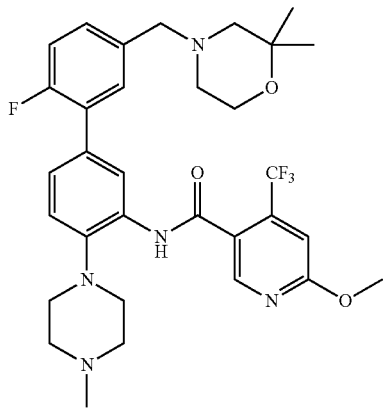 [SMILES: COc1cc(C(F)(F)F)c(C(=O)Nc2cc(-c3cc(CN4CCOC(C)(C)C4)ccc3F)ccc2N2CCN(C)CC2)cn1]

The title compound (white solid, 27.5 mg, 73%) was prepared according to the sequence described above for the preparation of example 51 using 2,2-dimethylmorpholine (6.69 mg, 0.058 mmol) in place of (R)-3-pyrrolidinol. $^1$H NMR (500 MHz, MeOD-d4) δ 8.48 (s, 1H), 8.12 (s, 1H), 7.40 (d, J=7.09 Hz, 1H), 7.29-7.34 (m, 1H), 7.20-7.27 (m, 2H), 7.11 (s, 1H), 7.00-7.07 (m, 1H), 3.96 (s, 3H), 3.65 (t, J=4.71 Hz, 2H), 3.40 (s, 2H), 2.93 (t, J=4.46 Hz, 4H), 2.55 (br. s., 4H), 2.32 (br. s., 2H), 2.26 (s, 3H), 2.14 (s, 2H), 1.14 (s, 6H); LCMS [M+H]$^+$=616.50 g/mol.

Example 60: N-(5-(2-fluoro-5-(morpholinomethyl)pyridin-3-yl)-2-((3S,5R)-3,4,5-trimethylpiperazin-1-yl)phenyl)-6-oxo-4-(trifluoromethyl)-1,6-dihydropyridine-3-carboxamide

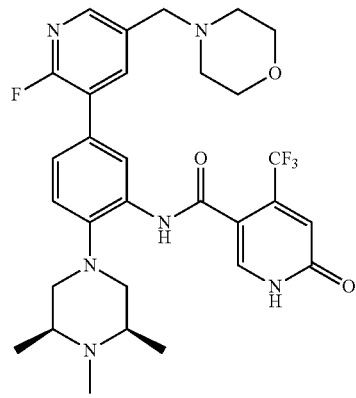 [SMILES: C[C@@H]1CN(c2ccc(-c3cc(CN4CCOCC4)cnc3F)cc2NC(=O)c2c[nH]c(=O)cc2C(F)(F)F)C[C@H](C)N1C]

The title compound (white solid, 11.5 mg, 30%) was prepared according to the sequence described above for the preparation of example 45 using 4-((6-fluoro-5-(4,4,5,5-tetramethyl-1,3,2-dioxaborolan-2-yl)pyridin-3-yl)methyl)morpholine (61.2 mg) in place of 5-(N-cyclohexylaminomethyl)-2-fluorophenylboronic acid, pinacol ester. $^1$H NMR (500 MHz, MeOD) δ 8.17 (s, 1H), 8.11 (d, J=2.7 Hz, 1H), 8.06 (dd, J=9.5, 2.4 Hz, 1H), 7.97 (s, 1H), 7.47 (dt, J=8.3, 2.2 Hz, 1H), 7.34 (d, J=8.4 Hz, 1H), 6.92 (s, 1H), 3.72-3.69 (m, 4H), 3.62 (s, 2H), 3.06 (dd, J=8.8, 2.4 Hz, 2H), 2.69 (t, J=11.2 Hz, 2H), 2.60 (dd, J=15.3, 9.2 Hz, 2H), 2.53-2.48 (m, 4H), 2.41 (s, 3H), 1.18 (d, J=6.1 Hz, 6H); LCMS [M+H]$^+$ 603.3 g/mol.

Example 61: N-(5-(2-fluoro-5-(morpholinomethyl)pyridin-3-yl)-2-(4-methylpiperazin-1-yl)phenyl)-6-oxo-4-(trifluoromethyl)-1,6-dihydropyridine-3-carboxamide

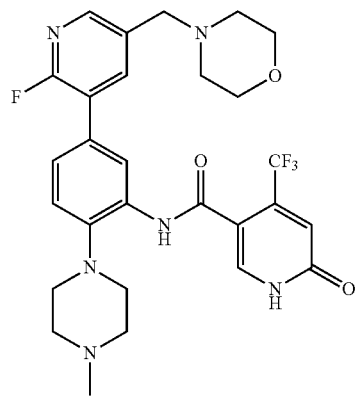

The title compound (white solid, 11.9 mg, 30%) was prepared according to the sequence described above for the preparation of example 1 4-((6-fluoro-5-(4,4,5,5-tetramethyl-1,3,2-dioxaborolan-2-yl)pyridin-3-yl)methyl)morpholine (64.2 mg) in place of (5-(((2S,6R)-2,6-dimethylmorpholino)methyl)-2-fluorophenyl)boronic acid. $^1$H NMR (500 MHz, MeOD) δ 8.19 (s, 1H), 8.11 (s, 1H), 8.06 (dd, J=9.6, 2.1 Hz, 1H), 7.98 (s, 1H), 7.47 (d, J=8.3 Hz, 1H), 7.37 (d, J=8.4 Hz, 1H), 6.93 (s, 1H), 3.72-3.69 (m, 4H), 3.62 (s, 2H), 3.03 (t, J=4.6 Hz, 4H), 2.69 (s, 4H), 2.51 (s, 4H), 2.39 (s, 3H); LCMS [M+H]+ 575.4 g/mol.

Example 62: N-(4-(4-ethylpiperazin-1-yl)-2'-fluoro-5'-(morpholinomethyl)-[1,1'-biphenyl]-3-yl)-6-oxo-4-(trifluoromethyl)-1,6-dihydropyridine-3-carboxamide

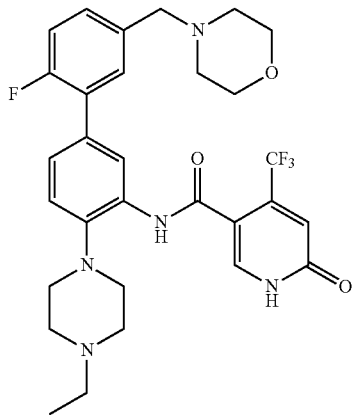 [SMILES: CCN1CCN(c2ccc(-c3cc(CN4CCOCC4)ccc3F)cc2NC(=O)c2c[nH]c(=O)cc2C(F)(F)F)CC1]

Step 1: N-(5-chloro-2-(4-ethylpiperazin-1-yl)phenyl)-6-oxo-4-(trifluoromethyl)-1,6-dihydropyridine-3-carboxamide

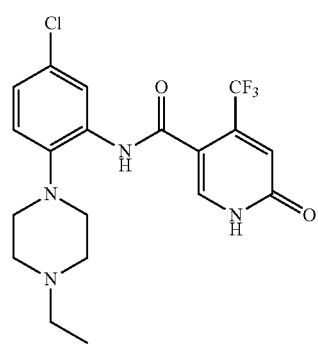 [SMILES: CCN1CCN(c2ccc(Cl)cc2NC(=O)c2c[nH]c(=O)cc2C(F)(F)F)CC1]

The title compound (red solid, 125 mg, 62%) was prepared according to the sequence described above for the preparation of example 30 using 5-chloro-2-(4-ethylpiperazin-1-yl)aniline in place of 5-bromo-4-fluoro-2-(4-methylpiperazin-1-yl)aniline. LCMS [M+1]+=429.08 g/mol.

Step 2: N-(4-(4-ethylpiperazin-1-yl)-2'-fluoro-5'-(morpholinomethyl)-[1,1'-biphenyl]-3-yl)-6-oxo-4-(trifluoromethyl)-1,6-dihydropyridine-3-carboxamide

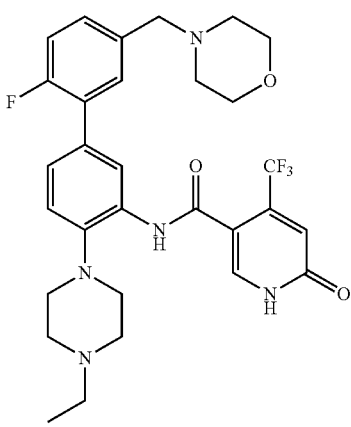 [SMILES: CCN1CCN(c2ccc(-c3cc(CN4CCOCC4)ccc3F)cc2NC(=O)c2c[nH]c(=O)cc2C(F)(F)F)CC1]

In a 5 mL MW vial N-(5-chloro-2-(4-ethylpiperazin-1-yl)phenyl)-6-oxo-4-(trifluoromethyl)-1,6-dihydropyridine-3-carboxamide (29.97 mg, 0.070 mmol), 4-(4-fluoro-3-(4,4,5,5-tetramethyl-1,3,2-dioxaborolan-2-yl)benzyl)morpholine (67.3 mg, 0.210 mmol), sodium carbonate (74.1 mg, 0.699 mmol), XPhos (6.66 mg, 0.014 mmol) and XPhos Pd G2 (11.00 mg, 0.014 mmol) were dissolved in water (1310 µL) and 1,4-dioxane (2184 µL) to give a white suspension. The suspension was stirred for 5 min, degassed, purged with $N_2$, and microwaved for 60 min at 120° C. The solvent was evaporated and 15 mL of $CH_2Cl_2$ were added. The suspension was sonicated and extracted from water. The solvent was evaporated in vacuo yielding the product that was purified by flash column chromatography on silica gel (0-100%, 89% $CH_2Cl_2$, 10% MeOH, 1% $NH_4Ac/CH_2Cl_2$) to afford the desired compound (32.1 mg, 75% yield). $^1$H NMR (500 MHz, MeOD) δ 8.15 (s, 1H), 7.98 (s, 1H), 7.49 (dd, J=7.6, 1.9 Hz, 1H), 7.41 (d, J=8.3 Hz, 1H), 7.34 (d, J=8.3 Hz, 1H), 7.33 (m, 1H), 7.15 (dd, J=10.6, 8.5 Hz, 1H), 6.92 (s, 1H), 3.71-3.69 (m, 4H), 3.56 (s, 2H), 3.04 (t, J=4.6 Hz, 4H), 2.73 (s, 4H), 2.57 (q, J=7.2 Hz, 2H), 2.49 (s, 4H), 1.17 (t, J=7.2 Hz, 3H)); LCMS [M+H]+ 588.5 g/mol.

Example 63: N-(5'-((cyclohexylamino)methyl)-4-(4-ethylpiperazin-1-yl)-2'-fluoro-[1,1'-biphenyl]-3-yl)-6-oxo-4-(trifluoromethyl)-1,6-dihydropyridine-3-carboxamide

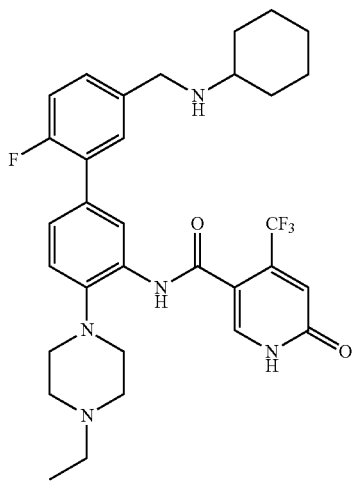 [SMILES: CCN1CCN(c2ccc(-c3cc(CNC4CCCCC4)ccc3F)cc2NC(=O)c2c[nH]c(=O)cc2C(F)(F)F)CC1]

The title compound (white solid, 28.9 mg, 68%) was prepared according to the sequence described above for the preparation of example 62 using 5-(N-cyclohexylaminomethyl)-2-fluorophenylboronic acid, pinacol ester (68.4 mg) in place of 4-(4-fluoro-3-(4,4,5,5-tetramethyl-1,3,2-dioxaborolan-2-yl)benzyl)morpholine. $^1$H NMR (500 MHz, MeOD) δ 8.22 (s, 1H), 8.10 (s, 1H), 7.58 (dd, J=7.4, 2.0 Hz, 1H), 7.40 (d, J=8.1 Hz, 1H), 7.40 (ddd, J=9.5, 5.0, 2.2 Hz, 1H), 7.34 (d, J=8.3 Hz, 1H), 7.21 (dd, J=10.5, 8.5 Hz, 1H), 6.79 (s, 1H), 4.02 (s, 2H), 3.02 (t, J=4.7 Hz, 4H), 2.79 (tt, J=10.3, 3.3 Hz, 1H), 2.69 (s, 4H), 2.53 (q, J=7.2 Hz, 2H), 2.08 (d, J=11.8 Hz, 2H), 1.83 (d, J=13.0 Hz, 2H), 1.69 (d, J=13.0 Hz, 1H), 1.34-1.21 (m, 5H), 1.15 (t, J=7.2 Hz, 3H); LCMS [M+H]$^+$ 600.55 g/mol.

Example 64: (4-(2'-fluoro-5'-(morpholinomethyl)-3-(6-oxo-4-(trifluoromethyl)-1,6-dihydropyridine-3-carboxamido)-[1,1'-biphenyl]-4-yl)-1-methylpiperazin-2-yl)methyl pivalate

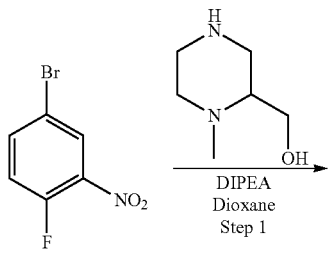

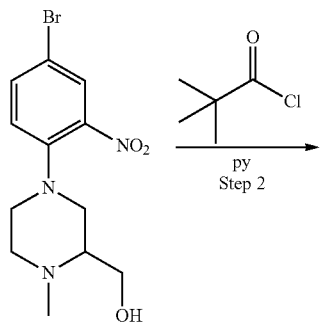

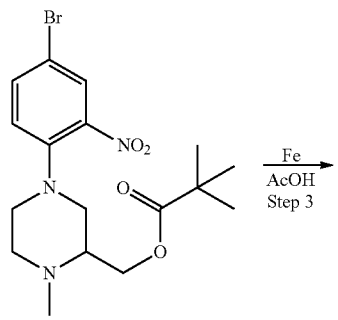

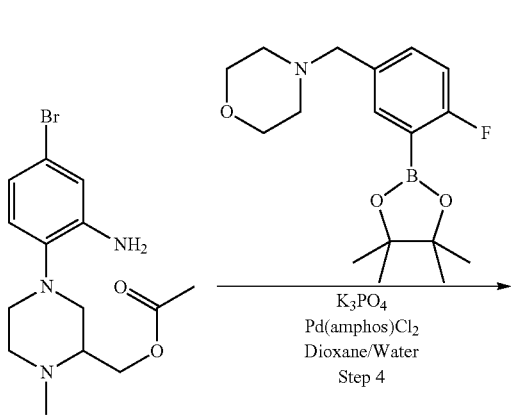

189
-continued

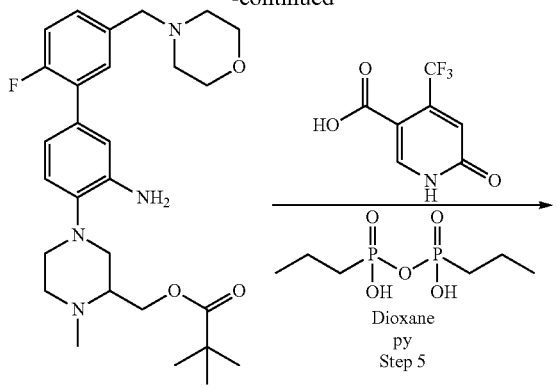

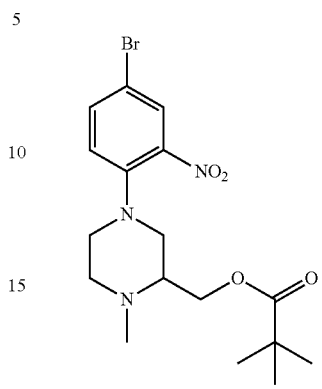

Dioxane
py
Step 5

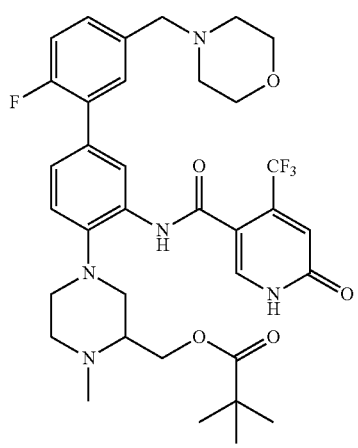

Step 1: (4-(4-bromo-2-nitrophenyl)-1-methylpiperazin-2-yl)methanol

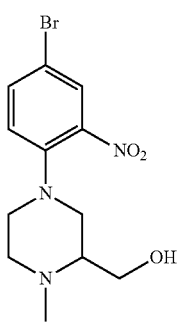

To a solution of 4-bromo-1-fluoro-2-nitrobenzene (0.185 g, 0.841 mmol) and N,N-diisopropylethylamine (0.517 g, 4.0 mmol) in dioxane (4 ml), (1-methyl-2-piperazinyl) methanol (0.223 g, 1.100 mmol) was added. The solution was heated at 80° C. for 16 hours. The solution was partitioned between EtOAc and water. The organic layer was separated and concentrated to get the crude product as a deep red oily residue, that was used in the following step without further purification (162 mg, 0.442 mmol, 44.2% yield), LCMS [M+H]⁺=330.1 g/mol.

190

Step 2: (4-(4-bromo-2-nitrophenyl)-1-methylpiperazin-2-yl)methyl pivalate

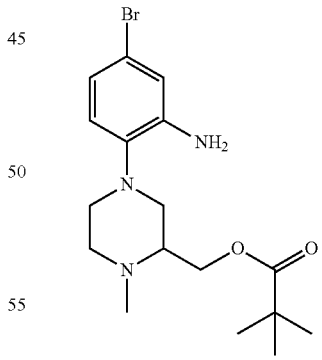

(4-(4-Bromo-2-nitrophenyl)-1-methylpiperazin-2-yl) methanol (162 mg, 0.442 mmol) was suspended in pyridine (1 ml) and charged with trimethylacetyl chloride (0.121 g, 1.000 mmol) at 23° C. The solution was agitated at 23° C. for 16 hours. After the reaction time the solution was partitioned between EtOAc/water. The organic layer was concentrated and purified by flash column chromatography on silica gel (0-20%, Hexane/EtOAc) to get the title compound product (128 mg, 0.294 mmol, 29.4% yield) as a yellow solid. $^1$H NMR (500 MHz, DMSO-d$_6$) δ=7.95 (d, J=2.3 Hz, 1H), 7.67 (dd, J=2.4, 8.9 Hz, 1H), 7.19 (d, J=8.8 Hz, 1H), 7.01-6.82 (m, 1H), 6.70-6.48 (m, 1H), 4.13 (s, 1H), 3.90-3.75 (m, 1H), 3.07-2.95 (m, 2H), 2.91-2.84 (m, 1H), 2.74-2.69 (m, 1H), 2.63 (dd, J=9.3, 11.7 Hz, 1H), 2.30 (d, J=3.7 Hz, 1H), 2.25-2.21 (m, 1H), 2.19 (s, 4H), 1.15-1.07 (m, 1H), 1.06 (s, 10H), 0.98 (s, 7H); LCMS [M+1]⁺=414.5 g/mol.

Step 3: (4-(4-bromo-2-nitrophenyl)-1-methylpiperazin-2-yl)methyl pivalate

To a solution of (4-(4-bromo-2-nitrophenyl)-1-methylpiperazin-2-yl)methyl pivalate (124 mg, 0.299 mmol) in acetic acid (2 mL), iron, powder (84 mg, 1.497 mmol) was added. The suspension was agitated at 80° C. 15 min. The suspension was diluted with ACN, filtered through celite, concentrated and purified by flash column chromatography on silica gel (0-20%, EtOAc/Hexane) to get the title compound (94 mg, 0.232 mmol, 78% yield) as a yellow solid. $^1$H NMR (500 MHz, DMSO-d$_6$) δ=7.07-6.93 (m, 1H), 6.87-6.75 (m, 2H), 6.66 (br. s., 1H), 5.01 (br. s., 2H), 4.27-3.92 (m, 2H), 3.13-2.60 (m, 5H), 2.30 (br. s., 3H), 1.33-0.90 (m, 15H); LCMS [M+1]⁺=385.2 g/mol.

Step 4: (4-(4-bromo-2-nitrophenyl)-1-methylpiperazin-2-yl)methyl pivalate

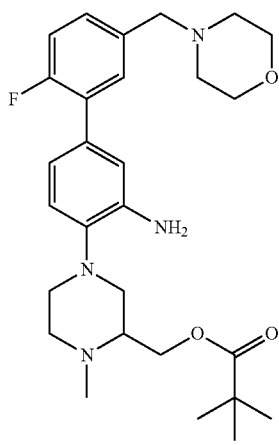 [SMILES: CN1CCN(c2ccc(-c3cc(CN4CCOCC4)ccc3F)cc2N)CC1COC(=O)C(C)(C)C]

To a solution of 4-(4-fluoro-3-(4,4,5,5-tetramethyl-1,3,2-dioxaborolan-2-yl)benzyl)morpholine (110 mg, 0.341 mmol), bis(di-tert-butyl(4-dimethylaminophenyl)phosphine)dichloropalladium(II) (7.55 mg, 10.67 μmol), (4-(2-amino-4-bromophenyl)-1-methylpiperazin-2-yl)methyl pivalate (82 mg, 0.213 mmol) and potassium phosphate tribasic reagent grade (91 mg, 0.427 mmol) in 1,4-dioxane (15 ml)/water (2 ml). The suspension was heated at 70° C. for 45 min. After the reaction time the mixture was concentrated, worked up using sat. aq. NH₄Cl and extracted with EtAOc. The organic layer was concentrated and purified by and purified by flash column chromatography (reverse phase, 0-90%, water/acetonitrile) to get the title compound (82 mg, 0.156 mmol, 73.2% yield), as a brown solid. ¹H NMR (500 MHz, DMSO-d6) δ=7.34 (d, J=7.6 Hz, 1H), 7.30-7.13 (m, 2H), 6.95 (d, J=8.1 Hz, 1H), 6.88 (s, 1H), 6.73 (d, J=8.1 Hz, 1H), 4.84 (s, 2H), 4.25 (d, J=8.9 Hz, 1H), 4.14-4.01 (m, 1H), 3.57 (t, J=4.1 Hz, 4H), 3.48 (s, 2H), 3.10 (d, J=6.6 Hz, 1H), 2.95 (d, J=10.8 Hz, 1H), 2.85 (d, J=11.2 Hz, 1H), 2.75 (t, J=9.7 Hz, 1H), 2.47-2.41 (m, 1H), 2.36 (br. s., 4H), 2.32 (s, 3H), 1.16 (s, 9H); LCMS [M+1]⁺=499.8 g/mol.

Step 5: 4-(2'-fluoro-5'-(morpholinomethyl)-3-(6-oxo-4-(trifluoromethyl)-1,6-dihydropyridine-3-carboxamido)-[1,1'-biphenyl]-4-yl)-1-methylpiperazin-2-yl)methyl pivalate

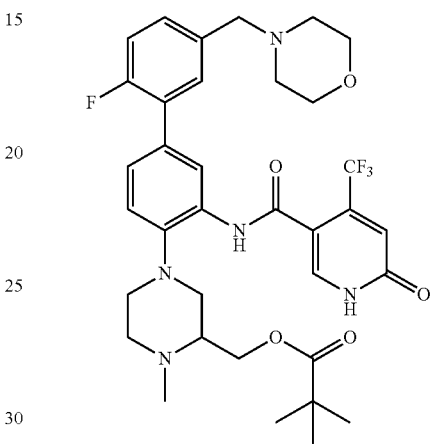

To a solution of (4-(3-amino-2'-fluoro-5'-(morpholinomethyl)-[1,1'-biphenyl]-4-yl)-1-methylpiperazin-2-yl)methyl pivalate (82 mg, 0.164 mmol) and 6-hydroxy-4-(trifluoromethyl)nicotinic acid (44.3 mg, 0.214 mmol) in 1,4-dioxane (4 mL), propylphosphonic anhydride solution (0.294 ml, 0.493 mmol) followed by pyridine (1 ml) were added. The suspension was heated to 80° C. for 16 hours. The reaction mixture was quenched with water and extracted with ethyl acetate. The organic layer was concentrated to dryness and loaded onto celite and purified by flash column chromatography on silica gel (0-100%, 89% CH₂Cl₂, 10% MeOH, 1% NH₄Ac/CH₂Cl₂) to get the title compound (64 mg, 0.088 mmol, 53.8% yield) as a brown solid. ¹H NMR (500 MHz, DMSO-d6) δ=12.55 (br. s., 1H), 9.49 (s, 1H), 7.97 (d, J=6.5 Hz, 2H), 7.42-7.38 (m, 1H), 7.37-7.30 (m, 2H), 7.29-7.23 (m, 2H), 6.81 (s, 1H), 4.15 (d, J=4.3 Hz, 1H), 4.07 (s, 1H), 3.57 (t, J=4.3 Hz, 4H), 3.50 (s, 2H), 3.11-2.97 (m, 2H), 2.86-2.82 (m, 1H), 2.71-2.61 (m, 1H), 2.47-2.41 (m, 1H), 2.37 (br. s., 5H), 2.31 (s, 3H), 1.11 (s, 9H); LCMS [M+1]⁺=688.8 g/mol.

Example 65: N-(2'-fluoro-4-(3-(hydroxymethyl)-4-methylpiperazin-1-yl)-5'-(morpholinomethyl)-[1,1'-biphenyl]-3-yl)-6-oxo-4-(trifluoromethyl)-1,6-dihydropyridine-3-carboxamide

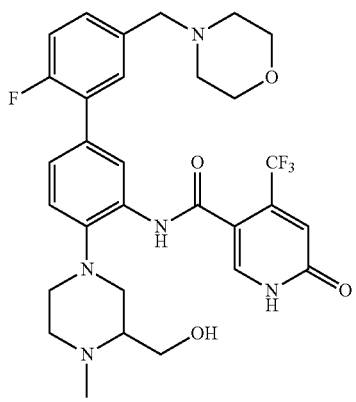 [SMILES: CN1CCN(c2ccc(-c3cc(CN4CCOCC4)ccc3F)cc2NC(=O)c2c[nH]c(=O)cc2C(F)(F)F)CC1CO]

To a solution mixture of (4-(2'-fluoro-5'-(morpholinomethyl)-3-(6-oxo-4-(trifluoromethyl)-1,6-dihydropyridine-3-carboxamido)-[1,1'-biphenyl]-4-yl)-1-methylpiperazin-2-yl)methyl pivalate (12 mg, 0.017 mmol) and lithium hydroxide monohydrate (7.32 mg, 0.174 mmol) in 1,4-dioxane (2 mL) and water (3 mL) was agitated at 23° C. over 5 hours. The reaction was neutralized with 1M HCl, concentrated to dryness and purified by prep HPLC (reverse phase, 0-90%, water/acetonitrile). The final product was lyophilized for 2 days to get the title compound (formic acid salt, 9.4 mg, 0.014 mmol, 79% yield), as a white solid. $^1$H NMR (500 MHz, MeOD-d4) δ=8.09 (br. s., 1H), 7.91 (s, 1H), 7.61 (dd, J=2.2, 7.2 Hz, 1H), 7.39 (s, 2H), 7.33-7.20 (m, 2H), 6.84 (s, 1H), 4.31 (s, 2H), 3.95 (br. s., 2H), 3.59 (d, J=12.3 Hz, 3H), 3.47 (d, J=11.4 Hz, 2H), 3.37-3.30 (m, 3H), 3.16-3.02 (m, 3H), 2.91 (s, 3H), 2.56 (s, 1H), 1.27-1.17 (m, 4H); LCMS [M+1]$^+$=604.3 g/mol.

Example 66: N-(5'-((4-(cyclopropylmethyl)piperazin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

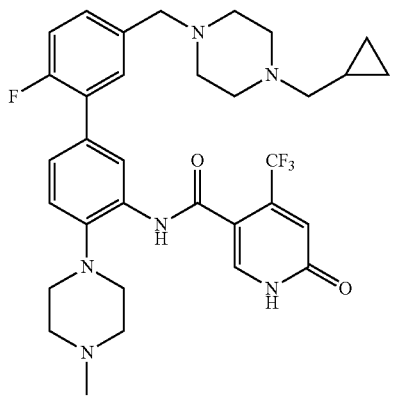 [SMILES: CN1CCN(c2ccc(-c3cc(CN4CCN(CC5CC5)CC4)ccc3F)cc2NC(=O)c2c[nH]c(=O)cc2C(F)(F)F)CC1]

To a solution of N-(5'-((4-(cyclopropylmethyl)piperazin-1-yl)methyl)-2'-fluoro-4-(4-methylpiperazin-1-yl)-[1,1'-biphenyl]-3-yl)-6-methoxy-4-(trifluoromethyl)nicotinamide (21 mg, 0.033 mmol) in methanol (0.75 mL) was added concentrated HCl (0.75 mL) and the reaction mixture was heated at 80° C. for 2.5 hours. The reaction mixture was allowed to cool to RT, concentrated and the residue was triturated with diethyl ether to yield the desired product as a pale green solid (HCl salt, 25 mg, 98%). $^1$H NMR (500 MHz, MeOD-d4) δ=8.21 (br. s., 1H), 8.07 (br. s., 1H), 7.84 (d, J=5.7 Hz, 1H), 7.61 (br. s., 1H), 7.56 (d, J=7.5 Hz, 1H), 7.42 (d, J=7.7 Hz, 1H), 7.35 (t, J=9.0 Hz, 1H), 7.01-6.88 (m, 1H), 4.44 (br. s., 2H), 4.04-3.82 (m, 2H), 3.73-3.53 (m, 6H), 3.20 (br. s., 4H), 2.99 (s, 3H), 2.68 (br. s., 8H), 1.17 (br. s., 1H), 0.81 (d, J=7.1 Hz, 2H), 0.50 (d, J=3.4 Hz, 2H); LCMS [M+H]$^+$=627.5 g/mol.

Example 67: N-(5'-(((cyclohexyl(methyl)amino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

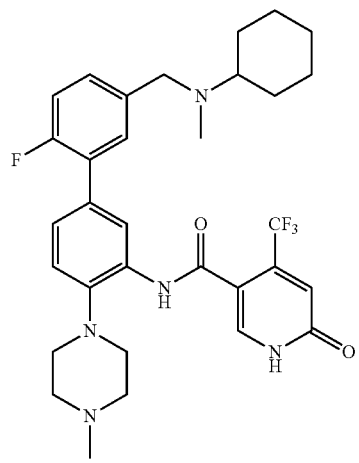 [SMILES: CN1CCN(c2ccc(-c3cc(CN(C)C4CCCCC4)ccc3F)cc2NC(=O)c2c[nH]c(=O)cc2C(F)(F)F)CC1]

The title compound (TFA salt, beige solid, 15 mg, 86%) was prepared according to the sequence described above for the preparation of example 42 using N-methylcyclohexylamine (9.86 mg, 0.087 mmol) in place of 4,4-difluorocyclohexylamine hydrochloride. $^1$H NMR (500 MHz, MeOD-d4) δ=8.20 (s, 1H), 8.03 (s, 1H), 7.72 (dd, J=2.0, 7.2 Hz, 1H), 7.59-7.54 (m, 1H), 7.51 (d, J=8.3 Hz, 1H), 7.43 (d, J=8.4 Hz, 1H), 7.37 (dd, J=8.6, 10.2 Hz, 1H), 7.00-6.93 (m, 1H), 4.57 (d, J=13.0 Hz, 1H), 4.32-4.21 (m, 1H), 3.64 (d, J=10.4 Hz, 2H), 3.24-3.14 (m, 2H), 3.03-2.95 (m, 3H), 2.77 (s, 3H), 2.68 (s, 5H), 2.19 (d, J=11.2 Hz, 1H), 2.12 (d, J=10.6 Hz, 1H), 2.05-1.94 (m, 2H), 1.76 (d, J=13.1 Hz, 1H), 1.65 (dq, J=3.4, 12.2 Hz, 2H), 1.49-1.39 (m, 2H), 1.33-1.26 (m, 1H); LCMS [M+H]$^+$=600.4 g/mol.

Example 68: N-(2'-fluoro-5'-((4-(4-fluorobenzyl) piperazin-1-yl)methyl)-4-(4-methylpiperazin-1-yl)-[, 1'-biphenyl]-3-yl)-6-oxo-4-(trifluoromethyl)-1,6-dihydropyridine-3-carboxamide

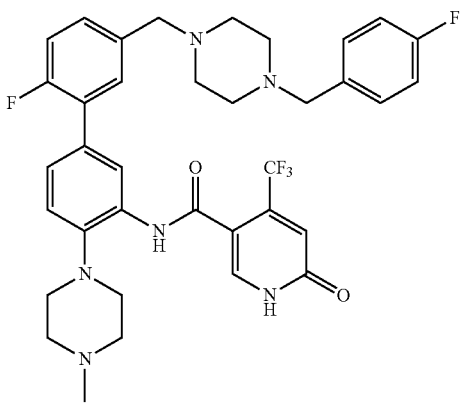 [SMILES: CN1CCN(c2ccc(-c3cc(CN4CCN(Cc5ccc(F)cc5)CC4)ccc3F)cc2NC(=O)c2c[nH]c(=O)cc2C(F)(F)F)CC1]

To a solution of N-(2'-fluoro-5'-((4-(4-fluorobenzyl)piperazin-1-yl)methyl)-4-(4-methylpiperazin-1-yl)-[1,1'-biphenyl]-3-yl)-6-methoxy-4-(trifluoromethyl)nicotinamide (10 mg, 0.014 mmol) in methanol (0.75 mL) was added concentrated HCl (0.75 mL) and the reaction mixture was heated at 80° C. for 2.5 hours. The reaction mixture was allowed to cool to RT, concentrated and the residue was triturated with diethyl ether to yield the desired product as a pale green solid (HCl salt, 7.5 mg, 63%). $^1$H NMR (500 MHz, MeOD-d4) δ=8.09 (s, 1H), 7.95 (s, 1H), 7.71 (d, J=6.0 Hz, 1H), 7.54-7.48 (m, 3H), 7.43 (d, J=8.4 Hz, 1H), 7.30 (d, J=8.4 Hz, 1H), 7.27-7.20 (m, 1H), 7.12 (t, J=8.6 Hz, 2H), 6.84 (s, 1H), 4.31 (d, J=16.8 Hz, 4H), 3.63-3.31 (m, 12H), 3.25 (br. s., 2H), 3.13-3.06 (m, 2H), 3.03-3.03 (m, 1H), 2.87 (s, 3H); LCMS [M+H]$^+$=681.5 g/mol.

Example 69: (R)—N-(2'-fluoro-5'-((3-hydroxypyrrolidin-1-yl)methyl)-4-(4-methylpiperazin-1-yl)-[1, 1'-biphenyl]-3-yl)-6-oxo-4-(trifluoromethyl)-1,6-dihydropyridine-3-carboxamide

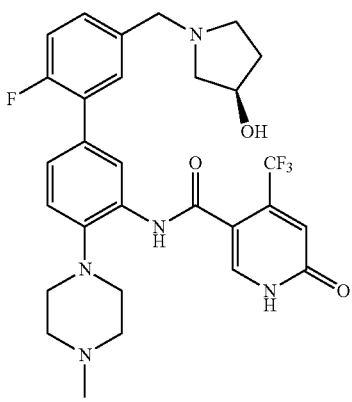 [SMILES: CN1CCN(c2ccc(-c3cc(CN4CC[C@@H](O)C4)ccc3F)cc2NC(=O)c2c[nH]c(=O)cc2C(F)(F)F)CC1]

To a solution of (R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide (26 mg, 0.044 mmol) in methanol (1.5 mL) was added concentrated HCl (0.75 mL) and the reaction mixture was heated at 80° C. for 2.5 hours. The reaction mixture was allowed to cool to RT, concentrated and the residue was triturated with diethyl ether to yield the desired product as a yellow solid (HCl salt, 25 mg, 79%). $^1$H NMR (500 MHz, MeOD-d4) δ=8.19 (s, 1H), 8.09-8.04 (m, 1H), 7.77 (ddd, J=2.1, 7.3, 12.8 Hz, 1H), 7.63-7.57 (m, 1H), 7.56-7.50 (m, 1H), 7.47-7.41 (m, 1H), 7.36 (dd, J=8.7, 10.3 Hz, 1H), 6.98-6.93 (m, 1H), 4.63-4.57 (m, 1H), 4.56-4.50 (m, 1H), 4.50-4.40 (m, 1H), 3.99-3.98 (m, 1H), 3.79-3.67 (m, 1H), 3.64 (d, J=11.5 Hz, 2H), 3.57-3.43 (m, 1H), 3.42-3.34 (m, 6H), 3.24 (d, J=12.2 Hz, 2H), 3.02-2.97 (m, 3H), 2.52-2.35 (m, 1H), 2.22-2.13 (m, 1H), 2.12-1.97 (m, 1H); LCMS [M+H]+=574.5 g/mol.

Example 70: N-(2'-fluoro-4-(4-methylpiperazin-1-yl)-5'-((4-morpholinopiperidin-1-yl)methyl)-[1,1'-biphenyl]-3-yl)-6-oxo-4-(trifluoromethyl)-1,6-dihydropyridine-3-carboxamide

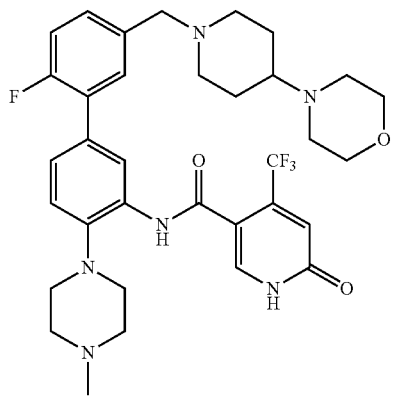 [SMILES: CN1CCN(c2ccc(-c3cc(CN4CCC(N5CCOCC5)CC4)ccc3F)cc2NC(=O)c2c[nH]c(=O)cc2C(F)(F)F)CC1]

To a solution of N-(2'-fluoro-4-(4-methylpiperazin-1-yl)-5'-((4-morpholinopiperidin-1-yl)methyl)-[1,1'-biphenyl]-3-yl)-6-methoxy-4-(trifluoromethyl)nicotinamide (26 mg, 0.039 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 28 mg, 85%). $^1$H NMR (500 MHz, MeOD-d4) δ=8.22 (s, 1H), 8.08 (s, 1H), 7.84 (d, J=6.0 Hz, 1H), 7.62 (br. s., 1H), 7.56 (d, J=8.4 Hz, 1H), 7.43 (d, J=8.3 Hz, 1H), 7.37 (t, J=9.4 Hz, 1H), 6.95 (s, 1H), 4.50-4.40 (m, 2H), 4.45 (s, 2H), 4.11 (d, J=12.5 Hz, 2H), 3.93-3.83 (m, 2H), 3.73 (d, J=12.5 Hz, 2H), 3.67-3.61 (m, 3H), 3.60-3.53 (m, 2H), 3.43-3.34 (m, 4H), 3.43-3.34 (m, 4H), 3.29-3.18 (m, 6H), 2.99 (s, 3H), 2.50 (d, J=13.0 Hz, 2H), 2.30-2.11 (m, 2H); LCMS [M+H]$^+$=657.5. g/mol.

Example 71: (R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

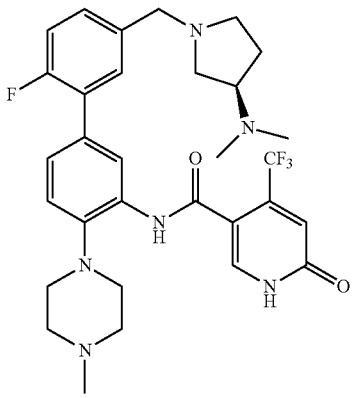 [SMILES: CN1CCN(c2ccc(-c3cc(CN4CC[C@@H](N(C)C)C4)ccc3F)cc2NC(=O)c2c[nH]c(=O)cc2C(F)(F)F)CC1]

To a solution of (R)—N-(5'-((3-(dimethylamino)pyrrolidin-1-yl)methyl)-2'-fluoro-4-(4-methylpiperazin-1-yl)-[1,1'-biphenyl]-3-yl)-6-methoxy-4-(trifluoromethyl)nicotinamide (16 mg, 0.026 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 18 mg, 88%). $^1$HNMR (500 MHz, MeOD-d4) δ=8.23 (s, 1H), 8.09 (s, 1H), 7.87 (dd, J=2.0, 7.2 Hz, 1H), 7.65 (br. s., 1H), 7.57 (d, J=8.2 Hz, 1H), 7.47-7.40 (m, 1H), 7.36 (dd, J=8.6, 10.3 Hz, 1H), 6.95 (s, 1H), 4.70-4.50 (m, 2H), 4.43-4.16 (m, 1H), 4.08-3.68 (m, 4H), 3.64 (d, J=11.7 Hz, 2H), 3.41-3.34 (m, 4H), 3.27-3.19 (m, 2H), 3.06-2.95 (m, 9H), 2.77-2.23 (m, 2H); LCMS [M+H]$^+$= 601.5 g/mol.

Example 72: N-(2'-fluoro-4-(4-methylpiperazin-1-yl)-5'-(piperazin-1-ylmethyl)-[1,1'-biphenyl]-3-yl)-6-oxo-4-(trifluoromethyl)-1,6-dihydropyridine-3-carboxamide

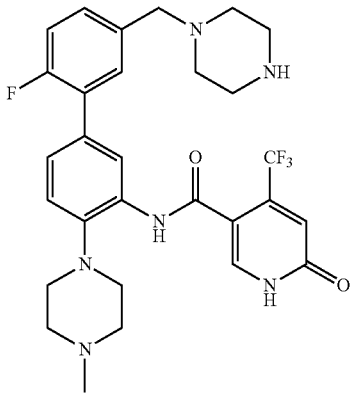

To a solution of N-(5'-((4-acetylpiperazin-1-yl)methyl)-2'-fluoro-4-(4-methylpiperazin-1-yl)-[1,1'-biphenyl]-3-yl)-6-methoxy-4-(trifluoromethyl)nicotinamide (26 mg, 0.041 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 25.5 mg, 86%). $^1$HNMR (500 MHz, MeOD-d4) δ=8.22 (s, 1H), 8.09 (s, 1H), 7.90 (dd, J=1.9, 7.2 Hz, 1H), 7.70-7.64 (m, 1H), 7.58 (d, J=8.3 Hz, 1H), 7.43 (d, J=8.3 Hz, 1H), 7.38 (dd, J=8.7, 10.2 Hz, 1H), 6.95 (s, 1H), 4.59-4.55 (m, 2H), 3.72-3.60 (m, 10H), 3.41-3.34 (m, 4H), 3.25-3.19 (m, 2H), 2.99 (s, 3H); LCMS [M+H]$^+$=573.3 g/mol.

Example 73: N-(2'-fluoro-5'-((4-fluoropiperidin-1-yl)methyl)-4-(4-methylpiperazin-1-yl)-[1,1'-biphenyl]-3-yl)-6-oxo-4-(trifluoromethyl)-1,6-dihydropyridine-3-carboxamide

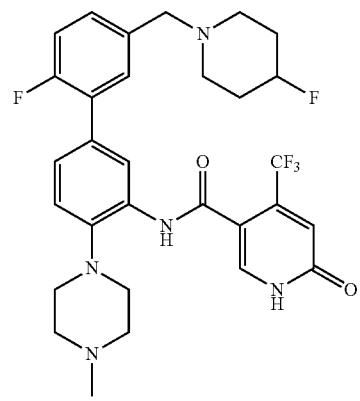 [SMILES: CN1CCN(c2ccc(-c3cc(CN4CCC(F)CC4)ccc3F)cc2NC(=O)c2c[nH]c(=O)cc2C(F)(F)F)CC1]

To a solution of N-(2'-fluoro-5'-((4-fluoropiperidin-1-yl)methyl)-4-(4-methylpiperazin-1-yl)-[1,1'-biphenyl]-3-yl)-6-methoxy-4-(trifluoromethyl)nicotinamide (20 mg, 0.033 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 19.5 mg, 80%). $^1$H NMR (500 MHz, MeOD-d4) δ=8.09 (s, 1H), 7.94 (s, 1H), 7.70-7.64 (m, 1H), 7.49-7.45 (m, 1H), 7.42 (d, J=8.4 Hz, 1H), 7.32 (d, J=8.4 Hz, 1H), 7.25 (dd, J=8.6, 10.4 Hz, 1H), 6.84 (s, 1H), 4.31 (s, 2H), 3.60-3.44 (m, 3H), 3.39-3.31 (m, 2H), 3.29-3.22 (m, 6H), 3.13-3.06 (m, 2H), 2.88 (s, 3H), 2.31-2.11 (m, 2H), 2.07-1.84 (m, 2H); LCMS [M+H]$^+$=590.5 g/mol.

Example 74: N-(5'-(3-oxa-6-azabicyclo[3.1.1]heptan-6-ylmethyl)-2'-fluoro-4-(4-methylpiperazin-1-yl)-[1,1'-biphenyl]-3-yl)-6-oxo-4-(trifluoromethyl)-1,6-dihydropyridine-3-carboxamide

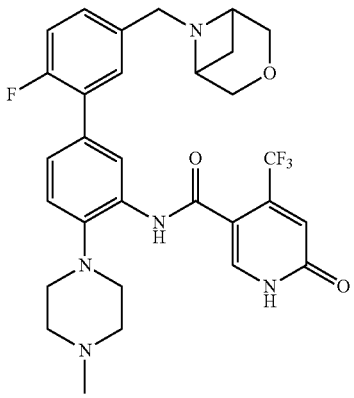 [SMILES: CN1CCN(c2ccc(-c3cc(CN4C5COCC4C5)ccc3F)cc2NC(=O)c2c[nH]c(=O)cc2C(F)(F)F)CC1]

To a solution of N-(5'-((3-oxa-6-azabicyclo[3.1.1]heptan-6-yl)methyl)-2'-fluoro-4-(4-methylpiperazin-1-yl)-[1,1'-biphenyl]-3-yl)-6-methoxy-4-(trifluoromethyl)nicotinamide (10 mg, 0.017 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 11 mg, 85%). $^1$H NMR (500 MHz, MeOD-d4) δ=8.20 (br. s., 1H), 8.06 (s, 1H), 7.82-7.71 (m, 1H), 7.65-7.56 (m, 1H), 7.53 (d, J=8.3 Hz, 1H), 7.44 (d, J=8.4 Hz, 1H), 7.40-7.30 (m, 1H), 6.96 (s, 1H), 4.77-4.66 (m, 2H), 4.60-4.54 (m, 1H), 4.49-4.49 (m, 1H), 4.46 (d, J=6.2 Hz, 1H), 4.41-4.32 (m, 3H), 4.41-4.32 (m, 3H), 4.28-4.13 (m, 2H), 3.79-3.58 (m, 3H), 3.55-3.45 (m, 1H), 3.43-3.34 (m, 4H), 3.27-3.18 (m, 2H), 2.99 (s, 3H); LCMS [M+H]$^+$=586.5 g/mol.

Example 75: (R)—N-(2'-fluoro-4-(4-methylpiperazin-1-yl)-5'-((3-(methylsulfonyl)pyrrolidin-1-yl)methyl)-[1,1'-biphenyl]-3-yl)-6-oxo-4-(trifluoromethyl)-1,6-dihydropyridine-3-carboxamide

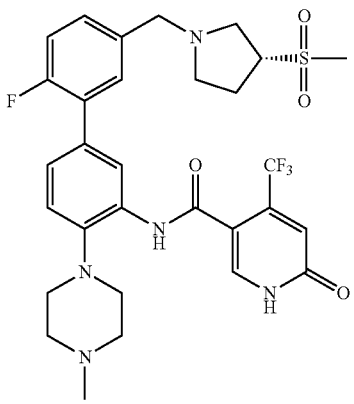 [SMILES: CN1CCN(c2ccc(-c3cc(CN4CC[C@@H](S(C)(=O)=O)C4)ccc3F)cc2NC(=O)c2c[nH]c(=O)cc2C(F)(F)F)CC1]

To a solution of (R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide (25 mg, 0.038 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 23 mg, 80%). $^1$H NMR (500 MHz, MeOD-d4) δ=8.08 (s, 1H), 7.98-7.92 (m, 1H), 7.69 (br. s., 1H), 7.50 (br. s., 1H), 7.42 (d, J=8.2 Hz, 1H), 7.32 (d, J=8.4 Hz, 1H), 7.25 (t, J=9.4 Hz, 1H), 6.84 (s, 1H), 4.51-4.40 (m, 2H), 4.26-4.05 (m, 1H), 3.96-3.77 (m, 1H), 3.72-3.57 (m, 2H), 3.55-3.51 (m, 2H), 3.55-3.51 (m, 2H), 3.55-3.51 (m, 2H), 3.35 (dd, J=1.7, 3.2 Hz, 1H), 3.29-3.23 (m, 4H), 3.15-3.08 (m, 2H), 2.99 (br. s., 3H), 2.87 (s, 3H), 2.57 (br. s., 1H), 2.40 (br. s., 1H); LCMS [M+H]$^+$=636.4 g/mol.

Example 76: (S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide

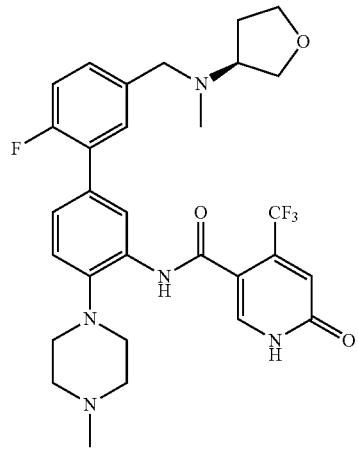 [SMILES: CN1CCN(c2ccc(-c3cc(CN(C)[C@H]4CCOC4)ccc3F)cc2NC(=O)c2c[nH]c(=O)cc2C(F)(F)F)CC1]

To a solution of (S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide (19 mg, 0.032 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 20 mg, 91%). $^1$H NMR (500 MHz, MeOD-d$_4$) δ=8.09 (s, 1H), 7.99-7.90 (m, 1H), 7.65 (d, J=7.2 Hz, 1H), 7.51-7.45 (m, 1H), 7.42 (d, J=8.4 Hz, 1H), 7.32 (d, J=8.3 Hz, 1H), 7.26 (t, J=9.4 Hz, 1H), 6.84 (s, 1H), 4.53-4.36 (m, 1H), 4.26-4.12 (m, 2H), 4.05 (dt, J=4.2, 8.3 Hz, 2H), 3.75 (dd, J=6.2, 11.4 Hz, 1H), 3.69-3.60 (m, 1H), 3.55-3.50 (m, 2H), 3.28-3.23 (m, 4H), 3.14-3.06 (m, 2H), 2.91-2.83 (m, 3H), 2.88 (s, 3H), 2.68 (d, J=13.8 Hz, 3H), 2.48-2.13 (m, 2H); LCMS [M+H]$^+$=588.4 g/mol.

Example 77: N-(5'-((2,2-dimethylmorpholino)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide

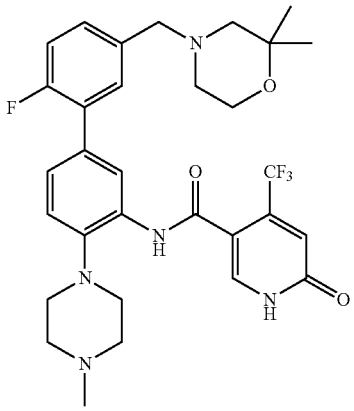 [SMILES: CN1CCN(c2ccc(-c3cc(CN4CCOC(C)(C)C4)ccc3F)cc2NC(=O)c2c[nH]c(=O)cc2C(F)(F)F)CC1]

To a solution of N-(5'-((2,2-dimethylmorpholino)methyl)-2'-fluoro-4-(4-methylpiperazin-1-yl)-[1,1'-biphenyl]-3-yl)-6-methoxy-4-(trifluoromethyl)nicotinamide (25 mg, 0.041 mmol) in methanol (1.5 mL) was added concentrated HCl (1.5 mL) and the reaction mixture was heated at 80° C. for 2.5 hours. The reaction mixture was allowed to cool to RT, concentrated and the residue was triturated with diethyl ether to yield the desired product as a white solid (HCl salt, 25 mg, 82%). $^1$H NMR (500 MHz, MeOD-d4) δ=8.10 (s, 1H), 7.94 (s, 1H), 7.70 (dd, J=2.1, 7.2 Hz, 1H), 7.54-7.47 (m, 1H), 7.42 (d, J=8.3 Hz, 1H), 7.32 (d, J=8.4 Hz, 1H), 7.25 (dd, J=8.6, 10.3 Hz, 1H), 6.84 (s, 1H), 4.39-4.26 (m, 2H), 3.95-3.86 (m, 1H), 3.83-3.75 (m, 1H), 3.56-3.50 (m, 2H), 3.33-3.24 (m, 8H), 3.14-3.07 (m, 2H), 2.88 (s, 3H), 1.30 (s, 3H), 1.18 (s, 3H); LCMS [M+H]$^+$=602.5 g/mol.

Example 78: N-(3'-cyano-2',6'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

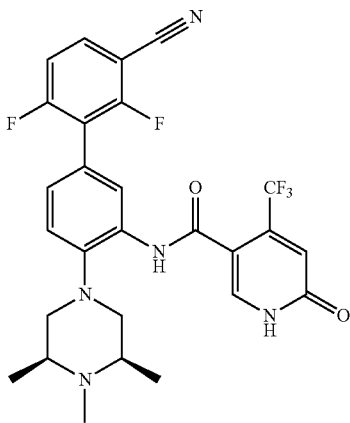 [SMILES: C[C@@H]1CN(c2ccc(-c3c(F)ccc(C#N)c3F)cc2NC(=O)c2c[nH]c(=O)cc2C(F)(F)F)C[C@H](C)N1C]

Step 1: N-(5-bromo-2-((3S,5R)-3,4,5-trimethylpiperazin-1-yl)phenyl)-6-methoxy-4-(trifluoromethyl)nicotinamide

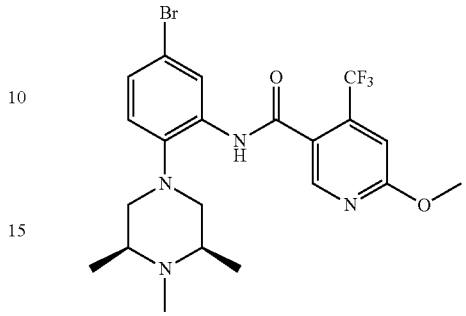

Propylphosphonic anhydride solution (7.99 mL, 13.43 mmol) was added dropwise to a mix of 6-methoxy-4-(trifluoromethyl)nicotinic acid (1.5 g, 6.44 mmol) and pyridine (1.730 mL, 21.48 mmol) in dry tetrahydrofuran (THF) (30 mL) under N$_2$ at RT. After 1.5 hour of stirring a pale yellow solution was obtained. Then 5-bromo-2-((3S,5R)-3,4,5-trimethylpiperazin-1-yl)aniline (1.601 g, 5.37 mmol) was added as a solid and the reaction mixture was heated at 50° C. The crude product was allowed to cool to RT, THF was removed and the residue was partitioned between ethyl acetate (50 mL) and sodium bicarbonate sat solution (50 mL). The organic phase was separated and the aqueous phase was extracted with additional ethyl acetate (50 mL). The solvent was evaporated in vacuo yielding the crude product by flash column chromatography on silica gel (0-100%, 89% CH$_2$Cl$_2$, 10% MeOH, 1% NH$_4$Ac/CH$_2$Cl$_2$) to afford the desired compound (1.6 mg, 58%) $^1$H NMR (500 MHz, DMSO-d6) δ=9.91-9.60 (m, 1H), 8.57 (s, 1H), 8.03 (s, 1H), 7.29 (s, 2H), 7.07 (d, J=8.6 Hz, 1H), 4.00-3.96 (m, 3H), 3.90-3.85 (m, 1H), 2.96 (d, J=10.8 Hz, 2H), 2.46-2.39 (m, 2H), 2.35-2.28 (m, 2H), 2.17 (s, 3H), 0.99 (d, J=6.1 Hz, 6H); LCMS [M+H]$^+$=501.6 g/mol.

Step 2: N-(3'-cyano-2',6'-difluoro-4-((3S,5R)-3,4,5-trimethylpiperazin-1-yl)-[1,1'-biphenyl]-3-yl)-6-methoxy-4-(trifluoromethyl)nicotinamide

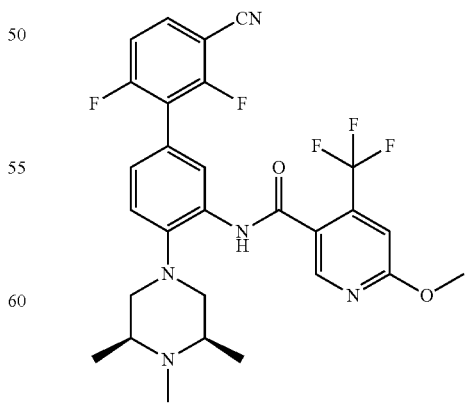

In a 5 mL MW vial N-(5-bromo-2-((3S,5R)-3,4,5-trimethylpiperazin-1-yl)phenyl)-6-methoxy-4-(trifluoromethyl)

nicotinamide (20 mg, 0.037 mmol), 2,4-difluoro-3-(4,4,5,5-tetramethyl-1,3,2-dioxaborolan-2-yl)benzonitrile (36.7 mg, 0.093 mmol), sodium carbonate, anhydrous (39.3 mg, 0.371 mmol), XPhos (3.54 mg, 0.007 mmol) and XPhos Pd G2 (5.84 mg, 0.007 mmol) were dissolved in water (2.5 mL) and 1,4-dioxane (2.5 mL) to give a white suspension. The suspension was stirred for 5 min, degassed, purged with $N_2$, and microwaved for 60 min at 120° C. The solvent was evaporated and 15 mL of $CH_2C_{12}$ were added. The suspension was sonicated and extracted from water. The solvent was evaporated in vacuo yielding the product that was purified by flash column chromatography on silica gel (0-100%, 89% $CH_2Cl_2$, 10% MeOH, 1% $NH_4Ac/CH_2Cl_2$) to afford the desired compound (10 mg, 48%). $^1H$ NMR (500 MHz, MeOD-d4) δ=8.46 (s, 1H), 8.09 (s, 1H), 7.79 (dt, J=6.5, 8.7 Hz, 1H), 7.34-7.29 (m, 1H), 7.28-7.22 (m, 2H), 7.12 (s, 1H), 3.96 (s, 3H), 2.97 (d, J=11.5 Hz, 2H), 2.59 (t, J=11.2 Hz, 2H), 2.51-2.44 (m, 2H), 2.31-2.28 (m, 3H), 1.08 (d, J=6.2 Hz, 6H); LCMS [M+1]$^+$=560.6 g/mol.

Step 3: N-(3'-cyano-2',6'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

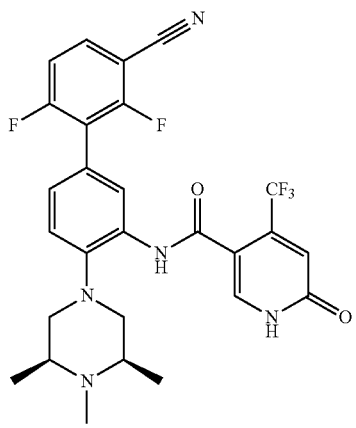 [SMILES: C[C@@H]1CN(c2ccc(-c3c(F)ccc(C#N)c3F)cc2NC(=O)c2c[nH]c(=O)cc2C(F)(F)F)C[C@H](C)N1C]

To a solution of N-(3'-cyano-2',6'-difluoro-4-((3S,5R)-3,4,5-trimethylpiperazin-1-yl)-[1,1'-biphenyl]-3-yl)-6-methoxy-4-(trifluoromethyl)nicotinamide (8 mg, 0.014 mmol) in methanol (1 mL) was added concentrated HCl (1 mL) and the reaction mixture was heated at 80° C. for 2.5 hours. The reaction mixture was allowed to cool to RT, concentrated and the residue was triturated with diethyl ether to yield the desired product as a white solid (HCl salt, 2 mg, 23%). $^1H$ NMR (500 MHz, MeOD-d4) δ=8.20-8.11 (m, 1H), 8.04 (s, 1H), 7.91 (dt, J=6.5, 8.7 Hz, 1H), 7.50-7.41 (m, 2H), 7.36 (t, J=8.7 Hz, 1H), 6.95 (s, 1H), 3.66-3.58 (m, 2H), 3.41-3.36 (m, 2H), 3.10-2.98 (m, 5H), 1.48 (d, J=6.4 Hz, 6H); LCMS [M+H]$^+$=546.6 g/mol.

Example 79: N-(5'-((cyclohexylamino)methyl)-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

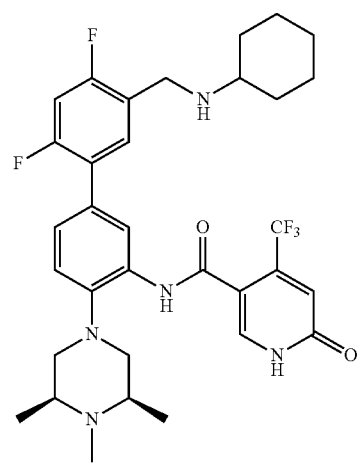

The title compound (HCl salt, white solid, 50 mg, 89%) was prepared according to the sequence described above for the preparation of example 51 using cyclohexylamine (17.98 mg, 0.181 mmol) in place of (R)-3-pyrrolidinol. $^1H$ NMR (500 MHz, MeOD-d4) δ=8.18 (s, 1H), 8.04 (s, 1H), 7.84-7.76 (m, 1H), 7.52-7.47 (m, 1H), 7.46-7.40 (m, 1H), 7.28 (t, J=10.0 Hz, 1H), 6.96 (s, 1H), 4.36 (s, 2H), 3.65-3.57 (m, 2H), 3.30-3.15 (m, 2H), 3.09-2.97 (m, 5H), 2.24 (br. s., 2H), 1.94 (d, J=8.3 Hz, 2H), 1.76 (d, J=12.8 Hz, 1H), 1.50-1.37 (m, 11H), 1.31-1.23 (m, 1H); LCMS [M+H]$^+$=632.7 g/mol.

Example 80: N-(2'-fluoro-5'-(phenylcarbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

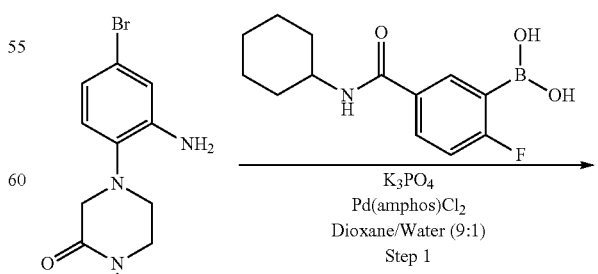

205
-continued

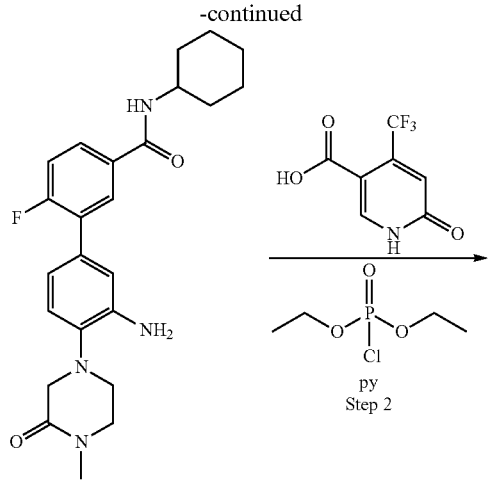

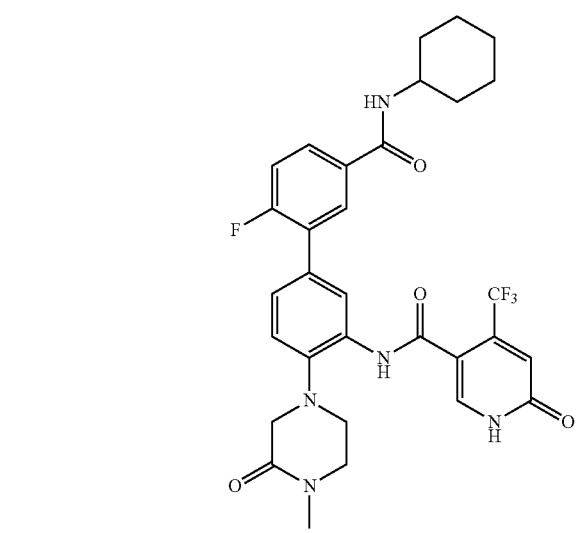

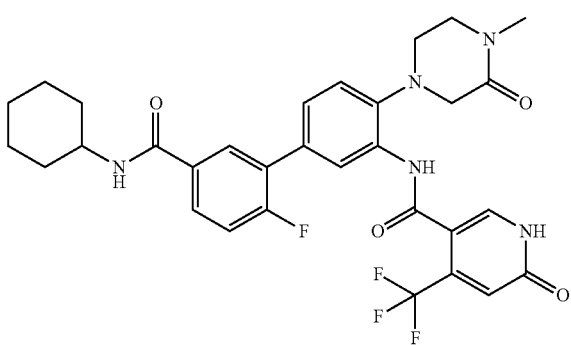

N-(5'-(cyclohexylcarbamoyl)-2'-fluoro-4-(4-methyl-3-oxopiperazin-1-yl)-[1,1'-biphenyl]-3-yl)-6-oxo-4-(trifluoromethyl)-1,6-dihydropyridine-3-carboxamide

206

Step 1: 5-bromo-2-((3S,5R)-3,4,5-trimethylpiperazin-1-yl)aniline

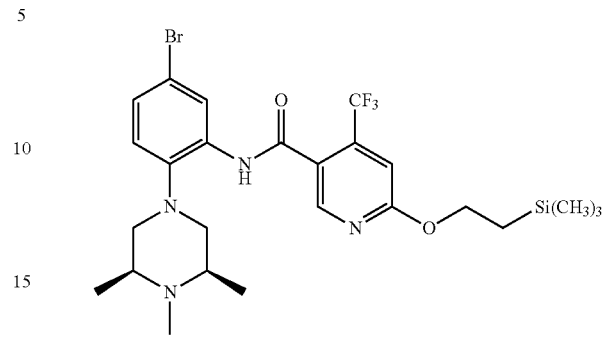

To a solution of 4-(trifluoromethyl)-6-(2-(trimethylsilyl)ethoxy)nicotinic acid (see example 42, step 6, 6 g, 19 mmol) in dry DMF (70 mL), HATU (11.1 g, 29.3 mmol) and DIPEA (6.6 mL, 39.0 mmol) were added at RT. The reaction mixture was stirred for 10 min. Then 5-bromo-2-((3S,5R)-3,4,5-trimethylpiperazin-1-yl)aniline (see example 45, step 2, 5.8 g, 19.5 mmol) was added and the reaction mixture was stirred for 48 hours. The reaction mixture was diluted with EtOAc (2×500 mL) washed with cold water (2×500 mL) and brine (2×200 mL). The organic layer was separated, dried over $Na_2SO_4$ and concentrated under reduced pressure to give the crude product which was purified by column chromatography (neutral $Al_2O_3$, 10%-20% pet ether/EtOAc) to give the title compound (4.5 g, 55.5%) as an off white compound. $^1$H NMR (500 MHz, MeOD-d4) δ=8.41 (s, 1H), 8.14 (s, 1H), 7.22 (dd, J=2.3, 8.6 Hz, 1H), 7.10-7.01 (m, 2H), 4.49-4.44 (m, 2H), 2.82 (d, J=11.4 Hz, 2H), 2.50 (t, J=11.1 Hz, 2H), 2.36-2.28 (m, 2H), 2.22-2.18 (m, 3H), 1.12-1.07 (m, 2H), 1.03 (d, J=6.4 Hz, 6H), 0.00 (s, 9H); LCMS [M+H]$^+$=587.6 g/mol.

Step 2: N-(2'-fluoro-5'-(phenylcarbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide

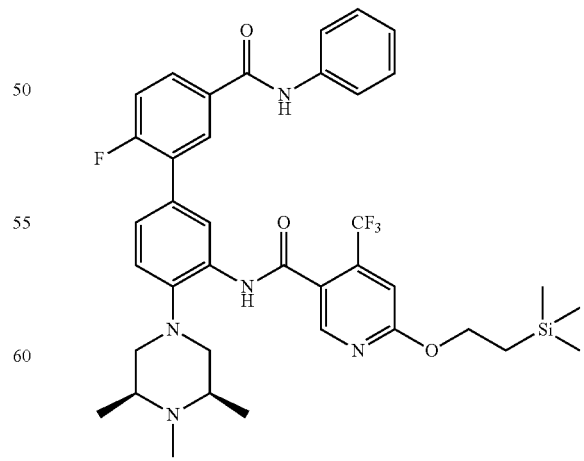

In a 5 mL MW vial 2-fluoro-5-(phenylaminocarbonyl)phenylboronic acid (33.1 mg, 0.128 mmol), N-(5-bromo-2-

((3S,5R)-3,4,5-trimethylpiperazin-1-yl)phenyl)-4-(trifluoromethyl)-6-(2-(trimethylsilyl)ethoxy)nicotinamide (50 mg, 0.085 mmol), bis(di-tert-butyl(4-dimethylaminophenyl)phosphine)dichloropalladium(II) (6.03 mg, 8.51 µmol) and potassium phosphate tribasic (0.036 g, 0.170 mmol) were dissolved in 1,4-dioxane (1.5 mL)/water (0.170 mL) (9:1 mixture) to give a white suspension. The suspension was stirred for 5 min, degassed, purged with $N_2$, and microwaved for 60 min at 110° C. The solvent was evaporated and 15 mL of $CH_2Cl_2$ were added. The suspension was sonicated and extracted from water (15 mL). The solvent was evaporated in vacuo yielding the crude product that was purified by flash column chromatography on silica gel (0-100%, 89% $CH_2Cl_2$, 10% MeOH, 1% $NH_4Ac/CH_2Cl_2$) to afford the title compound, that was used as is in for the following transformation. LCMS $[M+H]^+$=722.58 g/mol.

Step 3: N-(2'-fluoro-5'-(phenylcarbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

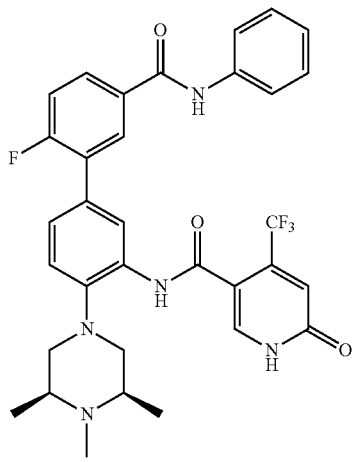 [SMILES: C[C@@H]1CN(c2ccc(-c3cc(C(=O)Nc4ccccc4)ccc3F)cc2NC(=O)c2c[nH]c(=O)cc2C(F)(F)F)C[C@H](C)N1C]

N-(2'-fluoro-5'-(phenylcarbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide from step 2 was dissolved in 2 mL of dichloromethane and trifluoroacetic acid (104 µL, 1.355 mmol) was added. The purple solution was stirred for 1 hour and the solvent was evaporated. The residue was purified using a cation exchange column eluting with MeOH:$NH_4OH$ and freeze dried for 2 days to afford the title compound (37.9 mg, over two steps 72%). $^1$H NMR (500 MHz, DMSO) δ 10.33 (s, 1H), 9.51 (s, 1H), 8.08 (dd, J=7.5, 2.0 Hz, 1H), 8.04 (s, 1H), 8.02-7.98 (m, 1H), 7.96 (s, 1H), 7.77 (d, J=7.7 Hz, 2H), 7.51-7.46 (m, 1H), 7.44 (d, J=8.4 Hz, 1H), 7.37 (t, J=7.9 Hz, 2H), 7.28 (d, J=8.3 Hz, 1H), 7.12 (t, J=7.4 Hz, 1H), 6.82 (s, 1H), 3.01 (d, J=10.5 Hz, 2H), 2.37 (s, 2H), 2.22 (s, 3H), 1.04 (d, J=5.9 Hz, 6H; LCMS $[M+1]^+$=622.52 g/mol.

Example 81: N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide

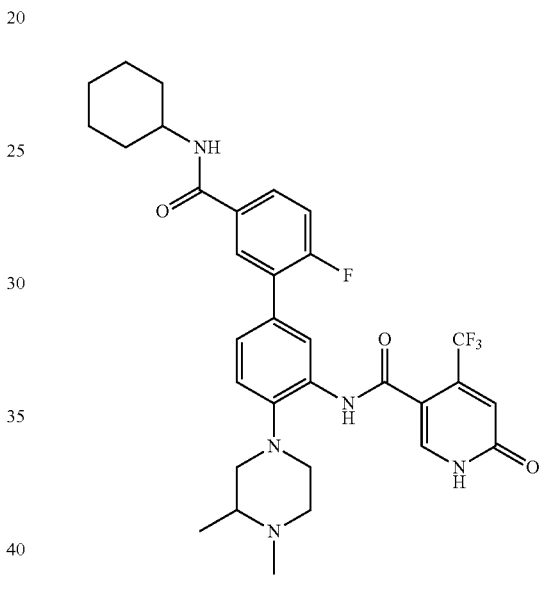

The title compound (white solid, 10 mg, 44%) was prepared in as similar manner as the sequence described above for the preparation of example 80 using 5-(cyclohexylcarbamoyl)-2-fluorophenylboronic acid (8.24 mg, 0.095 mmol) in place of 2-fluoro-5-(phenylaminocarbonyl)phenylboronic acid. $^1$H NMR (500 MHz, MeOD) δ 8.18 (s, 1H), 7.99 (s, 1H), 7.96 (dd, J=7.4, 1.7 Hz, 1H), 7.82 (d, J=2.5 Hz, 1H), 7.43 (d, J=8.1 Hz, 1H), 7.34 (d, J=8.4 Hz, 1H), 7.29-7.23 (m, 1H), 6.90 (s, 1H), 3.86 (s, 1H), 3.10 (d, J=10.4 Hz, 1H), 3.05-2.99 (m, 3H), 2.66 (t, J=10.6 Hz, 2H), 2.53 (s, 1H), 2.44 (s, 3H), 1.96 (d, J=9.4 Hz, 2H), 1.81 (d, J=11.4 Hz, 2H), 1.69 (d, J=12.6 Hz, 1H), 1.44-1.34 (m, 4H), 1.23 (s, 1H), 1.16 (d, J=5.7 Hz, 3H); LCMS HSS $[M+1]^+$=614.6 g/mol.

Example 82: N-(5-(6-(cyclopropylmethoxy)-2-fluoropyridin-3-yl)-2-((3R,5S)-3,4,5-trimethylpiperazin-1-yl)phenyl)-6-oxo-4-(trifluoromethyl)-1,6-dihydropyridine-3-carboxamide

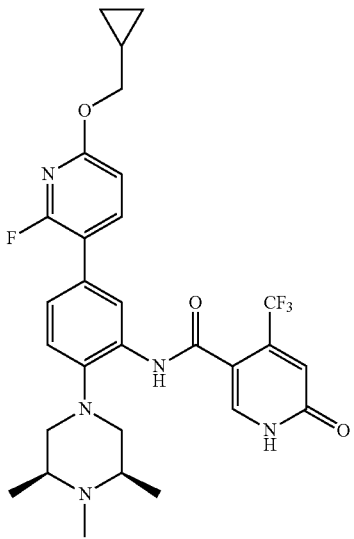 [SMILES: C[C@@H]1CN(c2ccc(-c3ccc(OCC4CC4)nc3F)cc2NC(=O)c2c[nH]c(=O)cc2C(F)(F)F)C[C@H](C)N1C]

The title compound (white solid, 10.5 mg, 27%) was prepared according to the sequence described above for the preparation of example 45 using 6-(cyclopropylmethoxy)-2-fluoropyridine-3-boronic acid (40.9 mg, 0.194 mmol) in place of 5-(N-cyclohexylaminomethyl)-2-fluorophenylboronic acid, pinacol ester. $^1$H NMR (500 MHz, MeOD) δ 8.10 (s, 1H), 7.97 (s, 1H), 7.91 (dd, J=10.2, 8.3 Hz, 1H), 7.40 (d, J=8.4 Hz, 1H), 7.31 (d, J=8.4 Hz, 1H), 6.93 (s, 1H), 6.77 (d, J=8.2 Hz, 1H), 4.13 (d, J=7.1 Hz, 2H), 3.09 (d, J=11.2 Hz, 2H), 2.81 (s, 2H), 2.74 (t, J=11.2 Hz, 2H), 2.54 (s, 3H), 1.31-1.27 (m, 1H), 1.24 (d, J=6.1 Hz, 6H), 0.64-0.59 (m, 2H), 0.39-0.35 (m, 2H); LCMS [M+1]$^+$=573.99 g/mol.

Example 83: N-(3'-((cyclohexylamino)methyl)-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

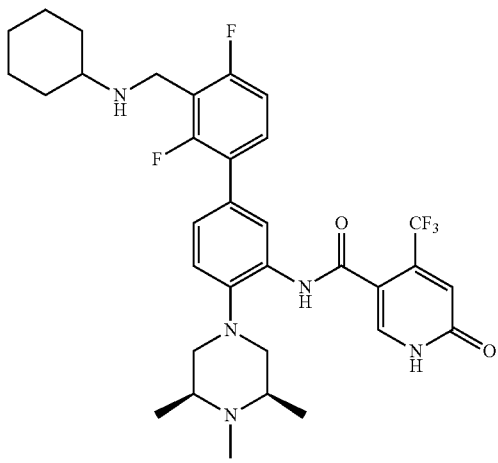 [SMILES: C[C@@H]1CN(c2ccc(-c3ccc(F)c(CNC4CCCCC4)c3F)cc2NC(=O)c2c[nH]c(=O)cc2C(F)(F)F)C[C@H](C)N1C]

The title compound (TFA salt, white solid, 29 mg, 81%) was prepared in as similar manner as the sequence described above for the preparation of example 42 using 2,4-difluoro-3-formylphenylboronic acid (60.7 mg, 0.327 mmol), in place of 2-fluoro-5-formylphenylboronic acid (60.9 mg, 0.363 mmol). $^1$H NMR (500 MHz, MeOD-d4) δ=8.21 (s, 1H), 8.01 (s, 1H), 7.76-7.66 (m, 1H), 7.49-7.39 (m, 2H), 7.27 (t, J=8.7 Hz, 1H), 7.00-6.93 (m, 1H), 4.44 (s, 2H), 3.62-3.50 (m, 2H), 3.32-3.21 (m, 2H), 3.14-2.96 (m, 5H), 2.25 (br. s., 2H), 1.94 (d, J=5.6 Hz, 2H), 1.77 (d, J=12.6 Hz, 1H), 1.56-1.36 (m, 11H), 1.33-1.26 (m, 1H); LCMS [M+H]$^+$=632.9 g/mol.

Example 84: N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide

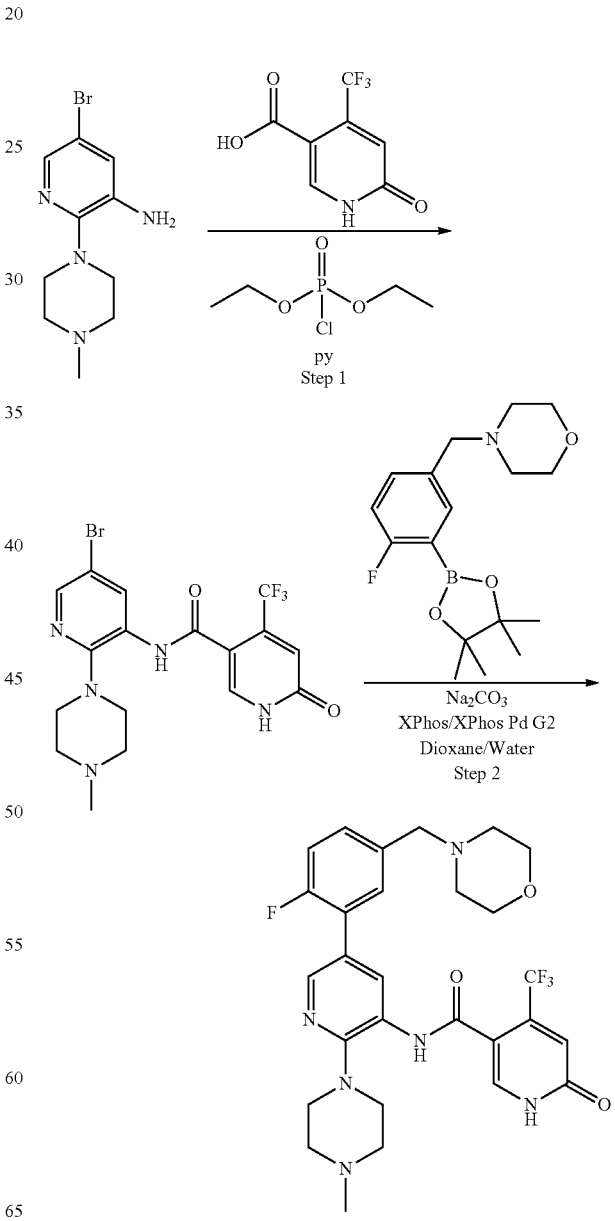

Step 1: N-(5-bromo-2-(4-methylpiperazin-1-yl)pyridin-3-yl)-6-oxo-4-(trifluoromethyl)-1,6-dihydropyridine-3-carboxamide

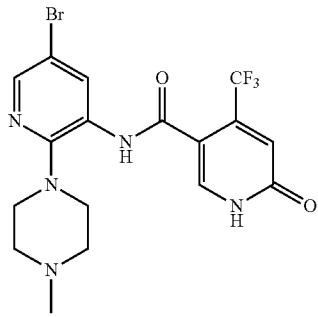 [SMILES: CN1CCN(c2ncc(Br)cc2NC(=O)c2c[nH]c(=O)cc2C(F)(F)F)CC1]

The title compound (red solid, 115 mg, 31%) was prepared according to the sequence described above for the preparation of example 45 using 5-bromo-2-(4-methylpiperazin-1-yl)pyridin-3-amine (200 mg, 0.738 mmol) in place of 5-bromo-2-((3R,5S)-3,4,5-trimethylpiperazin-1-yl)aniline. $^1$H NMR (500 MHz, MeOD) δ 8.32 (d, J=2.3 Hz, 1H), 8.19 (d, J=2.3 Hz, 1H), 7.94 (s, 1H), 6.91 (s, 1H), 3.25-3.22 (m, 4H), 2.68 (d, J=4.2 Hz, 4H), 2.39 (s, 3H); LCMS [M+1]$^+$=460.5 g/mol.

Step 2: N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide

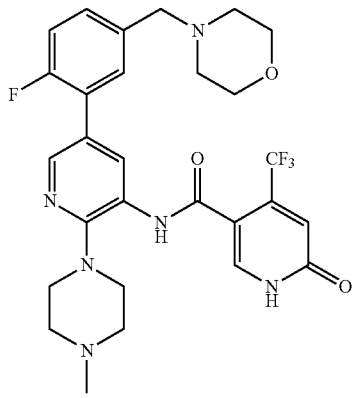

In a 5 mL MW vial 4-(4-fluoro-3-(4,4,5,5-tetramethyl-1,3,2-dioxaborolan-2-yl)benzyl)morpholine (63.3 mg, 0.197 mmol), N-(5-bromo-2-(4-methylpiperazin-1-yl)pyridin-3-yl)-6-oxo-4-(trifluoromethyl)-1,6-dihydropyridine-3-carboxamide (30.25 mg, 0.066 mmol), sodium carbonate, anhydrous (69.7 mg, 0.657 mmol) and XPhos (6.27 mg, 0.013 mmol), XPhos Pd G2 (10.34 mg, 0.013 mmol) were dissolved in water (1095 μL) and 1,4-dioxane (2191 μL) to give a white suspension. The suspension was stirred for 5 min, degassed, purged with N$_2$, and microwaved for 60 min at 120° C. The solvent was evaporated and 15 mL of CH$_2$Cl$_2$ were added. The suspension was sonicated and extracted from water. The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the desired compound (19 mg, 48%). $^1$H NMR (500 MHz, MeOD) δ 8.34 (s, 1H), 8.29 (s, 1H), 7.98 (s, 1H), 7.52 (dd, J=7.5, 1.7 Hz, 1H), 7.41-7.36 (m, 1H), 7.20 (dd, J=10.5, 8.5 Hz, 1H), 6.93 (s, 1H), 3.75-3.65 (m, 4H), 3.58 (s, 2H), 3.34 (s, 4H), 2.76 (s, 4H), 2.50 (s, 4H), 2.44 (s, 3H); LCMS [M+1]$^+$=575.6 g/mol.

Example 85: N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide

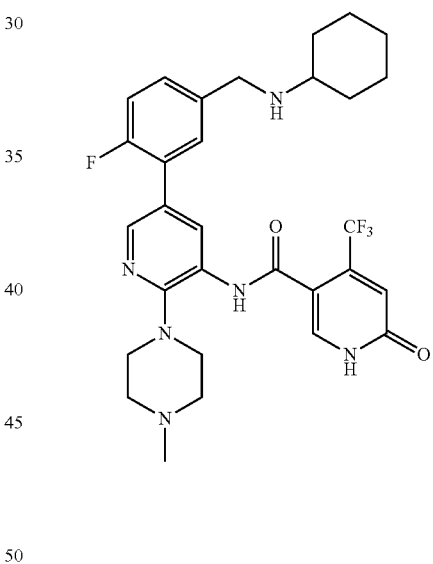

The title compound (white solid, 18.8 mg, 45%) was prepared according to the sequence described above for the preparation of example 84 using 5-(N-cyclohexylaminomethyl)-2-fluorophenylboronic acid, pinacol ester (65.2 mg, 0.196 mmol) in place of 4-(4-fluoro-3-(4,4,5,5-tetramethyl-1,3,2-dioxaborolan-2-yl)benzyl)morpholine. $^1$H NMR (500 MHz, MeOD) δ 8.34 (s, 1H), 8.31 (s, 1H), 8.07 (s, 1H), 7.60 (d, J=7.0 Hz, 1H), 7.45 (s, 1H), 7.29-7.23 (m, 1H), 6.82 (s, 1H), 4.03 (s, 2H), 2.80 (s, 1H), 2.66 (s, 4H), 2.36 (s, 3H), 2.09 (d, J=11.3 Hz, 2H), 1.83 (d, J=12.7 Hz, 2H), 1.69 (d, J=12.8 Hz, 1H), 1.39-1.17 (m, 7H); LCMS [M+1]$^+$=587.8 g/mol.

Example 86: N-(2'-chloro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

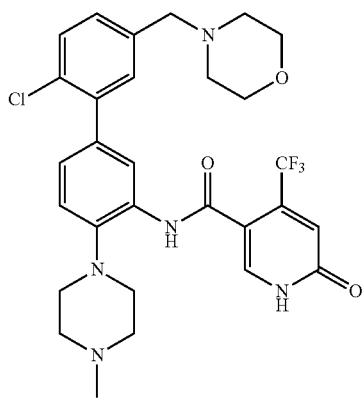 [SMILES: CN1CCN(c2ccc(-c3cc(CN4CCOCC4)ccc3Cl)cc2NC(=O)c2c[nH]c(=O)cc2C(F)(F)F)CC1]

The title compound (white solid, 39 mg, 52%) was prepared according to the sequence described above for the preparation of example 1 using (2-chloro-5-(morpholinomethyl)phenyl)boronic acid (0.085 g, 0.333 mmol) in place of (5-(((2S,6R)-2,6-dimethylmorpholino)methyl)-2-fluorophenyl)boronic acid. $^1$H NMR (500 MHz, MeOD) δ 8.05 (s, 1H), 7.96 (s, 1H), 7.43 (d, J=8.2 Hz, 1H), 7.37 (d, J=1.8 Hz, 1H), 7.32-7.26 (m, 3H), 6.91 (s, 1H), 3.69-3.65 (m, 4H), 3.53 (s, 2H), 3.02 (t, J=4.6 Hz, 4H), 2.69 (s, 4H), 2.47 (s, 4H), 2.39 (s, 3H); LCMS [M+H]$^+$=590.8 g/mol.

Example 87: N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide

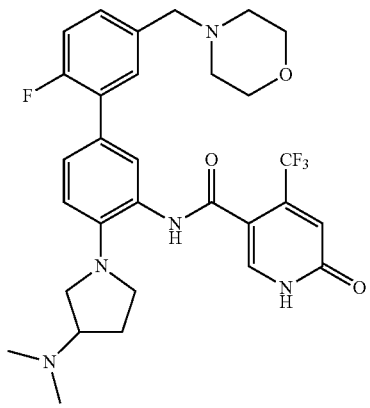 [SMILES: CN(C)C1CCN(c2ccc(-c3cc(CN4CCOCC4)ccc3F)cc2NC(=O)c2c[nH]c(=O)cc2C(F)(F)F)C1]

The title compound (white solid, 2.4 mg, 6% in the last step) was prepared according to the sequence described above for the preparation of example 26 using 3-(dimethylamino)pyrrolidine (0.260 g, 2.273 mmol) in place of 1,2-dimethyl-piperazine dichloride hydrate. $^1$H NMR (500 MHz, DMSO-d6) δ=9.83 (s, 1H), 7.93 (br. s., 1H), 7.41 (br. s., 1H), 7.37 (d, J=7.8 Hz, 1H), 7.33 (d, J=8.6 Hz, 1H), 7.29-7.18 (m, 3H), 6.92 (d, J=8.6 Hz, 1H), 6.81 (s, 1H), 4.12 (d, J=5.1 Hz, 1H), 3.62-3.54 (m, 7H), 3.48 (br. s., 4H), 3.18 (d, J=4.8 Hz, 3H), 2.37 (br. s., 6H), 2.21 (br. s., 6H), 2.14-2.07 (m, 1H), 1.92 (s, 1H); LCMS (M+H)+=588.8 g/mol.

Example 88: N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide

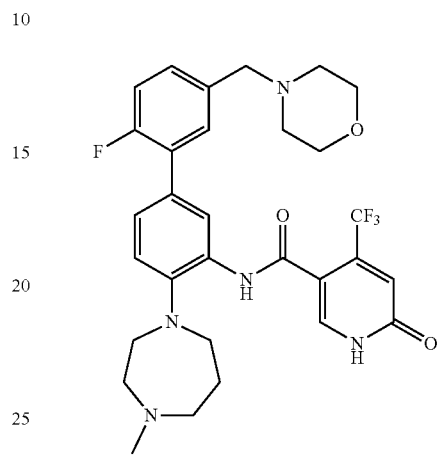

The title compound (white powder, 11 mg, 28% yield in the final step) was prepared according to the sequence described above for the preparation of example 26 using 1-methylhomopiperazine (0.623 g, 5.45 mmol) in place of 1,2-dimethyl-piperazine dichloride hydrate. $^1$H NMR (500 MHz, DMSO-d6) δ=9.67 (s, 2H), 8.28 (br. s., 3H), 8.00 (s, 1H), 7.87 (br. s., 1H), 7.38 (d, J=7.6 Hz, 1H), 7.29 (br. s., 2H), 7.27-7.21 (m, 2H), 6.81 (s, 1H), 3.57 (d, J=4.3 Hz, 12H), 3.23 (d, J=5.6 Hz, 12H), 2.63 (d, J=14.3 Hz, 7H), 2.37 (br. s., 5H), 2.25 (s, 3H), 1.83 (d, J=5.1 Hz, 2H); LCMS [M+H]+=588.8 g/mol.

Example 89: N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide

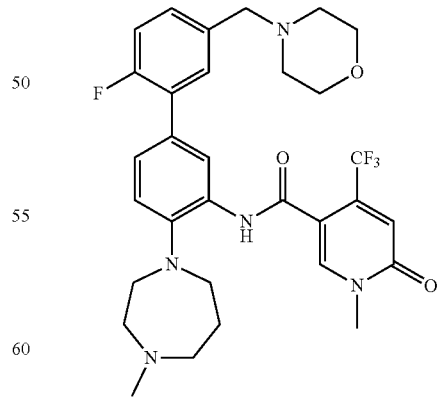

The title compound (brown oil, 9.7 mg, 24% yield in the final step) was prepared according to the sequence described above for the preparation of example 26 using 1-methylhomopiperazine (0.623 g, 5.45 mmol) in place of 1,2-dimethylpiperazine dichloride hydrate and 1-methyl-6-oxo-4-(trifluoromethyl)-1,6-dihydropyridine-3-carbonyl chloride (for preparation of chloride see example 1, 30.1 mg, 0.125 mmol) instead of the 6-hydroxy-4-(trifluoromethyl)nicotinic acid. $^1$H NMR (500 MHz, MeOD-d4) δ=8.32 (s, 1H), 8.06 (s, 1H), 7.50 (dd, J=1.9, 7.5 Hz, 1H), 7.40 (s, 1H), 7.37-7.32 (m, 2H), 7.23-7.13 (m, 1H), 6.96 (s, 1H), 3.72 (t, J=4.5 Hz, 5H), 3.68 (s, 3H), 3.58 (s, 2H), 3.37 (d, J=5.5 Hz, 2H), 3.24 (t, J=5.7 Hz, 2H), 2.99 (d, J=3.5 Hz, 4H), 2.56 (s, 3H), 2.51 (br. s., 4H), 2.06-1.98 (m, 2H); LCMS [M+H]$^+$=602.8 g/mol.

Example 90: N-(2'-fluoro-5'-(methylcarbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

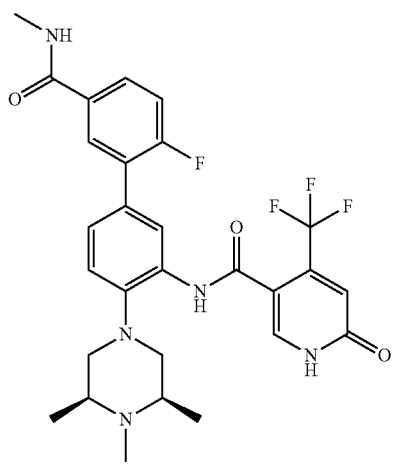 [SMILES: CNC(=O)c1ccc(F)c(-c2ccc(N3C[C@@H](C)N(C)[C@@H](C)C3)c(NC(=O)c3c[nH]c(=O)cc3C(F)(F)F)c2)c1]

The title compound (white solid, 37.3 mg, 71%) was prepared according to the sequence described above for the preparation of example 80 using 2-fluoro-5-(methylaminocarbonyl)phenylboronic acid (26.1 mg, 0.133 mmol) in place of 2-fluoro-5-(phenylaminocarbonyl)phenylboronic acid. $^1$H NMR (500 MHz, MeOD) δ 8.16 (s, 1H), 7.99-7.96 (m, 2H), 7.83 (ddd, J=8.3, 4.5, 2.3 Hz, 1H), 7.44 (d, J=8.3 Hz, 1H), 7.33 (d, J=8.4 Hz, 1H), 7.28 (dd, J=10.1, 8.9 Hz, 1H), 6.91 (s, 1H), 3.05 (d, J=10.9 Hz, 2H), 2.93 (s, 3H), 2.71 (t, J=11.0 Hz, 2H), 2.64 (s, 2H), 2.43 (s, 3H), 1.19 (d, J=5.9 Hz, 6H); LCMS [M+1]$^+$=560.5 g/mol.

Example 91: N-(4-(3-(dimethylamino)pyrrolidin-1-yl)-2'-fluoro-5'-(morpholinomethyl)-[1,1'-biphenyl]-3-yl)-4-fluoro-3,5-dimethylbenzamide

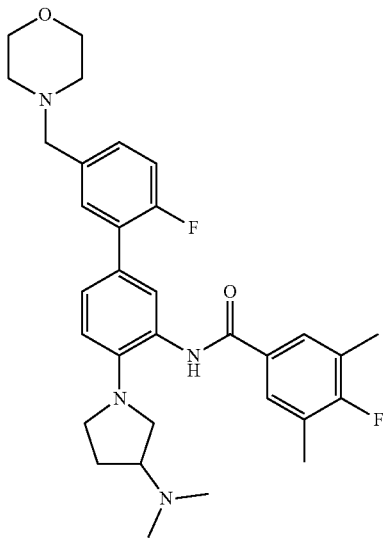 [SMILES: Cc1cc(C(=O)Nc2cc(-c3cc(CN4CCOCC4)ccc3F)ccc2N2CCC(N(C)C)C2)cc(C)c1F]

The title compound (red powder, 31.5 mg, 48.3% yield in the final step) was prepared according to the sequence described above for the preparation of example 26 using 3-(dimethylamino)pyrrolidine (0.260 g, 2.273 mmol) in place of 1,2-dimethyl-piperazine dichloride hydrate and 4-Fluoro-3,5-dimethylbenzoic acid (20.89 mg, 0.124 mmol) instead of the 6-hydroxy-4-(trifluoromethyl)nicotinic acid. $^1$H NMR (500 MHz, DMSO-d6) δ=9.86 (s, 1H), 7.76 (d, J=7.0 Hz, 2H), 7.43-7.32 (m, 3H), 7.29-7.17 (m, 2H), 6.93 (d, J=8.3 Hz, 1H), 3.57 (br.s., 5H), 3.49 (br. s., 4H), 2.45-2.08 (m, 18H), 1.86-1.69 (m, 1H); LCMS [M+1]$^+$= 549.9 g/mol.

Example 92: 4-fluoro-N-(2'-fluoro-4-(4-methyl-1,4-diazepan-1-yl)-5'-(morpholinomethyl)-[1,1'-biphenyl]-3-yl)-3,5-dimethylbenzamide The title compound (red powder, 15 mg, 43.1% yield in the final step) was prepared according to the sequence described above for the preparation of example 26 using 1-methylhomopiperazine (0.623 g, 5.45 mmol) in place of 1,2-dimethyl-piperazine dichloride hydrate and 4-Fluoro-3,5-dimethylbenzoic acid (11.14 mg, 0.066 mmol) instead of the 6-hydroxy-4-(trifluoromethyl)nicotinic acid. $^1$H NMR (500 MHz, DMSO-d6) δ=9.69 (s, 1H), 8.10-7.94 (m, 1H), 7.77 (d, J=6.7 Hz, 2H), 7.41 (d, J=7.6 Hz, 1H), 7.36-7.29 (m, 3H), 7.27 (d, J=10.5 Hz, 1H), 3.58 (br. s., 5H), 3.50 (s, 3H), 3.28-3.24 (m, 2H), 3.20 (t, J=6.0 Hz, 3H), 2.37 (br. s., 6H), 2.32 (s, 7H), 1.93 (d, J=9.0 Hz, 2H), 1.24 (br. s., 1H), 1.29-1.19 (m, 1H); LCMS [M+1]$^+$=548.7 g/mol.

Example 93: N-(5'-(cyclopropylcarbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

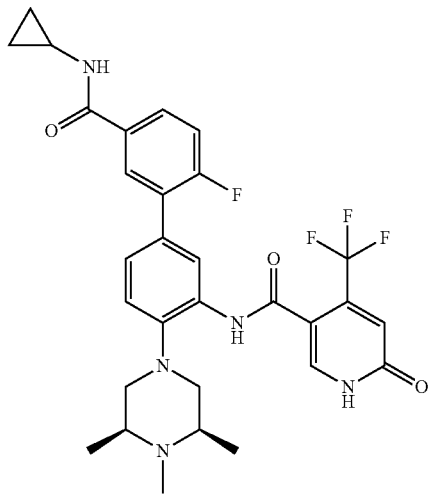 [SMILES: C[C@@H]1CN(c2ccc(-c3cc(C(=O)NC4CC4)ccc3F)cc2NC(=O)c2c[nH]c(=O)cc2C(F)(F)F)C[C@H](C)N1C]

The title compound (white solid, 8.0 mg, 15%) was prepared according to the sequence described above for the preparation of example 80 using 5-(cyclopropylcarbamoyl)-2-fluorophenylboronic acid (30.7 mg, 0.138 mmol), in place of 2-fluoro-5-(phenylaminocarbonyl)phenylboronic acid. $^1$H NMR (500 MHz, MeOD) δ 8.15 (s, 1H), 7.98 (s, 1H), 7.96 (dd, J=7.5, 1.8 Hz, 1H), 7.43 (d, J=8.3 Hz, 1H), 7.33 (d, J=8.2 Hz, 1H), 7.26 (t, J=9.5 Hz, 1H), 6.90 (s, 1H), 3.06 (d, J=7.9 Hz, 2H), 2.88-2.83 (m, 1H), 2.73 (s, 3H), 2.46 (s, 2H), 1.21 (s, 6H), 0.83-0.77 (m, 2H), 0.69-0.63 (m, 2H); LCMS [M+1]$^+$=586.56 g/mol.

Example 94: 4-fluoro-N-(2'-fluoro-4-(5-methylhexahydropyrrolo[3,4-c]pyrrol-2(1H)-yl)-5'-(morpholinomethyl)-[1,1'-biphenyl]-3-yl)-3,5-dimethylbenzamide

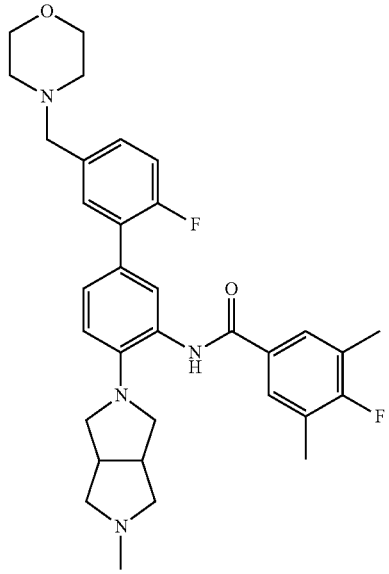 [SMILES: Cc1cc(C(=O)Nc2cc(-c3cc(CN4CCOCC4)ccc3F)ccc2N2CC3CN(C)CC3C2)cc(C)c1F]

The title compound (red-brown powder, 31.5 mg, 88% yield in the final step) was prepared according to the sequence described above for the preparation of example 26 using 1-2-Methyl-octahydro-pyrrolo[3,4-c]pyrrole (0.172 g, 1.364 mmol) in place of 1,2-dimethyl-piperazine dichloride hydrate and 4-fluoro-3,5-dimethylbenzoic acid (11.26 mg, 0.067 mmol) instead of the 6-hydroxy-4-(trifluoromethyl) nicotinic acid. $^1$H NMR (500 MHz, DMSO-d6) δ=9.61 (br. s., 1H), 7.91-7.74 (m, 2H), 7.50-7.05 (m, 4H), 3.58 (br. s., 4H), 3.50 (br. s., 2H), 3.24-3.11 (m, 2H), 3.00 (br. s., 2H), 2.64 (br. s., 3H), 2.37 (br. s., 3H), 2.34-2.22 (m, 6H), 1.31-1.19 (m, 2H); LCMS [M+1]$^+$=561.8 g/mol.

Example 95: 4-fluoro-N-(2'-fluoro-5'-(morpholinomethyl)-4-(4-(2,2,2-trifluoroethyl)piperazin-1-yl)-[,1'-biphenyl]-3-yl)-3,5-dimethylbenzamide

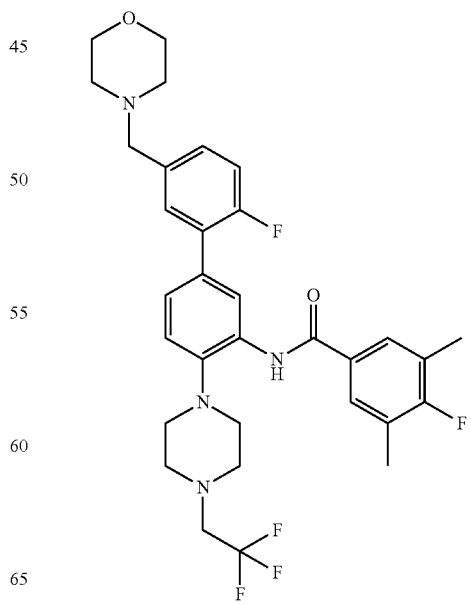

The title compound (brown powder, 9 mg, 27.6% yield in the final step) was prepared according to the sequence described above for the preparation of example 26 using 1-2-Methyl-octahydro-pyrrolo[3,4-c]pyrrole (0.172 g, 1.364 mmol) in place of 1,2-dimethyl-piperazine dichloride hydrate and 1-(2,2,2-Trifluoroethyl)piperazine dihydrochloride (250 mg, 1.037 mmol) instead of the 6-hydroxy-4-(trifluoromethyl)nicotinic acid. $^1$H NMR (500 MHz, DMSO-d6) δ=9.48 (s, 1H), 8.20 (s, 1H), 7.62 (d, J=6.8 Hz, 2H), 7.33 (d, J=7.7 Hz, 1H), 7.31-7.28 (m, 1H), 7.27-7.21 (m, 2H), 7.20-7.15 (m, 1H), 3.49 (t, J=4.3 Hz, 4H), 3.42 (s, 2H), 3.21-3.18 (m, 1H), 2.89-2.82 (m, 4H), 2.77 (d, J=3.8 Hz, 4H), 2.29 (br. s., 4H), 2.24 (s, 6H); LCMS [M+1]$^+$= 603.8 g/mol.

Example 96: (S)—N-(2-(3,4-dimethylpiperazin-1-yl)-5-(3-fluoropyridin-2-yl)phenyl)-6-oxo-4-(trifluoromethyl)-1,6-dihydropyridine-3-carboxamide

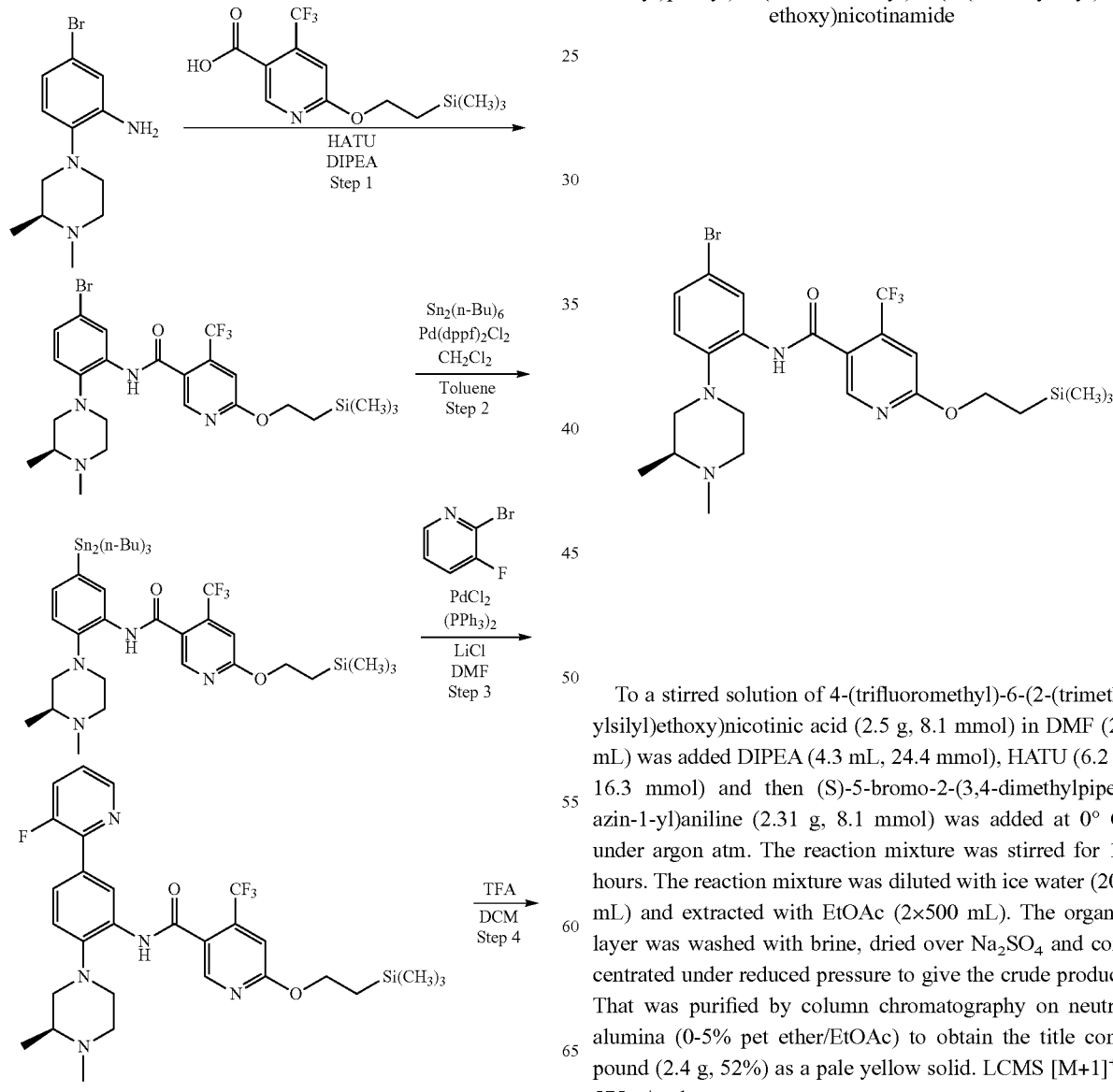

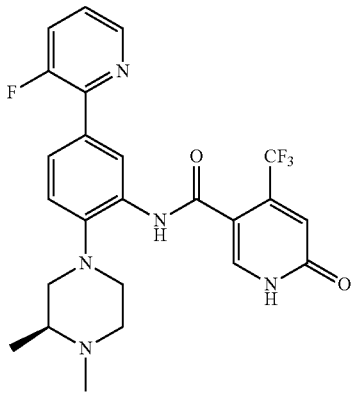

Step 1: (S)—N-(5-bromo-2-(3,4-dimethylpiperazin-1-yl)phenyl)-4-(trifluoromethyl)-6-(2-(trimethylsilyl)ethoxy)nicotinamide To a stirred solution of 4-(trifluoromethyl)-6-(2-(trimethylsilyl)ethoxy)nicotinic acid (2.5 g, 8.1 mmol) in DMF (25 mL) was added DIPEA (4.3 mL, 24.4 mmol), HATU (6.2 g, 16.3 mmol) and then (S)-5-bromo-2-(3,4-dimethylpiperazin-1-yl)aniline (2.31 g, 8.1 mmol) was added at 0° C. under argon atm. The reaction mixture was stirred for 16 hours. The reaction mixture was diluted with ice water (200 mL) and extracted with EtOAc (2×500 mL). The organic layer was washed with brine, dried over Na$_2$SO$_4$ and concentrated under reduced pressure to give the crude product. That was purified by column chromatography on neutral alumina (0-5% pet ether/EtOAc) to obtain the title compound (2.4 g, 52%) as a pale yellow solid. LCMS [M+1]$^+$= 575 g/mol.

Step 2: (S)—N-(2-(3,4-dimethylpiperazin-1-yl)-5-(tributylstannyl)phenyl)-4-(trifluoromethyl)-6-(2-(trimethylsilyl)ethoxy)nicotinamide

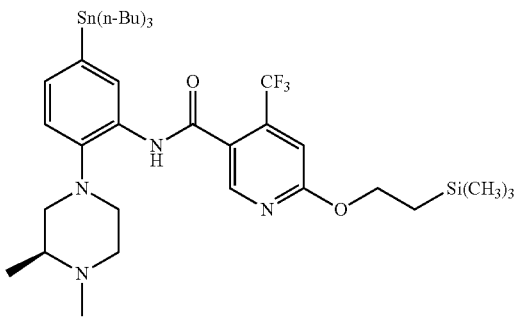

A stirred solution of (S)—N-(5-bromo-2-(3,4-dimethylpiperazin-1-yl)phenyl)-4-(trifluoromethyl)-6-(2-(trimethylsilyl)ethoxy)nicotinamide (2.4 g, 4.1 mmol) in toluene (48 mL) was degassed with argon for 15 min. Followed by addition of hexabutylditin (4.25 mL, 8.3 mmol), followed by $Pd_2(dppf)_2Cl_2$ (0.34 g, 0.41 mmol) after that the solution was heated to reflux under argon atmosphere for 16 hours. The reaction mixture was filtered through celite bed washed with EtOAc. The filtrated was evaporated under reduced pressure. The crude compound was purified by column chromatography with neutral alumina (0-30% pet ether/EtOAc) in the title compound (1.5 g, 45%) as a pale yellow liquid. $^1$H NMR (500 MHz, MeOD) δ 8.52 (s, 1H), 8.12 (s, J=11.5 Hz, 1H), 7.28 (d, J=7.8 Hz, 1H), 7.21 (d, J=7.7 Hz, 1H), 7.12 (s, 1H), 4.58-4.54 (m, 2H), 3.02 (d, J=11.2 Hz, 1H), 3.00-2.94 (m, 2H), 2.93-2.89 (m, 1H), 2.58 (dd, J=11.7, 9.8 Hz, 1H), 2.46 (td, J=11.2, 3.2 Hz, 1H), 2.33 (s, 3H), 1.62-1.56 (m, 5H), 1.40-1.33 (m, 7H), 1.22-1.16 (m, 3H), 1.13-1.06 (m, 9H), 0.91 (t, J=7.3 Hz, 9H), 0.11 (d, J=3.4 Hz, 9H); LCMS [M+1]$^+$=785.1 g/mol.

Step 3: (S)—N-(2-(3,4-dimethylpiperazin-1-yl)-5-(3-fluoropyridin-2-yl)phenyl)-4-(trifluoromethyl)-6-(2-(trimethylsilyl)ethoxy)nicotinamide

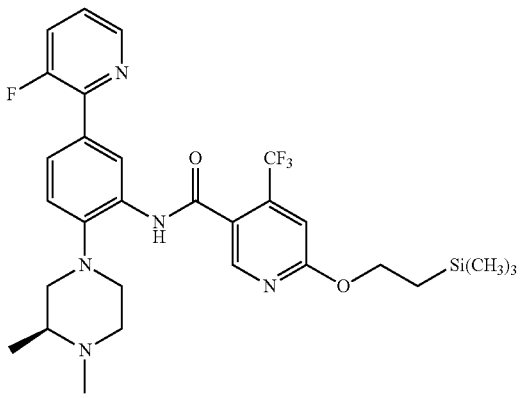

(S)—N-(2-(3,4-dimethylpiperazin-1-yl)-5-(tributylstannyl)phenyl)-4-(trifluoromethyl)-6-(2-(trimethylsilyl)ethoxy)nicotinamide (112 mg, 0.143 mmol) was dissolved in N,N-dimethylformamide (572 μL). 2-bromo-3-fluoropyridine (27.7 mg, 0.157 mmol), lithium chloride (18.17 mg, 0.429 mmol) and bis(triphenylphosphine)palladium(II) dichloride (5.52 mg, 7.86 μmol) were added to the solution at room temperature and then microwave it at 120° C. for 3 hours. The reaction mixture was quenched with water and then extracted with dichloromethane (3×10 mL). The organic layer was separated, concentrated and purified by column chromatography on silica gel (0-100%, 89% $CH_2Cl_2$, 10% MeOH, 1% $NH_4Ac/CH_2Cl_2$) to afford the title compound that was used in the next step without further purification. LCMS [M+1]$^+$=590 g/mol.

Step 4: (S)—N-(2-(3,4-dimethylpiperazin-1-yl)-5-(3-fluoropyridin-2-yl)phenyl)-6-oxo-4-(trifluoromethyl)-1,6-dihydropyridine-3-carboxamide

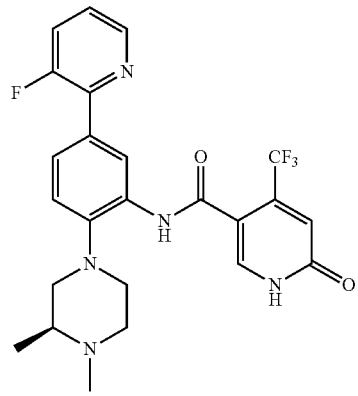 [SMILES: C[C@H]1CN(c2ccc(-c3ncccc3F)cc2NC(=O)c2c[nH]c(=O)cc2C(F)(F)F)CCN1C]

(S)—N-(2-(3,4-dimethylpiperazin-1-yl)-5-(3-fluoropyridin-2-yl)phenyl)-4-(trifluoromethyl)-6-(2-(trimethylsilyl)ethoxy)nicotinamide was dissolved in 2 mL of dichloromethane and trifluoroacetic acid (1094 μL, 14.29 mmol) was added. The purple solution was stirred for 1 hour and the solvent was evaporated. The residue was purified by a cation exchange column eluting with MeOH:NH$_4$OH and freeze dried for 2 days to afford the product as a white powder. $^1$H NMR (500 MHz, MeOD) δ 8.39 (s, 1H), 8.37 (dt, J=3.3, 1.4 Hz, 1H), 7.87 (s, 1H), 7.66 (dt, J=8.6, 2.1 Hz, 1H), 7.59 (ddd, J=11.2, 8.3, 1.1 Hz, 1H), 7.32 (dt, J=8.3, 4.2 Hz, 1H), 7.27-7.24 (m, 1H), 6.82 (s, 1H), 3.02 (ddd, J=11.7, 5.4, 2.7 Hz, 1H), 2.97 (dt, J=11.7, 2.7 Hz, 1H), 2.91 (td, J=11.5, 2.4 Hz, 1H), 2.85 (dt, J=11.7, 2.8 Hz, 1H), 2.53 (dd, J=11.9, 9.9 Hz, 1H), 2.47 (td, J=11.4, 3.1 Hz, 1H), 2.36-2.31 (m, 1H), 2.29 (s, 3H), 1.04 (d, J=6.1 Hz, 3H); LCMS [M+1]$^+$=490.3 g/mol.

Example 97: N-(2'-fluoro-5'-(morpholinomethyl)-4-(4-(2,2,2-trifluoroethyl)piperazin-1-yl)-[,1'-biphenyl]-3-yl)-6-oxo-4-(trifluoromethyl)-1,6-dihydropyridine-3-carboxamide

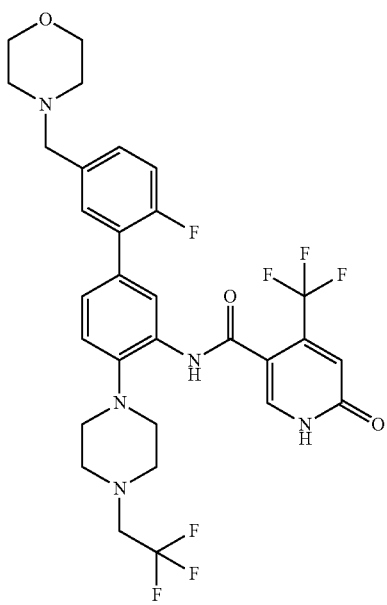 [SMILES: O=C(Nc1cc(-c2cc(CN3CCOCC3)ccc2F)ccc1N1CCN(CC(F)(F)F)CC1)c1c[nH]c(=O)cc1C(F)(F)F]

The title compound (white powder, 10.2 mg, 26.3% yield in the final step) was prepared according to the sequence described above for the preparation of example 26 using 1-(2,2,2-trifluoroethyl)piperazine dihydrochloride (250 mg, 1.037 mmol) in place of 1,2-dimethyl-piperazine dichloride hydrate. $^1$H NMR (500 MHz, DMSO-d6) δ=9.42 (s, 1H), 8.02 (d, J=13.9 Hz, 2H), 7.42-7.37 (m, 1H), 7.35-7.30 (m, 3H), 7.26 (d, J=10.5 Hz, 1H), 6.73 (s, 1H), 3.61-3.56 (m, 6H), 3.50 (s, 5H), 3.25 (d, J=10.1 Hz, 5H), 2.92 (d, J=4.5 Hz, 4H), 2.80 (br. s., 4H), 2.37 (br. s., 4H); LCMS [M+1]$^+$= 642.8 g/mol.

Example 98: N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

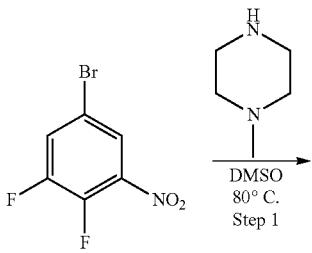

-continued

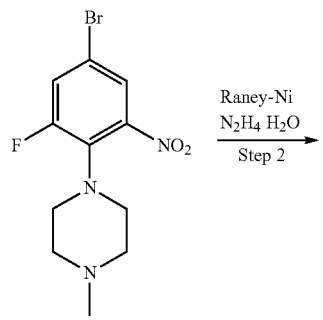

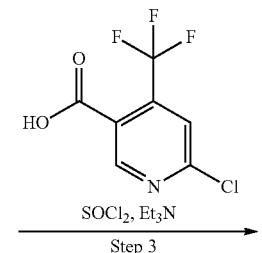

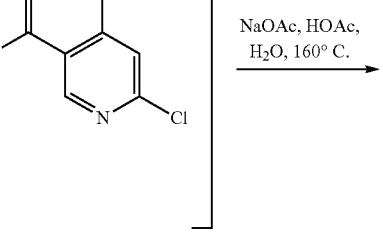

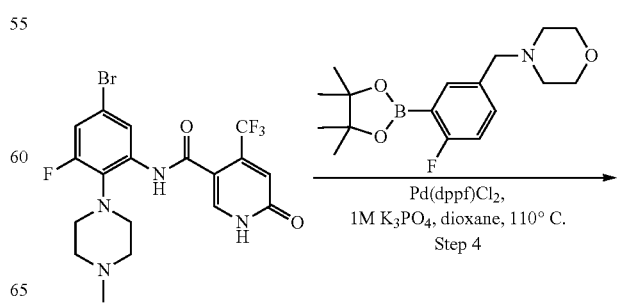

Step 2:
5-bromo-3-fluoro-2-(4-methylpiperazin-1-yl)aniline

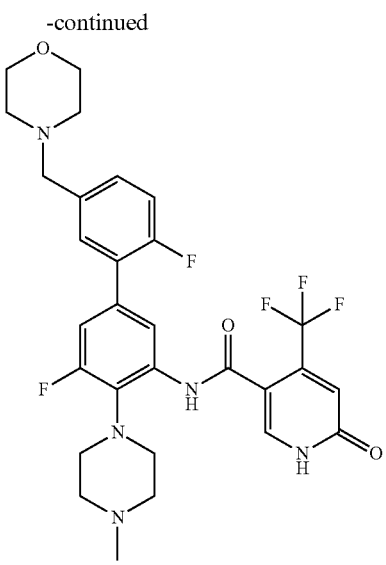
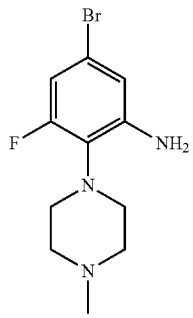 [SMILES: CN1CCN(c2c(F)cc(Br)cc2[N+](=O)[O-])CC1]

Step 1: 1-(4-bromo-2-fluoro-6-nitrophenyl)-4-methylpiperazine

To a solution 1-(4-bromo-2-fluoro-6-nitrophenyl)-4-methylpiperazine (1.428 g) and hydrazine monohydrate (0.728 mL, 15 mmol) in MeOH (15 mL) at 60° C. was added a suspension of Raney-Nickel (0.107 g, 1.25 mmol) in MeOH (5 mL) portion wise over 5 min. After addition, the resulting mixture was heated at 60° C. for 30 min and it turned from dark yellow to pale yellow. Raney-nickel was filtered off and the filtrated was concentrated, dried to give the title compound as a light beige solid (1.272 g, 88% over 2 steps). LCMS [M+H]$^+$=288.2 g/mol.

Step 3: N-(5-bromo-3-fluoro-2-(4-methylpiperazin-1-yl)phenyl)-6-oxo-4-(trifluoromethyl)-1,6-dihydropyridine-3-carboxamide

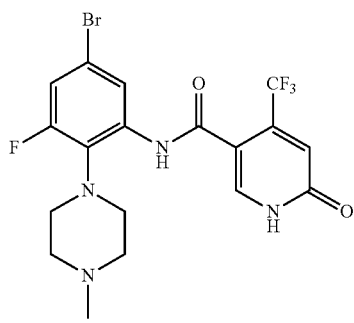 [SMILES: CN1CCN(c2c(F)cc(Br)cc2NC(=O)c2c[nH]c(=O)cc2C(F)(F)F)CC1]

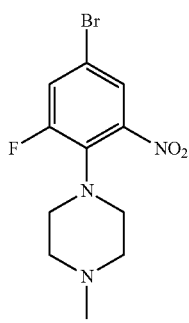

To a solution of 5-bromo-1,2-difluoro-3-nitrobenzene (1.190 g, 5 mmol) in DMSO (3 mL) was added 1-methylpiperazine (0.61 mL, 5.5 mmol). The resulting dark red solution was stirred at 80° C. for 1 hour. It was diluted with H$_2$O (80 mL), basified with 1 M aq NaOH (5 mL, 5 mmol) and extracted with EtOAc (60 mL+30 mL). The combined extracts were dried (Na$_2$SO$_4$), concentrated and dried under vacuum to give the title compound as a dark red oil (1.428 g). LCMS [M+H]$^+$=318.2 g/mol.

To a 25 mL RBF charged with 6-chloro-4-(trifluoromethyl)nicotinic acid (271 mg, 1.2 mmol) was added thionyl chloride (3.64 mL, 50 mmol). The resulting suspension was heated at 80° C. for 1 hour. It was evaporated to give a light yellow oil which was treated with DCM (10 mL), 5-bromo-3-fluoro-2-(4-methylpiperazin-1-yl)aniline (288 mg, 1 mmol) and Et$_3$N (0.42 mL, 3 mmol). The resulting mixture was stirred at RT for 1 hour. After quenching with sat. aq NaHCO$_3$ (10 mL), it was extracted with DCM (30 mL×2) and the combined extracts were evaporated and dried to give crude N-(5-bromo-3-fluoro-2-(4-methylpiperazin-1-yl)phenyl)-6-chloro-4-(trifluoromethyl)nicotinamide as a beige solid. LCMS [M+H]$^+$ 495.2. A mixture of the above solid, NaOAc (164 mg, 2 mmol) in AcOH/H$_2$O (7 mL/2 mL) in a 20 mL microwave vial was microwaved at 160° C. for 4 h. Solvents were removed and the residue was treated with sat. NaHCO$_3$ (20 mL) and extracted with DCM (60 mL+30 mL). The combined extracts were concentrated and purified by flash chromatography in silica gel (0-100% EtOAc/hex then 0-20% MeOH/DCM) to give the title compound as a white solid (349 mg, 88% over 2 steps). LCMS [M+H]⁺=477.2 g/mol.

Step 4: N-(3-fluoro-2-(4-methylpiperazin-1-yl)-5-(2-morpholinopyrimidin-5-yl)phenyl)-6-oxo-4-(trifluoromethyl)-1,6-dihydropyridine-3-carboxamide

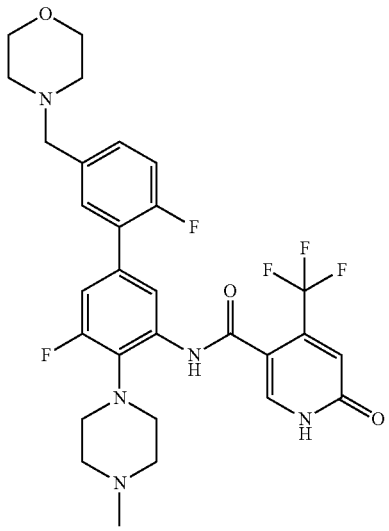 [SMILES: CN1CCN(c2c(F)cc(-c3cc(CN4CCOCC4)ccc3F)cc2NC(=O)c2c[nH]c(=O)cc2C(F)(F)F)CC1]

The title compound (white solid, 29.7 mg, 50%) was prepared according to the sequence described above for the preparation of example 1 using 4-(4-fluoro-3-(4,4,5,5-tetramethyl-1,3,2-dioxaborolan-2-yl)benzyl)morpholine (64.2 mg, 0.2 mmol) and N-(5-bromo-3-fluoro-2-(4-methylpiperazin-1-yl)phenyl)-6-oxo-4-(trifluoromethyl)-1,6-dihydropyridine-3-carboxamide (47.7 mg, 0.1 mmol). ¹H NMR (500 MHz, MeOD-d4) δ=8.26 (s, 1H), 8.06 (s, 1H), 7.52 (d, J=7.6 Hz, 1H), 7.40 (t, J=6.8 Hz, 1H), 7.22-7.14 (m, 2H), 6.94 (s, 1H), 3.72 (t, J=4.5 Hz, 4H), 3.59 (s, 2H), 3.31-3.13 (m, 4H), 2.66 (br. s., 4H), 2.51 (br. s., 4H), 2.38 (s, 3H); LCMS [M+H]⁺=592.4 g/mol.

Example 99: N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide

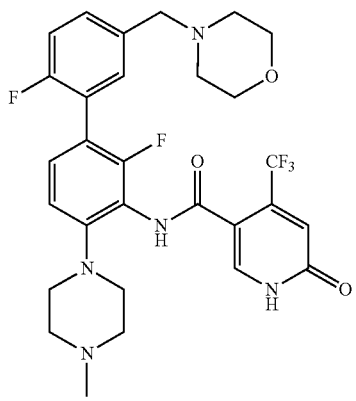

The title compound (white solid, 13.6 mg, 22%) was prepared according to the sequence described above for the preparation of example 1 (for a similar example see example 98) using 4-(4-fluoro-3-(4,4,5,5-tetramethyl-1,3,2-dioxaborolan-2-yl)benzyl)morpholine (64.2 mg, 0.2 mmol) and N-(3-bromo-2-fluoro-6-(4-methylpiperazin-1-yl)phenyl)-6-oxo-4-(trifluoromethyl)-1,6-dihydropyridine-3-carboxamide (47.7 mg, 0.1 mmol). ¹H NMR (500 MHz, MeOD-d4) δ=7.98 (s, 1H), 7.45-7.34 (m, 3H), 7.17 (dd, J=8.6, 9.7 Hz, 1H), 7.09 (d, J=8.4 Hz, 1H), 6.94 (s, 1H), 3.71 (t, J=4.6 Hz, 4H), 3.57 (s, 2H), 3.10 (br. s., 4H), 2.66 (br. s., 4H), 2.50 (br. s., 4H), 2.38 (s, 3H); LCMS [M+H]⁺=592.3 g/mol.

Example 100: N-(2'-fluoro-4-(5-methylhexahydropyrrolo[3,4-c]pyrrol-2(1H)-yl)-5'-(morpholinomethyl)-[1,1'-biphenyl]-3-yl)-6-oxo-4-(trifluoromethyl)-1,6-dihydropyridine-3-carboxamide

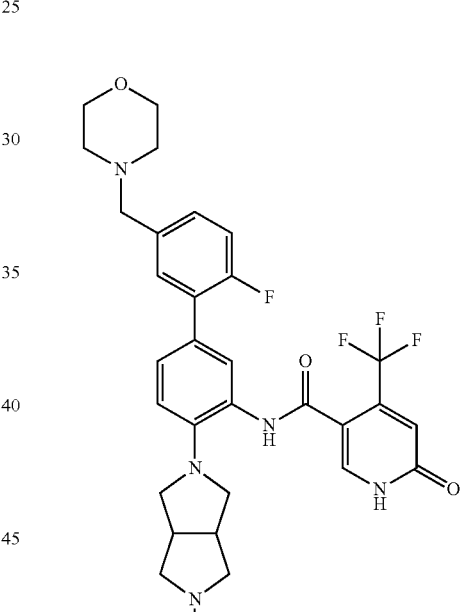

The title compound (yellow powder, 20 mg, 32.5% yield in the final step) was prepared according to the sequence described above for the preparation of example 26 using 1-2-Methyl-octahydro-pyrrolo[3,4-c]pyrrole (0.172 g, 1.364 mmol) in place of 1,2-dimethyl-piperazine dichloride hydrate. ¹H NMR (500 MHz, DMSO-d6) δ=10.06-9.63 (m, 1H), 8.07-7.99 (m, 1H), 7.85-7.74 (m, 1H), 7.39 (d, J=6.7 Hz, 1H), 7.36-7.28 (m, 3H), 7.25 (d, J=10.6 Hz, 1H), 7.15 (d, J=8.4 Hz, 1H), 6.82 (s, 1H), 3.64-3.54 (m, 8H), 3.52-3.48 (m, 5H), 3.17-3.04 (m, 5H), 2.43-2.33 (m, 7H), 1.94-1.88 (m, 3H). LCMS [M+1]⁺=600.7 g/mol.

Example 101: N-(4-(3-(dimethylamino)pyrrolidin-1-yl)-2'-fluoro-5'-(morpholinomethyl)-[1,1'-biphenyl]-3-yl)-1-methyl-6-oxo-4-(trifluoromethyl)-1,6-dihydropyridine-3-carboxamide

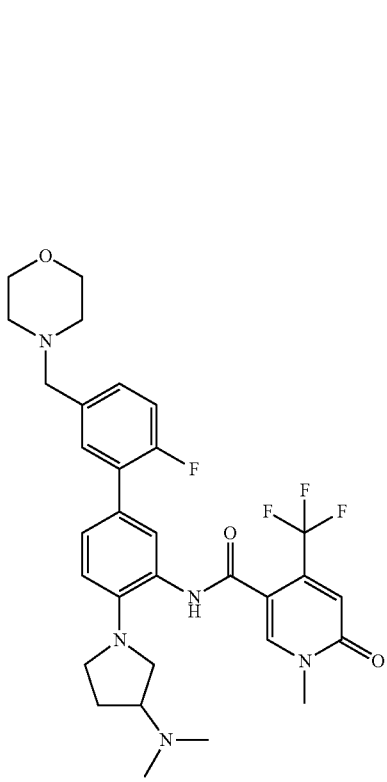 [SMILES: CN(C)C1CCN(c2ccc(-c3cc(CN4CCOCC4)ccc3F)cc2NC(=O)c2cn(C)c(=O)cc2C(F)(F)F)C1]

The title compound (brown oil, formic acid salt, 6.2 mg, 13.64% yield in the final step) was prepared according to the sequence described above for the preparation of example 26 using 3-(dimethylamino)pyrrolidine (0.260 g, 2.273 mmol) in place of 1,2-dimethyl-piperazine dichloride hydrate and 1-methyl-6-oxo-4-(trifluoromethyl)-1,6-dihydropyridine-3-carbonyl chloride (for preparation of chloride see example 1, 28.9 mg, 0.120 mmol), instead of the 6-hydroxy-4-(trifluoromethyl)nicotinic acid. $^1$H NMR (500 MHz, MeOD-d4) δ=8.50 (br. s., 4H), 8.31 (br. s., 1H), 7.75 (br. s., 1H), 7.50 (d, J=6.4 Hz, 1H), 7.43 (d, J=8.4 Hz, 1H), 7.35-7.29 (m, 1H), 7.36-7.27 (m, 1H), 7.22-7.10 (m, 2H), 6.95 (s, 1H), 3.72 (t, J=4.5 Hz, 4H), 3.67 (s, 3H), 3.60 (s, 2H), 2.56 (s, 5H), 2.55-2.51 (m, 4H), 2.40-2.30 (m, 1H), 2.11-1.93 (m, 1H); LCMS [M+1]$^+$=602.7 g/mol.

Example 102: 6-fluoro-N-(2'-fluoro-4-(4-methylpiperazin-1-yl)-5'-(morpholinomethyl)-[1,1'-biphenyl]-3-yl)-1H-benzo[d]imidazole-4-carboxamide

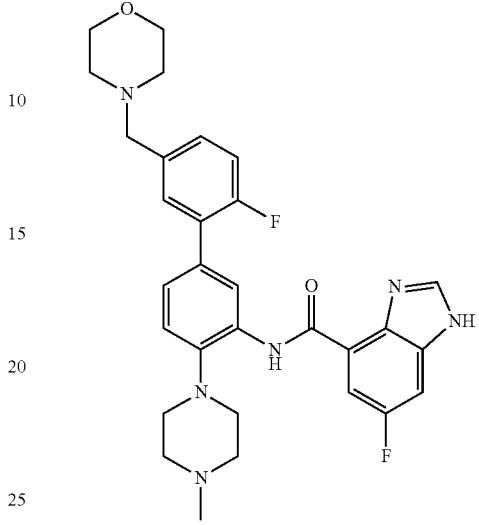

The title compound (brown powder, 16.7 mg, 39.9% yield) was prepared according to a similar procedure of the sequence described above for the preparation of example 9 using 6-Fluoro-1H-1,3-benzodiazole-4-carboxylic acid (17.05 mg, 0.095 mmol) in place of 6-oxo-1,6-dihydropyridazine-3-carboxylic acid. 1H NMR (500 MHz, DMSO-d6) δ=13.18 (br. s., 1H), 12.27 (br. s., 1H), 8.76 (br. s., 1H), 8.62 (s, 1H), 7.75 (dd, J=2.4, 10.6 Hz, 1H), 7.68 (dd, J=2.4, 8.3 Hz, 1H), 7.47-7.43 (m, 1H), 7.41-7.37 (m, 1H), 7.36-7.24 (m, 4H), 3.59 (t, J=4.3 Hz, 6H), 3.52 (s, 3H), 2.95 (br. s., 6H), 2.63 (br. s., 6H), 2.39 (br. s., 6H), 2.29 (s, 4H); LCMS [M+1]$^+$=547.6 g/mol.

Example 103: N-(2'-fluoro-4-(4-methylpiperazin-1-yl)-5'-(morpholinomethyl)-[1,1'-biphenyl]-3-yl)-1H-benzo[d]imidazole-2-carboxamide

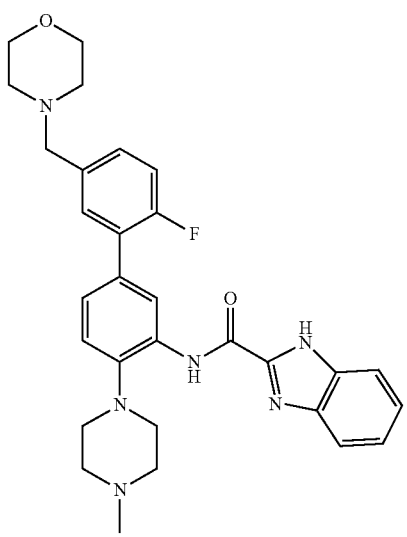 [SMILES: CN1CCN(c2ccc(-c3cc(CN4CCOCC4)ccc3F)cc2NC(=O)c2nc3ccccc3[nH]2)CC1]

The title compound (brown powder, 15.7 mg, 17.03% yield) was prepared according to a similar procedure of the sequence described above for the preparation of example 9 using 1H-benzimidazole-2-carboxylic acid (15.35 mg, 0.095 mmol) in place of 6-oxo-1,6-dihydropyridazine-3-carboxylic acid. $^1$H NMR (500 MHz, MeOD-d4) δ=8.65 (s, 1H), 7.93-7.61 (m, 2H), 7.53 (dd, J=2.1, 7.6 Hz, 1H), 7.47-7.30 (m, 5H), 7.19 (dd, J=8.4, 10.5 Hz, 1H), 3.73 (t, J=4.6 Hz, 4H), 3.60 (s, 2H), 3.11 (t, J=4.6 Hz, 4H), 2.93 (br. s., 4H), 2.53 (s, 7H); LCMS [M+1]$^+$=529.8 g/mol.

Example 104: (S)—N-(4-(2,4-dimethylpiperazin-1-yl)-2'-fluoro-5'-(morpholinomethyl)-[1,1'-biphenyl]-3-yl)-6-oxo-4-(trifluoromethyl)-1,6-dihydropyridine-3-carboxamide

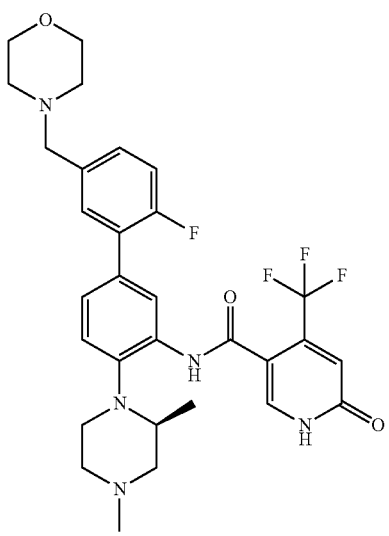 [SMILES: C[C@H]1CN(C)CCN1c1ccc(-c2cc(CN3CCOCC3)ccc2F)cc1NC(=O)c1c[nH]c(=O)cc1C(F)(F)F]

The title compound (yellow powder, 8.7 mg, 22.97% yield in the final step) was prepared according to the sequence described above for the preparation of example 26 using (R)-1,3-dimethylpiperazine dihydrochloride (106 mg, 0.568 mmol) in place of 1,2-dimethyl-piperazine dichloride hydrate. $^1$H NMR (500 MHz, MeOD-d4) δ=8.34 (s, 1H), 7.89 (s, 1H), 7.41 (dd, J=2.1, 7.6 Hz, 1H), 7.37-7.33 (m, 1H), 7.31 (s, 1H), 7.25 (d, J=2.3 Hz, 1H), 7.06 (dd, J=8.5, 10.6 Hz, 1H), 6.82 (s, 1H), 3.80 (s, 1H), 3.60 (t, J=4.5 Hz, 5H), 3.47 (s, 2H), 3.17-3.11 (m, 1H), 2.83 (d, J=7.0 Hz, 4H), 2.40 (br. s., 5H), 2.27 (s, 4H), 1.99 (s, 1H), 1.15 (t, J=7.1 Hz, 1H), 0.76 (d, J=6.2 Hz, 3H); LCMS [M+1]$^+$=588.7 g/mol.

Example 105: N-(2'-fluoro-4-(4-methylpiperazin-1-yl)-5'-(morpholinomethyl)-[1,1'-biphenyl]-3-yl)-6-oxo-1,6-dihydropyridine-3-carboxamide

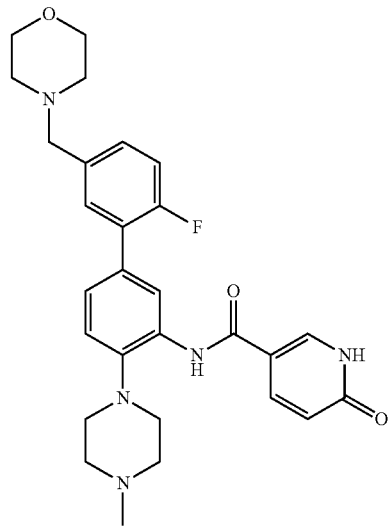 [SMILES: CN1CCN(c2ccc(-c3cc(CN4CCOCC4)ccc3F)cc2NC(=O)c2ccc(=O)[nH]c2)CC1]

The title compound (white solid, 66 mg, 60%) was prepared according to the sequence described above for the preparation of example 9 using 6-hydroxynicotinic acid (145 mg, 1.040 mmol) in place of 6-oxo-1,6-dihydropyridazine-3-carboxylic acid. $^1$H NMR (500 MHz, MeOD-d4) δ=8.15 (s, 1H), 8.09 (d, J=2.6 Hz, 1H), 7.98 (dd, J=2.7, 9.5 Hz, 1H), 7.38 (dd, J=1.9, 7.6 Hz, 1H), 7.30-7.19 (m, 3H), 7.04 (dd, J=8.5, 10.6 Hz, 1H), 6.53 (d, J=9.7 Hz, 1H), 5.39 (s, 1H), 3.60 (t, J=4.5 Hz, 4H), 3.45 (s, 2H), 2.92 (t, J=4.6 Hz, 4H), 2.58 (br. s., 3H), 2.39 (br. s., 4H), 2.29 (s, 3H); LCMS [M+1]$^+$=506.6 g/mol.

Example 106: 6-acetamido-N-(2'-fluoro-4-(4-methylpiperazin-1-yl)-5'-(morpholinomethyl)-[1,1'-biphenyl]-3-yl)-4-methylnicotinamide

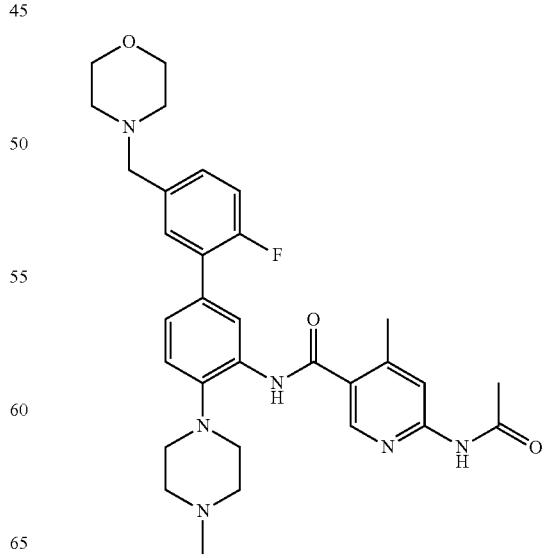

The title compound (white solid, 19 mg, 39.1% yield) was prepared according to the sequence described above for the preparation of example 9 using 6-acetamido-4-methylnicotinic acid (64 mg, 0.330 mmol) in place of 6-oxo-1,6-dihydropyridazine-3-carboxylic acid. $^1$H NMR (500 MHz, DMSO-d6) δ=10.71 (s, 1H), 9.46 (s, 1H), 8.53 (s, 1H), 8.22 (s, 3H), 8.06 (s, 1H), 7.42 (d, J=7.9 Hz, 1H), 7.34 (s, 3H), 7.28 (d, J=10.6 Hz, 1H), 3.58 (t, J=4.3 Hz, 4H), 3.52 (s, 3H), 2.94 (t, J=4.5 Hz, 4H), 2.38 (dd, J=2.3, 4.2 Hz, 9H), 2.23 (s, 3H), 2.13 (s, 3H); LCMS [M+1]$^+$=561.4 g/mol.

Example 107: N-(5'-((4-(cyclopropylmethyl)piperazin-1-yl)methyl)-2'-fluoro-4-(4-methylpiperazin-1-yl)-[1,1'-biphenyl]-3-yl)-6-methoxy-4-(trifluoromethyl)nicotinamide

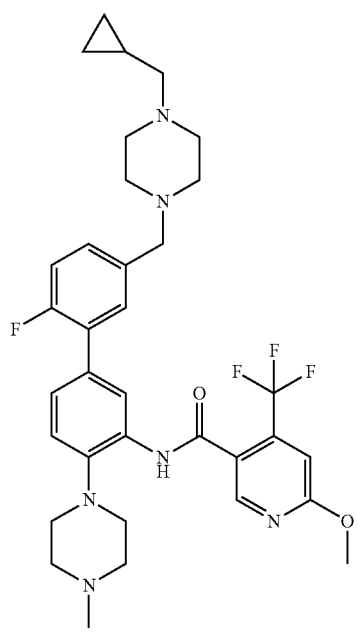 [SMILES: COc1cc(C(F)(F)F)c(C(=O)Nc2cc(-c3cc(CN4CCN(CC5CC5)CC4)ccc3F)ccc2N2CCN(C)CC2)cn1]

The title compound (white solid, 24 mg, 61%) was prepared according to the sequence described above for the preparation of example 51 using 1-(cyclopropylmethyl)piperazine (16.29 mg, 0.116 mmol) in place of (R)-3-pyrrolidinol. $^1$H NMR (500 MHz, MeOD-d4) δ=8.44 (s, 1H), 8.08 (s, 1H), 7.36 (d, J=6.4 Hz, 1H), 7.31-7.25 (m, 1H), 7.24-7.17 (m, 2H), 7.08 (s, 1H), 7.02 (dd, J=8.5, 10.5 Hz, 1H), 7.05-6.99 (m, 1H), 3.92 (s, 3H), 3.46 (s, 2H), 2.89 (t, J=4.5 Hz, 4H), 2.83-2.22 (m, 12H), 2.22-2.17 (m, 3H), 2.21 (s, 3H), 2.14 (d, J=6.6 Hz, 2H), 0.74 (dd, J=5.2, 6.7 Hz, 1H), 0.43-0.36 (m, 2H), −0.01 (q, J=5.0 Hz, 2H); LCMS [M+1]$^+$=641.3 g/mol.

Example 108: N-(2'-fluoro-4-(4-methylpiperazin-1-yl)-5'-(morpholinomethyl)-[1,1'-biphenyl]-3-yl)-6-(methylamino)-4-(trifluoromethyl)nicotinamide

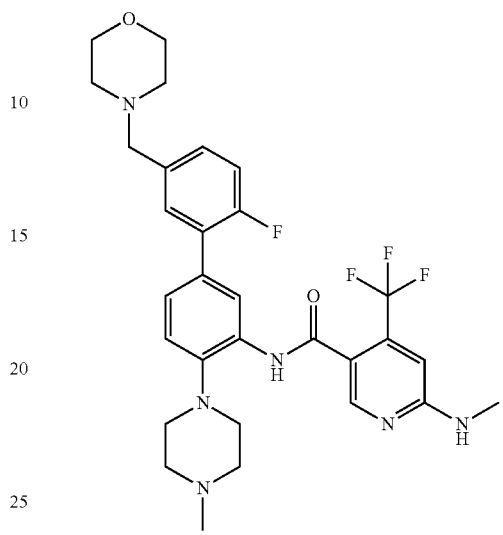

Step 1: 6-chloro-N-(2'-fluoro-4-(4-methylpiperazin-1-yl)-5'-(morpholinomethyl)-[1,1'-biphenyl]-3-yl)-4-(trifluoromethyl)nicotinamide

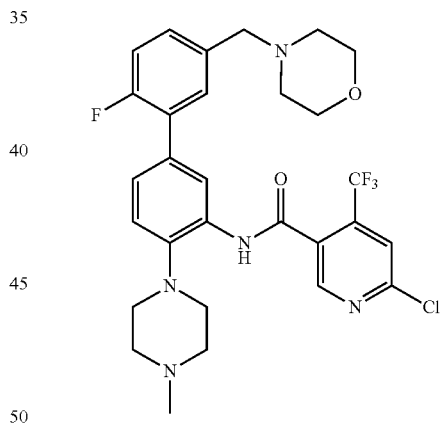

To a 25 mL RBF charged with 6-chloro-4-(trifluoromethyl)nicotinic acid (180 mg, 0.8 mmol) was added thionyl chloride (1.82 mL, 25 mmol). The resulting suspension was heated at 80° C. for 1 hour. The solution was evaporated to give a colorless oil which was treated with DCM (10 mL), 2'-fluoro-4-(4-methylpiperazin-1-yl)-5'-(morpholinomethyl)-[1,1'-biphenyl]-3-amine (192 mg, 0.5 mmol) and Et$_3$N (0.21 mL, 1.5 mmol). The resulting mixture was stirred at rt for 30 min. After quenching with 1 M aq NaHCO$_3$(10 mL), it was extracted with DCM (2×20 mL), dried (Na$_2$SO$_4$) and concentrated to give a brown oil which was purified by flash chromatography (0-34%, MeOH/EtOAc) to give the title compound as alight brown foam (174 mg, 58%). LCMS [M+H]$^+$=592.4 g/mol.

Step 2: Preparation of N-(2'-fluoro-4-(4-methylpiperazin-1-yl)-5'-(morpholinomethyl)-[1,1'-biphenyl]-3-yl)-6-(methylamino)-4-(trifluoromethyl)nicotinamide

Example 109: 6-amino-N-(2'-fluoro-4-(4-methylpiperazin-1-yl)-5'-(morpholinomethyl)-[1,1'-biphenyl]-3-yl)-4-(trifluoromethyl)nicotinamide

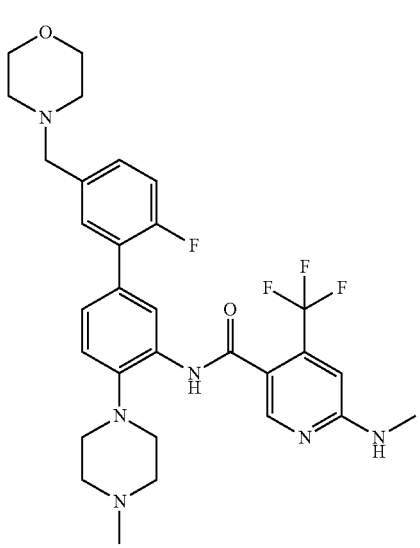 [SMILES: CNc1cc(C(F)(F)F)c(C(=O)Nc2cc(-c3cc(CN4CCOCC4)ccc3F)ccc2N2CCN(C)CC2)cn1]

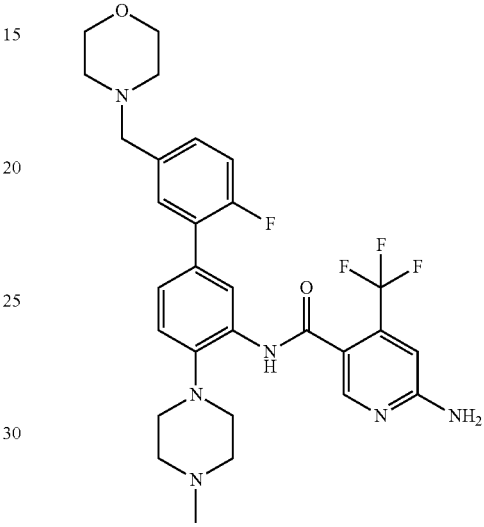

To a 20 mL microwave charge with 6-chloro-N-(2'-fluoro-4-(4-methylpiperazin-1-yl)-5'-(morpholinomethyl)-[1,1'-biphenyl]-3-yl)-4-(trifluoromethyl)nicotinamide (59 mg, 0.1 mmol) was added methylamine (33 wt. % in EtOH, 4 mL). The resulting mixture was irradiated in microwave at 120° C. for 1 h. It was connected to dryness and redissolved in DCM (20 mL). After basifying with 1 M aq NaHCO$_3$(10 mL), it was separated and the aqueous was extracted with DCM (20 mL). The combined extracts were concentrated and purified by flash chromatography (gradient: EtOAc/hex 0-100% then MeOH/DCM 0-20%) to give the title compound as a white solid (55.3 mg, 94%). $^1$H NMR (500 MHz, MeOD-d4) δ=8.44 (s, 1H), 8.25 (br. s., 1H), 7.51 (d, J=7.4 Hz, 1H), 7.43-7.33 (m, 3H), 7.17 (dd, J=8.5, 10.6 Hz, 1H), 6.88 (s, 1H), 3.72 (t, J=4.5 Hz, 4H), 3.58 (s, 2H), 3.04 (t, J=4.6 Hz, 4H), 3.00 (s, 3H), 2.69 (br. s., 4H), 2.51 (br. s., 4H), 2.39 (s, 3H); LCMS [M+H]$^+$=587.5 g/mol.

To a 20 mL microwave charge with 6-chloro-N-(2'-fluoro-4-(4-methylpiperazin-1-yl)-5'-(morpholinomethyl)-[1,1'-biphenyl]-3-yl)-4-(trifluoromethyl)nicotinamide (see example 108, step 1, 59 mg, 0.1 mmol) was added ammonia solution (7 M in methanol, 4 mL). The resulting mixture was irradiated in microwave at 100° C. for 10 hours. Solvents were removed and the residue was treated with ammonia solution (7 M in methanol, 4 mL). The resulting mixture was irradiated in microwave at 100° C. for additional 6 hours. Solvents were removed and the residue was redissolved in DCM (30 mL) and washed with 1 M NaHCO$_3$(10 mL). The aqueous layer was extracted with DCM (20 mL) and the combined organic layers were concentrated to dryness. The crude product was purified by flash chromatography (0-100%, Hex/EtOAc then 0-30% DCM/MeOH) to give the title compound as a white solid (30.5 mg, 52%). $^1$H NMR (500 MHz, MeOD-d4) δ 8.36 (s, 1H), 8.25 (br. s., 1H), 7.50 (d, J=7.34 Hz, 1H), 7.32-7.42 (m, 3H), 7.16 (dd, J=8.56, 10.39 Hz, 1H), 6.95 (s, 1H), 3.71 (t, J=4.46 Hz, 4H), 3.57 (s, 2H), 3.04 (t, J=4.52 Hz, 4H), 2.72 (br. s., 4H), 2.50 (br. s., 4H), 2.41 (s, 3H); LCMS [M+H]$^+$ 573.3 g/mol.

Example 110: N-(5'-(cyclohexyl(methyl)carbamoyl)-2'-fluoro-4-(4-methylpiperazin-1-yl)-[1,1'-biphenyl]-3-yl)-6-oxo-4-(trifluoromethyl)-1,6-dihydropyridine-3-carboxamide

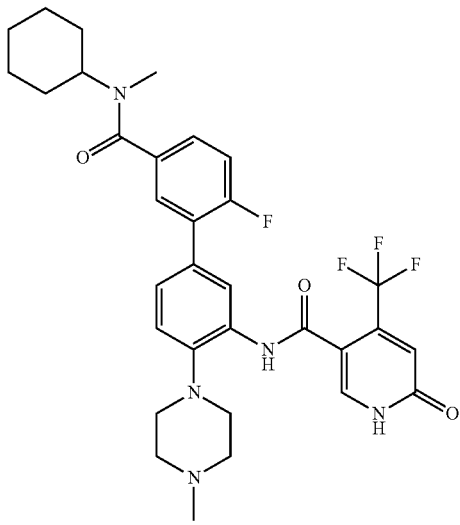 [SMILES: CN1CCN(c2ccc(-c3cc(C(=O)N(C)C4CCCCC4)ccc3F)cc2NC(=O)c2c[nH]c(=O)cc2C(F)(F)F)CC1]

The title compound (white solid, 31 mg, 54%) was prepared according to the sequence described above for the preparation of example 42 using 5-[cyclohexyl(methyl)carbamoyl]-2-fluorobenzeneboronic acid (0.039 g, 0.138 mmol) in place of 2-fluoro-5-formylphenylboronic acid. $^1$H NMR (500 MHz, MeOD) δ 8.15 (s, 1H), 7.98 (s, 1H), 7.52 (d, J=6.4 Hz, 1H), 7.42 (s, 1H), 7.39 (d, J=7.4 Hz, 1H), 7.35 (d, J=8.3 Hz, 1H), 7.33-7.25 (m, 1H), 6.91 (s, 1H), 3.54 (s, 1H), 3.03 (t, J=4.4 Hz, 4H), 2.94 (d, J=40.2 Hz, 3H), 2.68 (s, 4H), 2.38 (s, 3H), 1.89-1.42 (m, 8H), 1.26 (d, J=13.7 Hz, 2H) Major rotamer reported; LCMS [M+1]$^+$=614.3 g/mol.

Example 111: N-(5'-(cyclohexyl(methyl)carbamoyl)-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

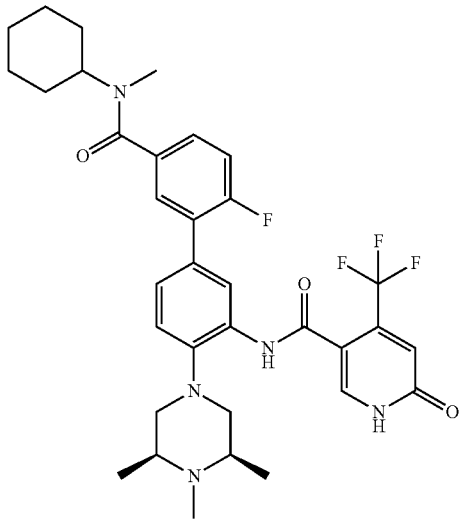 [SMILES: C[C@@H]1CN(c2ccc(-c3cc(C(=O)N(C)C4CCCCC4)ccc3F)cc2NC(=O)c2c[nH]c(=O)cc2C(F)(F)F)C[C@H](C)N1C]

In a 5 mL MW 5-[cyclohexyl(methyl)carbamoyl]-2-fluorobenzeneboronic acid (0.048 g, 0.172 mmol), N-(5-bromo-2-((3S,5R)-3,4,5-trimethylpiperazin-1-yl)phenyl)-4-(trifluoromethyl)-6-(2-(trimethylsilyl)ethoxy)nicotinamide (0.067 g, 0.114 mmol), bis(di-tert-butyl(4-dimethylaminophenyl)phosphine)dichloropalladium(II) (8.10 mg, 0.011 mmol) and potassium phosphate tribasic (0.073 g, 0.343 mmol) were dissolved in 1,4-dioxane (2.060 mL)/water (0.229 mL) (9:1 mixture) to give a white suspension. The suspension was stirred for 5 min, degassed, purged with N$_2$, and microwaved for 60 min at 110° C. The solvent was evaporated and 15 mL of CH$_2$Cl$_2$ were added. The suspension was sonicated and extracted from water (15 mL). The solvent was evaporated in vacuo yielding the crude product that was purified by flash column chromatography on silica gel (0-100%, 89% CH$_2$Cl$_2$, 10% MeOH, 1% NH$_4$Ac/CH$_2$Cl$_2$) to afford the protected intermediate. The product was dissolved in 2 mL of dichloromethane and trifluoroacetic acid (0.131 ml, 1.716 mmol) was added. The purple solution was stirred for 1 hour and the solvent was evaporated. The residue was purified using a cation exchange column eluting with MeOH:NH$_4$OH and freeze dried for 2 days to afford the title compound (white solid, 45 mg, 60%). $^1$H NMR (500 MHz, MeOD) δ 8.13 (s, 1H), 7.96 (s, 1H), 7.53 (s, 1H), 7.42 (d, J=8.3 Hz, 2H), 7.32 (d, J=8.4 Hz, 2H), 6.91 (s, 1H), 3.05 (s, 1H), 3.03 (s, 2H), 2.98 (s, 2H), 2.90 (s, 1H), 2.68 (t, J=11.1 Hz, 2H), 2.57 (s, 2H), 2.39 (s, 3H), 1.91-1.55 (m, 8H), 1.17 (d, J=6.2 Hz, 6H Major rotamer reported; LCMS [M+1]$^+$=642.5 g/mol.

Example 112: N-(2',4'-difluoro-3'-((methyl(oxetan-3-yl)amino)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

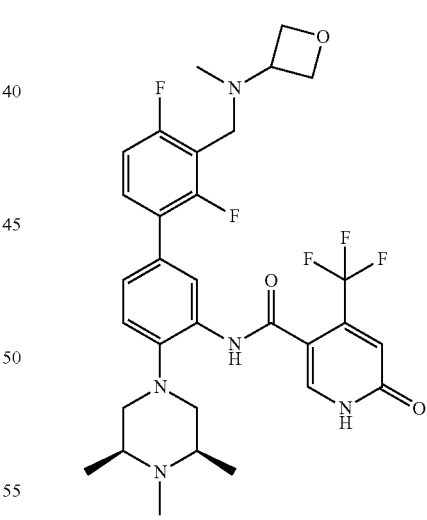

The title compound (white solid, 27 mg, 86%) was prepared in a similar manner than the sequence described above for the preparation of example 42 using N-methyl-3-oxetanamine (9.67 mg, 0.111 mmol) in place of 4,4-difluorocyclohexylamine hydrochloride, 2,4-difluoro-3-formylphenylboronic acid (60 mg, 0.327 mmol) in place of 2-fluoro-5-formylphenylboronic acid and 5-bromo-2-((3R,5S)-3,4,5-trimethylpiperazin-1-yl)aniline (preparation: example 45, step 2. 334 mg, 1.120 mmol) instead of 5-bromo-2-(4-methylpiperazin-1-yl)aniline. $^1$H NMR (500

MHz, MeOD-d4) δ=8.09 (s, 1H), 7.91 (s, 1H), 7.70-7.59 (m, 1H), 7.40-7.26 (m, 2H), 7.20 (t, J=8.7 Hz, 1H), 6.85 (s, 1H), 4.83-4.78 (m, 2H), 4.68 (t, J=6.7 Hz, 2H), 4.43 (br. s., 1H), 4.31 (br. s., 2H), 3.51-3.42 (m, 2H), 3.28-3.24 (m, 2H), 3.27 (br. s., 2H), 2.98-2.84 (m, 5H), 2.71 (br. s., 3H), 1.42-1.29 (m, 6H). LCMS [M+1]$^+$=620.6 g/mol.

Example 113: N-(2',4'-difluoro-5'-((methyl(oxetan-3-yl)amino)methyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

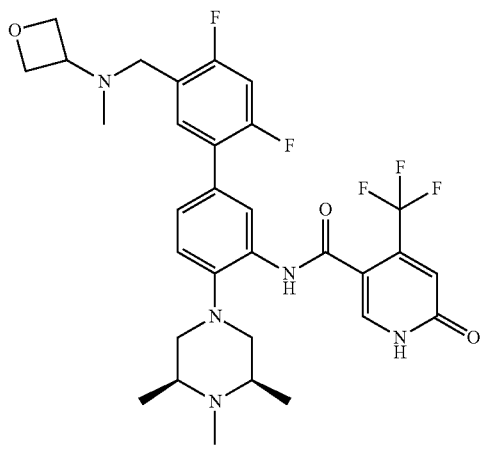 [SMILES: C[C@@H]1CN(c2ccc(-c3cc(CN(C)C4COC4)c(F)cc3F)cc2NC(=O)c2c[nH]c(=O)cc2C(F)(F)F)C[C@H](C)N1C]

The title compound (white solid, 39 mg, 89%) was prepared in a similar manner than the sequence described above for the preparation of example 42 using N-methyl-3-oxetanamine (15.58 mg, 0.179 mmol) in place of 4,4-difluorocyclohexylamine hydrochloride, 2,4-difluoro-5-(tetramethyl-1,3,2-dioxaborolan-2-yl)benzaldehyde (54 mg, 0.202 mmol) in place of 2-fluoro-5-formylphenylboronic acid and 5-bromo-2-((3R,5S)-3,4,5-trimethylpiperazin-1-yl)aniline (preparation: example 45, step 2. 334 mg, 1.120 mmol) instead of 5-bromo-2-(4-methylpiperazin-1-yl)aniline. $^1$H NMR (500 MHz, MeOD-d4) δ=8.09 (s, 1H), 7.93 (s, 1H), 7.68 (t, J=8.1 Hz, 1H), 7.43-7.37 (m, 1H), 7.36-7.31 (m, 1H), 7.24 (t, J=10.1 Hz, 1H), 6.88 (s, 1H), 4.78-4.74 (m, 2H), 4.72-4.66 (m, 2H), 4.51-4.38 (m, 1H), 4.27 (br. s., 2H), 3.52-3.44 (m, 2H), 3.28 (d, J=2.4 Hz, 2H), 2.98-2.89 (m, 5H), 2.71 (br. s., 3H), 1.38 (d, J=6.5 Hz, 6H); LCMS [M+1]$^+$=620.7 g/mol.

Example 114: N-(3'-((cyclohexylamino)methyl)-2',6'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

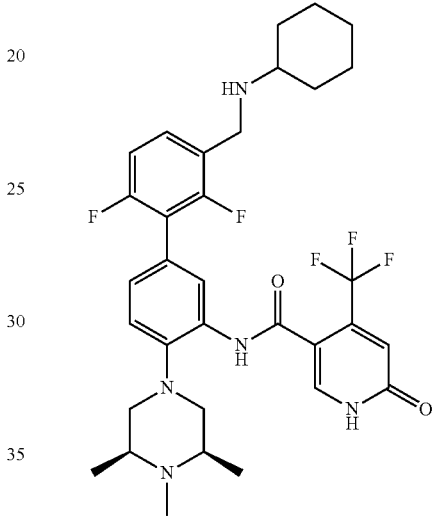

To a solution of N-(3'-((cyclohexylamino)methyl)-2',6'-difluoro-4-((3S,5R)-3,4,5-trimethylpiperazin-1-yl)-[1,1'-biphenyl]-3-yl)-6-methoxy-4-(trifluoromethyl)nicotinamide (28 mg, 0.043 mmol) in methanol (1.5 mL) was added concentrated HCl (1 mL) and the reaction mixture was heated at 80° C. for 2.5 hours. The reaction mixture was allowed to cool to RT, concentrated and the residue was triturated with diethyl ether to yield the desired product (HCl salt, white solid, 5.6 mg, 25%) as a yellow solid. $^1$H NMR (500 MHz, MeOD-d4) δ=8.08 (s, 1H), 7.86 (s, 1H), 7.62-7.53 (m, 1H), 7.34-7.24 (m, 2H), 7.14 (t, J=8.7 Hz, 1H), 6.89-6.80 (m, 1H), 4.28 (s, 2H), 3.08-3.03 (m, 2H), 2.95 (br. s., 2H), 2.81-2.71 (m, 2H), 2.56 (s, 3H), 2.20-2.07 (m, 2H), 2.12 (br. s., 2H), 1.82 (d, J=5.1 Hz, 2H), 1.64 (d, J=12.2 Hz, 1H), 1.35-1.29 (m, 4H), 1.20 (d, J=6.4 Hz, 6H); LCMS [M+1]$^+$=630.4 g/mol.

Example 115: N-(4'-((cyclohexylamino)methyl)-2',6'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

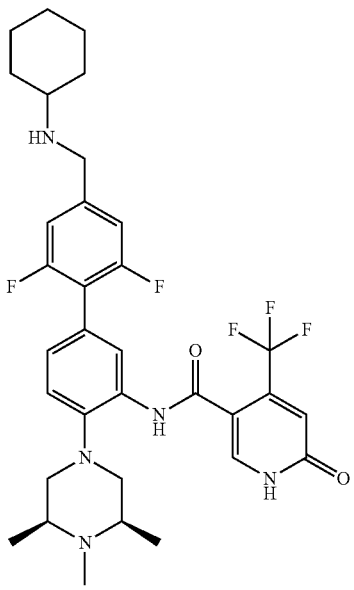 [SMILES: C[C@@H]1CN(c2ccc(-c3c(F)cc(CNC4CCCCC4)cc3F)cc2NC(=O)c2c[nH]c(=O)cc2C(F)(F)F)C[C@H](C)N1C]

To a solution of N-(4'-((cyclohexylamino)methyl)-2',6'-difluoro-4-((3S,5R)-3,4,5-trimethylpiperazin-1-yl)-[1,1'-biphenyl]-3-yl)-6-methoxy-4-(trifluoromethyl)nicotinamide (13 mg, 0.020 mmol) in methanol (1.5 mL) was added concentrated HCl (1 mL) and the reaction mixture was heated at 80° C. for 2.5 hours. The reaction mixture was allowed to cool to RT, concentrated and the residue was triturated with diethyl ether to yield the desired product (HCl salt, white solid, 8.5 mg, 64%) as a yellow solid. $^1$H NMR (500 MHz, MeOD-d4) δ=8.07 (s, 1H), 8.02 (s, 1H), 7.36-7.31 (m, 1H), 7.30-7.26 (m, 1H), 7.14 (d, J=8.3 Hz, 2H), 6.87 (s, 1H), 3.94 (s, 2H), 3.04 (d, J=11.2 Hz, 2H), 2.72-2.67 (m, 2H), 2.60-2.52 (m, 2H), 2.42-2.37 (m, 3H), 2.05 (d, J=11.1 Hz, 2H), 1.82 (d, J=13.0 Hz, 2H), 1.69 (d, J=12.5 Hz, 1H), 1.40-1.21 (m, 6H), 1.18 (d, J=6.2 Hz, 6H); LCMS [M+1]$^+$=632.7 g/mol.

Example 116: N-(2'-chloro-5'-(cyclohexylcarbamoyl)-4-(4-methylpiperazin-1-yl)-[1,1'-biphenyl]-3-yl)-6-oxo-4-(trifluoromethyl)-1,6-dihydropyridine-3-carboxamide

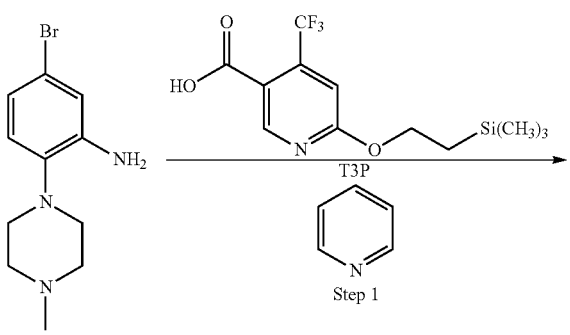

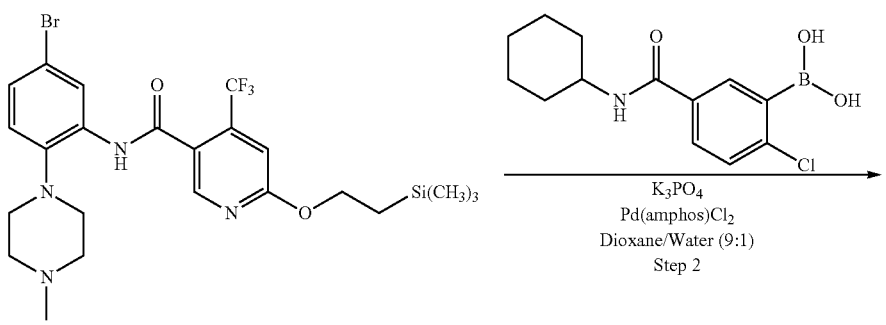

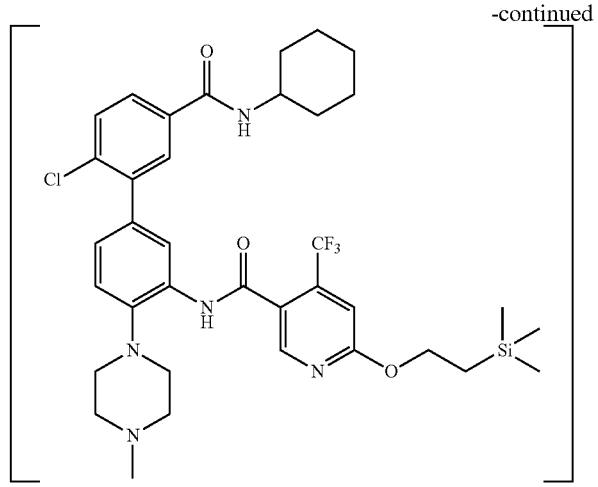

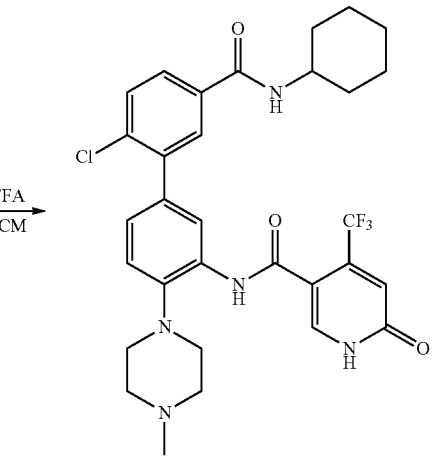

Step 1: N-(5-bromo-2-(4-methylpiperazin-1-yl)phenyl)-4-(trifluoromethyl)-6-(2-(trimethylsilyl)ethoxy) nicotinamide Step 2: N-(2'-chloro-5'-(cyclohexylcarbamoyl)-4-(4-methylpiperazin-1-yl)-[1,1'-biphenyl]-3-yl)-6-oxo-4-(trifluoromethyl)-1,6-dihydropyridine-3-carboxamide

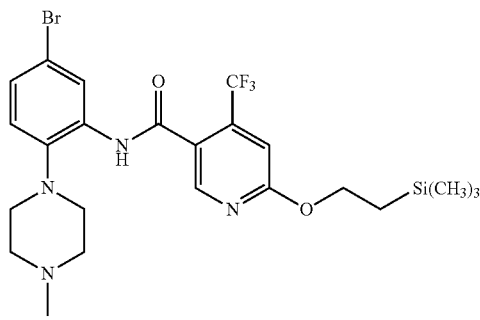

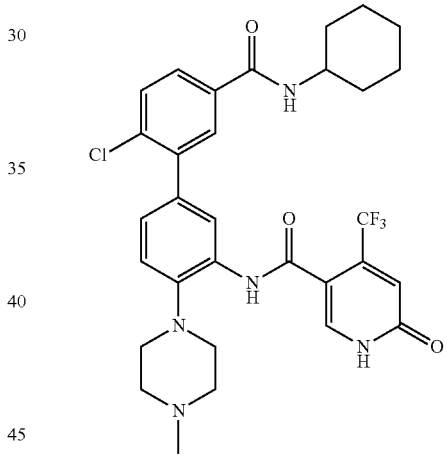

Propylphosphonic anhydride solution (0.881 mL, 1.481 mmol) was added dropwise to a mix of 5-bromo-2-(4-methylpiperazin-1-yl)aniline (0.250 g, 0.925 mmol) and pyridine (0.298 ml, 3.70 mmol) in dry tetrahydrofuran (THF) (9.25 mL) under $N_2$ at RT. After 1.5 hour of stirring a pale yellow solution was obtained. Then 5-bromo-2-(4-methylpiperazin-1-yl)aniline (0.250 g, 0.925 mmol) was added as a solid and the reaction mixture was heated at 50° C. The crude product was allowed to cool to RT, THF was removed and the residue was partitioned between ethyl acetate (25 mL) and sodium bicarbonate sat solution (25 mL). The organic phase was separated and the aqueous phase was extracted with additional ethyl acetate (25 mL). The solvent was evaporated in vacuo yielding the crude product by flash column chromatography on silica gel (0-100%, 89% $CH_2Cl_2$, 10% MeOH, 1% $NH_4Ac/CH_2Cl_2$) to afford the desired compound (283 mg, yield 53%); $^1H$ NMR (500 MHz, MeOD) δ 8.54 (s, 1H), 8.27 (s, 1H), 7.35 (dd, J=8.6, 2.3 Hz, 1H), 7.20 (d, J=8.6 Hz, 1H), 7.13 (s, 1H), 4.59-4.54 (m, 2H), 2.99 (t, J=4.7 Hz, 4H), 2.75 (s, 4H), 2.43 (s, 3H), 1.22-1.17 (m, 2H), 0.10 (s, 9H); $^{19}F$ NMR (471 MHz, MeOD) δ −62.85 (s); LCMS [M+1]$^+$=558.95 g/mol.

In a 5 mL MW vial 2-chloro-5-(cyclohexylcarbamoyl) benzeneboronic acid (0.038 g, 0.136 mmol), N-(5-bromo-2-(4-methylpiperazin-1-yl)phenyl)-4-(trifluoromethyl)-6-(2-(trimethylsilyl)ethoxy)nicotinamide (0.05055 g, 0.090 mmol), bis(di-tert-butyl(4-dimethylaminophenyl)phosphine)dichloropalladium(II) (6.40 mg, 9.03 µmol) and potassium phosphate tribasic reagent grade (0.038 g, 0.181 mmol) were dissolved in 1,4-dioxane (1.626 mL)/water (0.181 mL) (9:1 mixture) to give a white suspension. The suspension was stirred for 5 min, degassed, purged with $N_2$, and microwaved for 60 min at 110° C. The solvent was evaporated and 15 mL of $CH_2Cl_2$ were added. The suspension was sonicated and extracted from water (15 mL). The solvent was evaporated in vacuo yielding the crude product that was purified by flash column chromatography on silica gel (0-100%, 89% $CH_2Cl_2$, 10% MeOH, 1% $NH_4Ac/CH_2Cl_2$) to afford the protected intermediate. The product was dissolved in 2 mL of dichloromethane and trifluoroacetic acid (104 µl, 1.355 mmol) was added. The purple solution was stirred for 1 hour and the solvent was evaporated. The residue was purified using a cation exchange column eluting with MeOH:NH$_4$OH and freeze dried for 2 days to afford the title compound (11.73 mg, yield 19%). $^1$H NMR (500 MHz, MeOD) δ 7.96 (s, 1H), 7.88 (s, 1H), 7.73 (d, J=2.2 Hz, 1H), 7.67 (dd, J=8.4, 2.2 Hz, 1H), 7.49 (d, J=8.4 Hz, 1H), 7.25 (d, J=8.3 Hz, 1H), 7.21 (dd, J=8.3, 2.0 Hz, 1H), 6.81 (s, 1H), 3.77 (dd, J=9.4, 5.3 Hz, 1H), 2.93 (dd, J=5.8, 3.4 Hz, 4H), 2.58 (s, 4H), 2.28 (s, 3H), 1.85 (d, J=10.2 Hz, 2H), 1.71 (d, J=12.7 Hz, 2H), 1.59 (d, J=13.0 Hz, 1H), 1.29 (dd, J=17.3, 9.8 Hz, 4H), 1.16 (d, J=13.7 Hz, 1H); $^{19}$F NMR (471 MHz, MeOD) δ −63.91; LCMS HSS [M+1]$^+$= 616.28 g/mol.

Example 117: N-(4'-carbamoyl-2'-fluoro-4-((3S, 5R)-3,4,5-trimethylpiperazin-1-yl)-[1,1'-biphenyl]-3-yl)-6-oxo-4-(trifluoromethyl)-1,6-dihydropyridine-3-carboxamide

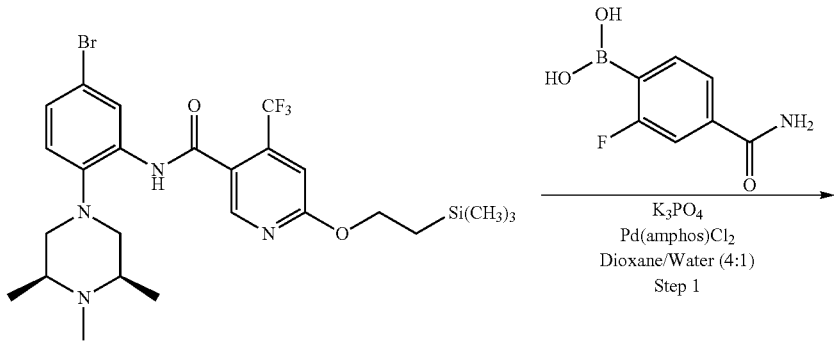

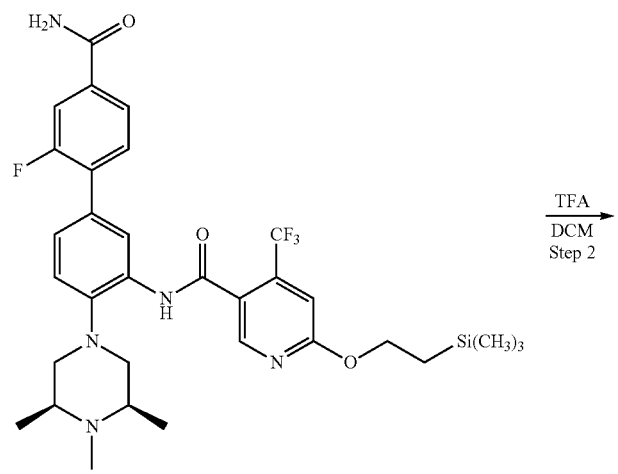

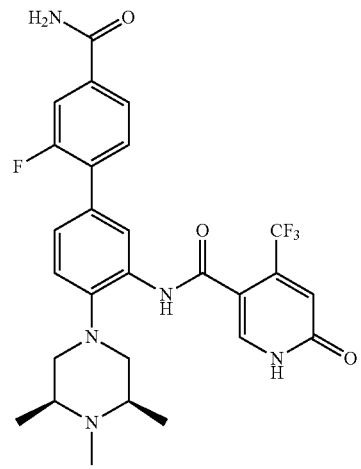

Step 1: N-(4'-carbamoyl-2'-fluoro-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide

Step 2: N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

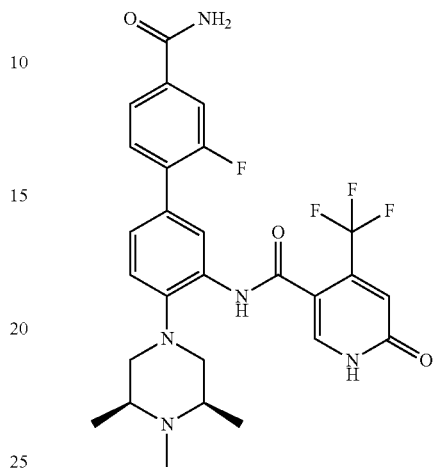

N-(4'-carbamoyl-2'-fluoro-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide (49 mg, 0.076 mmol) was dissolved in DCM (1.5 mL) then TFA (1.5 mL) was added. The mixture was stirred at RT. After about 1 hour. The solvents were evaporated under reduced pressure. The residue was dissolved in acetonitrile/water and lyophilized for 2 days to afford the title compound as an off-white powder (TFA, salt 53.1 mg, 86% yield). $^1$H NMR (500 MHz, MeOD-d4) δ=8.07 (s, 1H), 7.91 (s, 1H), 7.68 (dd, J=1.6, 7.9 Hz, 1H), 7.62 (dd, J=1.5, 11.5 Hz, 1H), 7.51 (t, J=7.9 Hz, 1H), 7.43-7.37 (m, 1H), 7.28 (d, J=8.3 Hz, 1H), 6.86-6.81 (m, 1H), 3.43 (ddd, J=2.9, 6.8, 10.1 Hz, 2H), 3.26 (br d, J=13.0 Hz, 2H), 2.90 (s, 3H), 2.89-2.75 (m, 2H), 1.35 (d, J=6.5 Hz, 6H); LCMS [M+H]$^+$ 546 g/mol.

Example 118: N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

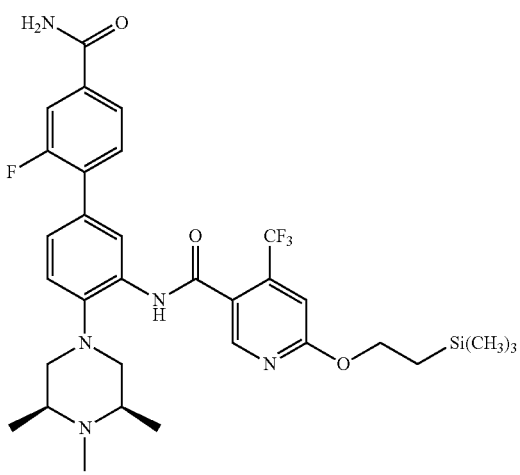

A small microwave vial was charged with (4-carbamoyl-2-fluorophenyl)boronic acid (23.35 mg, 0.128 mmol), potassium phosphate tribasic (54.2 mg, 0.255 mmol) and N-(5-bromo-2-((3S,5R)-3,4,5-trimethylpiperazin-1-yl)phenyl)-4-(trifluoromethyl)-6-(2-(trimethylsilyl)ethoxy)nicotinamide (see example 80 step 2, 50 mg, 0.085 mmol). 1,4-dioxane (3 mL) and water (0.75 mL) were added and the mixture was stirred at RT. Bis(di-tert-butyl(4-dimethylaminophenyl)phosphine)dichloropalladium(II) (6.03 mg, 8.51 μmol) was added, the head space was purged with N$_2$ then the vial was sealed. The mixture was then heated in the microwave at 100° C. for 45 min. The reaction mixture was then cooled, loaded directly onto celite and purified by reverse phase (10%-100%, water/acetonitrile) to afford Intermediate the title compound as a beige foamy solid (49 mg, 89%); LCMS [M+H]$^+$=646.0 g/mol.

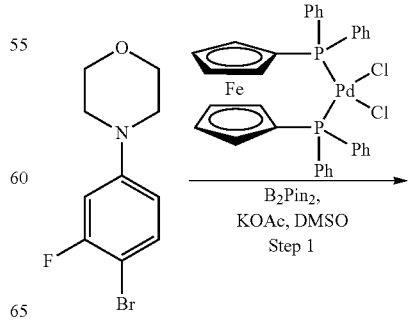

-continued

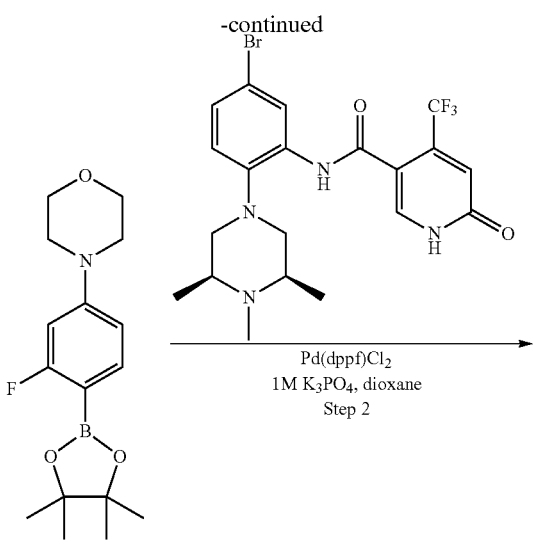

Step 1: 4-(3-fluoro-4-(4,4,5,5-tetramethyl-1,3,2-dioxaborolan-2-yl)phenyl)morpholine

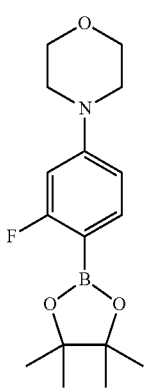

To a 20 mL microwave vial charged with 4-(4-bromo-3-fluorophenyl)morpholine (1.0 g, 3.84 mmol), bis(pinacolato)diboron (1.95 mg, 7.68 mmol), Pd(dppf)Cl$_2$ (141 mg, 0.192 mmol, 5 mol %) and KOAc (1.13 g, 11.5 mmol) was added DMSO (10 mL). The resulting mixture was heated at 100° C. (oil bath) for 4 h. Additional Pd(dppf)Cl$_2$ (71 mg, 0.096 mmol, 2.5 mol %) and DMSO (2 mL) were added and the reaction mixture was heated at 120° C. (oil bath) for 4 h. After diluting with brine (5 mL), it was extracted with EtOAc (2×15 mL). The combined extracts were concentrated and purified by flash chromatography (EtOAc/hex 0-100% then MeOH/DCM 0-20%) to give the title compound as a light green solid (1.789 g). LCMS [M+H]$^+$ 308.3 g/mol.

Step 2: Preparation of N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

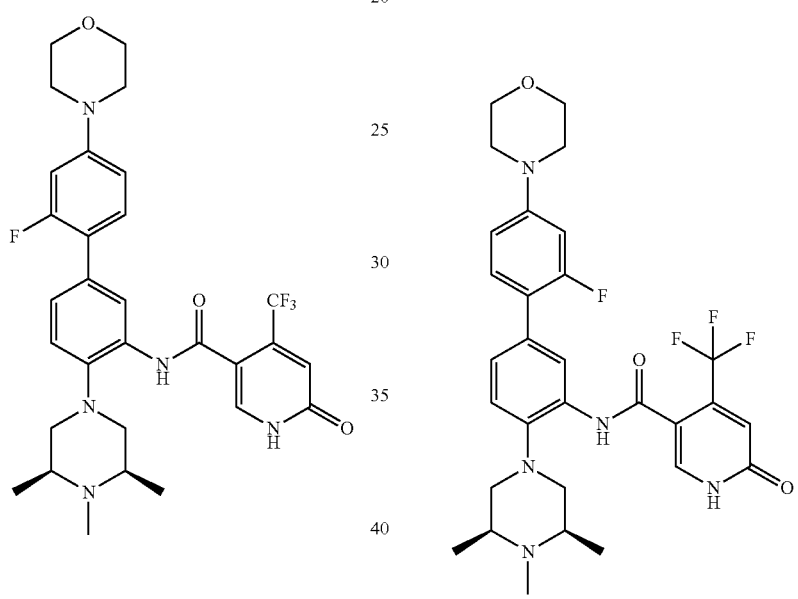

To a microwave vial charged with N-(5-bromo-2-((3S,5R)-3,4,5-trimethylpiperazin-1-yl)phenyl)-6-oxo-4-(trifluoromethyl)-1,6-dihydropyridine-3-carboxamide (48.7 mg, 0.1 mmol), 4-(3-fluoro-4-(4,4,5,5-tetramethyl-1,3,2-dioxaborolan-2-yl)phenyl)morpholine (assuming 60% purity, 102 mg, 0.2 mmol), Pd(dppf)Cl2 (20 mol %) was added dioxane, followed by 1 M aq K3PO4 (3-6 equiv). The resulting mixture was irradiated in microwave at 100-110° C. for 2 h. It was diluted with H$_2$O and extracted with EtOAc. The combined extracts were evaporated and purified by flash chromatography (0-30% Hexane/EtOAc then 0-10% DCM/MeOH) to give the Suzuki coupling product (light yellow solid, 18.3 mg, 29%). $^1$H NMR (500 MHz, MeOD-d4) δ=8.09 (br s, 1H), 7.95 (s, 1H), 7.40-7.32 (m, 2H), 7.25 (d, J=8.4 Hz, 1H), 6.90 (s, 1H), 6.82 (dd, J=2.3, 8.6 Hz, 1H), 6.74 (dd, J=2.3, 14.4 Hz, 1H), 3.86-3.79 (m, 4H), 3.23-3.15 (m, 4H), 2.99 (br d, J=11.1 Hz, 2H), 2.72-2.62 (m, 2H), 2.62-2.52 (m, 2H), 2.40 (s, 3H), 1.17 (br d, J=5.9 Hz, 6H); LCMS [M+H]$^+$ 588.5 g/mol.

Example 119: N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

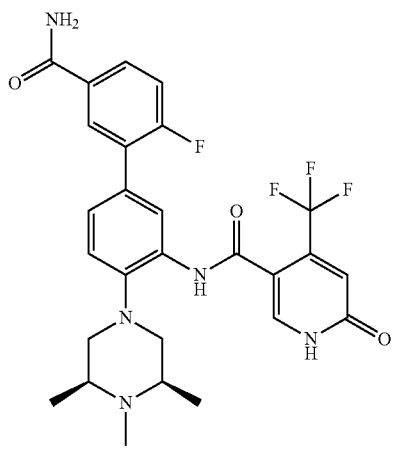 [SMILES: C[C@@H]1CN(c2ccc(-c3cc(C(N)=O)ccc3F)cc2NC(=O)c2c[nH]c(=O)cc2C(F)(F)F)C[C@H](C)N1C]

The title compound (off-white powder, 57.5 mg, 89% yield in the final step) was prepared according to the sequence described above for the preparation of example 117 using 4-fluoro-3-(4,4,5,5-tetramethyl-1,3,2-dioxaborolan-2-yl)benzamide (106 mg, 0.568 mmol) in place of (4-carbamoyl-2-fluorophenyl)boronic acid. $^1$H NMR (500 MHz, MeOD-d4) δ=8.17 (s, 1H), 8.07 (dd, J=2.2, 7.5 Hz, 1H), 8.03 (s, 1H), 7.93 (ddd, J=2.4, 4.6, 8.5 Hz, 1H), 7.54-7.47 (m, 1H), 7.40 (d, J=8.4 Hz, 1H), 7.32 (dd, J=8.7, 10.2 Hz, 1H), 6.97-6.91 (m, 1H), 3.61-3.50 (m, 2H), 3.37 (br d, J=13.0 Hz, 2H), 3.05-2.96 (m, 5H), 1.47 (d, J=6.5 Hz, 6H); LCMS [M+H]$^+$=546 g/mol.

Example 120: N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

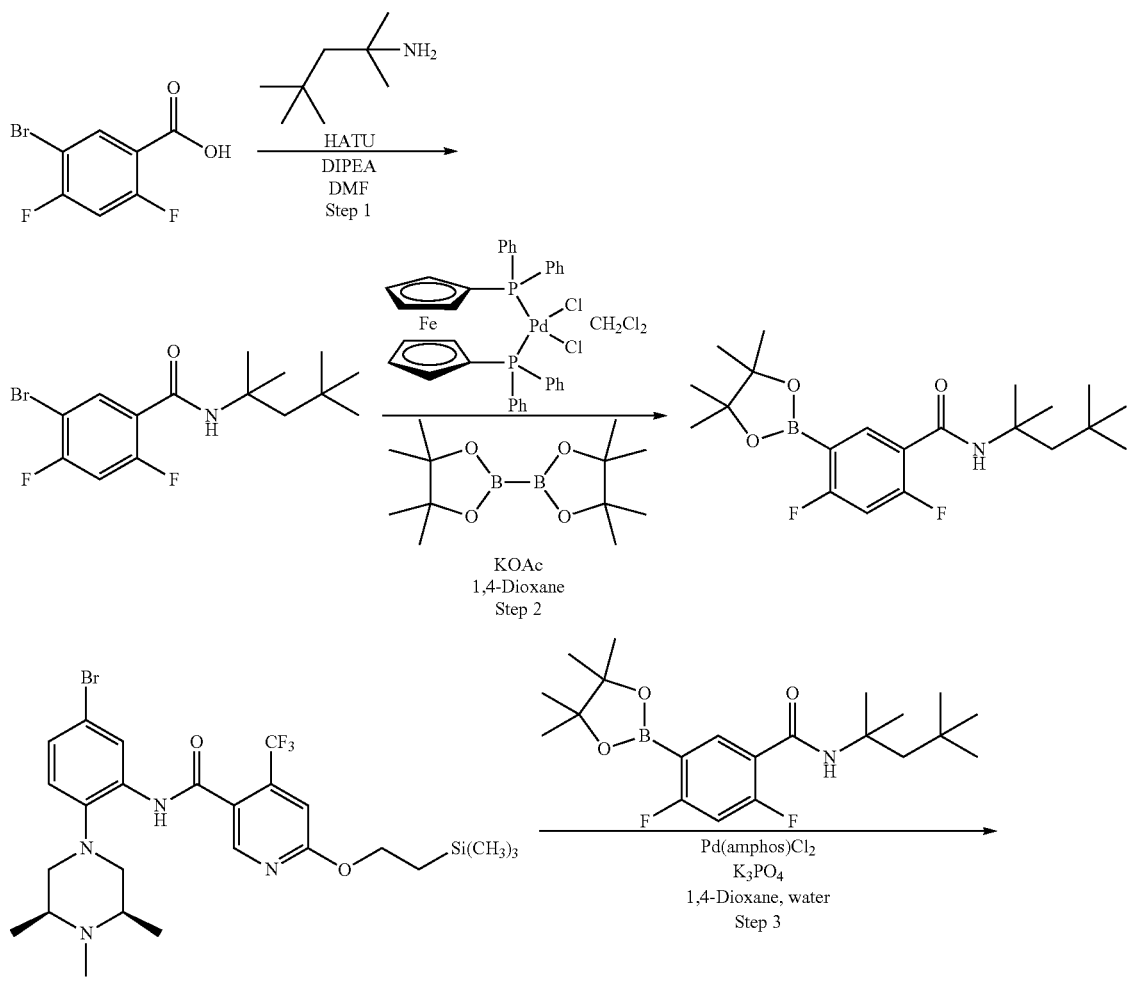

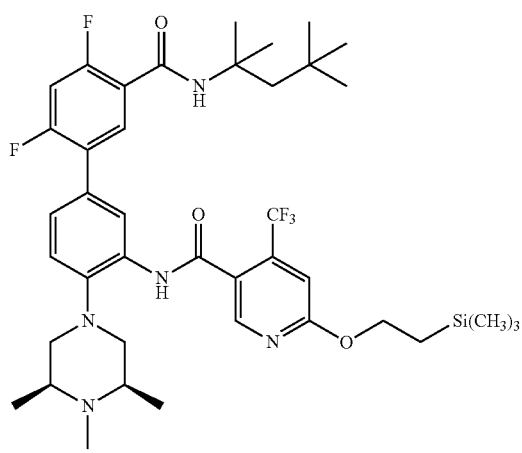

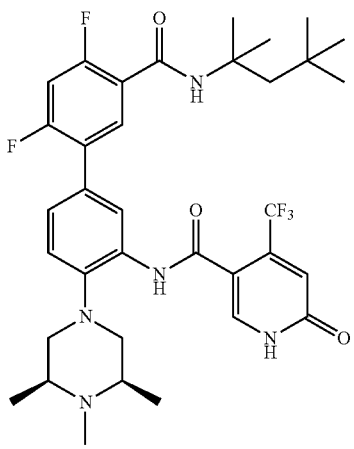

Step 1: 5-bromo-2,4-difluoro-N-(2,4,4-trimethylpentan-2-yl)benzamide

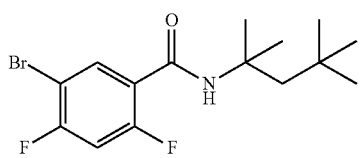 [SMILES: CC(C)(C)CC(C)(C)NC(=O)c1cc(Br)c(F)cc1F]

A 250 mL round bottom flask was charged with 5-bromo-2,4-difluorobenzoic acid (1 g, 4.22 mmol), HATU (2.407 g, 6.33 mmol) and tert-octylamine (1.023 mL, 6.33 mmol). N,N-Dimethylformamide (10 mL) was then added and the mixture was stirred at RT for 5 min. N,N-Diisopropylethylamine (2.94 mL, 16.88 mmol) was added and the reaction mixture was stirred for 16 hours at RT. The mixture was then diluted with EtOAc, washed with water (3×10 mL) and brine, dried over Na$_2$SO$_4$ and concentrated in vacuo. The crude residue was loaded onto celite and purified by purified by flash column chromatography on silica gel (0-40% Hexane/EtOAc). The title compound was obtained as a light grey solid (1.275 g, 87% yield); LCMS [M+H]$^+$=348 g/mol.

Step 2: 2,4-difluoro-5-(4,4,5,5-tetramethyl-1,3,2-dioxaborolan-2-yl)-N-(2,4,4-trimethylpentan-2-yl)benzamide

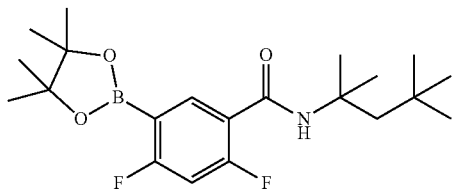 [SMILES: CC(C)(C)CC(C)(C)NC(=O)c1cc(B2OC(C)(C)C(C)(C)O2)c(F)cc1F]

5-Bromo-2,4-difluoro-N-(2,4,4-trimethylpentan-2-yl)benzamide (1.273 g, 3.66 mmol), bis(pinacolato)diboron (1.392 g, 5.48 mmol) and potassium acetate (1.076 g, 10.97 mmol) were mixed in 1,4-dioxane (12 mL) in an 20 mL microwave vial. The mixture was degassed with a stream of N$_2$ for 10 min then [1,12-bis(diphenylphosphino)ferrocene]dichloropalladium(II) CH$_2$Cl$_2$ complex (0.299 g, 0.366 mmol) was added. The headspace was flushed with N$_2$ and the vial was sealed. The mixture was heated in the microwave at 110° C. for 2 hours. The reaction mixture was concentrated onto celite and purified by flash column chromatography on silica gel (0-20% Hexane/EtOAc) The product was collected as dark orange oil that solidified upon standing (1.37 g, 95% yield); LCMS [M+H]$^+$=396 g/mol.

Step 3: N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide

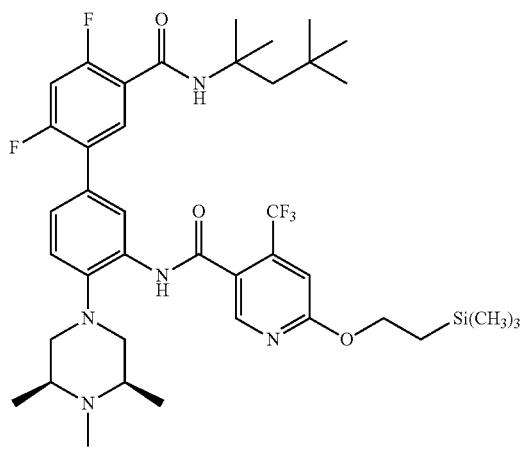

2,4-difluoro-5-(4,4,5,5-tetramethyl-1,3,2-dioxaborolan-2-yl)-N-(2,4,4-trimethylpentan-2-yl)benzamide (53.8 mg, 0.136 mmol), potassium phosphate tribasic (54.2 mg, 0.255 mmol) and N-(5-bromo-2-((3S,5R)-3,4,5-trimethylpiperazin-1-yl)phenyl)-4-(trifluoromethyl)-6-(2-(trimethylsilyl)ethoxy)nicotinamide (50 mg, 0.085 mmol) were charged in a small microwave vial. 1,4-dioxane (3 mL) and water (0.75 mL) were added then the mixture was stirred at room temperature. Bis(di-tert-butyl(4-dimethylaminophenyl)phosphine)dichloropalladium(II) (6.03 mg, 8.51 µmol) was added to the mixture. The head space was purged with N₂ then the vial was sealed and heated in the microwave at 100° C. for 30 min. The reaction mixture was loaded on celite, dried under vacuum and purified by reverse phase (10-100%, water/aceonitrile). The title compound was collected as a beige foamy solid (55 m, 83% yield); LCMS [M+H]⁺= 776 g/mol.

Step 4: N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

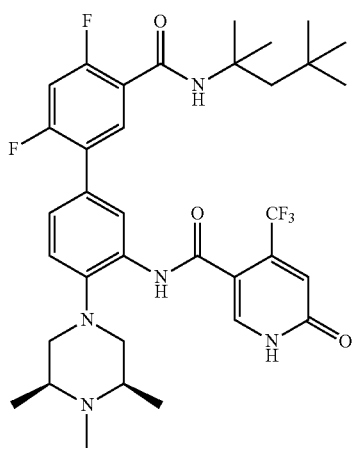 [SMILES: C[C@@H]1CN(c2ccc(-c3cc(C(=O)NC(C)(C)CC(C)(C)C)c(F)cc3F)cc2NC(=O)c2c[nH]c(=O)cc2C(F)(F)F)C[C@H](C)N1C]

N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide (10 mg, 0.013 mmol) was dissolved in DCM (1 mL) then TFA (0.5 mL) was added. The mixture was stirred at RT for about 10 min. The solvents were evaporated under vacuum and the residue was dissolved in acetonitrile/water then lyophilized to afford the title compound as a white powder (TFA salt, 10 mg, 93% yield). ¹H NMR (500 MHz, MeOD-d4) δ=8.02 (s, 1H), 7.90 (s, 1H), 7.68 (br d, J=2.3 Hz, 1H), 7.63 (t, J=8.3 Hz, 1H), 7.35-7.24 (m, 2H), 7.07 (t, J=10.3 Hz, 1H), 6.85-6.81 (m, 1H), 3.48-3.37 (m, 2H), 3.25 (br d, J=13.3 Hz, 2H), 2.90 (s, 3H), 2.89-2.82 (m, 2H), 1.84 (s, 2H), 1.39 (s, 6H), 1.35 (d, J=6.4 Hz, 6H), 0.95 (s, 9H); LCMS [M+H]⁺=676 g/mol.

Example 121: N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

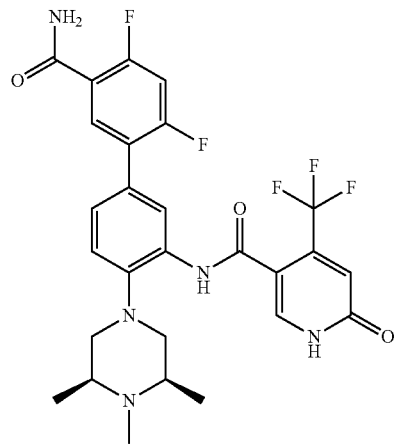 [SMILES: C[C@@H]1CN(c2ccc(-c3cc(C(N)=O)c(F)cc3F)cc2NC(=O)c2c[nH]c(=O)cc2C(F)(F)F)C[C@H](C)N1C]

N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide (45 mg, 0.058 mmol) was dissolved in DCM (1.5 mL) then TFA (1.5 mL) was added. The mixture was stirred for about 5 hours at 60° C. The solvents were evaporated under reduced pressure. The residue was dissolved in an acetonitrile-water mixture and lyophilized to afford the title compound as an off-white powder (TFA salt, 41 mg, 99% yield). ¹H NMR (500 MHz, MeOD-d4) δ=8.03 (s, 1H), 7.91 (s, 1H), 7.88 (t, J=8.5 Hz, 1H), 7.36-7.25 (m, 2H), 7.12 (t, J=10.5 Hz, 1H), 6.86-6.80 (m, 1H), 3.47-3.37 (m, 2H), 3.25 (br d, J=13.1 Hz, 2H), 2.92-2.83 (m, 5H), 1.35 (d, J=6.5 Hz, 6H); LCMS [M+H]⁺=564 g/mol.

Example 122: N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

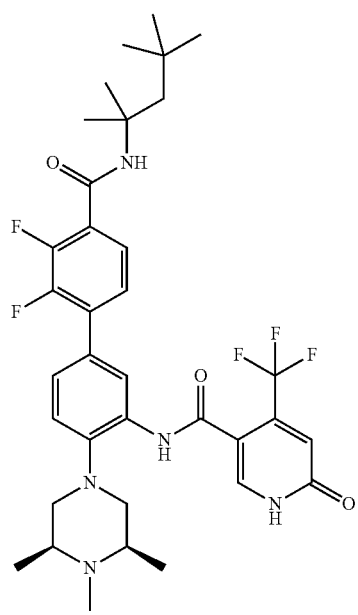 [SMILES: C[C@@H]1CN(c2ccc(-c3ccc(C(=O)NC(C)(C)CC(C)(C)C)c(F)c3F)cc2NC(=O)c2c[nH]c(=O)cc2C(F)(F)F)C[C@H](C)N1C]

The title compound (white powder, 14 mg, 77% yield in the final step) was prepared according to the sequence described above for the preparation of example 120 using 4-bromo-2,3-difluorobenzoic acid (1.022 g, 4.31 mmol) in place of 5-bromo-2,4-difluorobenzoic acid. (TFA salt, 14 mg, 0.017 mmol, 77% yield). ¹H NMR (500 MHz, MeOD-d4) δ=8.06 (s, 1H), 7.90 (s, 1H), 7.79 (s, 1H), 7.38 (br d, J=8.2 Hz, 1H), 7.31 (br d, J=1.6 Hz, 1H), 7.30 (s, 1H), 7.29-7.24 (m, 1H), 6.86-6.80 (m, 1H), 3.42 (br s, 2H), 3.25 (br s, 2H), 2.89 (s, 3H), 2.89-2.83 (m, 2H), 1.85 (s, 2H), 1.40 (s, 6H), 1.35 (br d, J=6.4 Hz, 6H), 0.96 (s, 9H); LCMS [M+H]⁺=676 g/mol.

Example 123: N-(4'-carbamoyl-2',3'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide

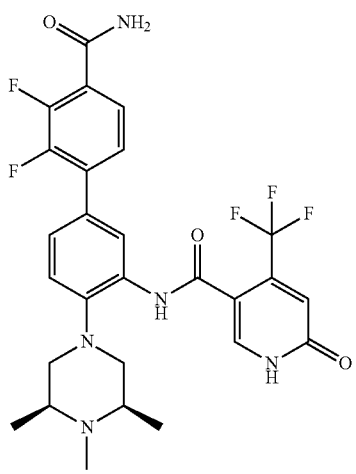 [SMILES: C[C@@H]1CN(c2ccc(-c3ccc(C(N)=O)c(F)c3F)cc2NC(=O)c2c[nH]c(=O)cc2C(F)(F)F)C[C@H](C)N1C]

N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-4-(trifluoromethyl)-6-(2-(trimethylsilyl)ethoxy)nicotinamide (50 mg, 0.064 mmol) was dissolved in DCM (1.5 mL) then TFA (1.5 mL) was added the mixture was heated at 62° C. for about 4.5 h. The solvents were removed in vacuo and the residue was dissolved in acetonitrile-water mixture and lyophilized to afford the title compound as an off-white powder (TFA salt, 42 mg, 91% yield). ¹H NMR (500 MHz, MeOD-d4) δ=8.08 (s, 1H), 7.91 (s, 1H), 7.55-7.50 (m, 1H), 7.40 (br d, J=8.2 Hz, 1H), 7.31 (s, 1H), 7.30-7.24 (m, 1H), 6.85-6.80 (m, 1H), 3.48-3.37 (m, 2H), 3.26 (br d, J=13.2 Hz, 2H), 2.92-2.81 (m, 5H), 1.35 (d, J=6.5 Hz, 6H); LCMS [M+H]⁺=564 g/mol.

Example 124: N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide

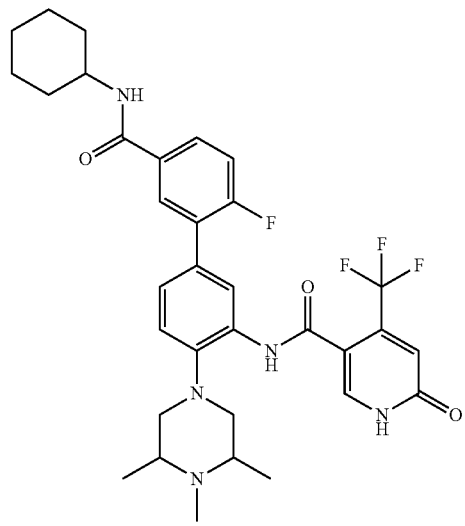 [SMILES: CC1CN(c2ccc(-c3cc(C(=O)NC4CCCCC4)ccc3F)cc2NC(=O)c2c[nH]c(=O)cc2C(F)(F)F)CC(C)N1C]

The title compound (white solid, 11.4 mg, 18%) was prepared according to the sequence described above for the preparation of example 26 using 1,2,6-trimethylpiperazine (47 mg) in place of 1,2-dimethyl-piperazine dichloride hydrate. ¹H NMR (500 MHz, MeOD) δ 8.17 (s, 1H), 7.98 (s, 1H), 7.96 (dd, J=7.5, 1.9 Hz, 1H), 7.84-7.80 (m, 1H), 7.63 (t, J=8.6 Hz, 1H), 7.43 (d, J=8.2 Hz, 1H), 7.33 (d, J=8.3 Hz, 1H), 7.29-7.23 (m, 1H), 6.89 (s, 1H), 6.83 (dd, J=9.1, 2.0 Hz, 1H), 3.86 (s, 1H), 3.05 (s, 2H), 2.70 (dd, J=25.6, 14.8 Hz, 4H), 2.43 (s, 3H), 1.96 (d, J=9.6 Hz, 2H), 1.81 (d, J=11.8 Hz, 2H), 1.69 (d, J=12.5 Hz, 1H), 1.44-1.34 (m, 4H), 1.23 (s, 1H), 1.19 (d, J=4.9 Hz, 6H); LCMS [M+H]⁺ 628.54 g/mol.

Example 125: N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide

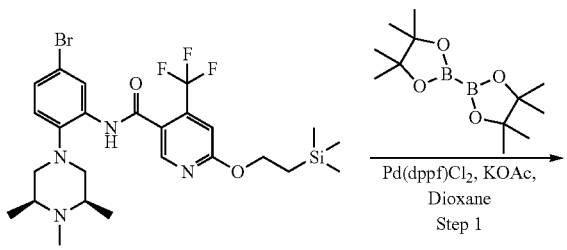

259
-continued

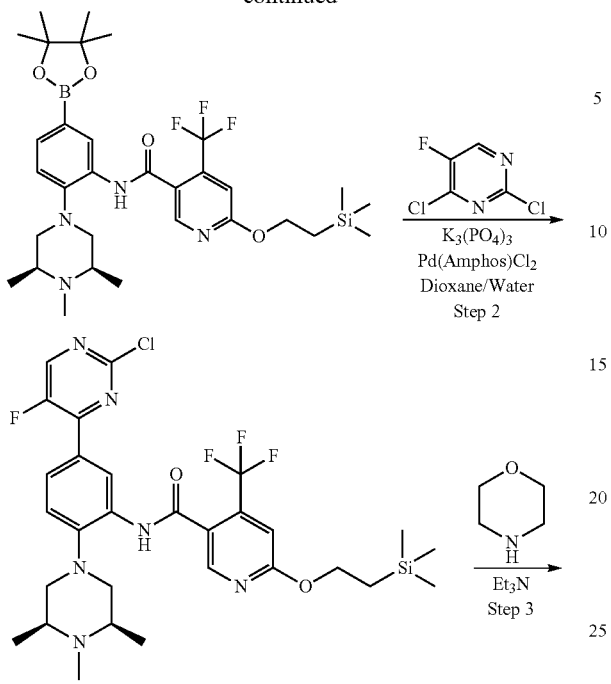

260

Step 1: N-(5-(4,4,5,5-tetramethyl-1,3,2-dioxaborolan-2-yl)-2-((3R,5S)-3,4,5-trimethylpiperazin-1-yl)phenyl)-4-(trifluoromethyl)-6-(2-(trimethylsilyl)ethoxy)nicotinamide

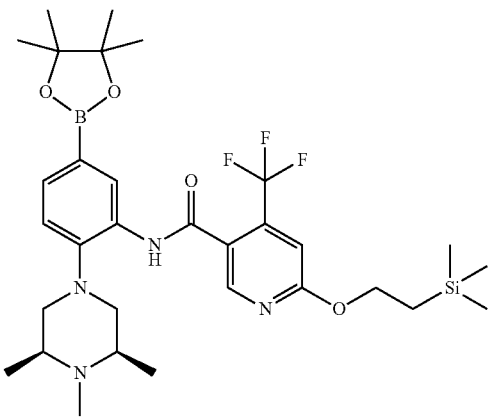

A suspension of N-(5-bromo-2-((3S,5R)-3,4,5-trimethylpiperazin-1-yl)phenyl)-4-(trifluoromethyl)-6-(2-(trimethylsilyl)ethoxy)nicotinamide (616 mg, 1.048 mmol), potassium acetate (0.601 g, 6.12 mmol), bis(pinacolato)diboron (0.745 g, 2.040 mmol) in dioxane (12 mL) was degassed with $N_2$ for 10 min, then treated with Pd(dppf)Cl$_2$ (0.050 g, 0.061 mmol). The reaction was sparged with $N_2$ for an additional 10 min. The mixture was heated to 80° C. overnight, then allowed to cool to room temperature. LCMS analysis indicated quantitative conversion to the desired boronate ester. The crude reaction mixture was used directly in the next step. LCMS [M+H]$^+$=635.0 g/mol.

Step 2: N-(5-(5-fluoro-2-morpholinopyrimidin-4-yl)-2-((3S,5R)-3,4,5-trimethylpiperazin-1-yl)phenyl)-4-(trifluoromethyl)-6-(2-(trimethylsilyl)ethoxy)nicotinamide

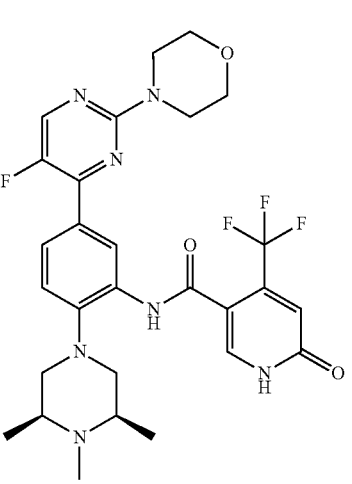

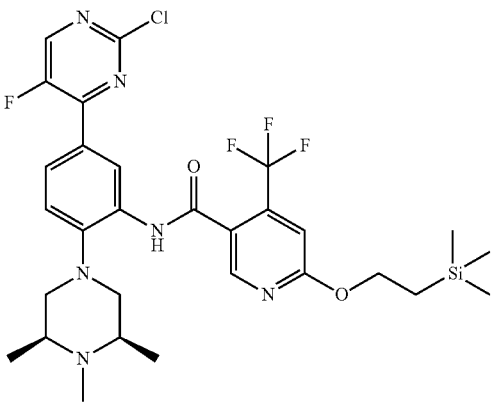

To a microwave vial charged with N-(5-(4,4,5,5-tetramethyl-1,3,2-dioxaborolan-2-yl)-2-((3R,5S)-3,4,5-trimethylpiperazin-1-yl)phenyl)-4-(trifluoromethyl)-6-(2-(trimethylsilyl)ethoxy)nicotinamide (0.050, 0.079 mmol), 2,4-dichloro-5-fluoropyrimidine (0.040 g, 0.236 mmol), K$_3$PO$_4$ (0.0334 g, 0.158 mmol) was added dioxane (2 ml) and water (2 ml) and the vial was flushed with N$_2$. Bis(di-tert-butyl (4-dimethylaminophenyl)phosphine)dichloropalladium(II) (0.011 g, 0.016 mmol) was added, the vial was sealed, and the mixture heated in a microwave reactor to 110° C. for 30 minutes. The crude mixture was concentrated onto celite and purified using flash column chromatography on silica gel [0-100%, 89% CH$_2$Cl$_2$, 10% MeOH, 1% NH$_4$Ac/CH$_2$Cl$_2$] The product was dried under vacuum to give the title compound as a yellowish-brown solid (0.033 g). LCMS [M+H]$^+$=639.0 g/mol.

Step 3: N-(5-(5-fluoro-2-morpholinopyrimidin-4-yl)-2-((3S,5R)-3,4,5-trimethylpiperazin-1-yl)phenyl)-4-(trifluoromethyl)-6-(2-(trimethylsilyl)ethoxy)nicotinamide

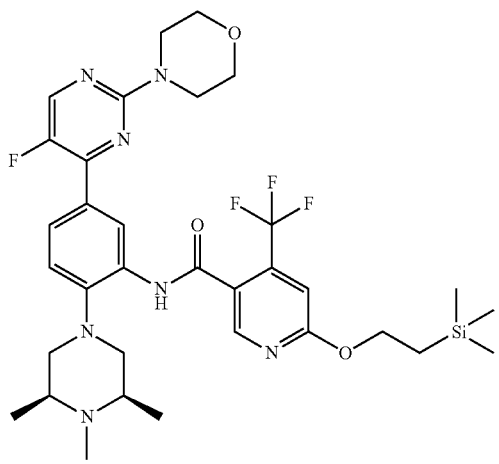

To a vial charged with N-(5-(2-chloro-5-fluoropyrimidin-4-yl)-2-((3R,5S)-3,4,5-trimethylpiperazin-1-yl)phenyl)-4-(trifluoromethyl)-6-(2-(trimethylsilyl)ethoxy)nicotinamide (0.033, 0.052 mmol), morpholine (0.5 ml, 5.8 mmol), and Et$_3$N (1 ml, 7.17 mmol) was added and the vial was heated neat to 120° C. for 30 minutes. LCMS analysis indicated quantitative conversion to the desired product. The mixture was concentrated in vacuo and the crude mixture was used directly in the next step. LCMS [M+H]$^+$=690 g/mol.

Step 4: N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide

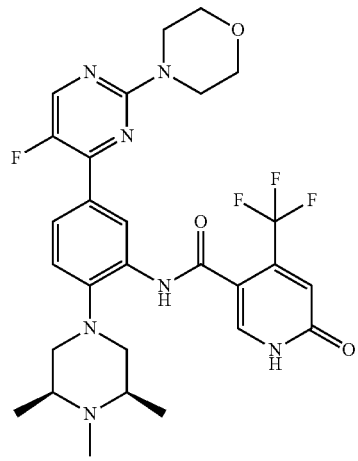 [SMILES: C[C@@H]1CN(c2ccc(-c3nc(N4CCOCC4)ncc3F)cc2NC(=O)c2c[nH]c(=O)cc2C(F)(F)F)C[C@H](C)N1C]

N-(5-(5-fluoro-2-morpholinopyrimidin-4-yl)-2-((3S,5R)-3,4,5-trimethylpiperazin-1-yl)phenyl)-4-(trifluoromethyl)-6-(2-(trimethylsilyl)ethoxy)nicotinamide was dissolved in 2 mL of dichloromethane and trifluoroacetic acid (104 µl, 1.355 mmol) was added. The purple solution was stirred for 1 hour and the solvent was evaporated. The residue was purified using prepHPLC (20%-90%, H$_2$O/acetonitrile) followed by a cation exchange column eluting with MeOH: NH$_4$OH and freeze dried for 2 days to afford the title compound (10.3 mg). $^1$H NMR (500 MHz, MeOD) δ 8.66 (s, 1H), 8.32 (d, J=3.9 Hz, 1H), 7.98 (d, J=9.1 Hz, 1H), 7.95 (s, 1H), 7.30 (d, J=8.5 Hz, 1H), 6.92 (s, 1H), 3.78 (dd, J=13.8, 4.7 Hz, 8H), 3.11 (d, J=11.4 Hz, 2H), 2.69 (t, J=11.2 Hz, 2H), 2.60 (s, 2H), 2.40 (s, 3H), 1.18 (d, J=6.1 Hz, 6H); LCMS [M+H]$^+$=590.4 g/mol.

(c) Biological Assays

Compounds of the present application display inhibition of the interaction between WDR5 and its binding partners in the following assays:

(i) Surface Plasmon Resonance (SPR) Assay

Exemplary compounds of the application were dissolved in 100% DMSO at 10 mM, assayed fresh, and then stored at −20° C. for repeat studies and other experiments. Full length WDR5 with an N-terminal His tag and C-terminal AviTag (Avidity Inc.) was expressed in *E. coli* with coexpression of BirA to biotin label the protein in vivo. Purification was via Ni-NTA. The purified WDR5 protein has a molecular weight of 41976 Da.

SPR studies were performed using a Biacore™ T200 instrument (GE Health Sciences Inc.). Biotinylated WDR5 protein (approximately 3000RU) was stably captured to streptavidin coupled SA chips according to the manufacture's protocol (GE Health Sciences Inc.). The running buffer used was HBS-EP (20 mM Hepes pH 7.4, 150 mM NaCl, 3 mM EDTA, 0.05% P-20) plus 5% DMSO with a flow rate of 40pl/min. For SPR analysis, 5 different concentrations of each exemplary compound of the application were sprayed into 96 or 384 well plates using an HP D300 digital dispenser. The concentration ranged from about 195 nM to about 12 nM in a two-fold series. Concentration ranges were adjusted higher or lower for weaker or more potent compounds, respectively, when necessary. For the $K_D$ determinations, single cycle kinetic analysis was performed with an on time of 60 seconds, and an off time of 300 or 600 seconds. Curve fitting and $K_D$ calculations were performed with the Biacore T200 Evaluation software (GE Health Sciences Inc).

(1) Results

Table 1 shows the binding affinity values ($K_D$) of exemplary compounds of the application for the WDR5 protein. The exemplary compounds of the application have binding affinities ranging in the nanomolar concentrations.

(ii) MLL1-WRAD2 Enzyme Assay

Compound potency was assessed through incorporation of 3H-SAM into oligonucleosomes purified from HeLa cells. Specifically, recombinant human MLL1 (aa 3745-3969, GenBank Accession No. NM_005933), WDR5 (aa 22-334, GenBank Accession No. NM 017588), RbBP5 (aa 1-538, GenBank Accession No. NM_005057), Ash2L (aa 2-534, GenBank Accession No. NM_001105214), and DPY-30 (aa 1-99, GenBank Accession No. NM_0325742), all with N-terminal His tag, were expressed in E. coli and mixed at a molar ratio of 1:1:1:1:2. 10 nM of the assembled MLL1-WRAD2 complex was mixed with 100 nM WRAD2 to enhance complex formation before incubation with 0.05 mg/ml nucleosome substrate and compounds (as 10 point duplicate dose response titrations) for 15 min in a buffer consisting of 50 mM Tris (pH 8.5), 5 mM $MgCl_2$, 50 mM NaCl, 1 mM DTT, 0.01% Brij-35, and 1% DMSO. Reaction was initiated with 1 µM 3H-SAM and incubated for 1 hour at 30° C. Reaction mixture was transferred to P81 filterpaper and washed with PBS before detection.

(1) Results

Table 2 shows the inhibitory activity of representative of compounds of the invention in the in vitro methyl transferase assay (MLL1-WRAD2 assay).

(iii) Detection of In-Cell H3K4 Dimethylation

T24 cells were seeded into a 96-well plate at 400 cells/well in 150 µl medium (McCoy 5A containing 10% FBS, 100 µg/ml Normocin, and 50 µg/ml Gentamycin, Invitrogen). A HP D300 digital dispenser was used to dose cells with DMSO or test compounds across a 10-point range of concentrations (high dose of 10 µM), and cultures were grown in a humidified 5% $CO_2$ incubator at 37° C. After five days, plates were removed from incubator, media was aspirated, and the cells washed in PBS. Cell lysis, histone extraction, and detection of H3K4 dimethylation (H3K4me2) were performed using an AlphaLisa kit according to the manufacturer's instructions (Perkin Elmer). Signal was measured using an Envision plate reader.

(1) Results

Example 2 shows an $IC_{50}$ of 0.952 µM.

(iv) Cell Proliferation Assay

MV4-11 cells were seeded into a 96-well plate at 1,000 cells/well in 150 µl medium (Alpha-MEM containing 10% FBS, 100 µg/ml Normocin, and 50 µg/ml Gentamycin, Invitrogen). A HP D300 digital dispenser was used to dose cells with DMSO or test compounds across a 10-point range of concentrations (high dose of 10 µM), and cultures were grown in a humidified 5% $CO_2$ incubator at 37° C. After five days, plates were removed from incubator and equilibrated to room temperature. An equal volume of ATPlite assay reagent was added to each well, and samples were processed according to manufacturer's instructions (Perkin Elmer). Luminescent signal was measured using an Envision plate reader equipped with a US-Luminescence detector.

(1) Results

Table 3 illustrates the whole-cell potency of exemplary compounds of the application.

(v) Residency Time

Biochemical and cellular assays of drug interactions with their target macromolecules have traditionally been based on measures of drug-target binding affinity under thermodynamic equilibrium conditions. Equilibrium binding metrics such as the half-maximal inhibitory concentration ($IC_{50}$), the effector concentration for half-maximal response ($EC_{50}$), the equilibrium dissociation constant ($K_D$) and the inhibition constant ($K_i$), all pertain to in vitro assays run under closed system conditions, in which the drug molecule and target are present at invariant concentrations throughout the time course of the experiment [*Nat. Rev. Drug Discov.* 2006, 5, 730-739; *Biochemistry* 2008, 47, 5481-5492; *Expert Opin. Drug Discov.* 2010, 5, 305-310]. In living organisms, the concentration of drug available for interaction with a localized protein target is in constant flux because of various physiological processes. Such processes include gastrointestinal absorption, hepatic and renal metabolism, and tissue distribution. Hence, equilibrium measures of drug-target interactions are not entirely valid in the context of the open, non-equilibrium conditions of in vivo pharmacology. It has been suggested that the key determinant of in vivo pharmacological activity and duration is not the binding affinity of a drug for its intended target but the lifetime, or residence time, of the binary drug-target complex. Pharmacological activity typically depends on the binding of the drug to its intended target, and pharmacological activity will usually only persist while the drug remains bound. As soon as a drug dissociates from its target, that target protein is then free to resume its pathophysiological function, which is presumably the molecular progenitor of disease.

The lifetime of a drug on its target is determined by two rate constants: the association rate constant ($k_{on}$) and the dissociation rate constant ($k_{off}$). In principle, the lifetime of the binary drug-target complex is thus extended by a rapid rate of drug binding and/or a slow rate of drug-target complex dissociation. The in vivo lifetime of a drug-target complex is most critically dependent on the value of the $k_{off}$ [*Nat. Rev. Drug Discov.* 2006, 5, 730-739; *Biochemistry* 2008, 47, 5481-5492; *Expert Opin. Drug Discov.* 2010, 5, 305-310]. Drug-target residence time is defined as the reciprocal of $k_{off}$ ($\tau=1/k_{off}$), making the residence time a parameter that is easily measured by routine in vitro assay methods. Moreover, residence time contributes to the multiple, critical parameters that influence in vivo pharmacodynamics [*Anal. Biochem.* 2014, 468, 42-49].

The potency of drug-target binding interactions (as measured by the $K_D$) and residence time are distinct parameters, they are nevertheless interdependent. This interdependency is clear from the mathematical definitions of the $K_D$ for various modalities of binding (see below). The simplest binding interaction is a 1:1 binding reaction in which one molecule of ligand (L, in this case a drug molecule) interacts with one molecule of the protein target (R, the target of pharmacological intervention), that is held in a single conformational state. The association of ligand and target occurs in a single kinetic step, defined by the $k_{on}$; similarly, binary complex dissociation occurs in a single kinetic step, defined by the $k_{off}$. For this binding mode, the $K_D$ is defined by equation shown below.

$$K_D = k_{off}/k_{on}$$

Hence, from this model, the $K_D$ would be expected to be directly related to the $k_{off}$ and inversely related to both the residence time (1/$k_{off}$) and the $k_{on}$. However, in many cases of high-potency ligand binding to protein targets, one finds that the value of $k_{on}$ is invariant over a series of chemically related ligands (for example, a pharmacophore series) binding to a protein target, or for a specific ligand binding to variants of a protein target.

The drug-target residence time model was formulated on the basis of a foundation of experimental data suggesting that slow binding and particularly slow drug-target complex dissociation might be a critical molecular antecedent of durable pharmacological activity in vivo [*Proc. Natl Acad. Sci. USA* 1994, 91, 11202-11206; *J. Am. Chem. Soc. USA* 1996, 118, 2359-2365; *Proc. Natl Acad. Sci. USA* 2006, 103, 7625-7630]. The mathematical basis for analyzing slow binding and dissociating enzyme inhibition kinetics was developed in the seminal work of Morrison and Walsh [*Adv. Enzymol. Relat. Areas Mol. Biol.* 1988, 61, 201-299]. The advent of surface plasmon resonance (SPR) methods led to the ability to measure, and therefore renewed interest in, protein-ligand association and dissociation kinetics [*Future Med. Chem.* 2009, 1, 1399-1414].

Based on a number of experimental studies, the drug-target residence time model predicts that durable pharmacodynamics can be achieved by developing drug molecules with long residence times on their intended target. If the residence time of the drug on its target exceeds the pharmacokinetic half-life of the drug in systemic circulation, one could even achieve the seemingly paradoxical situation of sustained pharmacodynamics activity, even after the bulk of drug has been cleared from the body [*Nat. Rev. Drug Discov.* 2006, 5, 730-739; *Biochemistry* 2008, 47, 5481-5492; *Drug Discov. Today* 2013, 18: 697-707 (2013). Indeed, numerous examples of long-residence-time drugs that exhibit this unexpected pharmacokinetics-pharmacodynamics temporal relationship now exist [*Curr. Opin. Drug Discov.* 2009, 12 488-496; *Curr. Opin. Chem. Biol.* 2010, 14, 467-474]. The ability to sustain durable pharmacodynamics after the clearance of bulk drug from the circulation can provide important advantages in terms of convenient dosing schedules for patients and avoiding off-target mediated toxicities[*Nat Rev Drug Discov.* 2016, 15(2):87-95].

Over the past 10 years, the drug-target residence time model has been further refined and applied to drug discovery and development efforts. We have discovered a novel class of compounds which inhibit the WDR5 protein-protein binding. In addition, structure-activity relationship studies demonstrated that specific chemical features contribute to longer residence times. WDR5 inhibitors with longer residence times has demonstrated increased inhibition of MLL1 catalytic activity resulting in significantly improved growth inhibition observed in hematologic and solid tumors (Table 3 and 4).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Binding affinities ($K_D$) derived from surface plasmon resonance (SPR) assays.

| Compound ID | IUPAC Name | WDR5 binding affinity ($K_D$, μM) |
|---|---|---|
| 1 | N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide | 0.017 |
| 2 | N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide | 0.011 |
| 3 | N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide | 0.011 |
| 4 | N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide | 0.086 |
| 5 | N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide | 0.029 |
| 6 | N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide | 0.076 |
| 7 | N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide | 0.004 |
| 8 | N-[5-[2-fluoro-6-(oxan-4-yloxy)pyridin-3-yl]-2-(4-methylpiperazin-1-yl)phenyl]-6-oxo-4-(trifluoromethyl)-1H-pyridine-3-carboxamide | 0.005 |
| 9 | N-[5-[2-fluoro-5-(morpholin-4-ylmethyl)phenyl]-2-(4-methylpiperazin-1-yl)phenyl]-6-oxo-1H-pyridazine-3-carboxamide | 1.60 |
| 10 | N-[5-[2-fluoro-5-(morpholin-4-ylmethyl)phenyl]-2-(4-methylpiperazin-1-yl)phenyl]-3-methoxybenzamide | 1.00 |

TABLE 1-continued

Binding affinities ($K_D$) derived from surface plasmon resonance (SPR) assays.

| Compound ID | IUPAC Name | WDR5 binding affinity ($K_D$, μM) |
|---|---|---|
| 11 | 4-fluoro-N-[5-[2-fluoro-5-(morpholin-4-ylmethyl)phenyl]-2-(4-methylpiperazin-1-yl)phenyl]-3,5-dimethylbenzamide | 0.006 |
| 12 | 2-chloro-4-fluoro-N-[5-[2-fluoro-5-(morpholin-4-ylmethyl)phenyl]-2-(4-methylpiperazin-1-yl)phenyl]-3-methylbenzamide | 0.093 |
| 13 | N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide | 0.015 |
| 14 | methyl 4-fluoro-3-[4-(4-methylpiperazin-1-yl)-3-[[6-oxo-4-(trifluoromethyl)-1H-pyridine-3-carbonyl]amino]phenyl]benzoate | 0.026 |
| 15 | N-[5-[2-(cyclopropylmethoxy)-5-fluoropyridin-4-yl]-2-(4-methylpiperazin-1-yl)phenyl]-6-oxo-4-(trifluoromethyl)-1H-pyridine-3-carboxamide | 0.009 |
| 16 | N-[5-[6-(cyclopropylmethoxy)-2-fluoropyridin-3-yl]-2-(4-methylpiperazin-1-yl)phenyl]-6-oxo-4-(trifluoromethyl)-1H-pyridine-3-carboxamide | 0.010 |
| 17 | N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide | 0.014 |
| 18 | N-[5-[5-[(cyclohexylamino)methyl]-2-fluorophenyl]-2-(4-methylpiperazin-1-yl)phenyl]-4-fluoro-3,5-dimethylbenzamide | 0.027 |
| 19 | 4-fluoro-N-[5-[2-fluoro-6-(oxan-4-yloxy)pyridin-3-yl]-2-(4-methylpiperazin-1-yl)phenyl]-3,5-dimethylbenzamide | 0.071 |
| 20 | N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide | 0.076 |
| 21 | N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide | 0.019 |
| 22 | N-[5-(2-fluoro-6-pyrrolidin-1-ylpyridin-3-yl)-2-(4-methylpiperazin-1-yl)phenyl]-6-oxo-4-(trifluoromethyl)-1H-pyridine-3-carboxamide | 0.017 |
| 23 | N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide | 0.079 |
| 24 | N-[5-[2-fluoro-5-(morpholin-4-ylmethyl)phenyl]-2-(4-methylpiperazin-1-yl)phenyl]-3-methylbenzamide | 5.030 |
| 25 | N-[5-(2-fluorophenyl)-2-(4-methylpiperazin-1-yl)phenyl]-6-oxo-4-(trifluoromethyl)-1H-pyridine-3-carboxamide | 0.102 |
| 26 | N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide | 0.009 |
| 27 | N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.008 |
| 28 | N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide | 4.00 |
| 29 | N-[5-[2-fluoro-5-(morpholin-4-ylmethyl)phenyl]-2-(4-methylpiperazin-1-yl)phenyl]-4-methyl-6-oxo-1H-pyridine-3-carboxamide | 0.262 |
| 30 | N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide | 0.019 |
| 31 | N-[5-[5-fluoro-2-(oxan-4-yloxy)pyridin-4-yl]-2-(4-methylpiperazin-1-yl)phenyl]-6-oxo-4-(trifluoromethyl)-1H-pyridine-3-carboxamide | 0.009 |
| 32 | N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide | 0.006 |
| 33 | N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide | 0.023 |

TABLE 1-continued

Binding affinities ($K_D$) derived from surface plasmon resonance (SPR) assays.

| Compound ID | IUPAC Name | WDR5 binding affinity ($K_D$, μM) |
|---|---|---|
| 34 | N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide | 0.021 |
| 35 | N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide | 0.009 |
| 36 | 4-fluoro-N-[5-[2-fluoro-5-(morpholin-4-ylmethyl)phenyl]-2-(4-methylpiperazin-1-yl)phenyl]-3-methylbenzamide | 0.004 |
| 37 | N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide | 0.005 |
| 38 | N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide | 0.008 |
| 39 | N-[5-(3-fluoro-2-morpholin-4-ylpyridin-4-yl)-2-(4-methylpiperazin-1-yl)phenyl]-6-oxo-4-(trifluoromethyl)-1H-pyridine-3-carboxamide | 0.028 |
| 40 | N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide | 0.009 |
| 41 | 4-fluoro-N-[5-[2-fluoro-5-(morpholin-4-ylmethyl)phenyl]-2-(4-methylpiperazin-1-yl)phenyl]-3-methyl-5-(trifluoromethyl)benzamide | 0.055 |
| 42 | N-[5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide | 0.005 |
| 43 | N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide | 0.007 |
| 44 | N-[5-[2-fluoro-5-(morpholin-4-ylmethyl)phenyl]-2-(4-methylpiperazin-1-yl)phenyl]-4-hydroxy-2-(trifluoromethyl)benzamide | 0.069 |
| 45 | N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide | 0.002 |
| 46 | N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide | 0.00095 |
| 47 | N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide | 0.008 |
| 48 | 2,3-difluoro-N-[5-[2-fluoro-5-(morpholin-4-ylmethyl)phenyl]-2-(4-methylpiperazin-1-yl)phenyl]-5-hydroxybenzamide | 0.093 |
| 49 | 4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide | 0.007 |
| 50 | N-[5-[2-(cyclopropylmethoxy)-5-fluoropyridin-4-yl]-2-[(3R,5S)-3,4,5-trimethylpiperazin-1-yl]phenyl]-6-oxo-4-(trifluoromethyl)-1H-pyridine-3-carboxamide | 0.004 |
| 51 | (R)-N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide | >0.200 |
| 52 | N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide | >0.200 |
| 53 | N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide | >0.200 |

TABLE 1-continued

Binding affinities ($K_D$) derived from surface plasmon resonance (SPR) assays.

| Compound ID | IUPAC Name | WDR5 binding affinity ($K_D$, μM) |
|---|---|---|
| 54 | N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide | >0.200 |
| 55 | N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide | >0.200 |
| 56 | N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide | >0.200 |
| 57 | (R)-N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide | >0.200 |
| 58 | (S)-N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide | >0.200 |
| 59 | N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide | >0.200 |
| 60 | N-[5-[2-fluoro-5-(morpholin-4-ylmethyl)pyridin-3-yl]-2-[(3R,5S)-3,4,5-trimethylpiperazin-1-yl]phenyl]-6-oxo-4-(trifluoromethyl)-1H-pyridine-3-carboxamide | 0.007 |
| 61 | N-[5-[2-fluoro-5-(morpholin-4-ylmethyl)pyridin-3-yl]-2-(4-methylpiperazin-1-yl)phenyl]-6-oxo-4-(trifluoromethyl)-1H-pyridine-3-carboxamide | 0.007 |
| 62 | N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide | >0.200 |
| 63 | N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide | >0.200 |
| 64 | [4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate | >0.200 |
| 65 | N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide | 0.0094 |
| 66 | N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide | 0.0072 |
| 67 | N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide | 0.0032 |
| 68 | N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide | 0.0077 |
| 69 | (R)-N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide. | 0.0054 |
| 70 | N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide | 0.0044 |
| 71 | (R)-N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide | 0.0048 |
| 72 | N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide | 0.0051 |

TABLE 1-continued

Binding affinities (K$_D$) derived from surface plasmon resonance (SPR) assays.

| Compound ID | IUPAC Name | WDR5 binding affinity (K$_D$, μM) |
|---|---|---|
| 73 | N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide | 0.0042 |
| 74 | N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide | 0.0048 |
| 75 | N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide | 0.0059 |
| 76 | (S)-N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide | 0.0055 |
| 77 | N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide | 0.0045 |
| 78 | N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide | 0.039 |
| 79 | N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide | 0.0025 |
| 80 | N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide | 0.0040 |
| 81 | N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide | 0.0063 |
| 82 | N-[5-[6-(cyclopropylmethoxy)-2-fluoropyridin-3-yl]-2-[(3S,5R)-3,4,5-trimethylpiperazin-1-yl]phenyl]-6-oxo-4-(trifluoromethyl)-1H-pyridine-3-carboxamide | 0.0007 |
| 83 | N-[5-[3-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide | 0.010 |
| 84 | N-(5-(2-fluoro-5-(morpholinomethyl)phenyl)-2-(4-methylpiperazin-1-yl)pyridin-3-yl)-6-oxo-4-(trifluoromethyl)-1,6-dihydropyridine-3-carboxamide | 0.022 |
| 85 | N-(5-(5-((cyclohexylamino)methyl)-2-fluorophenyl)-2-(4-methylpiperazin-1-yl)pyridin-3-yl)-6-oxo-4-(trifluoromethyl)-1,6-dihydropyridine-3-carboxamide | 0.015 |
| 86 Comparative compound | N-(2'-chloro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide | 0.035 |
| 87 | N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide | 0.012 |
| 88 | N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide | 0.018 |
| 89 | N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide | 0.235 |
| 90 | N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide | 0.0065 |
| 91 | N-[2-[3-(dimethylamino)pyrrolidin-1-yl]-5-[2-fluoro-5-(morpholin-4-ylmethyl)phenyl]phenyl]-4-fluoro-3,5-dimethylbenzamide | 0.316 |

TABLE 1-continued

Binding affinities ($K_D$) derived from surface plasmon resonance (SPR) assays.

| Compound ID | IUPAC Name | WDR5 binding affinity ($K_D$, µM) |
|---|---|---|
| 92 | 4-fluoro-N-[5-[2-fluoro-5-(morpholin-4-ylmethyl)phenyl]-2-(4-methyl-1,4-diazepan-1-yl)phenyl]-3,5-dimethylbenzamide | 0.394 |
| 93 | N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide | 0.0031 |
| 94 | 4-fluoro-N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-3,5-dimethylbenzamide | >0.200 |
| 95 | 4-fluoro-N-[5-[2-fluoro-5-(morpholin-4-ylmethyl)phenyl]-2-[4-(2,2,2-trifluoroethyl)piperazin-1-yl]phenyl]-3,5-dimethylbenzamide | >0.200 |
| 96 | (S)-N-(2-(3,4-dimethylpiperazin-1-yl)-5-(3-fluoropyridin-2-yl)phenyl)-6-oxo-4-(trifluoromethyl)-1,6-dihydropyridine-3-carboxamide | 0.0026 |
| 97 | N-[5-[2-fluoro-5-(morpholin-4-ylmethyl)phenyl]-2-[4-(2,2,2-trifluoroethyl)piperazin-1-yl]phenyl]-6-oxo-4-(trifluoromethyl)-1H-pyridine-3-carboxamide | >0.200 |
| 98 | N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide | 0.017 |
| 99 | N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide | 0.014 |
| 100 | N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-6-oxo-4-(trifluoromethyl)-1H-pyridine-3-carboxamide | 5.930 |
| 101 | N-[2-[3-(dimethylamino)pyrrolidin-1-yl]-5-[2-fluoro-5-(morpholin-4-ylmethyl)phenyl]phenyl]-1-methyl-6-oxo-4-(trifluoromethyl)pyridine-3-carboxamide | 2.270 |
| 102 | 6-fluoro-N-[5-[2-fluoro-5-(morpholin-4-ylmethyl)phenyl]-2-(4-methylpiperazin-1-yl)phenyl]-1H-benzimidazole-4-carboxamide | >0.200 |
| 103 | N-[5-[2-fluoro-5-(morpholin-4-ylmethyl)phenyl]-2-(4-methylpiperazin-1-yl)phenyl]-1H-benzimidazole-2-carboxamide | >0.200 |
| 104 | N-[5-[2-fluoro-5-(morpholin-4-ylmethyl)phenyl]-2-[(2R)-2,4-dimethylpiperazin-1-yl]phenyl]-6-oxo-4-(trifluoromethyl)-1H-pyridine-3-carboxamide | 4 |
| 105 | N-[5-[2-fluoro-5-(morpholin-4-ylmethyl)phenyl]-2-(4-methylpiperazin-1-yl)phenyl]-6-oxo-1H-pyridine-3-carboxamide | 1.95 |
| 106 | 6-acetamido-N-[5-[2-fluoro-5-(morpholin-4-ylmethyl)phenyl]-2-(4-methylpiperazin-1-yl)phenyl]-4-methylpyridine-3-carboxamide | 0.0083 |
| 107 | N-[5-[5-[[4-(cyclopropylmethyl)piperazin-1-yl]methyl]-2-fluorophenyl]-2-(4-methylpiperazin-1-yl)phenyl]-6-methoxy-4-(trifluoromethyl)pyridine-3-carboxamide | >0.200 |
| 108 | N-[5-[2-fluoro-5-(morpholin-4-ylmethyl)phenyl]-2-(4-methylpiperazin-1-yl)phenyl]-6-(methylamino)-4-(trifluoromethyl)pyridine-3-carboxamide | >0.200 |
| 109 | 6-amino-N-[5-[2-fluoro-5-(morpholin-4-ylmethyl)phenyl]-2-(4-methylpiperazin-1-yl)phenyl]-4-(trifluoromethyl)pyridine-3-carboxamide | >0.200 |
| 110 | N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide | 0.0042 |
| 111 | N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide | 0.0024 |

TABLE 1-continued

Binding affinities (K$_D$) derived from surface plasmon resonance (SPR) assays.

| Compound ID | IUPAC Name | WDR5 binding affinity (K$_D$, μM) |
|---|---|---|
| 112 | N-[5-[2,4-difluoro-3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide | 0.023 |
| 113 | N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide | 0.0082 |
| 114 | N-[5-[3-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide | 0.013 |
| 115 | N-[5-[4-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide | 0.055 |
| 116 Comparative compound | N-[5-[2-chloro-5-(cyclohexylcarbamoyl)phenyl]-2-(4-methylpiperazin-1-yl)phenyl]-6-oxo-4-(trifluoromethyl)-1H-pyridine-3-carboxamide | 0.013 |
| 117 | N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0017 |
| 118 | N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0056 |
| 119 | N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0037 |
| 120 | N-(2',4'-difluoro-5'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0060 |
| 121 | N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0092 |
| 122 | N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0076 |
| 123 | N-(4'-carbamoyl-2',3'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide | 0.0036 |
| 124 | N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide | 0.0017 |
| 125 | N-(5-(5-fluoro-2-morpholinopyrimidin-4-yl)-2-((3S,5R)-3,4,5-trimethylpiperazin-1-yl)phenyl)-6-oxo-4-(trifluoromethyl)-1,6-dihydropyridine-3-carboxamide | 0.0030 |

TABLE 2

Inhibitory activity of exemplary compounds of the application in the in vitro methyl transferase assay (MLL1-WRAD2 assay).

| Example | WDR5 binding affinity SPR (K$_D$, μM) | Residence Time (t, min) | In vitro MLL1 activity (IC$_{50}$, μM) |
|---|---|---|---|
| 1 | 0.017 | 2.55 | 0.764 |
| 2 | 0.011 | 3.73 | 0.939 |
| 3 | 0.011 | 6.40 | 0.966 |
| 4 | 0.086 | 0.88 | NT |
| 5 | 0.029 | 1.88 | NT |
| 6 | 0.076 | 0.19 | 2.51 |
| 7 | 0.004 | 7.88 | 0.216 |
| 8 | 0.005 | 5.85 | 1.48 |
| 9 | 1.60 | NT | NT |
| 10 | 1.00 | NT | NT |

TABLE 2-continued

Inhibitory activity of exemplary compounds of the application in the in vitro methyl transferase assay (MLL1-WRAD2 assay).

| Example | WDR5 binding affinity SPR ($K_D$, μM) | Residence Time (t, min) | In vitro MLL1 activity ($IC_{50}$, μM) |
|---|---|---|---|
| 11 | 0.006 | 1.04 | 4.43 |
| 12 | 0.093 | 0.60 | NT |
| 13 | 0.015 | 0.30 | 8.98 |
| 14 | 0.026 | 1.36 | NT |
| 15 | 0.009 | 4.04 | 2.25 |
| 16 | 0.010 | 5.25 | 1.47 |
| 17 | 0.014 | 4.25 | NT |
| 18 | 0.027 | 2.67 | NT |
| 19 | 0.071 | 1.44 | NT |
| 20 | 0.076 | 0.41 | NT |
| 21 | 0.019 | 1.75 | NT |
| 22 | 0.017 | 2.30 | NT |
| 23 | 0.079 | 0.56 | NT |
| 24 | 5.03 | ND | NT |
| 25 | 0.102 | 0.94 | NT |
| 26 | 0.009 | 3.07 | 0.779 |
| 27 | 0.008 | 5.84 | 0.529 |
| 28 | 4.00 | ND | NT |
| 29 | 0.262 | 0.42 | 26.7 |
| 30 | 0.020 | 1.35 | 15.7 |
| 31 | 0.009 | 5.76 | 1.74 |
| 32 | 0.006 | 9.48 | 0.332 |
| 33 | 0.023 | 1.37 | 8.45 |
| 34 | 0.021 | 0.26 | 13.7 |
| 35 | 0.009 | 4.59 | 2.39 |
| 36 | 0.004 | 0.12 | >30 |
| 37 | 0.006 | 4.38 | 1.3 |
| 38 | 0.008 | 3.42 | 3.99 |
| 39 | 0.028 | 1.46 | 2.51 |
| 40 | 0.009 | 2.52 | 6.29 |
| 41 | 0.055 | 0.77 | >30 |
| 42 | 0.005 | 4.43 | 2.28 |
| 43 | 0.007 | 3.64 | 3.25 |
| 44 | 0.069 | 0.23 | >30 |
| 45 | 0.002 | 31.9 | 0.514 |
| 46 | 0.00095 | 74.4 | 0.290 |
| 47 | 0.008 | 9.58 | 2.39 |
| 48 | 0.093 | 0.61 | 21.3 |
| 49 | 0.007 | 3.89 | 1.57 |
| 50 | 0.004 | 12.6 | 1.79 |
| 51 | >0.200 | ND | NT |
| 52 | >0.200 | ND | NT |
| 53 | >0.200 | ND | NT |
| 54 | >0.200 | ND | NT |
| 55 | >0.200 | ND | NT |
| 56 | >0.200 | ND | NT |
| 57 | >0.200 | ND | NT |
| 58 | >0.200 | ND | NT |
| 59 | >0.200 | ND | NT |
| 60 | 0.007 | 9.50 | 1.41 |
| 61 | 0.007 | 2.29 | 4.49 |
| 62 | >0.200 | ND | 13.5 |
| 63 | >0.200 | ND | 5.63 |
| 64 | 0.102 | ND | NT |
| 65 | 0.0094 | 9.93 | 7.3 |
| 66 | 0.0072 | 3.79 | 1.10 |
| 67 | 0.0032 | 8.80 | 1.15 |
| 68 | 0.0077 | 3.81 | 1.89 |
| 69 | 0.0054 | 2.36 | 2.89 |
| 70 | 0.0044 | 5.80 | 1.11 |
| 71 | 0.0048 | 4.29 | 2.07 |
| 72 | 0.0051 | 1.16 | 5.93 |
| 73 | 0.0042 | 5.44 | 0.592 |
| 74 | 0.0048 | 3.90 | 1.75 |
| 75 | 0.0059 | 5.13 | 2.09 |
| 76 | 0.0055 | 3.81 | 1.90 |
| 77 | 0.0045 | 5.41 | 0.907 |
| 78 | 0.0390 | 2.50 | NT |
| 79 | 0.0025 | 16.4 | NT |
| 80 | 0.0140 | 2.18 | 3.99 |
| 81 | 0.0175 | 0.78 | >30 |
| 82 | 0.0007 | 23.0 | 0.549 |
| 83 | 0.0103 | 3.24 | NT |
| 84 | 0.022 | 0.91 | >30 |
| 85 | 0.0148 | 0.78 | NT |
| 86 | 0.0345 | 2.72 | NT |
| 87 | 0.012 | 5.76 | 3.89 |
| 88 | 0.018 | 1.71 | NT |
| 89 | 0.235 | 0.07 | NT |
| 90 | 0.0064 | 3 | 1.093 |
| 91 | 0.316 | ND | NT |
| 92 | 0.394 | ND | NT |
| 93 | 0.003 | 9.6 | 0.197 |
| 94 | >0.200 | ND | NT |
| 95 | >0.200 | ND | NT |
| 96 | 0.003 | 7.2 | 2.534 |
| 97 | >0.200 | ND | NT |
| 98 | 0.017 | 0.78 | 40.12 |
| 99 | 0.014 | 2.2 | 3.985 |
| 100 | 5.930 | ND | NT |
| 101 | 2.274 | ND | NT |
| 102 | >0.200 | ND | NT |
| 103 | >0.200 | ND | NT |
| 104 | 4 | ND | NT |
| 105 | 1.95 | ND | NT |
| 106 | 0.829 | 3.2 | NT |
| 107 | >0.200 | ND | NT |
| 108 | >0.200 | ND | NT |
| 109 | >0.200 | ND | NT |
| 110 | 0.004 | 7.2 | 0.607 |
| 111 | 0.024 | 34 | 0.203 |
| 112 | 0.023 | 1.3 | NT |
| 113 | 0.008 | 5.5 | 2.1 |
| 114 | 0.013 | 4.3 | 11.1 |
| 115 | 0.055 | 1.5 | NT |
| 116 | 0.013 | 3.7 | 1.9 |
| 117 | 0.0016 | 7.9 | NT |
| 118 | 0.006 | 7.2 | NT |
| 119 | 0.004 | 2.8 | NT |
| 120 | 0.006 | 12.5 | NT |
| 121 | 0.009 | 2.3 | NT |
| 122 | 0.008 | 6.7 | NT |
| 123 | 0.004 | 4.2 | NT |
| 124 | 0.0017 | 20.6 | 0.293 |
| 125 | 0.0031 | 11.6 | 0.049 |

ND: Not determined;
NT: Not tested

TABLE 3

Whole cell potency of exemplary compounds of the application in MV-411 cells.

| Compound ID | In vitro whole cell potency in MV-411 cells, ($IC_{50}$, μM) |
|---|---|
| 2 | 0.634 |
| 3 | 3.18 |
| 7 | 0.410 |
| 15 | 2.26 |
| 16 | 5.97 |
| 26 | 0.491 |
| 27 | 0.737 |
| 31 | 1.28 |
| 32 | 0.680 |
| 37 | 2.91 |
| 38 | >10 |
| 39 | >10 |
| 45 | 0.074 |
| 46 | 0.118 |
| 47 | 1.99 |
| 49 | 2.24 |

TABLE 3-continued

Whole cell potency of exemplary compounds of the application in MV-411 cells.

| Compound ID | In vitro whole cell potency in MV-411 cells, (IC$_{50}$, μM) |
|---|---|
| 50 | 0.943 |
| 63 | >10 |
| 66 | 1.13 |
| 67 | 0.292 |
| 68 | 1.79 |
| 69 | >10 |
| 70 | 1.14 |
| 71 | 2.71 |
| 72 | >10 |
| 73 | 0.502 |
| 74 | 5.43 |
| 75 | 1.22 |
| 76 | 0.787 |
| 77 | 1.28 |
| 80 | 2.18 |
| 81 | >10 |
| 82 | 0.536 |
| 125 | 0.087 |

TABLE 4

Representative examples of the effect of Fluoro-substitution at

| Structure | Assay Results | Compound | Assay Results |
|---|---|---|---|
| (structure) | K$_D$ (SPR) = 0.036 μM<br>τ = 0.78 min<br>IC$_{50}$ (HMT) = 9.5 μM | (structure) | K$_D$ (SPR) = 0.011 μM<br>τ = 3.73 min<br>IC$_{50}$ (MLL1) = 0.939 μM |
| (structure) | K$_D$ (SPR) = 0.030 μM<br>τ = 0.91 min<br>IC$_{50}$ (HMT) = NT | (structure) | K$_D$ (SPR) = 0.011 μM<br>τ = 5.44 min<br>IC$_{50}$ (MLL1) = 0.592 μM |

TABLE 4-continued

Representative examples of the effect of Fluoro-substitution at

| Structure | Assay Results | Compound | Assay Results |
|---|---|---|---|
| | $K_D$ (SPR) = 0.0345 µM<br>τ = min<br>$IC_{50}$ (MLL1) = µM | | $K_D$ (SPR) = 0.011 µM<br>τ = 3.73 min<br>$IC_{50}$ (MLL1) = 0.939 µM |
| | $K_D$ (SPR) = 0.0132 µM | | $K_D$ (SPR) = 0.006 µM |

NT: Not tested

The invention claimed is:

1. A compound of Formula (I):

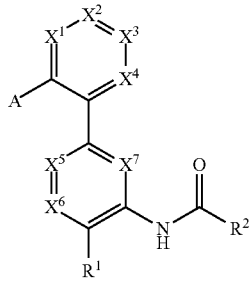

(I)

or a pharmaceutically acceptable salt thereof, wherein:

A is F;
$X^1$ is $CR^{10}$;
$X^2$ is $CR^{10}$;
$X^3$ is $CR^{10}$;
$X^4$ is $CR^{10}$;
$X^5$ is CH;
$X^6$ is CH;
$X^7$ is CH;
$R^1$ is heterocycloalkyl, optionally substituted with one or more substituents independently selected from the group consisting of halo, $C_{1-6}$ alkyl, $C_{1-6}$ fluoroalkyl, $C_{1-6}$ alkylene-$NR^5R^6$, $C_{1-6}$ alkylene-$OR^4$, $C_{1-6}$ alkylene-$SR^4$, $NR^5R^6$, $OR^4$, $SR^4$, and $C_{3-10}$ cycloalkyl;

$R^2$ is selected from the group consisting of:

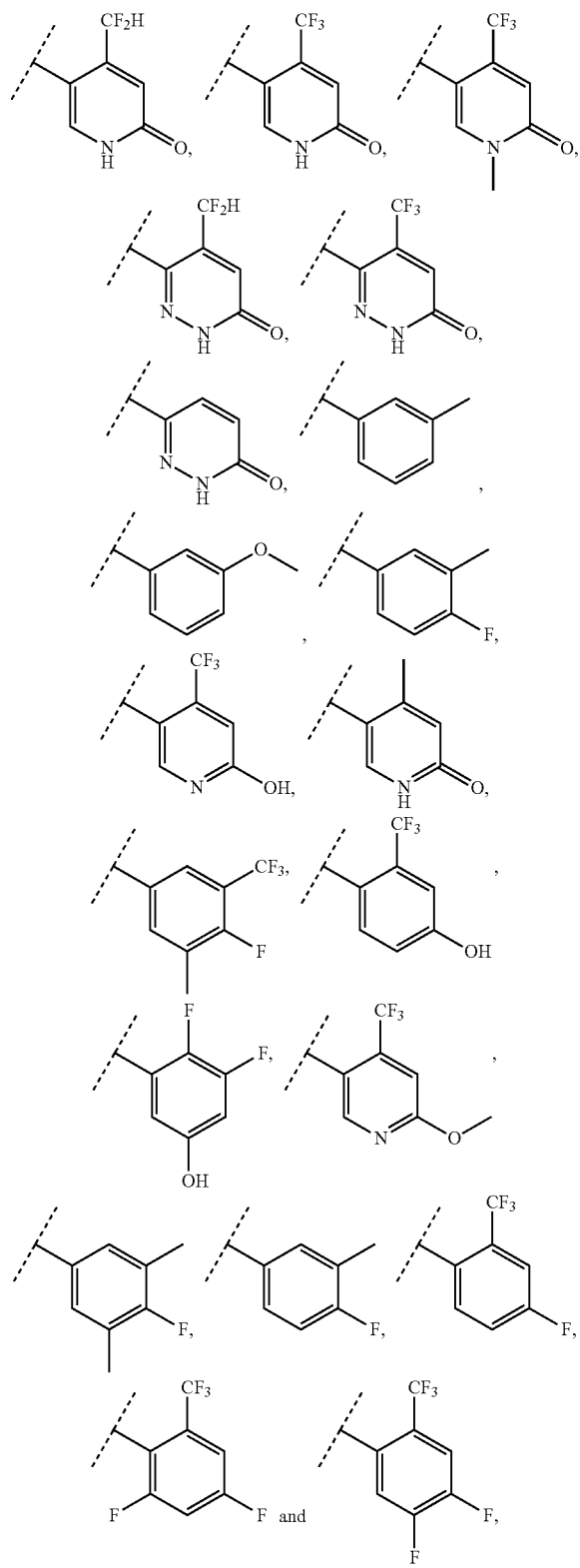

or a tautomer thereof;

$R^4$ is H, $C_{1-6}$ alkyl, $C_{1-6}$ fluoroalkyl, C(O)CH—, alkyl, or C(O)$C_{1-6}$ fluoroalkyl;

$R^5$ is H, $C_{1-6}$ alkyl, $C_{1-6}$ fluoroalkyl, $C_{1-6}$ alkylene-NH—$C_{1-6}$ alkyl, $C_{1-6}$ alkylene-N($C_{1-6}$ alkyl)($C_{1-6}$ alkyl), $C_{1-6}$ alkylene-O—$C_{1-6}$ alkyl, $C_{1-6}$ alkylene-$C_{3-6}$ cycloalkyl, $C_{1-6}$ alkylene-heterocycloalkyl, $C_{1-6}$ alkylene-$C_{6-10}$ aryl, $C_{1-6}$ alkylene-heteroaryl, C(O)$C_{1-6}$ alkyl, C(O)$C_{1-6}$ fluoroalkyl, C(O)NH$C_{1-6}$ alkyl, C(O)O$C_{1-6}$ alkyl, S(O)$_2 C_{1-6}$ alkyl, S(O)$_2$NH$C_{1-6}$ alkyl, or heterocycloalkyl;

$R^6$ is H, $C_{1-6}$ alkyl, $C_{1-6}$ fluoroalkyl, $C_{1-6}$ alkylene-NH—$C_{1-6}$ alkyl, $C_{1-6}$ alkylene-N($C_{1-6}$ alkyl)($C_{1-6}$ alkyl), $C_{1-6}$ alkylene-O—$C_{1-6}$ alkyl, $C_{1-6}$ alkylene-$C_{3-6}$ cycloalkyl, $C_{1-6}$ alkylene-heterocycloalkyl, $C_{1-6}$ alkylene-$C_{6-10}$ aryl, $C_{1-6}$ alkylene-heteroaryl, C(O)$C_{1-6}$ alkyl, C(O)$C_{1-6}$ fluoroalkyl, C(O)NH$C_{1-6}$ alkyl, C(O)O$C_{1-6}$ alkyl, S(O)$_2 C_{1-6}$ alkyl, S(O)$_2$NH$C_{1-6}$ alkyl, or heterocycloalkyl; or $R^5$ and $R^6$, together with the nitrogen atom to which they are attached, form a 3-10 membered heterocyclyl, optionally substituted with one or more substituents independently selected from the group consisting of halo, CN, $C_{1-6}$ alkyl, $C_{1-6}$ fluoroalkyl, $C_{1-6}$ alkylene-O—$C_{1-6}$ alkyl, $C_{1-6}$ alkylene-NH—$C_{1-6}$ alkyl, $C_{1-6}$ alkylene-N($C_{1-6}$ alkyl)($C_{1-6}$ alkyl),$C_{1-6}$ alkylene-$C_{3-6}$ cycloalkyl, $C_{1-6}$ alkylene-heterocycloalkyl, $C_{1-6}$ alkylene-$C_{6-10}$ aryl, $C_{1-6}$ alkylene-heteroaryl, C(O)$C_{1-6}$ alkyl, C(O)$C_{1-6}$ fluoroalkyl, C(O)NH$C_{1-6}$ alkyl, C(O)O$C_{1-6}$ alkyl, OH, O$C_{1-6}$ alkyl, O$C_{1-6}$ fluoroalkyl, S(O)$_2 C_{1-6}$ alkyl, and S(O)$_2$NH$C_{1-6}$ alkyl;

$R^7$ is H, $C_{1-6}$ alkyl, $C_{1-6}$ fluoroalkyl, C(O)$C_{1-6}$ alkyl, or C(O)$C_{1-6}$ fluoroalkyl;

$R^8$ is H, $C_{1-6}$ alkyl, $C_{1-6}$ fluoroalkyl, C(O)$C_{1-6}$ alkyl, or C(O)$C_{1-6}$ fluoroalkyl;

$R^9$ is H, $C_{1-6}$ alkyl, $C_{1-6}$ fluoroalkyl, C(O)$C_{1-6}$ alkyl, or C(O)$C_{1-6}$ fluoroalkyl; or $R^8$ and $R^9$, together with the nitrogen atom to which they are attached, form a 3-10 membered heterocyclyl, optionally substituted with one or more substituents independently selected from the group consisting of halo, CN, $C_{1-6}$ alkyl, $C_{1-6}$ fluoroalkyl, OH, O$C_{1-6}$ alkyl, or O$C_{1-6}$ fluoroalkyl;

$R^{10}$ is H, halo, CN, $C_{1-6}$ alkyl, $C_{1-6}$ fluoroalkyl, $C_{1-6}$ alkylene-$R^{14}$, $C_{1-6}$ alkylene-$NR^{12}R^{13}$, $C_{1-6}$ alkylene-$OR^{11}$, $C_{1-6}$ alkylene-$SR^{11}$, C(O)$NR^{12}R^{13}$, C(O)$OR^{11}$, C(S)$NR^{12}R^{13}$, C(S)$OR^{11}$, $NR^{12}R^{13}$, $OR^{11}$, O$C_{1-6}$ alkylene-$R^{14}$, O$C_{1-6}$ alkylene-$NR^{12}R^{13}$, O$C_{1-6}$ alkylene-$OR^{11}$, O$C_{1-6}$alkylene-$SR^{11}$, $SR^{11}$, S$C_{1-6}$ alkylene-$R^{14}$, S$C_{1-6}$ alkylene-$NR^{12}R^{13}$, S$C_{1-6}$ alkylene-$OR^{11}$, S$C_{1-6}$ alkylene-$SR^{11}$, or $R^{14}$;

$R^{11}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, C(O)$C_{1-6}$ alkyl, C(O)$C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, CN, $C_{1-6}$ alkyl, $C_{1-6}$ alkylene-$NR^{16}R^{17}$, $C_{1-6}$ alkylene-$OR^{15}$, $C_{1-6}$ alkylene-$SR^{15}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{15}$, C(O)$NR^{16}R^{17}$, C(O)$OR^{15}$, C(O)$R^{15}$, $NR^{16}R^{17}$, $OR^{15}$, $SR^{15}$, S(O)$C_{1-6}$ alkyl, S(O)$_2 C_{1-6}$ alkyl, $C_{3-10}$ cycloalkyl, heterocycloalkyl, $C_{6-10}$ aryl, and heteroaryl;

$R^{12}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, C(O)$C_{1-6}$ alkyl, C(O)$C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, CN, $C_{1-6}$ alkyl, $C_{1-6}$ alkylene-$NR^{16}R^{17}$, $C_{1-6}$ alkylene-$OR^{15}$, $C_{1-6}$ alkylene-$SR^{15}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{15}$, $C(O)NR^{16}R^{17}$, $C(O)OR^{15}$, $C(O)R^{15}$, $NR^{16}R^{17}$, $OR^{15}$, $SR^{15}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{13}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, CN, $C_{1-6}$ alkyl, $C_{1-6}$ alkylene-$NR^{16}R^{17}$, $C_{1-6}$ alkylene-$OR^{15}$, $C_{1-6}$ alkylene-$SR^{15}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{15}$, $C(O)NR^{16}R^{17}$, $C(O)OR^{15}$, $C(O)R^{15}$, $NR^{16}R^{17}$, $OR^{15}$, $SR^{15}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; or $R^{12}$ and $R^{13}$, together with the nitrogen atom to which they are attached, form a 3-10 membered heterocyclyl, optionally substituted with one or more substituents independently selected from the group consisting of halo, CN, $C_{1-6}$ alkyl, $C_{1-6}$ alkylene-$NR^{16}R^{17}$, $C_{1-6}$ alkylene-$OR^{15}$, $C_{1-6}$ alkylene-$SR^{15}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{15}$, $C(O)NR^{16}R^{17}$, $C(O)OR^{15}$, $C(O)R^{15}$, $NR^{16}R^{17}$, $OR^{15}$, $SR^{15}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{14}$ is $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, CN, $C_{1-6}$ alkyl, $C_{1-6}$ alkylene-$NR^{16}R^{17}$, $C_{1-6}$ alkylene-$OR^{15}$, $C_{1-6}$ alkylene-$SR^{15}$, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C_{1-6}$ alkylene-$R^5$, $C(O)R^{15}$, $C(O)OR^5$, $C(O)NR^{16}R^{17}$, $NR^{16}R^{17}$, $OR^{15}$, $SR^{15}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{15}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C(O)C_{1-6}$ fluoroalkyl, $C_{3-10}$ cycloalkyl, heterocycloalkyl, or $C_{6-10}$ aryl, each optionally substituted with one or more substituents independently selected from the group consisting of halo, CN, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)$(C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)$(C_{1-6}$ alkyl), $C(O)OH$, $C(O)OC_{1-6}$ alkyl, $NH_2$, $NHC_{1-6}$ alkyl, $N(C_{1-6}$ alkyl)$(C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{16}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, CN, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)$(C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)$(C_{1-6}$ alkyl), $C(O)OH$, $C(O)OC_{1-6}$ alkyl, $NH_2$, $NHC_{1-6}$ alkyl, $N(C_{1-6}$ alkyl)$(C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; and $R^{17}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, CN, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)$(C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)$(C_{1-6}$ alkyl), $C(O)OH$, $C(O)OC_{1-6}$ alkyl, $NH_2$, $NHC_{1-6}$ alkyl, $N(C_{1-6}$ alkyl)$(C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; or $R^{16}$ and $R^{17}$, together with the nitrogen atom to which they are attached, form a 3-10 membered heterocyclyl, optionally substituted with one or more substituents independently selected from the group consisting of halo, CN, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)$(C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)$(C_{1-6}$ alkyl), $C(O)OH$, $C(O)OC_{1-6}$ alkyl, $NH_2$, $NHC_{1-6}$ alkyl, $N(C_{1-6}$ alkyl)$(C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

with the proviso that:
(1) $R^1$ comprises at least one basic nitrogen atom; and
(2) all alkyl and alkylene groups not otherwise specified are optionally substituted with fluoro.

2. The compound of claim 1, or a pharmaceutically acceptable salt thereof, wherein:
$X^1$ is CH;
$X^2$ is CH;
$X^3$ is CH; and
$X^4$ is CH.

3. The compound of claim 1, or a pharmaceutically acceptable salt thereof, wherein:

$X^5$ is CH;

$X^6$ is CH; and $X^7$ is CH.

4. The compound of claim 1, or a pharmaceutically acceptable salt thereof, wherein $R^1$ is heterocycloalkyl, optionally substituted with one, two, or three substituents independently selected from the group consisting of halo, $C_{1-6}$ alkyl, $C_{1-6}$ fluoroalkyl, $C_{1-6}$ alkylene-$NR^5R^6$, $C_{1-6}$ alkylene-$OR^4$, and $NR^5R^6$.

5. The compound of claim 1, or a pharmaceutically acceptable salt thereof, wherein $R^1$ is selected from the group consisting of:

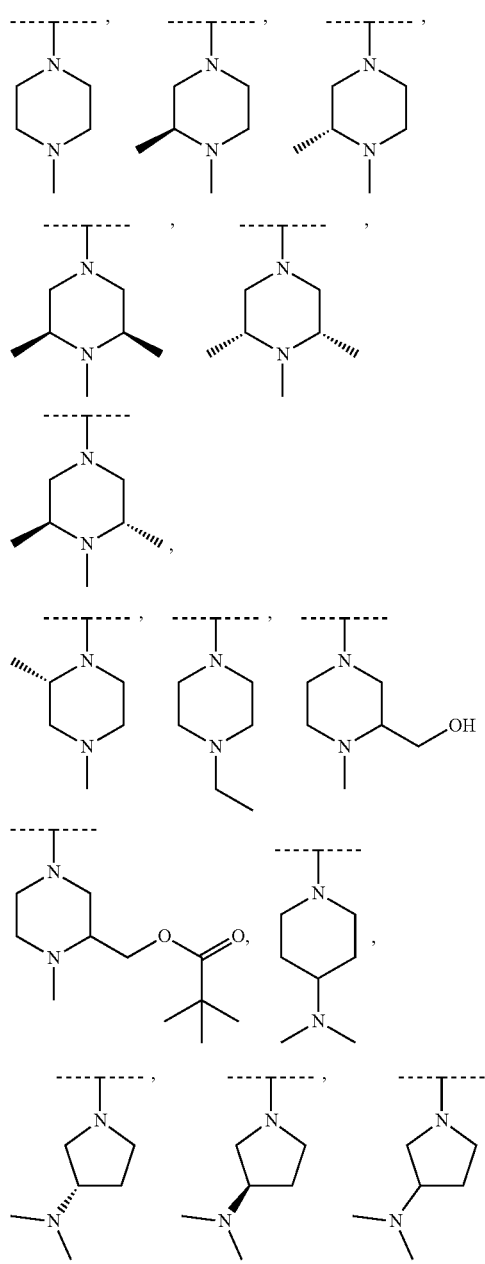

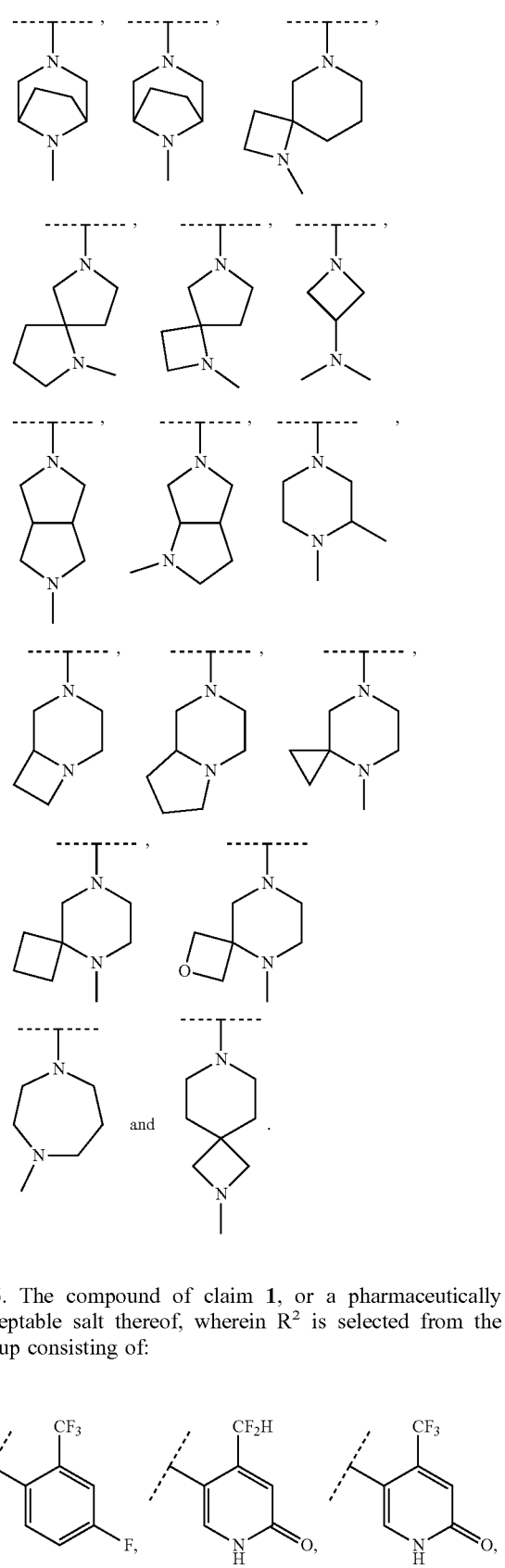

6. The compound of claim 1, or a pharmaceutically acceptable salt thereof, wherein $R^2$ is selected from the group consisting of:

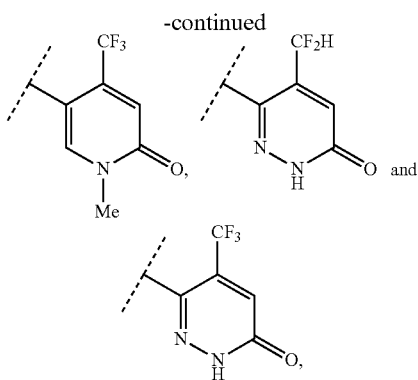

or a tautomer thereof.

7. The compound of claim 1, or a pharmaceutically acceptable salt thereof, wherein $R^4$ is H, $C_{1-6}$ alkyl, or $C(O)C_{1-6}$ alkyl.

8. The compound of claim 1, or a pharmaceutically acceptable salt thereof, wherein $R^5$ is H, $C_{1-6}$ alkyl, or heterocycloalkyl; and $R^6$ is H, $C_{1-6}$ alkyl, or heterocycloalkyl.

9. The compound of claim 1, or a pharmaceutically acceptable salt thereof, wherein $R^5$ and $R^6$, together with the nitrogen atom to which they are attached, form a 3-10 membered heterocyclyl, optionally substituted with one, two, or three substituents independently selected from the group consisting of halo and $C_{1-6}$ alkyl.

10. The compound of claim 1, or a pharmaceutically acceptable salt thereof, wherein $R^7$ is H or $C_{1-6}$ alkyl.

11. The compound of claim 1, or a pharmaceutically acceptable salt thereof, wherein $R^{10}$ is H, halo, CN, $C_{1-6}$ alkyl, $C_{1-6}$ fluoroalkyl, $C_{1-6}$ alkylene-$R^{14}$, $C_{1-6}$ alkylene-$NR^{12}R^{13}$, $C_{1-6}$ alkylene-$OR^{11}$, $C(O)NR^{12}R^{13}$, $C(O)OR^{11}$, $NR^{12}R^{13}$, $OR^{11}$, $OC_{1-6}$ alkylene-$R^{14}$, $OC_{1-6}$ alkylene-$NR^{12}R^{13}$, $OC_{1-6}$ alkylene-$OR^{11}$, or $R^{14}$.

12. The compound of claim 1, or a pharmaceutically acceptable salt thereof, wherein $R^{11}$ is H, $C_{1-6}$ alkyl, $C_{1-6}$ fluoroalkyl, $C_{3-10}$ cycloalkyl, heterocycloalkyl, $C_{6-10}$ aryl, or heteroaryl.

13. The compound of claim 1, or a pharmaceutically acceptable salt thereof, wherein:

$R^{12}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo and $C_{1-6}$ alkyl; and $R^{13}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo and $C_{1-6}$ alkyl.

14. The compound of claim 1, or a pharmaceutically acceptable salt thereof, wherein $R^{12}$ and $R^{13}$, together with the nitrogen atom to which they are attached, form a 3-10 membered heterocyclyl, optionally substituted with one or more substituents independently selected from the group consisting of halo, $C_{1-6}$ alkyl, $C_{1-6}$ alkylene-$C_{3-10}$ cycloalkyl, $C_{1-6}$ alkylene-$R^{15}$, $NR^{16}R^{17}$, $OR^{15}$, $S(O)_2C_{1-6}$ alkyl, and heterocycloalkyl.

15. The compound of claim 1, or a pharmaceutically acceptable salt thereof, wherein $R^{14}$ is $C_{3-10}$ cycloalkyl or heterocycloalkyl.

16. The compound of claim 1, or a pharmaceutically acceptable salt thereof, wherein $R^{15}$ is H, $C_{1-6}$ alkylene-$C_{6-10}$ aryl, or $C_{6-10}$ aryl, wherein $C_{1-6}$ alkylene-$C_{6-10}$ aryl and $C_{6-10}$ aryl are each optionally substituted with one or more substituents independently selected from the group consisting of halo and $C_{1-6}$ alkyl.

17. The compound of claim 1, or a pharmaceutically acceptable salt thereof, wherein:

$R^{16}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{3-10}$ cycloalkyl, heterocycloalkyl, or $C_{6-10}$ aryl; and $R^{17}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{3-10}$ cycloalkyl, heterocycloalkyl, or $C_{6-10}$ aryl.

18. The compound of claim 1, wherein the compound is selected from the group consisting of:

N-[5-[5-[[(2S,6R)-2,6-dimethylmorpholin-4-yl]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-4-(methoxymethoxy)-5-(2,4,4-trimethylpentan-2-ylcarbamoyl)phenyl]-2-(4-methylpiperazin-1-yl)phenyl]-6-oxo-4-(trifluoromethyl)-1H-pyridine-3-carboxamide;

N-[5-(5-carbamoyl-2-fluoro-4-hydroxyphenyl)-2-(4-methylpiperazin-1-yl)phenyl]-6-oxo-4-(trifluoromethyl)-1H-pyridine-3-carboxamide;

N-[5-[2-fluoro-5-(trifluoromethoxy)phenyl]-2-(4-methylpiperazin-1-yl)phenyl]-6-oxo-4-(trifluoromethyl)-1H-pyridine-3-carboxamide;

N-[5-[2-fluoro-5-(2-methylpropoxy)phenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridazine-3-carboxamide;

N-[5-[2-fluoro-5-(morpholin-4-ylmethyl)phenyl]-2-(4-methylpiperazin-1-yl)phenyl]-3-methoxybenzamide;

4-fluoro-N-[5-[2-fluoro-5-(morpholin-4-ylmethyl)phenyl]-2-(4-methylpiperazin-1-yl)phenyl]-3,5-dimethylbenzamide;

N-[5-[2-fluoro-5-(morpholin-4-ylmethyl)phenyl]-2-(4-methylpiperazin-1-yl)phenyl]-1-methyl-6-oxo-4-(trifluoromethyl)pyridine-3-carboxamide;

methyl 4-fluoro-3-[4-(4-methylpiperazin-1-yl)-3-[[6-oxo-4-(trifluoromethyl)-1H-pyridine-3-carbonyl]amino]phenyl]benzoate;

N-[5-[5-[(cyclopropylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(cyclohexylamino)methyl]-2-fluorophenyl]-2-(4-methylpiperazin-1-yl)phenyl]-4-fluoro-3,5-dimethylbenzamide;

N-[5-[2-fluoro-5-(morpholin-4-ylmethyl)phenyl]-2-(4-methylpiperazin-1-yl)phenyl]-6-oxo-4-(trifluoromethyl)-1H-pyridazine-3-carboxamide;

N-[5-[5-(cyclopropylmethoxy)-2,4-difluorophenyl]-2-(4-methylpiperazin-1-yl)phenyl]-6-oxo-4-(trifluoromethyl)-1H-pyridine-3-carboxamide;

N-[5-[2-fluoro-3-(morpholin-4-ylmethyl)phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-3-methylbenzamide;

N-[5-(2-fluorophenyl)-2-(4-methylpiperazin-1-yl)phenyl]-6-oxo-4-(trifluoromethyl)-1H-pyridine-3-carboxamide;

N-[2-(3,4-dimethylpiperazin-1-yl)-5-[2-fluoro-5-(morpholin-4-ylmethyl)phenyl]phenyl]-6-hydroxy-4-(trifluoromethyl)pyridine-3-carboxamide;

N-(2'-fluoro-5'-(morpholinomethyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-[2-[(2S)-2,4-dimethylpiperazin-1-yl]-5-[2-fluoro-5-(morpholin-4-ylmethyl)phenyl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-methyl-6-oxo-1H-pyridine-3-carboxamide;

N-(2',6-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-[5-[5-(cyclohexylcarbamoyl)-2-fluorophenyl]-2-(4-methylpiperazin-1-yl)phenyl]-6-oxo-4-(trifluoromethyl)-1H-pyridine-3-carboxamide;

N-[5-[4-[(cyclopentylamino)methyl]-2-fluorophenyl]-2-(4-methylpiperazin-1-yl)phenyl]-6-oxo-4-(trifluoromethyl)-1H-pyridine-3-carboxamide;

N-[5-[4-[(cyclohexylamino)methyl]-2-fluorophenyl]-2-(4-methylpiperazin-1-yl)phenyl]-6-oxo-4-(trifluoromethyl)-1H-pyridine-3-carboxamide;

N-[5-[5-[(tert-butylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methylbenzamide;

N-[5-[2-fluoro-5-[(oxan-4-ylamino)methyl]phenyl]-2-(4-methylpiperazin-1-yl)phenyl]-6-oxo-4-(trifluoromethyl)-1H-pyridine-3-carboxamide;

N-[5-[2-fluoro-4-(morpholin-4-ylmethyl)phenyl]-2-(4-methylpiperazin-1-yl)phenyl]-6-oxo-4-(trifluoromethyl)-1H-pyridine-3-carboxamide;

N-[5-[5-[(dimethylamino)methyl]-2-fluorophenyl]-2-(4-methylpiperazin-1-yl)phenyl]-6-oxo-4-(trifluoromethyl)-1H-pyridine-3-carboxamide;

4-fluoro-N-[5-[2-fluoro-5-(morpholin-4-ylmethyl)phenyl]-2-(4-methylpiperazin-1-yl)phenyl]-3-methyl-5-(trifluoromethyl)benzamide;

N-[5-[5-[[(4,4-difluorocyclohexyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[methyl(oxetan-3-yl)amino]methyl]phenyl]-2-(4-methylpiperazin-1-yl)phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-4-hydroxy-2-(trifluoromethyl)benzamide;

N-[5-[5-[(cyclohexylamino)methyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[5-(cyclohexylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2-fluoro-5-(morpholine-4-carbonyl)phenyl]-2-[(3R,5S)-3,4,5-trimethylpiperazin-1-yl]phenyl]-6-oxo-4-(trifluoromethyl)-1H-pyridine-3-carboxamide;

2,3-difluoro-N-[5-[2-fluoro-5-(morpholin-4-ylmethyl)phenyl]-2-(4-methylpiperazin-1-yl)phenyl]-5-hydroxybenzamide;

4-(difluoromethyl)-N-[5-[2-fluoro-5-(morpholin-4-ylmethyl)phenyl]-2-(4-methylpiperazin-1-yl)phenyl]-6-oxo-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-methoxy-4-(trifluoromethyl)nicotinamide;

N-[5-[2-fluoro-5-[(4-morpholin-4-ylpiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-[[(3S)-3-propan-2-ylpyrrolidin-1-yl]methyl]phenyl]-2-(4-methylpiperazin-1-yl)phenyl]-6-methoxy-4-(trifluoromethyl)pyridine-3-carboxamide;

N-[5-[5-[(4-acetylpiperazin-1-yl)methyl]-2-fluorophenyl]-2-(4-methylpiperazin-1-yl)phenyl]-6-methoxy-4-(trifluoromethyl)pyridine-3-carboxamide;

N-[5-[2-fluoro-5-[(4-fluoropiperidin-1-yl)methyl]phenyl]-2-(4-methylpiperazin-1-yl)phenyl]-6-methoxy-4-(trifluoromethyl)pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-methoxy-4-(trifluoromethyl)pyridine-3-carboxamide;

(R)—N-(2'-fluoro-4-(4-methylpiperazin-1-yl)-5'-((3-(methylsulfonyl)pyrrolidin-1-yl)methyl)-[1,1'-biphenyl]-3-yl)-6-methoxy-4-(trifluoromethyl)nicotinamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-methoxy-4-(trifluoromethyl)nicotinamide;

N-[5-[5-[(2,2-dimethylmorpholin-4-yl)methyl]-2-fluorophenyl]-2-(4-methylpiperazin-1-yl)phenyl]-6-methoxy-4-(trifluoromethyl)pyridine-3-carboxamide;

N-[2-(4-ethylpiperazin-1-yl)-5-[2-fluoro-5-(morpholin-4-ylmethyl)phenyl]phenyl]-6-oxo-4-(trifluoromethyl)-1H-pyridine-3-carboxamide;

N-[5-[5-[(cyclohexylamino)methyl]-2-fluorophenyl]-2-(4-ethylpiperazin-1-yl)phenyl]-6-oxo-4-(trifluoromethyl)-1H-pyridine-3-carboxamide;

[4-[4-[2-fluoro-5-(morpholin-4-ylmethyl)phenyl]-2-[[6-oxo-4-(trifluoromethyl)-1H-pyridine-3-carbonyl]amino]phenyl]-1-methylpiperazin-2-yl]methyl 2,2-dimethylpropanoate;

N-[5-[2-fluoro-5-(morpholin-4-ylmethyl)phenyl]-2-[3-(hydroxymethyl)-4-methylpiperazin-1-yl]phenyl]-6-oxo-4-(trifluoromethyl)-1H-pyridine-3-carboxamide;

N-[5-[5-[[4-(cyclopropylmethyl)piperazin-1-yl]methyl]-2-fluorophenyl]-2-(4-methylpiperazin-1-yl)phenyl]-6-oxo-4-(trifluoromethyl)-1H-pyridine-3-carboxamide;

N-[5-[5-[[cyclohexyl(methyl)amino]methyl]-2-fluorophenyl]-2-(4-methylpiperazin-1-yl)phenyl]-6-oxo-4-(trifluoromethyl)-1H-pyridine-3-carboxamide;

N-[5-[2-fluoro-5-[[4-[(4-fluorophenyl)methyl]piperazin-1-yl]methyl]phenyl]-2-(4-methylpiperazin-1-yl)phenyl]-6-oxo-4-(trifluoromethyl)-1H-pyridine-3-carboxamide;

(R)—N-(2'-fluoro-5'-((3-hydroxypyrrolidin-1-yl)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-[(4-morpholin-4-ylpiperidin-1-yl)methyl]phenyl]-2-(4-methylpiperazin-1-yl)phenyl]-6-oxo-4-(trifluoromethyl)-1H-pyridine-3-carboxamide;

(R)—N-(5'-((3-(dimethylamino)pyrrolidin-1-yl)methyl)-2'-fluoro-4-(4-methylpiperazin-1-yl)-[1,1'-biphenyl]-3-yl)-6-oxo-4-(trifluoromethyl)-1,6-dihydropyridine-3-carboxamide;

N-[5-[2-fluoro-5-(piperazin-1-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[(4-fluoropiperidin-1-yl)methyl]phenyl]-2-(4-methylpiperazin-1-yl)phenyl]-6-oxo-4-(trifluoromethyl)-1H-pyridine-3-carboxamide;

N-[5-[2-fluoro-5-(3-oxa-6-azabicyclo[3.1.1]heptan-6-ylmethyl)phenyl]-2-(4-methylpiperazin-1-yl)phenyl]-6-oxo-4-(trifluoromethyl)-1H-pyridine-3-carboxamide;

N-[5-[2-fluoro-5-[[(3R)-3-methylsulfonylpyrrolidin-1-yl]methyl]phenyl]-2-(4-methylpiperazin-1-yl)phenyl]-6-oxo-4-(trifluoromethyl)-1H-pyridine-3-carboxamide;

(S)—N-(2'-fluoro-5'-((methyl(tetrahydrofuran-3-yl)amino)methyl)-4-(4-methylpiperazin-1-yl)-[1,1'-biphenyl]-3-yl)-6-oxo-4-(trifluoromethyl)-1,6-dihydropyridine-3-carboxamide;

N-[5-[5-[(2,2-dimethylmorpholin-4-yl)methyl]-2-fluorophenyl]-2-(4-methylpiperazin-1-yl)phenyl]-6-oxo-4-(trifluoromethyl)-1H-pyridine-3-carboxamide;

N-[5-(3-cyano-2,6-difluorophenyl)-2-[(3R,5S)-3,4,5-trimethylpiperazin-1-yl]phenyl]-6-oxo-4-(trifluoromethyl)-1H-pyridine-3-carboxamide;

N-[5-[5-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-[5-[2-fluoro-5-(phenylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-(5'-(cyclohexylcarbamoyl)-4-(3,4-dimethylpiperazin-1-yl)-2'-fluoro-[1,1'-biphenyl]-3-yl)-6-oxo-4-(trifluoromethyl)-1,6-dihydropyridine-3-carboxamide;

N-[5-[3-[(cyclohexylamino)methyl]-2,4-difluorophenyl]-2-[(3S,5R)-3,4,5-trimethylpiperazin-1-yl]phenyl]-6-oxo-4-(trifluoromethyl)-1H-pyridine-3-carboxamide;

N-(4-(3-(dimethylamino)pyrrolidin-1-yl)-2'-fluoro-5'-(morpholinomethyl)-[1,1'-biphenyl]-3-yl)-6-oxo-4-(trifluoromethyl)-1,6-dihydropyridine-3-carboxamide;

N-(2'-fluoro-4-(4-methyl-1,4-diazepan-1-yl)-5'-(morpholinomethyl)-[1,1'-biphenyl]-3-yl)-6-oxo-4-(trifluoromethyl)-1,6-dihydropyridine-3-carboxamide;

N-(2'-fluoro-4-(4-methyl-1,4-diazepan-1-yl)-5'-(morpholinomethyl)-[1,1'-biphenyl]-3-yl)-1-methyl-6-oxo-4-(trifluoromethyl)-1,6-dihydropyridine-3-carboxamide;

N-[5-[2-fluoro-5-(methylcarbamoyl)phenyl]-2-[(3R,5S)-3,4,5-trimethylpiperazin-1-yl]phenyl]-6-oxo-4-(trifluoromethyl)-1H-pyridine-3-carboxamide;

N-[2-[3-(dimethylamino)pyrrolidin-1-yl]-5-[2-fluoro-5-(morpholin-4-ylmethyl)phenyl]phenyl]-4-fluoro-3,5-dimethylbenzamide;

4-fluoro-N-[5-[2-fluoro-5-(morpholin-4-ylmethyl)phenyl]-2-(4-methyl-1,4-diazepan-1-yl)phenyl]-3,5-dimethylbenzamide;

N-[5-[5-(cyclopropylcarbamoyl)-2-fluorophenyl]-2-[(3R,5S)-3,4,5-trimethylpiperazin-1-yl]phenyl]-6-oxo-4-(trifluoromethyl)-1H-pyridine-3-carboxamide;

4-fluoro-N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-3,5-dimethylbenzamide;

4-fluoro-N-[5-[2-fluoro-5-(morpholin-4-ylmethyl)phenyl]-2-[4-(2,2,2-trifluoroethyl)piperazin-1-yl]phenyl]-3,5-dimethylbenzamide;

N-[5-[2-fluoro-5-(morpholin-4-ylmethyl)phenyl]-2-[4-(2,2,2-trifluoroethyl)piperazin-1-yl]phenyl]-6-oxo-4-(trifluoromethyl)-1H-pyridine-3-carboxamide;

N-(2',5-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-(2,2'-difluoro-4-(4-methylpiperazin-1-yl)-5'-(morpholinomethyl)-[1,1'-biphenyl]-3-yl)-6-oxo-4-(trifluoromethyl)-1,6-dihydropyridine-3-carboxamide;

N-[5-[2-fluoro-5-(morpholin-4-ylmethyl)phenyl]-2-(2-methyl-1,3,3a,4,6,6a-hexahydropyrrolo[3,4-c]pyrrol-5-yl)phenyl]-6-oxo-4-(trifluoromethyl)-1H-pyridine-3-carboxamide;

N-[2-[3-(dimethylamino)pyrrolidin-1-yl]-5-[2-fluoro-5-(morpholin-4-ylmethyl)phenyl]phenyl]-1-methyl-6-oxo-4-(trifluoromethyl)pyridine-3-carboxamide;

N-[5-[2-fluoro-5-(morpholin-4-ylmethyl)phenyl]-2-[(2R)-2,4-dimethylpiperazin-1-yl]phenyl]-6-oxo-4-(trifluoromethyl)-1H-pyridine-3-carboxamide;

N-[5-[2-fluoro-5-(morpholin-4-ylmethyl)phenyl]-2-(4-methylpiperazin-1-yl)phenyl]-6-oxo-1H-pyridine-3-carboxamide;

6-acetamido-N-[5-[2-fluoro-5-(morpholin-4-ylmethyl)phenyl]-2-(4-methylpiperazin-1-yl)phenyl]-4-methylpyridine-3-carboxamide;

N-[5-[5-[[4-(cyclopropylmethyl)piperazin-1-yl]methyl]-2-fluorophenyl]-2-(4-methylpiperazin-1-yl)phenyl]-6-methoxy-4-(trifluoromethyl)pyridine-3-carboxamide;

N-[5-[5-[cyclohexyl(methyl)carbamoyl]-2-fluorophenyl]-2-(4-methylpiperazin-1-yl)phenyl]-6-oxo-4-(trifluoromethyl)-1H-pyridine-3-carboxamide;

N-[5-[5-[cyclohexyl(methyl)carbamoyl]-2-fluorophenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-3-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[2,4-difluoro-5-[[methyl(oxetan-3-yl)amino]methyl]phenyl]-2-[(3R,5S)-3,4,5-trimethylpiperazin-1-yl]phenyl]-6-oxo-4-(trifluoromethyl)-1H-pyridine-3-carboxamide;

N-[5-[3-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;

N-[5-[4-[(cyclohexylamino)methyl]-2,6-difluorophenyl]-2-[(3R,5S)-3,4,5-trimethylpiperazin-1-yl]phenyl]-6-oxo-4-(trifluoromethyl)-1H-pyridine-3-carboxamide;

N-(4'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2'-fluoro-4'-morpholino-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(5'-carbamoyl-2'-fluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;

N-(2',4'-difluoro-5'-((2,4,4-trimethylpentan-2-yl)carbamoyl)-4-((3S,5R)-3,4,5-trimethylpiperazin-1-yl)-[1,1'- biphenyl]-3-yl)-6-oxo-4-(trifluoromethyl)-1,6-dihydropyridine-3-carboxamide;
N-(5'-carbamoyl-2',4'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(2',3'-difluoro-4'-((2,4,4-trimethylpentan-2-yl)carbamoyl)-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide;
N-(4'-carbamoyl-2',3'-difluoro-4-((3S,5R)-3,4,5-trimethylpiperazin-1-yl)-[1,1'-biphenyl]-3-yl)-6-oxo-4-(trifluoromethyl)-1,6-dihydropyridine-3-carboxamide; and
N-(5'-(cyclohexylcarbamoyl)-2'-fluoro-4-(3,4,5-trimethylpiperazin-1-yl)-[1,1'-biphenyl]-3-yl)-6-oxo-4-(trifluoromethyl)-1,6-dihydropyridine-3-carboxamide,
or a pharmaceutically acceptable salt thereof.

19. A pharmaceutical composition comprising a pharmaceutically acceptable carrier and/or diluent and a compound of claim 1, or a pharmaceutically acceptable salt thereof.

20. A method for inhibiting WD repeat domain 5-mixed lineage leukemia 1 protein-protein binding in a subject in need thereof, comprising administering to the subject a therapeutically effective amount of at least one compound of claim 1, or a pharmaceutically acceptable salt thereof.

21. The method of claim 20, wherein the subject has a disease selected from the group consisting of bladder cancer, breast cancer, Burkitt's lymphoma, colorectal cancer, gastric cancer, glioma, leukemia, medulloblastoma, MYCN-amplified neuroblastoma, pancreatic cancer, prostate cancer, testicular cancer, and thyroid cancer.

22. A compound of Formula (Ia):

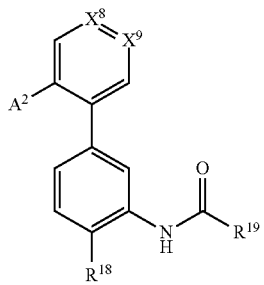

or a pharmaceutically acceptable salt thereof,
wherein:
$A^2$ is F;
$X^8$ is $CR^{26}$;
$X^9$ is $CR^{26}$;
$R^{18}$ is heterocycloalkyl, optionally substituted with one or more substituents independently selected from the group consisting of halo, $C_{1-6}$ alkyl, $C_{1-6}$ fluoroalkyl, $C_{1-6}$ alkylene-$NR^{21}R^{22}$, $C_{1-6}$ alkylene-$OR^{20}$, $C_{1-6}$ alkylene-$SR^{20}$, $NR^{21}R^{22}$, $OR^{20}$, and $SR^{20}$;
$R^{19}$ is selected from the group consisting of:

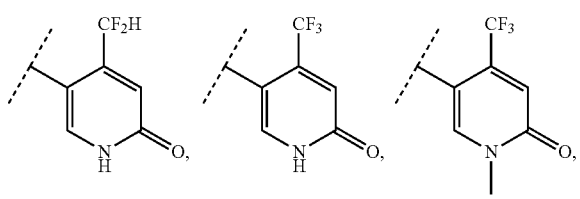

-continued or a tautomer thereof;
$R^{20}$ is H, $C_{1-6}$ alkyl, $C_{1-6}$ fluoroalkyl, $C(O)C_{1-6}$ alkyl, or $C(O)C_{1-6}$ fluoroalkyl;
$R^{21}$ is H, $C_{1-6}$ alkyl, $C_{1-6}$ fluoroalkyl, $C(O)C_{1-6}$ alkyl, $C(O)C_{1-6}$ fluoroalkyl, or heterocycloalkyl;
$R^{21}$ is H, $C_{1-6}$ alkyl, $C_{1-6}$ fluoroalkyl, $C(O)C_{1-6}$ alkyl, $C(O)C_{1-6}$ fluoroalkyl, or heterocycloalkyl;
$R^{22}$ is H, $C_{1-6}$ alkyl, $C_{1-6}$ fluoroalkyl, $C(O)C_{1-6}$ alkyl, $C(O)C_{1-6}$ fluoroalkyl, or heterocycloalkyl; or
$R^{21}$ and $R^{22}$, together with the nitrogen atom to which they are attached, form a 3-10 membered heterocyclyl, optionally substituted with one or more substituents independently selected from the group consisting of halo, $C_{1-6}$ alkyl, $C_{1-6}$ fluoroalkyl, $C(O)C_{1-6}$ alkyl, $C(O)$ $C_{1-6}$ fluoroalkyl, OH, $OC_{1-6}$ alkyl, and $OC_{1-6}$ fluoroalkyl;

$R^{24}$ is H, $C_{1-6}$ alkyl, $C_{1-6}$ fluoroalkyl, $C(O)C_{1-6}$ alkyl, or $C(O)C_{1-6}$ fluoroalkyl;

$R^{25}$ is H, $C_{1-6}$ alkyl, $C_{1-6}$ fluoroalkyl, $C(O)C_{1-6}$ alkyl, or $C(O)C_{1-6}$ fluoroalkyl; or $R^{24}$ and $R^{25}$, together with the nitrogen atom to which they are attached, form a 3-10 membered heterocyclyl, optionally substituted with one or more substituents independently selected from the group consisting of halo, $C_{1-6}$ alkyl, $C_{1-6}$ fluoroalkyl, OH, $OC_{1-6}$ alkyl, and $OC_{1-6}$ fluoroalkyl;

each $R^{26}$ is independently H, halo, CN, $C_{1-6}$ alkyl, $C_{1-6}$ fluoroalkyl, $C_{1-6}$ alkylene-$R^{30}$, $C_{1-6}$ alkylene-$NR^{28}R^{29}$, $C_{1-6}$ alkylene-$OR^{27}$, $C_{1-6}$ alkylene-$SR^{27}$, $C(O)NR^{28}R^{29}$, $C(O)OR^{27}$, $C(S)NR^{28}R^{29}$, $C(S)OR^{27}$, $NR^{28}R^{29}$, $OR^{27}$, $OC_{1-6}$ alkylene-$R^{30}$, $OC_{1-6}$ alkylene-$NR^{28}R^{29}$, $OC_{1-6}$ alkylene-$OR^{27}$, $OC_{1-6}$ alkylene-$SR^{27}$, $SR^{27}$, $SC_{1-6}$ alkylene-$R^{30}$, $SC_{1-6}$ alkylene-$NR^{28}R^{29}$, $SC_{1-6}$ alkylene-$OR^{27}$, $SC_{1-6}$ alkylene-$SR^{27}$, or $R^{30}$;

$R^{27}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, optionally substituted with one or more substituents independently selected from the group consisting of halo, $C_{1-6}$ alkyl, $C_{1-6}$ alkylene-$NR^{32}R^{33}$, $C_{1-6}$ alkylene-$OR^{31}$, $C_{1-6}$ alkylene-$SR^{31}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{31}$, $C(O)NR^{32}R^{33}$, $C(O)OR^{31}$, $C(O)R^{31}$, $NR^{32}R^{33}$, $OR^{31}$, $SR^{31}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{28}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{32}R^{33}$, $C_{1-6}$ alkylene-$OR^{31}$, $C_{1-6}$ alkylene-$SR^{31}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{31}$, $C(O)NR^{32}R^{33}$, $C(O)OR^{31}$, $C(O)R^{31}$, $NR^{32}R^{33}$, $OR^{31}$, $SR^{31}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{29}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{32}R^{33}$, $C_{1-6}$ alkylene-$OR^{31}$, $C_{1-6}$ alkylene-$SR^{31}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{31}$, $C(O)NR^{32}R^{33}$, $C(O)OR^{31}$, $C(O)R^{31}$, $NR^{32}R^{33}$, $OR^{31}$, $SR^{31}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; or $R^{28}$ and $R^{29}$, together with the nitrogen atom to which they are attached, form a 3-10 membered heterocyclyl, optionally substituted with one or more substituents independently selected from the group consisting of halo, $C_{1-6}$ alkyl, $C_{1-6}$ alkylene-$NR^{32}R^{33}$, $C_{1-6}$ alkylene-$OR^{31}$, $C_{1-6}$ alkylene-$SR^{31}$, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C_{1-6}$ alkylene-$R^{31}$, $C(O)NR^{32}R^{33}$, $C(O)OR^{31}$, $C(O)R^{31}$, $NR^{32}R^{33}$, $OR^{31}$, $SR^{31}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{30}$ is $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{32}R^{33}$, $C_{1-6}$ alkylene-$OR^{31}$, $C_{1-6}$ alkylene-$SR^{31}$, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C_{1-6}$ alkylene-$R^{31}$, $C(O)R^{31}$, $C(O)OR^{31}$, $C(O)NR^{32}R^{33}$, $NR^{32}R^{33}$, $OR^{31}$, $SR^{31}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{31}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C(O)C_{1-6}$ fluoroalkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{32}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; and $R^{33}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl$)(C_{1-6}$ alkyl$)$, $C(O)OH$, $C(O)OC_{1-6}$ alkyl, $NH_2$, $NHC_{1-6}$ alkyl, $N(C_{1-6}$ alkyl$)(C_{1-6}$ alkyl$)$, $OH$, $OC_{1-6}$ alkyl, $OC_{1-6}$ fluoroalkyl, $SH$, $SC_{1-6}$ alkyl, $SC_{1-6}$ fluoroalkyl, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl; or $R^{32}$ and $R^{33}$, together with the nitrogen atom to which they are attached, form a 3-10 membered heterocyclyl, optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl$)(C_{1-6}$ alkyl$)$, $C_{1-6}$ alkylene-$OH$, $C_{1-6}$ alkylene-$O$—$C_{1-6}$ alkyl, $C_{1-6}$ alkylene-$SH$, $C_{1-6}$ alkylene-$S$—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl$)(C_{1-6}$ alkyl$)$, $C(O)OH$, $C(O)OC_{1-6}$ alkyl, $NH_2$, $NHC_{1-6}$ alkyl, $N(C_{1-6}$ alkyl$)(C_{1-6}$ alkyl$)$, $OH$, $OC_{1-6}$ alkyl, $OC_{1-6}$ fluoroalkyl, $SH$, $SC_{1-6}$ alkyl, $SC_{1-6}$ fluoroalkyl, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl;

with the proviso that:
(1) $R^{18}$ comprises at least one basic nitrogen atom; and
(2) all alkyl and alkylene groups not otherwise specified are optionally substituted with fluoro.

23. A compound of Formula (Ib):

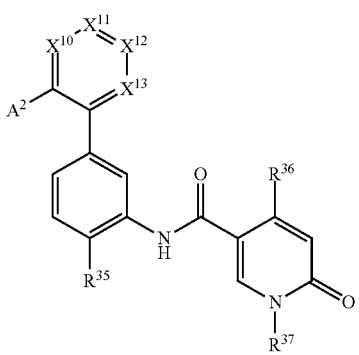

(Ib)

or a pharmaceutically acceptable salt thereof, wherein:
$X^{10}$ is CH;
$X^{11}$ is CH;
$X^{12}$ is $CR^{38}$;
$X^{13}$ is CH;
$R^{35}$ is

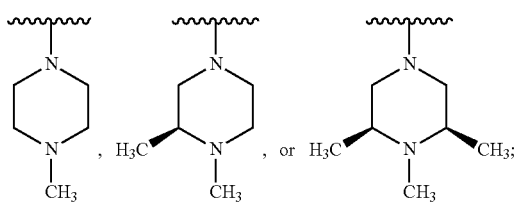

$R^{36}$ is $CHF_2$ or $CF_3$;
$R^{37}$ is H or $CH_3$;
$R^{38}$ is H, halo, CN, $C_{1-6}$ alkyl, $C_{1-6}$ fluoroalkyl, $C_{1-6}$ alkylene-$NR^{40}R^{41}$, $C_{1-6}$ alkylene-$OR^{39}$, $C_{1-6}$ alkylene-$SR^{39}$, $C_{1-6}$ alkylene-$R^{42}$, $C(O)NR^{40}R^{41}$, $C(O)OR^{39}$, $C(S)NR^{40}R^{41}$, $C(S)OR^{39}$, $NR^{40}R^{41}$, $OC_{1-6}$ alkylene-$NR^{40}R^{41}$, $OC_{1-6}$ alkylene-$OR^{39}$, $OC_{1-6}$ alkylene-$SR^{39}$, $OC_{1-6}$ alkylene-$R^{42}$, $OR^{39}$, $SC_{1-6}$ alkylene-$NR^{40}R^{41}$, $SC_{1-6}$ alkylene-$OR^{39}$, $SC_{1-6}$ alkylene-$SR^{39}$, $SC_{1-6}$ alkylene-$R^{42}$, or $SR^{39}$;
$R^{39}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{44}R^{45}$, $C_{1-6}$ alkylene-$OR^{43}$, $C_{1-6}$ alkylene-$SR^{43}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{43}$, $C(O)NR^{44}R^{45}$, $C(O)OR^{43}$, $C(O)R^{43}$, $NR^{44}R^{45}$, $OR^{43}$, $SR^{43}$, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl;
$R^{40}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{44}R^{45}$, $C_{1-6}$ alkylene-$OR^{43}$, $C_{1-6}$ alkylene-$SR^{43}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{43}$, $C(O)NR^{44}R^{45}$, $C(O)OR^{43}$, $C(O)R^{43}$, $NR^{44}R^{45}$, $OR^{43}$, $SR^{43}$, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl;
$R^{41}$ is H, $C_{1-10}$ alkyl, $C_{1-10}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{44}R^{45}$, $C_{1-6}$ alkylene-$OR^{43}$, $C_{1-6}$ alkylene-$SR^{43}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{43}$, $C(O)NR^{44}R^{45}$, $C(O)OR^{43}$, $C(O)R^{43}$, $NR^{44}R^{45}$, $OR^{43}$, $SR^{43}$, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl; or
$R^{40}$ and $R^{41}$, together with the nitrogen atom to which they are attached, form a 3-10 membered heterocyclyl, optionally substituted with one or more substituents independently selected from the group consisting of halo, $C_{1-6}$ alkyl, $C_{1-6}$ alkylene-$NR^{44}R^{45}$, $C_{1-6}$ alkylene-$OR^{43}$, $C_{1-6}$ alkylene-$SR^{43}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{43}$, $C(O)NR^{44}R^{45}$, $C(O)OR^{43}$, $C(O)R^{43}$, $NR^{44}R^{45}$, $OR^{43}$, $SR^{43}$, $S(O)C_{1-6}$ alkyl, $S(O)_2 C_{1-6}$ alkyl, $C_{3-10}$ cycloalkyl, heterocycloalkyl, $C_{6-10}$ aryl, and heteroaryl;
$R^{42}$ is $C(O)C_{1-6}$ alkyl, $C(O)C_{1-6}$ fluoroalkyl, $C_{3-10}$ cycloalkyl, heterocycloalkyl, $C_{6-10}$ aryl, or heteroaryl, each optionally substituted with one or more substituents independently selected from the group consisting of halo, $C_{1-6}$ alkyl, $C_{1-6}$ alkylene-$NR^{44}R^{45}$, $C_{1-6}$ alkylene-$OR^{43}$, $C_{1-6}$ alkylene-$SR^{43}$, $C_{1-6}$ alkylene-$C_{3-10}$ cycloalkyl, $C_{1-6}$ alkylene-$C_{6-10}$ aryl, $C_{1-6}$ alkylene-heterocycloalkyl, $C_{1-6}$ alkylene-heteroaryl, $C_{1-6}$ alkylene-$R^{43}$, $C(O)NR^{44}R^{45}$, $C(O)OR^{43}$, $C(O)R^{43}$, $NR^{44}R^{45}$, $OR^{43}$, $SR^{43}$, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{43}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C(O)C_{1-6}$ fluoroalkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

$R^{44}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; and $R^{45}$ is H, $C_{1-6}$ alkyl, $C_{1-6}$ fluoroalkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C(O)C_{1-6}$ alkyl, $C_{3-10}$ cycloalkyl, heterocycloalkyl, or $C_{6-10}$ aryl, each optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl; or $R^{44}$ and $R^{45}$, together with the nitrogen atom to which they are attached, form a 3-10 membered heterocyclyl, optionally substituted with one or more substituents independently selected from the group consisting of halo, $C_{1-6}$ alkyl, $C_{1-6}$ fluoroalkyl, $C_{1-6}$ alkylene-$NH_2$, $C_{1-6}$ alkylene-$NHC_{1-6}$ alkyl, $C_{1-6}$ alkylene-$N(C_{1-6}$ alkyl)($C_{1-6}$ alkyl), $C_{1-6}$ alkylene-OH, $C_{1-6}$ alkylene-O—$C_{1-6}$ alkyl, $C_{1-6}$ alkylene-SH, $C_{1-6}$ alkylene-S—$C_{1-6}$ alkyl, $C_{1-6}$ alkylene-$C_{3-10}$ cycloalkyl, $C_{1-6}$ alkylene-heterocycloalkyl, $C_{1-6}$ alkylene-$C_{6-10}$ aryl, $C_{1-6}$ alkylene-heteroaryl, $C(O)C_{1-6}$ alkyl, $C(O)C_{1-6}$ fluoroalkyl, $C(O)NH_2$, $C(O)NHC_{1-6}$ alkyl, $C(O)N(C_{1-6}$ alkyl)($C_{1-6}$ alkyl), $C(O)OH$, $C(O)OC_{1-6}$ alkyl, $NH_2$, $NHC_{1-6}$ alkyl, $N(C_{1-6}$ alkyl)($C_{1-6}$ alkyl), OH, $OC_{1-6}$ alkyl, $OC_{1-6}$ fluoroalkyl, SH, $SC_{1-6}$ alkyl, $SC_{1-6}$ fluoroalkyl, $S(O)C_{1-6}$ alkyl, $S(O)_2C_{1-6}$ alkyl, $C_{3-10}$ cycloalkyl, heterocycloalkyl, $C_{6-10}$ aryl, and heteroaryl;

with the proviso that:
(1) all alkyl and alkylene groups not otherwise specified are optionally substituted with fluoro.

\* \* \* \* \*